United States Patent
Lau et al.

(10) Patent No.: US 8,946,268 B2
(45) Date of Patent: Feb. 3, 2015

(54) MODULATORS OF HEC1 ACTIVITY AND METHODS THEREFOR

(75) Inventors: Johnson Lau, Newport Beach, CA (US); Huang Jiann-Jyh, Yilan County (TW)

(73) Assignee: Taivex Therapeutics, Inc., Taipei (TW)

( * ) Notice: Subject to any disclaimer, the term of this patent is extended or adjusted under 35 U.S.C. 154(b) by 250 days.

(21) Appl. No.: 13/048,709

(22) Filed: Mar. 15, 2011

(65) Prior Publication Data

US 2011/0230486 A1   Sep. 22, 2011

Related U.S. Application Data

(60) Provisional application No. 61/314,798, filed on Mar. 17, 2010.

(51) Int. Cl.
| | |
|---|---|
| *A61K 31/429* | (2006.01) |
| *C07D 417/12* | (2006.01) |
| *A61K 31/427* | (2006.01) |
| *A61K 31/4439* | (2006.01) |
| *A61K 31/496* | (2006.01) |
| *A61K 31/501* | (2006.01) |
| *A61K 31/506* | (2006.01) |
| *A61K 31/5377* | (2006.01) |

(52) U.S. Cl.
CPC .......... *A61K 31/427* (2013.01); *A61K 31/4439* (2013.01); *A61K 31/496* (2013.01); *A61K 31/501* (2013.01); *A61K 31/506* (2013.01); *A61K 31/5377* (2013.01); *C07D 417/12* (2013.01)
USPC ........................................ 514/342; 546/270.7

(58) Field of Classification Search
USPC ........................................ 546/270.7; 514/342
See application file for complete search history.

(56) References Cited

U.S. PATENT DOCUMENTS

| | | | | |
|---|---|---|---|---|
| 8,324,385 | B2 * | 12/2012 | Bolin et al. | 544/360 |
| 2005/0113420 | A1 * | 5/2005 | Nan et al. | 514/340 |
| 2006/0140956 | A1 | 6/2006 | Lee et al. | |

FOREIGN PATENT DOCUMENTS

| | | | |
|---|---|---|---|
| WO | 03/105891 | | 12/2003 |
| WO | 2004/033666 | | 4/2004 |
| WO | 2005/026137 | | 3/2005 |
| WO | 2007/004038 | | 1/2007 |
| WO | 2007008541 | * | 1/2007 |
| WO | 2007/131071 | | 11/2007 |
| WO | 2009014674 | * | 1/2009 |
| WO | 2009-140621 | | 11/2009 |
| WO | 2010/056506 | | 5/2010 |

OTHER PUBLICATIONS

Banerjee et al., "Synthesis of some, etc.," CA 88:165278 (1978).*
Bilinski et al., "Oscillopolarographic analysis, etc.," CA 66:46364 (1967).*
Sahu et al., "Condensed heterocycles. etc," CA 107:58982 (1987).*
Wu, G., et al, "Small Molecule Targeting the Hec1/Nek2 Pathway Suppresses Tumor Cell Growth in Culture and in Animal", American Association for Cancer Research, 2008:68:8393-8399, Published Online Oct. 15, 2008.
Qiu, X.L., et al., "Synthesis and Biological Evaluation of a Series of Novel Inhibitor of Nek2/Hec1 Analogues", Journal of Medical Chemistry, National Institutes of Health, Mar. 26, 2009, 52(6): 1757-1767.
PubChem, "F5773-1986—Compound Summary", http://pubchem.ncbi.nl.m.nih.gov/summary/summary.cgi?cid=4551765#x304, Feb. 2, 2013.
PubChem, "F5773-1987—Compound Summary", http://pubchem.ncbi.nl.m.nih.gov/summary/summary.cgi?cid=4551766#x304, Feb. 2, 2013.
PubChem, "F5773-1988—Compound Summary", http://pubchem.ncbi.nl.m.nih.gov/summary/summary.cgi?cid=4551767#x304, Feb. 2, 2013.
PubChem, "ZINC04072672—Compound Summary", http://pubchem.ncbi.nl.m.nih.gov/summary/summary.cgi?cid=4168446#x304, Feb. 2, 2013.
PubChem, "ZINC00946516—Compound Summary", http://pubchem.ncbi.nl.m.nih.gov/summary/summary.cgi?cid=1185425#x304, Feb. 2, 2013.
PubChem, "ZINC01746105—Compound Summary", http://pubchem.ncbi.nl.m.nih.gov/summary/summary.cgi?cid=155416#x304, Feb. 2, 2013.

* cited by examiner

*Primary Examiner* — Patricia L Morris
(74) *Attorney, Agent, or Firm* — Fish & Tsang, LLP

(57) ABSTRACT

Compounds, compositions, and methods for modulation of Hec1/Nek2 interaction are provided. Especially preferred compounds disrupt Nek2/Hec1 binding and are therefore useful as chemotherapeutic agent for neoplastic diseases.

15 Claims, 5 Drawing Sheets

| IC$_{50}$ in μM | Solid Tumor Cell Line | | | | Leukemia | | | |
|---|---|---|---|---|---|---|---|---|
| | Hela | MDA-MB468 | MDA-MB231 | PC-3 | K562 | *KG-1 | MV4-11 | RS4;11 |
| 1 | 0.6731 | 0.3500 | 0.3000 | 0.545 | 0.4296 | 0.5206 | 1.504 | 1.287 |
| 82 | 0.1620 | 0.1200 | 0.0960 | 0.165 | 0.0520 | 0.1092 | 0.560 | 0.218 |
| 95 | 0.0486 | 0.0370 | 0.0320 | 0.0600 | 0.0349 | 0.0289 | 0.231 | 0.254 |
| 99 | 0.0427 | 0.0400 | 0.0200 | 0.0580 | 0.0163 | 0.0187 | 0.188 | 0.096 |

Figure 1A

| IC$_{50}$ in μM | Normal Cell | | | |
|---|---|---|---|---|
| | WI-38[#2] | RPTEC | *HuVec | *HAoSMC |
| 1 | >10 | >10 | >9 | >9 |
| 82 | >10 | >10 | >9 | >9 |
| 95 | >10 | >10 | >9 | >9 |
| 99 | >10 | >10 | >9 | >9 |

Figure 1B

| IC$_{50}$(μM) or % inhibition | | | |
|---|---|---|---|
| Kinase \ Compounds | "82" | "95" | "99" |
| CHK1 | > 10 | > 10 | > 10 |
| CHK2 | > 10 | > 10 | > 10 |
| Cdk1/cyclin B | > 10 | > 10 | > 10 |
| Aurora A | > 10 | > 10 | > 10 |
| Aurora B | > 10 | > 10 | > 10 |
| mTOR | > 10 | > 10 | > 10 |
| PI3Kα | > 10 | > 10 | > 10 |
| PI3Kβ | > 10 | > 10 | > 10 |
| VEGFR-2 | > 10 | > 10 | > 10 |
| PDGFR-β | > 10 | > 10 | > 10 |
| FGFR-1 | > 10 | > 10 | > 10 |
| EGFR | > 10 | > 10 | > 10 |
| EGFR(T790M) | > 10 | > 10 | > 10 |
| IGF1-R | > 10 | > 10 | > 10 |
| B-Raf | > 10 | > 10 | > 10 |
| B-Raf(V600E) | > 10 | > 10 | > 10 |
| C-Raf | > 10 | > 10 | > 10 |
| Flt3 | > 10 | > 1 | > 10 |
| c-Met | > 10 | > 10 | > 10 |
| Kit | > 10 | > 10 | > 10 |

Figure 4

MODULATORS OF HEC1 ACTIVITY AND METHODS THEREFOR

This application claims priority to our copending U.S. provisional application with the Ser. No. 61/314,798, which was filed Mar. 17, 2010.

FIELD OF THE INVENTION

The field of the invention is various compounds, compositions, and methods related to modulation of activity of HEC1, particularly as it related to inhibition of tumor cell propagation.

BACKGROUND

While mechanisms associated with mitotic regulation are conceptually an attractive target in attempts to reduce tumor cell growth, compounds with high specific activity and selectivity and desirable pharmacological profile have been elusive. For example, the spindle apparatus can be targeted with spindle poisons (e.g., taxanes, vinca alkaloids, etc.) with relatively high activity, but many spindle poisons are unacceptable for pharmaceutical intervention as such poisons are often non-specific.

To improve specificity of treatment, components for spindle and kinetochore regulation or mitotic checkpoint control may be selected that have been shown to be functionally associated with cancer. For example, Hec1 is a critical component in spindle checkpoint signaling that is highly expressed in cancer and helps assure correct segregation of chromosomes during cell division. Hec1 interacts with various other kinetochore components including Nuf2, Spc 24, Spc25, and Zwint-1, as well as with mitotic kinases Nek2 and Aurora B. Overexpression of Hec1 is common among a large variety of cancers and cancer cell lines, and can often serve as a prognostic marker in primary breast cancer and other cancers. Based on the apparent importance of Hec1 in tumor cell growth, RNAi has been used to reduce Hec1 expression and shown considerable promise, at least in an animal model. However, in vivo delivery of siRNA with high specificity to the tumor is often problematic.

More recently, various small molecule inhibitors have been developed that interfere with the Nek2/Hec1 interaction. Since Nek2 is a regulatory component of Hec1 in mitosis, abrogation of the Hec1/Nek2 function was expected to result in chromosome mis-segregation and cell death. Several promising compounds have been reported (see *J. Med. Chem.*, 2009, 52 (6), pp 1757-1767, *Cancer Res.* 2008 Oct. 15; 68(20):8393-9) that had significant cell killing activity and directly targeted the Hec1/Nek2 pathway. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply. However, while the observed activity was in at least some cases promising, problems associated with solubility, toxicity, and relatively high half-maximal inhibitory concentrations nevertheless remained.

Thus, there is still a need for improved compounds, compositions, and methods for Hec1 inhibition, particularly as it relates to use of such compounds in the treatment of cancer.

SUMMARY OF THE INVENTION

The inventive subject matter is drawn to various compounds, compositions, and methods for Hec1 inhibition. More particularly, contemplated compounds will include those according to Formula I

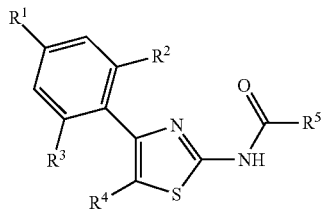

Formula I where $R^1$, $R^2$, $R^3$, $R^4$, and $R^5$ are described as further below. Further especially preferred compounds will have a structure according to Formulae II and III (with respective radicals also described in more detail below).

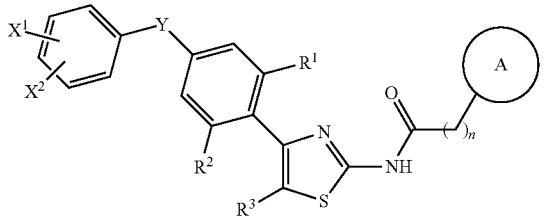

Formula II

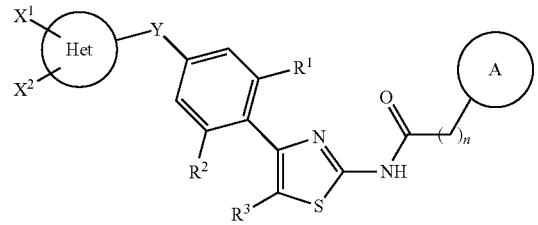

Formula III

In one aspect of the inventive subject matter, contemplated compounds are inhibitors of Hec1, and/or may be characterized as disrupting Hec1/Nek2 interaction. Consequently, the compounds presented herein are particularly suitable for use as therapeutic agents that disrupt the mitotic pathway. Therefore, and viewed from yet another perspective, especially contemplated compositions include pharmaceutical compositions that comprise one or more of contemplated compounds at a concentration effective to disrupt Hec1/Nek2 binding in a patient when the composition is administered to the patient.

Thus, in another aspect of the inventive subject matter, a method of disrupting Nek2/Hec1 interaction is contemplated and will include a step of contacting a Nek2/Hec1 complex with one or more compounds presented herein in an amount that is effective to disrupt Nek2/Hec1 binding. While all manners of contacting are generally contemplated, it is typically preferred that the step of contacting the Nek2/Hec1 complex is performed in vivo in a mammal, and that the step of contacting may also be performed in combination with an agent that interferes with microtubule formation or degradation.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIGS. 1A and 1B are tables illustrating the cytotoxic effect of selected compounds on tumor cells (1A) and normal cells (1B).

FIG. 4 is a table illustrating high specificity of contemplated compounds with respect to protein kinases.

DETAILED DESCRIPTION

Contemplated Compounds

Figure 2A:
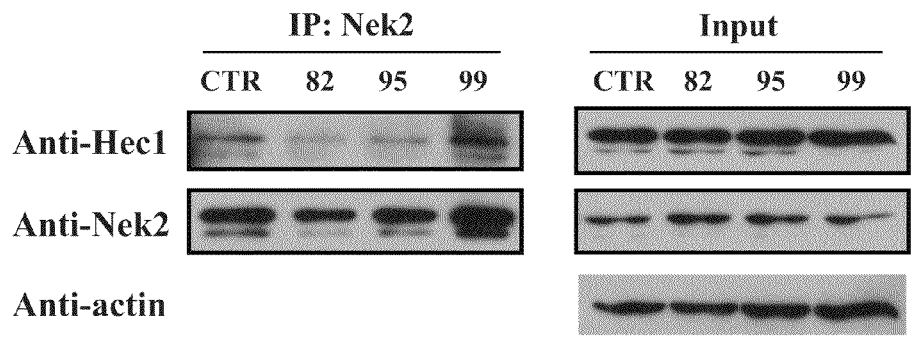
FIGS. 2A-2D are photographs of western blots depicting disruption of Hec1/Nek2 interaction (2A, 2B), Nek2 degradation (2C), and Nek2 instability (2D) caused by selected compounds.

The inventors have discovered that certain compounds according to Formula I can be prepared and have advantageous properties as moieties that interfere with Hec1. Particularly preferred compounds will include those according to Formula I

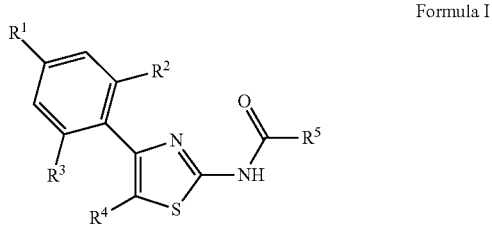

Formula I

In especially preferred aspects, $R^1$ is hydrogen, alkyl, alkenyl, alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —$N=CR_aR_b$, or —$NR_aC(O)NHR_b$; $R_a$ and $R_b$ are independently hydrogen, alkyl, alkenyl, alkynyl, aryl, aryloxy, alkoxy, hydroxy, heteroaryl, cycloalkyl, heterocycloalkyl, cycloalkenyl, or heterocycloalkenyl, or $R_a$ and $R_b$, together with a nitrogen atom to which they are bonded, are heteroaryl, heterocycloalkyl, or heterocycloalkenyl; $R^2$, $R^3$, and $R^4$ are independently hydrogen, $C_1$-$C_6$ alkyl, halogen, or $OR_a$; and $R^5$ is alkyl, phenylalkyl, heteroarylalkyl, phenyalkenyl, heteroarylalkenyl, phenyl, heteroaryl, heterocycloalkyl, or heterocycloalkenyl; wherein each of $R^1$, $R^2$, $R^3$, $R^4$, $R^5$, $R_a$, and $R_b$ are independently optionally substituted. Less preferred compounds include those where (I) $R^1$ and $R^2$ are methyl and where $R^3$ is hydrogen, $R^5$ is not thiazolyl, N-methylimidazolyl, pyrazinyl, pyridinyl, morpholinyl, phenyl, or dimethoxyphenyl; (II) where $R^1$, $R^2$, and $R^3$ are methyl, $R^5$ is not thiazolyl, N-methylimidazolyl, pyrazinyl, pyridinyl, morpholinyl, phenyl, methoxyphenyl, dihydroxyphenyl, hydroxymethoxyphenyl, trifluoromethylphenyl, or dimethoxyphenyl; and (III) where $R^1$ and $R^2$ are methyl and where $R^3$ is hydroxyl or methoxy, $R^5$ is not phenyl.

It is particularly preferred that $R^1$ is alkoxy, $SR_a$, $OR_a$, or, —$S(O)_2R_a$, that $R_a$ is alkyl or optionally substituted aryl, that $R^2$, $R^3$, and $R^4$ are independently hydrogen or $C_1$-$C_6$ alkyl, and that $R^5$ is optionally substituted heteroaryl. Even more preferred compounds among those are compounds where $R^1$ is alkoxy, $SR_a$, $OR_a$, or, —$S(O)_2R_a$, where $R_a$ is alkyl or an optionally substituted aryl, where $R^2$ and $R^3$ are $C_1$-$C_6$ alkyl, and where $R^5$ is optionally substituted (e.g., halogenated) pyridinyl. Most preferably, $R^1$ is $OR_a$, wherein $R_a$ is optionally substituted aryl, $R^2$ and $R^3$ are $C_1$-$C_6$ alkyl, and $R^5$ is an optionally substituted pyridinyl.

Consequently, and viewed from a different perspective, compounds are also preferred that have a structure according to Formula II

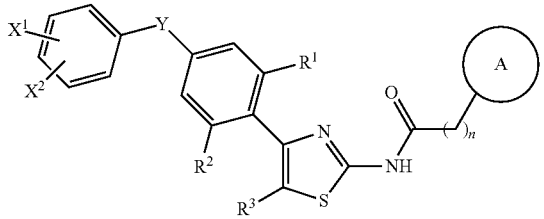

Formula II in which wherein $X^1$ and $X^2$ are independently H, alkyl, alkenyl, alkynyl, halogen, nitro, cyano, cycloalkyl, heterocycloalkyl, cycloalkenyl, heterocycloalkenyl, $OR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —$N=CR_aR_b$, or —$NR_aC(O)NHR_b$; Y is $CH_2$, $CHR_a$, $CR_aR_b$, O, NH, $NR_a$, S, SO, or $SO_2$; $R^1$, $R^2$, and $R^3$ are independently H, alkyl, alkoxy, or halogen; n is 0, 1, or 2; and in which A is an optionally substituted aryl or an optionally substituted heteroaryl, and most preferably a compound as shown below

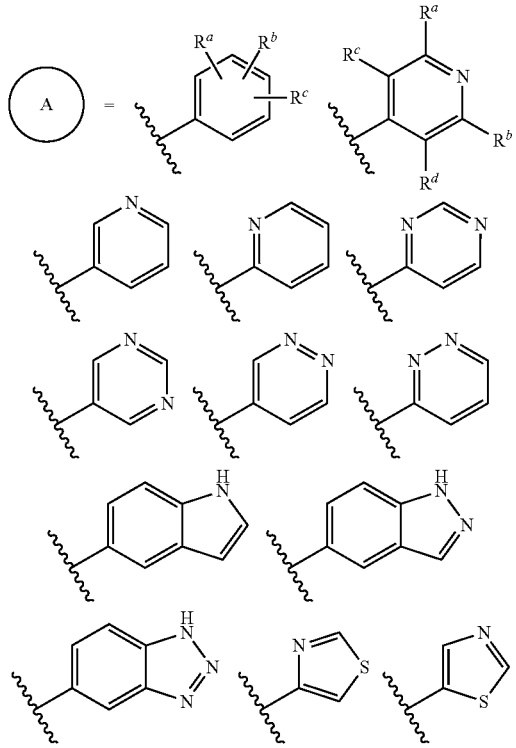

wherein each of $X^1$ and $X^2$ is independently optionally substituted, and wherein $R_c$ and $R_d$ are independently $R_a$. Among such compounds, it is further preferred that Y is O, S, or $SO_2$, and/or that A is an optionally substituted pyridinyl. Most typically, $X^1$ and $X^2$ in such compounds will be independently H, alkyl, and alkoxy, and n is 0 or 1. With respect to remaining radicals, the same considerations as provided for Formula I apply.

Still further preferred compounds have a structure according to Formula III

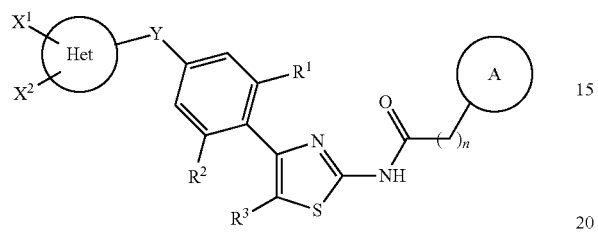

Formula III in which wherein $X^1$, $X^2$, and $X^3$ are independently H, alkyl, alkenyl, alkynyl, halogen, nitro, cyano, cycloalkyl, heterocycloalkyl, cycloalkenyl, heterocycloalkenyl, $OR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —$N=CR_aR_b$, or —$NR_aC(O)NHR_b$; Y is $CH_2$, $CHR_a$, $CR_aR_b$, O, NH, $NR_a$, S, SO, or $SO_2$; $R^1$, $R^2$, and $R^3$ are independently H, alkyl, alkoxy, or halogen; n is 0, 1, or 2; wherein each of $X^1$ and $X^2$ is independently optionally substituted; wherein $R_c$ and $R_d$ is independently $R_a$, and in which A and Het are independently and preferably an aromatic and optionally substituted aryl or heteroaryl. Among other suitable choices, it is typically preferred that

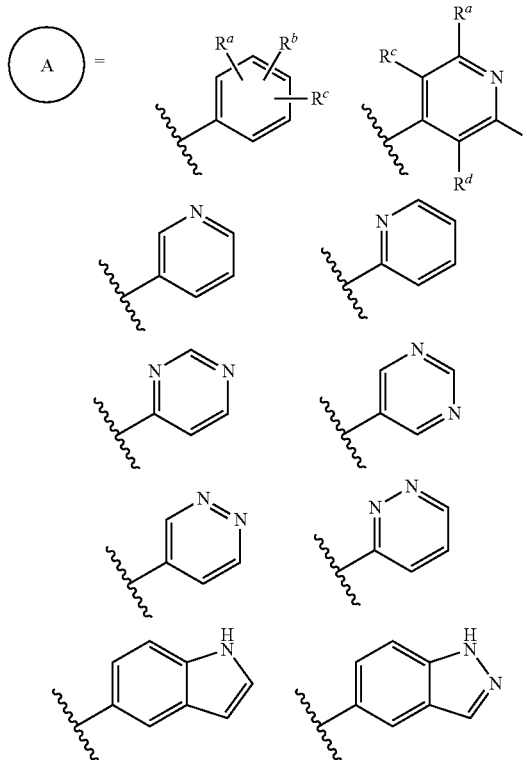

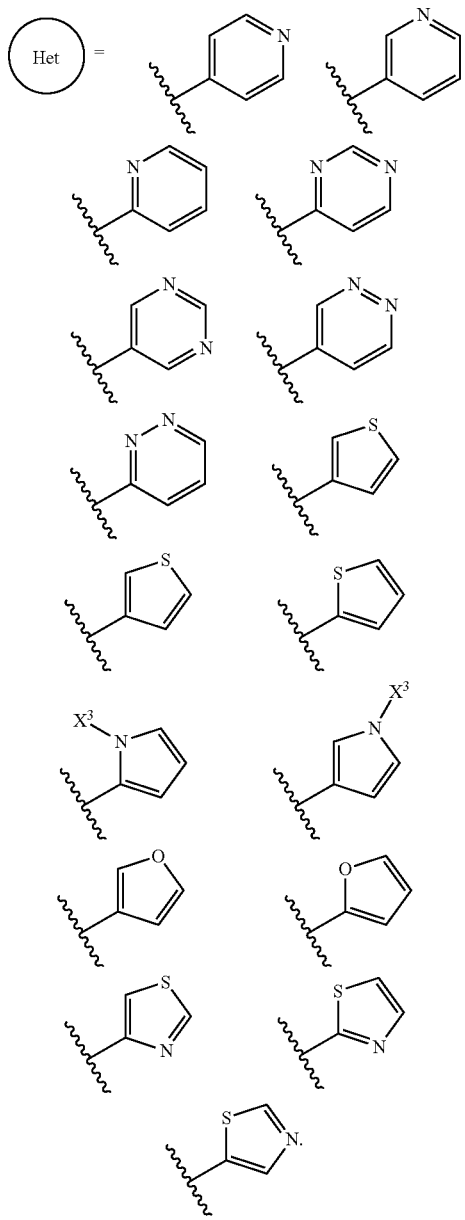

With respect to remaining radicals, the same considerations as noted for Formula I apply. Especially preferred compounds according to Formula II will include those in which A is an optionally substituted pyridinyl, and/or that Y is O, S, or $SO_2$.

In view of the above and further experimental data (see below), particularly preferred compounds will have a structure as shown below

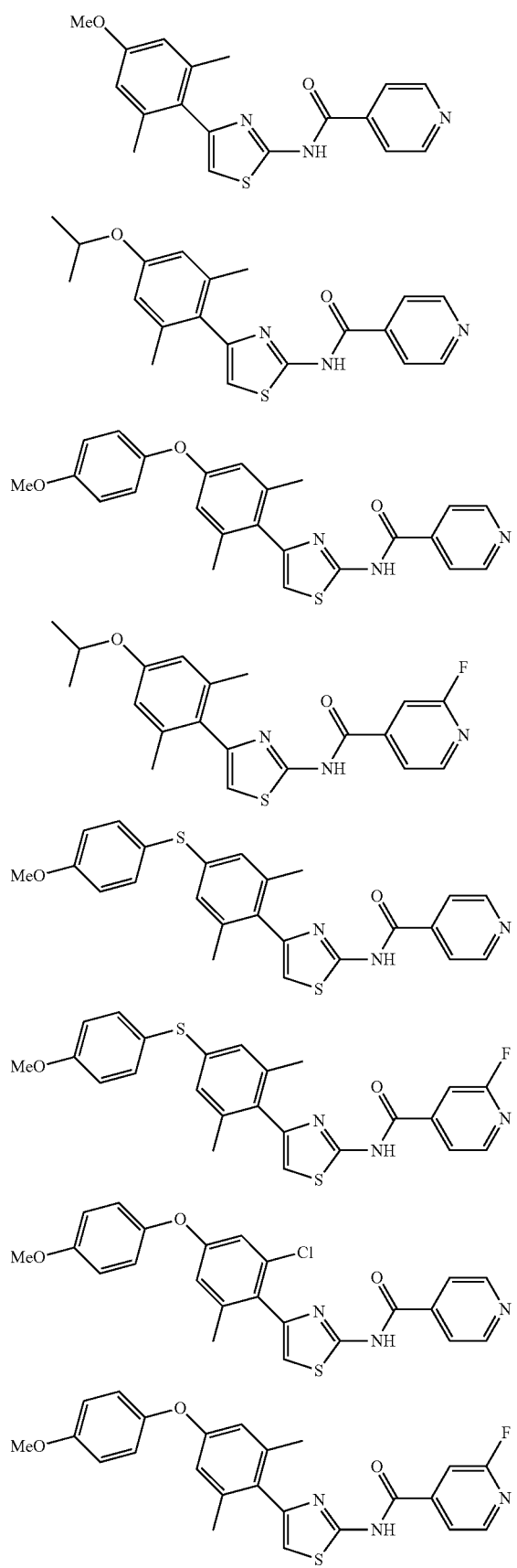

-continued

The term "alkyl" as used herein refers to a hydrocarbon radical, which may be straight, cyclic, or branched. The term "alkenyl", refers to an alkyl having at least one double bond. Where more than one double bond is present, it is contemplated that the double bonds may be conjugated or un-conjugated. The term "alkynyl", as used herein refers to an alkyl having at least one triple bond. Contemplated alkynyls may further include another triple bond or double bond, which may or may not be conjugated with the first triple bond. The term "alkoxy", as used herein, refers to an O-alkyl group, wherein the "alkyl" is defined as provided above.

A "cycloalkyl" as used herein refers to a non-aromatic monovalent monocyclic or polycyclic radical having from 3 to 14 carbon atoms, each of which may be saturated or unsaturated, and may be un-substituted or substituted by one or more suitable substituents as defined herein, and to which may be fused one or more aryl groups, heteroaryl groups, cycloalkyl groups, or heterocycloalkyl groups which themselves may be un-substituted or substituted by one or more substituents. Examples of cycloalkyl groups include cyclopropyl, cycloheptyl, cyclooctyl, cyclodecyl, cyclobutyl, adamantyl, norpinanyl, decalinyl, norbornyl, cyclohexyl, and cyclopentyl.

A "heterocycloalkyl" as used herein refers to a non-aromatic monovalent monocyclic or polycyclic radical having 1-5 heteroatoms selected from nitrogen, oxygen, and sulfur, and may be unsubstituted or substituted by one or more suitable substituents as defined herein, and to which may be fused one or more aryl groups, heteroaryl groups, cycloalkyl groups, or heterocycloalkyl groups which themselves may be un-substituted or substituted by one or more substituents. Examples of heterocycloalkyl groups include oxiranyl, pyrrolidinyl, piperidyl, tetrahydropyran, and morpholinyl.

An "aryl" (Ar) as used herein refers to an aromatic monocyclic or polycyclic radical comprising generally between 5 and 18 carbon ring members, which may be un-substituted or substituted by one or more suitable substituents as defined herein, and to which may be fused one or more cycloalkyl groups, heterocycloalkyl groups, or heteroaryl groups, which themselves may be un-substituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

A "heteroaryl" as used herein refers to an aromatic monocyclic or polycyclic radical comprising generally between 4 and 18 ring members, including 1-5 heteroatoms selected from nitrogen, oxygen, and sulfur, which may be un-substituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

The term "heterocycle" or "heterocyclic" as used herein refers to aromatic and non-aromatic heterocyclic groups, typically with 4 to 10 atoms forming a ring, and containing one or more heteroatoms (typically O, S, or N). Non-aromatic heterocyclic groups include groups having only 4 atoms in their ring system, but aromatic heterocyclic groups typically have at least 5 atoms in their ring system. Examples of non-aromatic heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2 H-pyranyl, 4 H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.i.0]hexanyl, 3 H-indolyl, and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, is benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, quinazolinyl, benzothiazolyl, benzoxazolyl, quinoxalinyl, naphthyridinyl, and furopyridinyl. Contemplated 4-10 membered heterocycles may be C-attached or N-attached (where appropriate). For instance, a group derived from pyrrole may be pyrrol-1-yl (N-attached) or pyrrol-3-yl (C-attached).

As still further used herein, the term "substituted" as used herein refers to a replacement or modification of an atom (radical) or chemical group (e.g., $NH_2$, or OH) in a molecule with a functional group to produce a substituted molecule, and particularly contemplated functional groups include nucleophilic groups (e.g., —$NH_2$, —OH, —SH, —NC, etc.), electrophilic groups (e.g., C(O)OR, C(O)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof. For example, where the molecule is an alkyl, the replaced radical is a hydrogen radical, and the functional group is a hydroxyl group, the H-atom is substituted by an OH group to form a substituted alkyl. In another example, where the molecule is an amino acid, the modified group is the amino group, and the functional group is an alkyl group, the amino group is alkylated to form an N-substituted amino acid.

For example, suitable substituents include halogen (chloro, iodo, bromo, or fluoro); $C_{1-6}$-alkyl; $C_{1-6}$-alkenyl; $C_{1-6}$-alkynyl, hydroxyl, $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; etc. It should be further noted that all substituents contemplated herein may further optionally be substituted by one or more substituents noted above. Especially preferred substituents include hydroxyl groups, halogens, oxo groups, alkyl groups (and especially lower alkyl), acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups.

Moreover, it should be appreciated that the compounds according to the inventive subject matter may comprise one or more asymmetric centers, and may therefore exist in different enantiomeric forms, and all enantiomeric forms of contemplated compounds are specifically contemplated herein. Similarly, where contemplated compounds exhibit optical activity and/or have stereoisomers, all optical activities and/or isomeric forms are contemplated herein. Similarly, where double bonds distinguish a Z-form from an E-form (or cis- from trans-), both isomers are contemplated. Moreover, it is noted that the compounds according to the inventive subject matter may also be isotopically-labeled. Examples of suitable isotopes $^2H$, $^3H$, $^{13}C$, $^{14}C$, $^{15}N$, $^{18}O$, $^{17}O$, $^{18}F$, or $^{36}Cl$. Certain isotopically-labeled compounds of the inventive subject matter, for example those into which $^{14}C$ or $^3H$ is incorporated, may be useful in drug and/or substrate tissue distribution assays. On the other hand, substitution with non-radioactive isotopes (e.g., $^2H$ or $^{13}C$) can afford certain therapeutic advantages resulting from greater metabolic stability, for example increased in vivo half-life or reduced dosage requirements and, hence, may be preferred in some circumstances.

Contemplated compounds may be prepared as pharmaceutically acceptable salt(s), which especially include salts of acidic or basic groups which may be present in the contemplated compounds. For example, where contemplated compounds are basic in nature it should be noted that such compounds may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate [1,1'-methylene-bis-(2-hydroxy-3-naphthoate)] anions. Similarly, where contemplated compounds are acidic in nature, it should be noted that such compounds may form base salts with various pharmacologically acceptable cations, and especially suitable cations include alkali metal or alkaline earth metal ions (e.g., sodium and potassium cations).

In still further contemplated aspects, the compounds presented herein may be prepared as prodrugs, and all known manners and types of prodrugs are considered suitable for use herein, so long as such prodrug will increase the concentration of the drug (or metabolite of the prodrug) at a target organ, target cell, and/or Hec1. For example, where contemplated compounds have a free amino, amido, hydroxy, thio, or carboxylic group, it is contemplated that such groups can be employed to covalently and releasably bind a moiety that converts the drug into a prodrug. Therefore, prodrugs particularly include those in which contemplated compounds form an ester, amide, or disulfide bond with another cleavable moiety. Such moieties may assist in organ or cell-specific delivery of the drug and therefore particularly include receptor ligands and their analogs, antibody fragments or other high-affinity ligands ($K_d<10^6M$).

For instance, a carboxyl group can be derived to form an amide or alkyl ester, which may include an ether, amine-, and/or carboxylic acid group. Free hydroxyl groups may be derived using hemisuccinates, phosphate esters, dimethylaminoacetates, and phosphoryloxymethyloxycarbonyls, as outlined in D. Fleisher, R. Bong, B. H. Stewart, Advanced Drug Delivery 40 Reviews (1996) 19, 115. Carbamate prodrugs of hydroxyl and amino groups are also included, as are carbonate prodrugs and sulfate esters of hydroxyl groups. Deriving hydroxyl groups as (acyloxy)methyl and (acyloxy) ethylethers, wherein the acyl group may be an alkyl ester (optionally substituted), or where the acyl group is an amino acid ester are also contemplated (prodrugs of this type are described in R. P. Robinson et al., J. Medicinal Chemistry (1996) 39:p. 10).

In still further contemplated aspects, it should be appreciated that the compounds according to the inventive subject matter may also be active as a metabolite (of a prodrug or non-prodrug form) and that all of such metabolites are especially contemplated herein. For example, suitable metabolites include hydroxylated forms, oxidized forms, glucuronidated forms, sulfated forms, etc. Moreover, it is also noted that the metabolites may be more active that the originally administered form.

Contemplated Compositions and Formulations

Based on the activity of the compounds as Hec1 modulators, the inventors contemplate that the compounds and compositions according to the inventive subject matter may be employed for prophylaxis and/or treatment of various diseases associated with Hec1 dysfunction and/or overexpression, and in fact for all diseases that positively respond to administration of contemplated compounds. The term "dysfunction of Hec1" as used herein refers to any abnormality in Hec1, especially as it relates to its association with Nek2 function and spindle checkpoint signaling. Such abnormalities may be due to one or more of a mutation (e.g., increasing or reducing affinity to a binding partner), temporary or permanent overexpression (e.g., activated by inappropriate or mutated promoter), irreversible or tighter binding of an activator, inappropriate activation by non-physiological molecule, etc. Consequently, particularly contemplated diseases include neoplastic diseases, and especially cancerous neoplastic diseases (e.g., breast cancer, squamous cell cancer, bladder cancer, gastric cancer, pancreatic cancer, head cancer, neck cancer, oesophageal cancer, prostate cancer, colorectal cancer, lung cancer, renal cancer, gynecological cancer, or thyroid cancer). Non cancerous neoplastic diseases include benign hyperplasia of the skin (e.g., psoriasis) or prostate (e.g., benign prostatic hypertrophy (BPH).

Therefore, the inventor also contemplates numerous pharmaceutical compositions that include the compounds presented herein and it is generally contemplated that the compounds according to the inventive subject matter may be formulated into pharmaceutical compositions that have a therapeutically effective amount of contemplated compounds (or pharmaceutically acceptable salt, hydrate, or prodrug thereof), and a pharmaceutically acceptable carrier.

Activity, toxicity, and other pharmacological and pharmacodynamic parameters can be established for the compounds presented herein using numerous known protocols. Similarly, cytotoxicity can be established via MTS assay in various cell lines, while disruption of Hec1-Nek2 interaction can be monitored via co-immunoprecipitation or a yeast two-hybrid system. Cell cycle analysis can be performed by monitoring various stage populations (e.g., sub-G1, G0/G1, S, etc.), and metaphase chromosomal misalignment quantitation can be performed using immunofluorescence methods well known in the art. In vivo activity can be established using various animal models, and especially xenograft models. Exemplary results are provided in the attached table and normalized data. Consequently, the inventors contemplate a pharmaceutical composition that includes a pharmaceutically acceptable carrier and contemplated compounds herein wherein the compounds are present in a concentration effective to disrupt Hec1/Nek2 binding in a patient when the composition is administered to the patient. The inventors have also discovered that numerous compounds according to the inventive subject matter were bioavailable upon oral administration and could be detected in serum over prolonged periods after oral administration or intravenous (i.v.), administration (see below).

Most preferably, contemplated compounds are formulated with one or more non-toxic pharmaceutically acceptable carriers, preferably formulated for oral administration in solid or liquid form, or for parenteral injection. Thus, it should be appreciated that pharmaceutical compositions according to the inventive subject matter may be administered to humans and other animals using various routes, including orally, rectally, parenterally, intraperitoneally, vaginally, or topically.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compounds according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally, dosage levels of about 0.01 mg to about 500 mg, more preferably of about 0.5 mg to about 50 mg of contemplated compound per kilogram of body weight per day are administered orally to a mammalian patient. If desired, the effective daily dose may be divided into multiple doses for purposes of administration, e.g., two to four separate doses per day. Therefore, contemplated formulations especially include those suitable for oral administration, parenteral administration, for administration as cream, or as eye-drops or other liquid topical formulation.

Furthermore, preliminary data showed that various Hec1 inhibitors, exhibited synergistic effect with selected chemotherapeutic inhibitors. Among other chemotherapeutic inhibitors, compounds including Taxol, vincristine, and vinblastine showed synergistic effect, and are also expected to have synergistic effect with respect to tubulin formation or polymerization inhibitors, as well as pretubulin inhibitors. Thus, suitable chemotherapeutic inhibitors especially include one or more drugs that interfere with microtubule formation or degradation. Therefore, any drugs that affect cell division and any anti-metabolites are deemed useful in combination with the Hec1 inhibitors contemplated herein. In contrast, anthracyclines (e.g., doxorubicin) were shown only to have at most additive effect and no synergistic effect with Hec1 inhibitors.

It should still further be appreciated that contemplated pharmaceutical compositions may also include additional pharmaceutically active compounds, and especially contemplated additional pharmaceutically active compounds include antineoplastic agents, which may act on DNA replication, cell cycle, cell metabolism, angiogenesis, or induce apoptosis. Further suitable active agents include immunologically active agents (e.g., anti-inflammatory agents, immunosuppressants, steroids, interferons (alpha, beta, or gamma) and fragments thereof, and those molecules that selectively increase or suppress Th1 and/or Th2 cytokine expression). Still other suitable active agents include antibacterial and antiviral agents, drugs that stimulate or modify metabolism, neurologically active drugs, and/or analgesic drugs. Of course, it should be recognized that additional pharmaceutically active compounds may be included in the same pharmaceutical composition, or may be administered separately, and a person of ordinary skill in the art will readily determine schedule and route of suitable co-administration of the additional pharmaceutically active compounds.

EXAMPLES/EXPERIMENTS

Exemplary Synthesis of 4-Aryl-2-amidothiazoles

Contemplated 4-aryl-2-amidothiazole compounds can be prepared by numerous synthetic routes, and the following is provided to give exemplary guidance only. While the below scheme can be used to prepare most of the compounds presented herein, other compounds may require minor modifications top the general scheme that will be readily apparent to the skilled artisan.

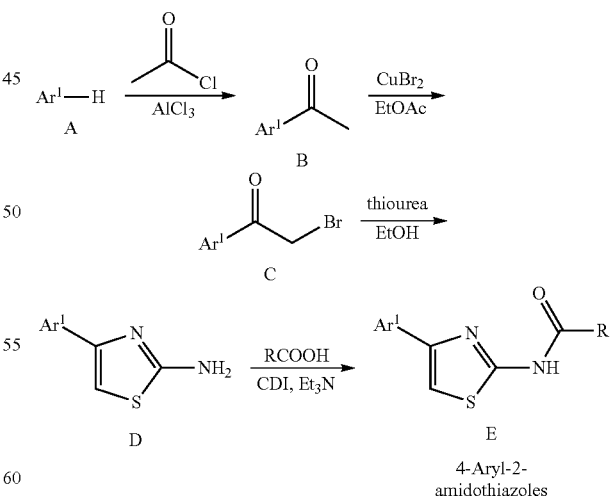

4-Aryl-2-amidothiazoles

The above scheme illustrates a method for the synthesis of 4-aryl-2-aminothiazoles E. Aromatic compounds of structure A, including substituted benzene, pyridine, or other heterocyclic compound (5-, 6-, or 7-membered) are reacted with acetyl chloride in the presence of $AlCl_3$ to afford acetylated arenes B. Bromination of B give α-Br-acetylated arenes C, which are allowed to react with thiourea to generate aminothiazoles D with an aryl substituent at the C-4 position. The so prepared aminothiazoles then react with different acids give the final 4-aryl-2-amidothiazoles E.

Acetylation of Ar¹:

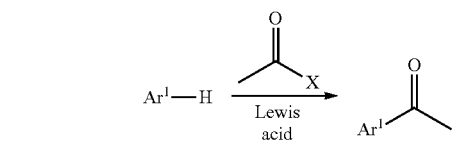

X = OH, Cl, Br, OAlkyl, OAryl
Lewis acid = AlCl₃, ZnCl₃, BiCl₃, conc. acid

The acetylation of Ar¹ can be achieved by use of different reagents as shown in the above Scheme.

Bromination of Acetyl Ar¹:

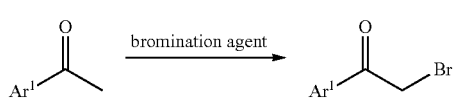

Suitable bromination agents include Br₂, HBr, NBS, TBABr₃, CuBr₂, etc. in various solvents, including ether, THF, halogenated hydrocarbons, ester, etc.

Amidation of Aminothiazoles:

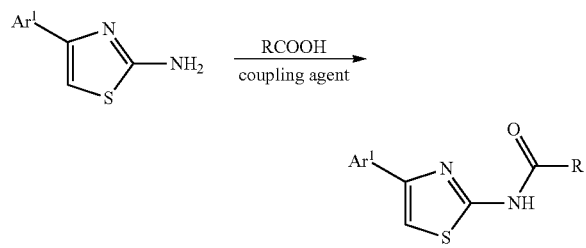

Suitable coupling agents include CDI, EDC, CDC, etc.

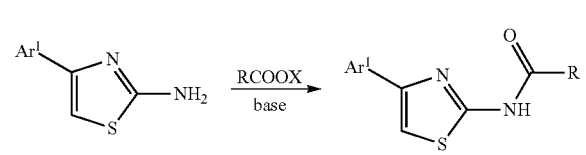

X is typically Cl or Br; base is typically Et₃N, Me₃N, DIPEA, K₂CO₃, Na₂CO₃, DMAP, etc. Alternatively, 4-Aryl-2-amidothiazoles can be prepared as follows:

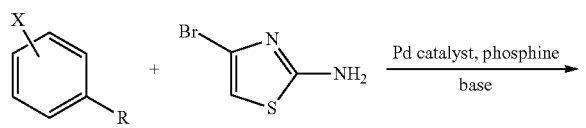

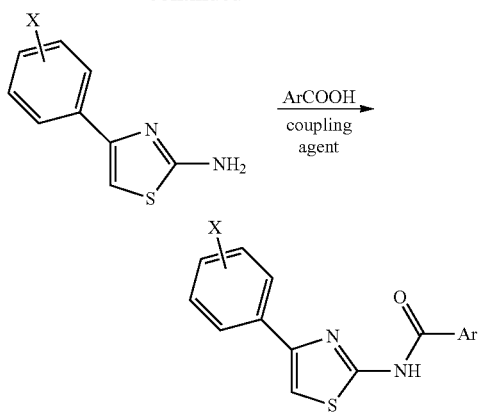

Alternatively, coupling may also be performed as follows:

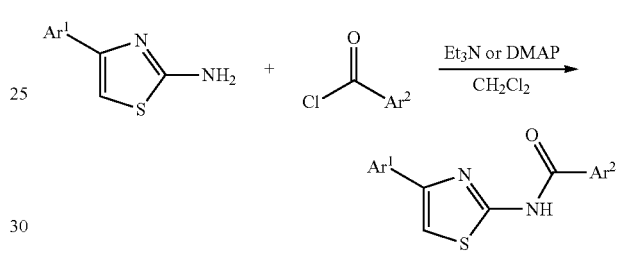

To a solution of 4-arylthiazol-2-amine (1.0 equiv) in CH₂Cl₂ was added triethylamine (3.0 equiv) or DMAP (3.0 equiv) followed by aryloxy chloride (1.5 equiv) or aryloxy-chloride hydrochloride (1.5 equiv). The reaction mixture was stirred at room temperature overnight. The solution was concentrated under reduced pressure and added with hot water. The resultant precipitate was filtered, and dried under vacuum to give the corresponding 4-aryl-2-amidothiazoles. For specific examples of synthesis, see below.

Synthesis of Exemplary Aminothiazoles and the Related Intermediates

2-Bromo-1-mesitylethanone. To a solution of 1-mesitylethanone (1.02 g, 6.27 mmol) in EtOAc (50 mL) was added copper(II) bromide (CuBr₂, 2.85 g, 12.8 mmol). The reaction mixture was heated at reflux for 90 min. The solution was allowed to cool down, and the resultant solids were filtered off and washed with EtOAc. The filtrate was concentrated under reduced pressure to give crude 2-bromo-1-mesitylethanone (1.67 g) as yellow oil: $^1$H NMR (500 MHz, CDCl₃) δ 6.87 (2 H, s), 4.27 (2 H, s), 2.31 (3 H, s), 2.22 (6 H, s).

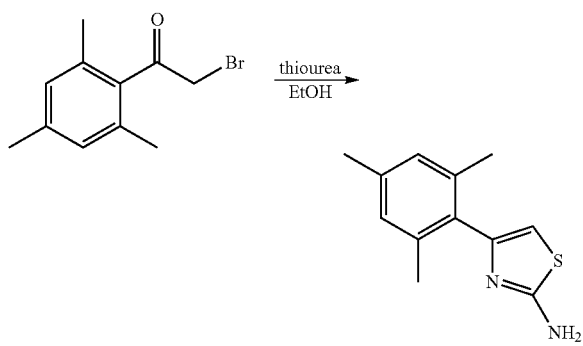

4-Mesitylthiazol-2-amine. 2-Bromo-1-mesitylethanone (2.43 g, 10.1 mmol) and thiourea (0.810 g, 10.6 mmol) were dissolved in 95% ethanol (20 mL). The reaction mixture was heated at reflux for 2.0 h. The solution was concentrated under reduced pressure, and the residue was recrystallized from 2-propanol to give the desired 4-mesitylthiazol-2-amine (2.36 g) as white solids: $^1$H NMR (500 MHz, CD$_3$OD) δ 7.00 (2 H, s), 6.67 (1 H, s), 2.31 (3 H, s), 2.19 (6 H, s).

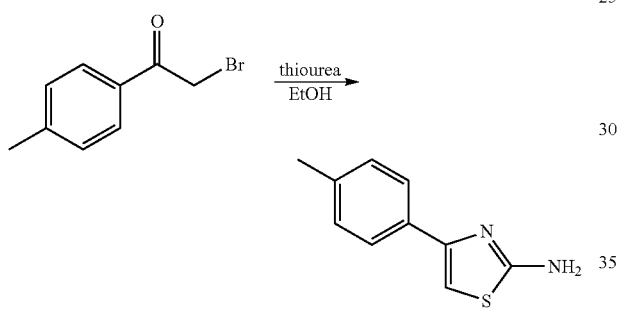

4-(p-Tolyl)thiazol-2-amine. A mixture of 2-bromo-1-(p-tolyl)ethanone (5.00 g, 23.5 mmol) and thiourea (1.97 g, 25.9 mmol) in 95% EtOH (33.5 mL) was heated at reflux for 60 min. The solution was concentrated and added with water (50 mL) and saturated aqueous Na$_2$CO$_3$ (1.0 mL). The resultant precipitate was filtered and washed with hot water. The solids were filtered and dried under vacuum to give 4-(p-tolyl)thiazol-2-amine (4.40 g) as white solids in 99% yield: $^1$H NMR (500 MHz, CDCl$_3$) δ 7.66 (d, J=8.0 Hz, 2 H), 7.18 (d, J=7.5 Hz, 2 H), 6.66 (s, 1 H), 5.25 (bs, 2 H), 2.36 (s, 6 H).

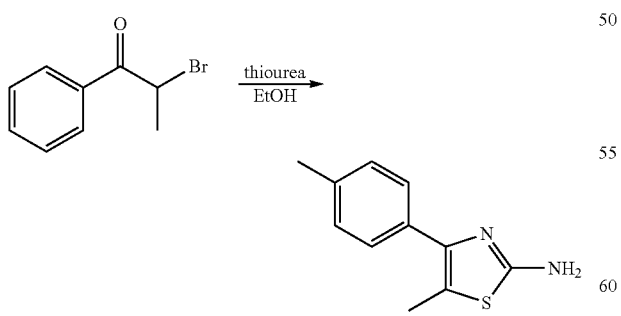

5-Methyl-4-(p-tolyl)thiazol-2-amine. A mixture of 2-bromo-1-(p-tolyl)propan-1-one (6.88 g, 30.3 mmol) and thiourea (2.54 g, 33.4 mmol) in 95% EtOH (43 mL) was heated at reflux for 60 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 5-methyl-4-(p-tolyl)thiazol-2-amine (6.10 g) as white solids in 99% yield: $^1$H NMR (500 MHz, CDCl$_3$) δ 7.40 (d, J=8.0 Hz, 2 H), 7.23 (d, J=8.0 Hz, 2 H), 3.18 (bs, 2 H), 2.37 (s, 3 H), 2.35 (s, 3 H).

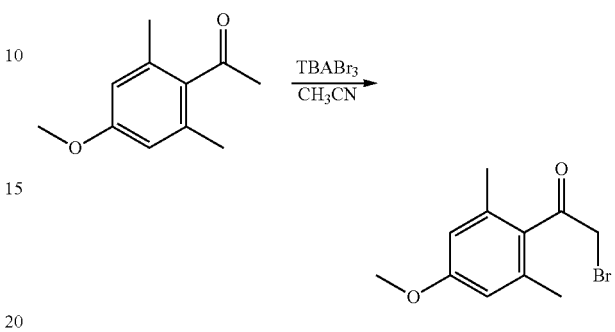

2-Bromo-1-(4-methoxy-2,6-dimethylphenyl)ethanone. To a solution of 1-(4-methoxy-2,6-dimethylphenyl)ethanone (5.7 g, 32 mmol) in acetonitrile (64 mL) was added tetrabutylammoniumtribromide (TBABr$_3$, 15.4 g, 32.0 mmol). The reaction was stirred at room temperature for 80 min. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-methoxy-2,6-dimethylphenyl)ethanone (9.14 g), which was used directly for the next step without further purification.

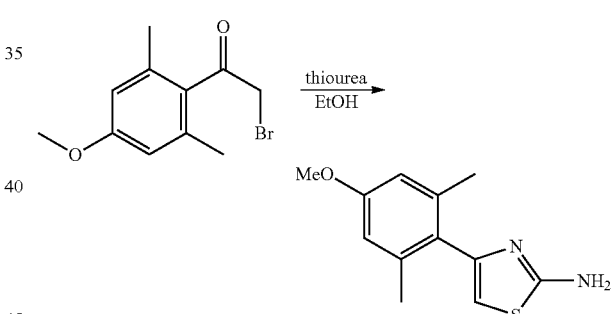

4-(4-Methoxy-2,6-dimethylphenyl)thiazol-2-amine. A mixture of 2-bromo-1-(4-methoxy-2,6-dimethylphenyl)ethanone (8.65 g, 33.6 mmol) and thiourea (2.56 g, 33.6 mmol) in 95% EtOH (48 mL) was heated at reflux for 60 min. The solution was concentrated and added with water (50 mL) and saturated aqueous Na$_2$CO$_3$ (5.0 mL). The resultant precipitate was filtered and recrystallized in toluene (50 mL). The solids were filtered and dried under vacuum to give 4-(4-methoxy-2,6-dimethylphenyl)thiazol-2-amine (5.9 g) as white solids in 66% yield: $^1$H NMR (500 MHz, CDCl$_3$) δ 6.61 (s, 2 H), 6.27(s, 1 H), 4.91 (bs, 2 H), 3.79 (s, 3 H), 2.15 (s, 6 H).

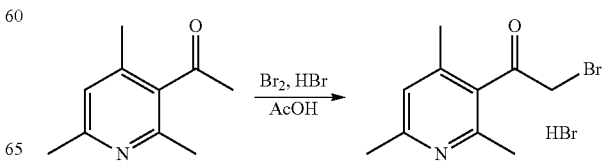

2-Bromo-1-(2,4,6-trimethylpyridin-3-yl)ethanone hydrobromide. To a solution of 1-(2,4,6-trimethylpyridin-3-yl)ethanone (5.0 g, 30.6 mmol) in 33% HBr in acetic acid solution (10.2 mL) was added bromine (1.57 ml, 30.6 mmol) in acetic acid (10.2 mL) dropwisely. The reaction was stirred at 70° C. for 2.0 h. The solution was cooled to room temperature and washed with ether. The residue was dried under reduced pressure to give 2-bromo-1-(2,4,6-trimethylpyridin-3-yl)ethanone hydrobromide, which was used directly for the next step without further purification.

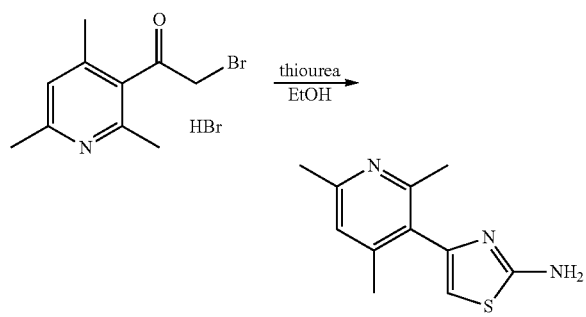

4-(2,4,6-Trimethylpyridin-3-yl)thiazol-2-amine. A mixture of 2-bromo-1-(2,4,6-trimethylpyridin-3-yl)ethanone hydrobromide (9.00 g, 27.9 mmol) and thiourea (2.12 g, 27.9 mmol) in 95% EtOH (39.8 mL) was heated at reflux for 120 min. The solution was concentrated and added with water (50 mL) and saturated aqueous $Na_2CO_3$ (5.0 mL). The resultant precipitate was filtered and recrystallized in toluene. The solids were filtered and dried under vacuum to give 4-(2,4,6-trimethylpyridin-3-yl)thiazol-2-amine (3.80 g) as yellow solids in 62% yield: $^1$H NMR (500 MHz, $CDCl_3$) δ 6.87 (s, 1 H), 6.31 (s, 1 H), 5.07 (bs, 2 H), 2.49 (s, 3 H), 2.38 (s, 3 H), 2.14 (s, 3 H).

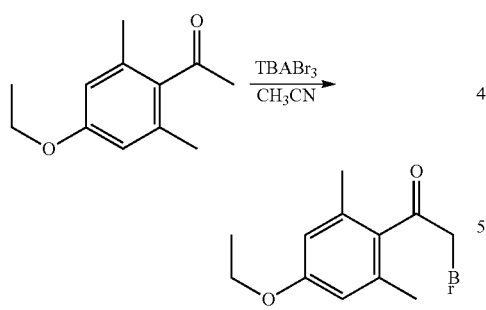

2-Bromo-1-(4-ethoxy-2,6-dimethylphenyl)ethanone. To a solution of 1-(4-ethoxy-2,6-dimethylphenyl)ethanone (4.00 g, 20.8 mmol) in acetonitrile (41.6 mL) was added tetrabutylammoniumtribromide ($TBABr_3$, 10.0 g, 20.8 mmol). The reaction was stirred at room temperature overnight. The solution was concentrated under reduced pressure, added with water, and extracted with ethyl acetate. The organic layer was washed with brine, dried over anhydrous $MgSO_4(s)$, and concentrated under reduced pressure to give 2-bromo-1-(4-ethoxy-2,6-dimethylphenyl)ethanone (6.40 g), which was used directly for the next step without further purification.

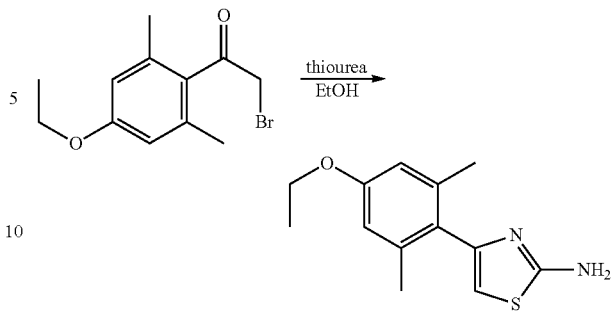

4-(4-Ethoxy-2,6-dimethylphenyl)thiazol-2-amine. A mixture of 2-bromo-1-(4-ethoxy-2,6-dimethylphenyl)ethanone (6.35 g, 23.4 mmol) and thiourea (1.78 g, 23.4 mmol) in 95% EtOH (33.5 mL) was heated at reflux for 60 min. The solution was concentrated and added with water (50 mL) and saturated aqueous $Na_2CO_3$ (5.0 mL). The resultant precipitate was filtered and recrystallized in toluene (30 mL). The solids were filtered and dried under vacuum to give 4-(4-ethoxy-2,6-dimethylphenyl)thiazol-2-amine (4.18 g) as white solids in 72% yield: $^1$H NMR (500 MHz, DMSO-$d_6$) δ 6.84 (s, 2 H), 6.60 (s, 2 H), 6.27(s, 1 H), 3.99 (q, J=6.5 Hz, 2 H), 2.06 (s, 6 H), 1.31 (t, J=6.95 Hz, 3 H).

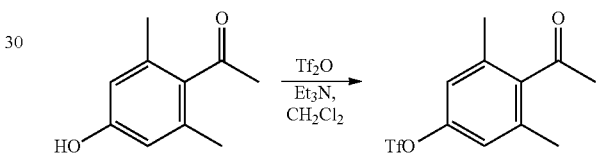

4-Acetyl-3,5-dimethylphenyl trifluoromethanesulfonate. A solution of 1-(4-hydroxy-2,6-dimethylphenyl)ethanone (3.30 g, 20.1 mmol), triethylamine (4.07 g, 40.2 mmol) in anhydrous $CH_2Cl_2$ (20.1 mL) was cooled to 0° C., and then added with trifluoromethanesulfonic anhydride (4.0 mL, 24 mmol) dropwisely. After the addition was completed, the reaction mixture was warmed to room temperature and stirred for 1.0 h. The solution was added with water and extracted with ethyl acetate (60 mL). The organic layer was separated, dried over $MgSO_4(s)$, concentrated under reduced pressure. The residue was purified by flash chromatography on silica gel to give 4-acetyl-3,5-dimethylphenyl trifluoromethanesulfonate (5.0 g) as yellow oil in 85% yield.

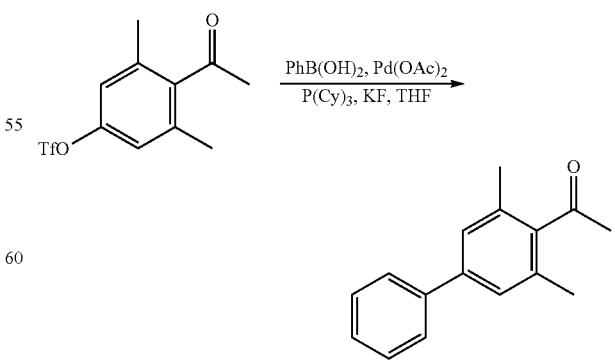

1-(3,5-Dimethyl-[1,1'-biphenyl]-4-yl)ethanone. To a solution of 4-acetyl-3,5-dimethylphenyl trifluoromethanesulfonate (1.00 g, 3.38 mmol), KF (0.65 g, 11 mmol), and phenylboronic acid (0.49 g, 4.0 mmol) in THF (4.0 mL) was added tricyclohexylphosphine (11.4 mg, 0.04 mmol) and Pd(OAc)$_2$ (7.6 mg, 0.03 mmol). The reaction mixture was stirred at room temperature for 5.0 h under N$_2$. The reaction mixture was filtered through a small pad of Celite, and the cake was washed with ethyl acetate (40 mL). The filtrate was concentrated under reduced pressure, and the residue was purified by flash chromatography on silica gel to give 1-(3,5-dimethyl-[1,1'-biphenyl]-4-yl)ethanone (0.68 g) in 90% yield: $^1$H NMR (500 MHz, CDCl$_3$) δ 7.56 (d, J=8.0 Hz, 2 H), 7.44 (t, J=7.0 Hz, 2 H), 7.35 (m, 1 H), 7.25 (s, 2 H), 2.52 (s, 3 H), 2.33 (s, 6 H).

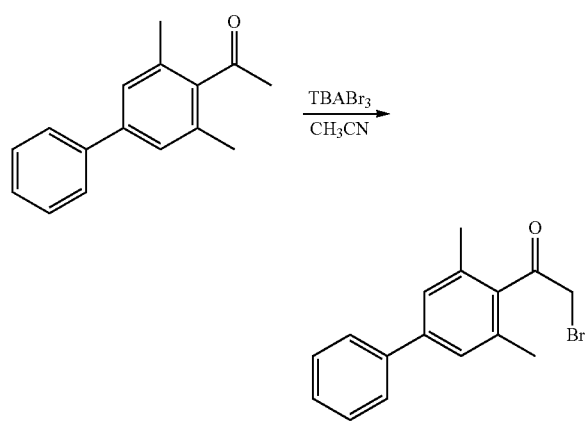

2-Bromo-1-(3,5-dimethyl-[1,1'-biphenyl]-4-yl)ethanon. To a solution of 1-(3,5-dimethyl-[1,1'-biphenyl]-4-yl)ethanone (1.89 g, 8.43 mmol) in acetonitrile (16.9 mL) was added tetrabutylammoniumtribromide (TBABr$_3$, 4.07 g, 8.43 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(3,5-dimethyl-[1,1'-biphenyl]-4-yl)ethanone (3.2 g), which was used directly for the next step without further purification.

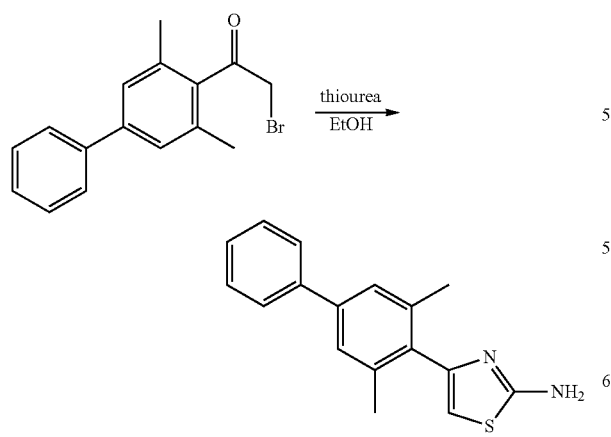

4-(3,5-Dimethyl-[1,1'-biphenyl]-4-yl)thiazol-2-amine. A mixture of 2-bromo-1-(3,5-dimethyl-[1,1'-biphenyl]-4-yl) ethanone (2.56 g, 8.44 mmol) and thiourea (0.64 g, 8.44 mmol) in 95% EtOH (12.1 mL) was heated at reflux for 60 min. The solution was concentrated and added with water (50 mL) and saturated aqueous Na$_2$CO$_3$ (1.0 mL). The resultant precipitate was filtered and recrystallized in toluene (10 mL). The solids were filtered and dried under vacuum to give 4-(3,5-dimethyl-[1,1'-biphenyl]-4-yl)thiazol-2-amine (0.66 g) as yellow solids in 28% yield: $^1$H NMR (500 MHz, CDCl3) δ 7.60 (d, J=1 Hz, 2 H), 7.43 (t, J=7.5 Hz, 1 H), 7.32 (m, 1 H), 7.25 (s, 2 H), 6.34 (s, 1 H), 5.03 (bs, 2 H), 2.24 (s, 6 H).

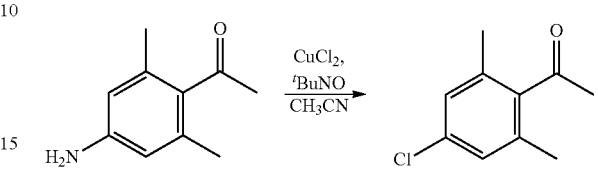

1-(4-Chloro-2,6-dimethylphenyl)ethanone. Anhydrous copper(II) chloride (98.9 g, 0.74 mol) was mixed with tert-butyl nitrite (94.8 g, 0.83 mol) in acetonitrile (1.02 L). The solution was cooled to 0° C. and slowly added with 1-(4-amino-2,6-dimethylphenyl)ethanone (100 g, 0.61 mol) in a period of 5.0 min. After the addition was completed, the reaction mixture was warmed to room temperature, and was poured into an aqueous hydrochloric acid solution (20%, 1.0 L). The solution was extracted with EtOAc (800 mL), and the organic layer was separated, washed with H$_2$O (1.0 L), dried over MgSO$_4$ (s), and concentrated under reduced pressure. The liquid was distilled to give 1-(4-chloro-2,6-dimethylphenyl)ethanone (85.0 g) as yellow oil in 76% yield: $^1$H NMR (500 MHz, CDCl3) δ 7.02 (s, 2 H), 2.45 (s, 3 H), 2.22 (s, 6 H).

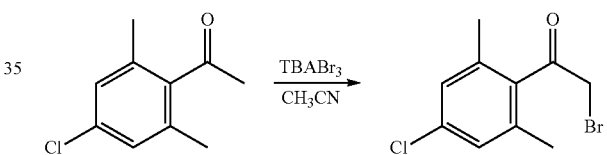

2-Bromo-1-(4-chloro-2,6-dimethylphenyl)ethanone. To a solution of 1-(4-chloro-2,6-dimethylphenyl)ethanone (5.0 g, 27 mmol) in acetonitrile (54.8 mL) was added tetrabutylammoniumtribromide (TBABr$_3$, 13.2 g, 27.4 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-chloro-2,6-dimethylphenyl)ethanone (7.2 g), which was used directly for the next step without further purification.

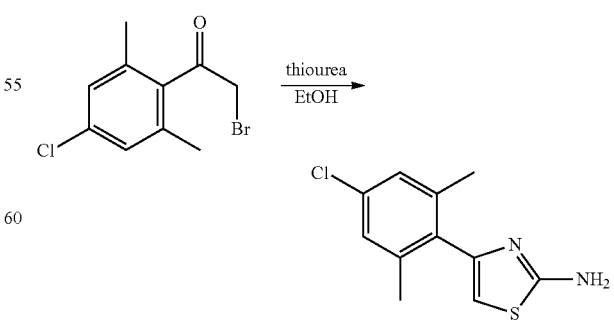

4-(4-Chloro-2,6-dimethylphenyl)thiazol-2-amine. A mixture of 2-bromo-1-(4-chloro-2,6-dimethylphenyl)ethanone (6.54 g, 25.0 mmol) and thiourea (1.90 g, 25.0 mmol) in 95% EtOH (35.7 mL) was heated at reflux for 60 min. The solution was concentrated and added with water (50 mL) followed by saturated aqueous Na$_2$CO$_3$ (4.0 mL). The resultant precipitate was filtered and recrystallized in toluene (30 mL). The solids were filtered and dried under vacuum to give 4-(4-chloro-2,6-dimethylphenyl)thiazol-2-amine (4.30 g) as white solids in 72% yield: $^1$H NMR (500 MHz, DMSO-d$_6$) δ 7.16 (s, 2 H), 6.43 (s, 1 H), 2.10 (s, 6 H).

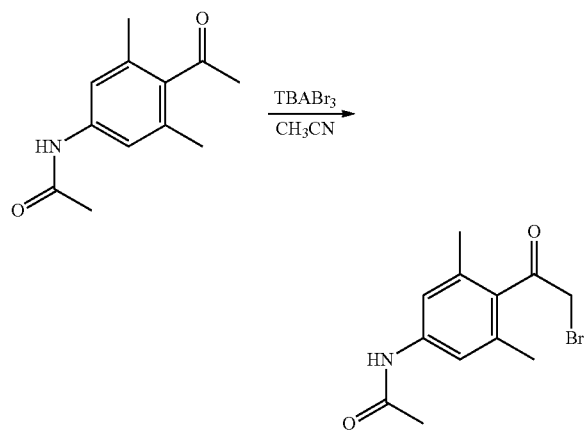

N-(4-(2-Bromoacetyl)-3,5-dimethylphenyl)acetamide. To a solution of N-(4-acetyl-3,5-dimethylphenyl)acetamide (5.00 g, 24.4 mmol) in acetonitrile (48.7 mL) was added tetrabutylammoniumtribromide (TBABr$_3$, 11.7 g, 24.4 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give N-(4-(2-bromoacetyl)-3,5-dimethylphenyl)acetamide (7.00 g), which was used directly for the next step without further purification.

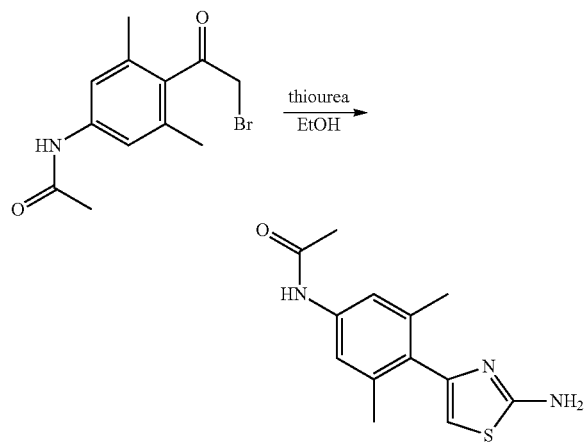

N-(4-(2-aminothiazol-4-yl)-3,5-dimethylphenyl)acetamide. A mixture of N-(4-(2-bromoacetyl)-3,5-dimethylphenyl)acetamide (7.34 g, 25.8 mmol) and thiourea (1.97 g, 25.9 mmol) in 95% EtOH (36.9 mL) was heated at reflux for 120 min. The solution was concentrated and added with water (100 mL) and saturated aqueous Na$_2$CO$_3$ (5.0 mL). The resultant precipitate was filtered and recrystallized in toluene (50 mL). The solids were filtered and dried under vacuum to give N-(4-(2-aminothiazol-4-yl)-3,5-dimethylphenyl)acetamide (5.83 g) as yellow solids in 86% yield: $^1$H NMR (500 MHz, DMSO-d$_6$) δ 9.80 (s, 1 H), 7.26 (s, 2 H), 6.90 (bs, 2 H), 6.30 (s, 1 H), 2.06 (s, 6 H), 2.02 (s, 3 H).

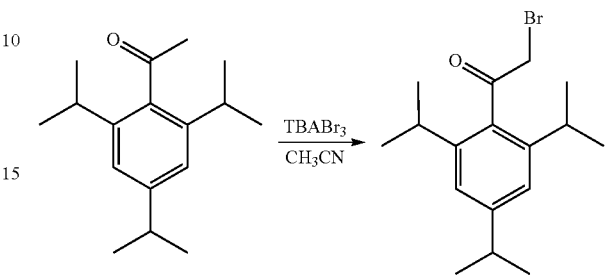

2-Bromo-1-(2,4,6-triisopropylphenyl)ethanone. To a solution of 1-(2,4,6-triisopropylphenyl)ethanone (10.0 g, 65.3 mmol) in acetonitrile (81 mL) was added tetrabutylammoniumtribromide (TBABr$_3$, 19.6 g, 40.6 mmol). The reaction was stirred at room temperature for 3.0 h. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,4,6-triisopropylphenyl)ethanone (13.2 g), which was used directly for the next step without further purification.

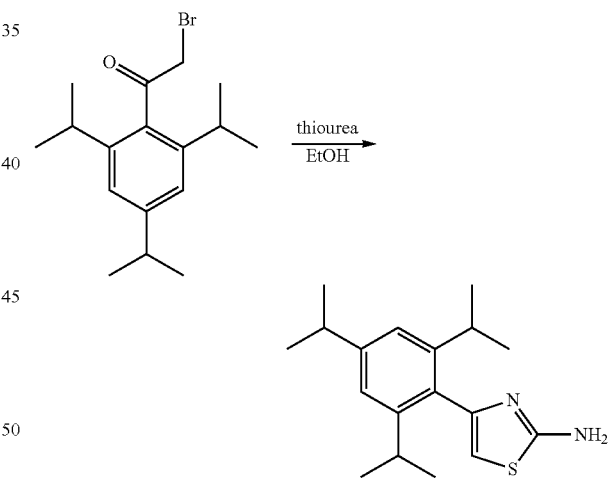

4-(2,4,6-Triisopropylphenyl)thiazol-2-amine. A mixture of 2-bromo-1-(2,4,6-triisopropylphenyl)ethanone (13.9 g, 42.7 mmol) and thiourea (3.24 g, 42.6 mmol) in 95% EtOH (60.9 mL) was heated at reflux overnight. The solution was concentrated and added with water (100 mL), saturated aqueous Na$_2$CO$_3$ (10 mL), and extracted with ethyl acetate. The organic layer was washed with brine, dried over anhydrous MgSO$_4$(s), and concentrated under reduced pressure, which was purified by column chromatography on silica gel (33% EtOAc in hexanes as eluant) to give 4-(2,4,6-triisopropylphenyl)thiazol-2-amine (3.28 g) as white solids in 25% yield: $^1$H NMR (500 MHz, CDCl3) δ 7.03 (s, 2 H), 6.22 (s, 1 H), 4.75 (bs, 2 H), 2.89 (m, 1 H), 2.68 (m, 2 H), 1.27-1.14 (m, 18 H).

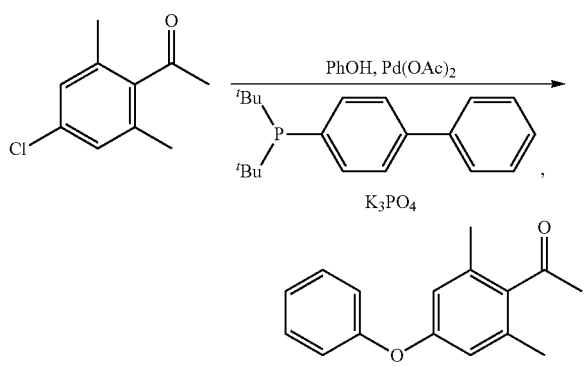

1-(2,6-Dimethyl-4-phenoxyphenyl)ethanone. To a solution of 1-(4-chloro-2,6-dimethylphenyl)ethanone (4.50 g, 24.6 mmol), K$_3$PO$_4$ (10.5 g, 49.3 mmol), and phenol (2.78 g, 29.5 mmol) in toluene (49.3 mL) was added 2-(di-tert-butylphosphino)biphenyl (221 mg, 0.74 mmol) and Pd(OAc)$_2$ (233 mg, 1.04 mmol). The reaction was heated at 100° C. for 2.0 h under N$_2$. The solution was cooled to room temperature and filtered through a small pad of Celite. The cake was washed with ethyl acetate (50 mL) and the combined filtrate was concentrated under reduced pressure. The residue was purified by flash column chromatography on silica gel to give 1-(2,6-dimethyl-4-phenoxyphenyl)ethanone as a yellow oil in 68% yield: $^1$H NMR (500 MHz, CDCl3) δ 7.35 (t, J=8.0 Hz, 2 H), 7.12 (t, J=7.5 Hz, 1 H), 7.00 (d, J=7.5 Hz, 2 H), 6.65 (s, 2 H), 2.48 (s, 3 H), 2.22 (s, 6 H).

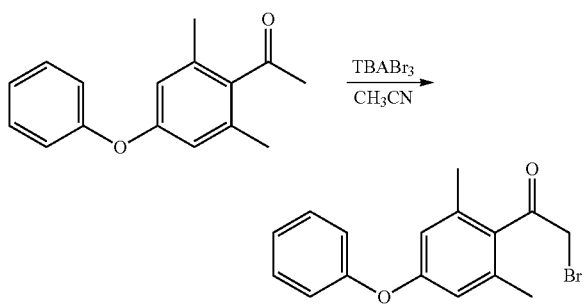

2-Bromo-1-(2,6-dimethyl-4-phenoxyphenyl)ethanone. To a solution of 1-(2,6-dimethyl-4-phenoxyphenyl)ethanone (3.60 g, 15.0 mmol) in acetonitrile (30 mL) was added tetrabutylammoniumtribromide (TBABr$_3$, 7.95 g, 15.0 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,6-dimethyl-4-phenoxyphenyl)ethanone (4.8 g), which was used directly for the next step without further purification.

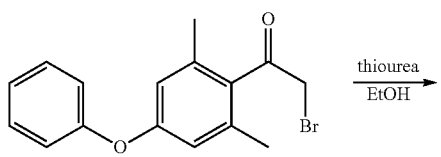

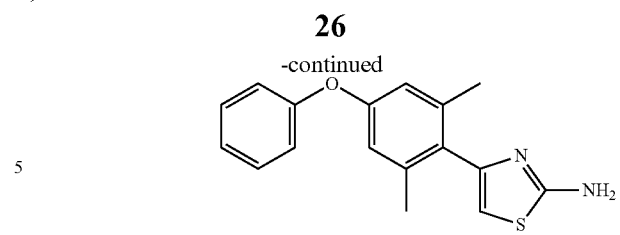

4-(2,6-Dimethyl-4-phenoxyphenyl)thiazol-2-amine. A mixture of 2-bromo-1-(2,6-dimethyl-4-phenoxyphenyl)ethanone (5.18 g, 16.2 mmol) and thiourea (1.24 g, 16.3 mmol) in 95% EtOH (23.2 mL) was heated at reflux for 60 min. The solution was concentrated and added with water (50 mL) and saturated aqueous Na$_2$CO$_3$ (5.0 mL). The resultant precipitate was filtered and recrystallized in toluene (30 mL). The solids were filtered and dried under vacuum to give 4-(2,6-dimethyl-4-phenoxyphenyl)thiazol-2-amine (2.84 g) as yellow solids in 59% yield: $^1$H NMR (500 MHz, CDCl$_3$) δ 7.33 (t, J=7.5 Hz, 2 H), 7.26 (t, J=7.5 Hz, 1 H), 7.10 (d, J=7.3, 2 H), 6.72 (s, 2 H), 6.30 (s, 1 H), 5.18 (bs, 2 H), 2.14 (s, 6 H).

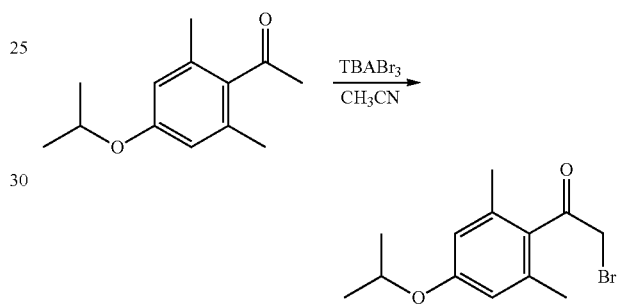

2-Bromo-1-(4-isopropoxy-2,6-dimethylphenyl)ethanone. To a solution of 1-(4-isopropoxy-2,6-dimethylphenyl)ethanone (4.3 g, 20.9 mmol) in acetonitrile (41.7 mL) was added tetrabutylammoniumtribromide (TBABr$_3$, 11.1 g, 22.9 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-isopropoxy-2,6-dimethylphenyl)ethanone (5.9 g), which was used directly for the next step without further purification.

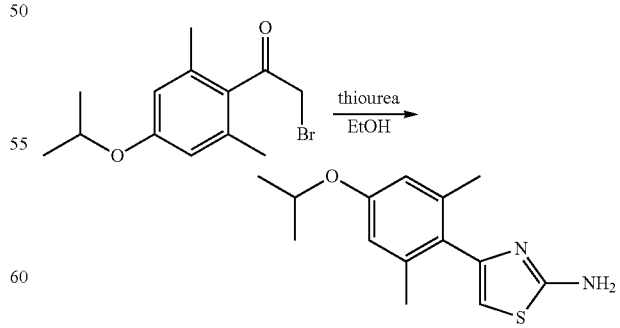

4-(4-Isopropoxy-2,6-dimethylphenyl)thiazol-2-amine. A mixture of 2-bromo-1-(4-isopropoxy-2,6-dimethylphenyl)ethanone (5.18 g, 18.2 mmol) and thiourea (1.38 g, 18.2 mmol) in 95% EtOH (26 mL) was heated at reflux for 60 min.

The solution was concentrated and added with water (50 mL) and saturated aqueous Na₂CO₃ (5.0 mL). The resultant precipitate was filtered and recrystallized in toluene (30 mL). The solids were filtered and dried under vacuum to give 4-(4-isopropoxy-2,6-dimethylphenyl)thiazol-2-amine (3.44 g) as yellow solids in 72.2% yield: $^1$H NMR (500 MHz, CDCl3) δ 6.60 (s, 2 H), 6.26 (s, 1 H), 4.97 (bs, 2 H), 4.54 (m, 1 H), 2.13 (s, 6 H), 1.32 (d, J=6.1 Hz, 6 H).

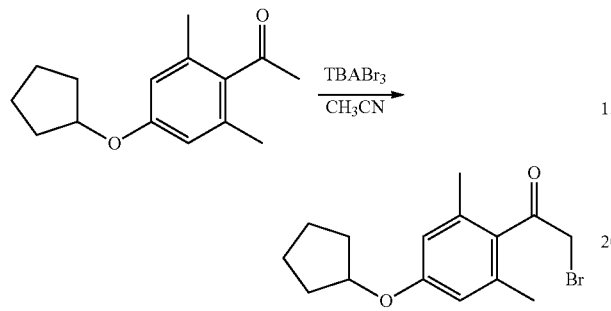

2-Bromo-1-(4-(cyclopentyloxy)-2,6-dimethylphenyl) ethanone. To a solution of 1-(4-(cyclopentyloxy)-2,6-dimethylphenyl)ethanone (4.60 g, 19.8 mmol) in acetonitrile (39.6 mL) was added tetrabutylammoniumtribromide (TBABr₃, 10.5 g, 21.8 mmol). The reaction was stirred at room temperature overnight. The solution was concentrated under reduced pressure, added with water, and extracted with ethyl acetate. The organic layer was washed with brine, dried over anhydrous MgSO₄(s), and concentrated under reduced pressure to give 2-bromo-1-(4-(cyclopentyloxy)-2,6-dimethylphenyl)ethanone (6.2 g), which was used directly for the next step without further purification.

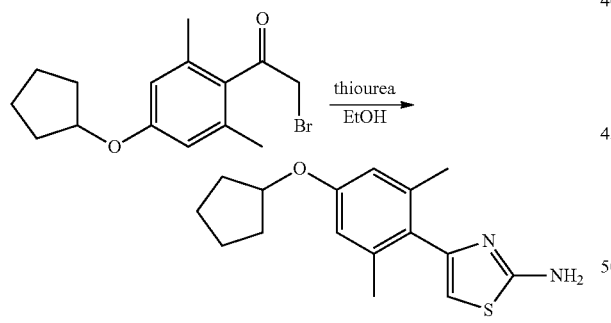

4-(4-(Cyclopentyloxy)-2,6-dimethylphenyl)thiazol-2-amine. A mixture of 2-bromo-1-(4-(cyclopentyloxy)-2,6-dimethylphenyl)ethanone (6.16 g, 19.8 mmol) and thiourea (1.51 g, 19.8 mmol) in 95% EtOH (28.3 mL) was heated at reflux for 90 min. The solution was concentrated and added with water (50 mL) and saturated aqueous Na₂CO₃ (5.0 mL). The resultant precipitate was filtered and recrystallized in toluene (30 mL). The solids were filtered and dried under vacuum to give 4-(4-(cyclopentyloxy)-2,6-dimethylphenyl) thiazol-2-amine (4.2 g) as white solids in 73.7% yield: $^1$H NMR (500 MHz, CDCl₃) δ 6.58 (s, 2 H), 6.24 (s, 1 H), 4.75 (m, 1 H), 2.13 (s, 6 H), 1.88-1.78 (m, 6 H), 1.62-1.59 (m, 2 H).

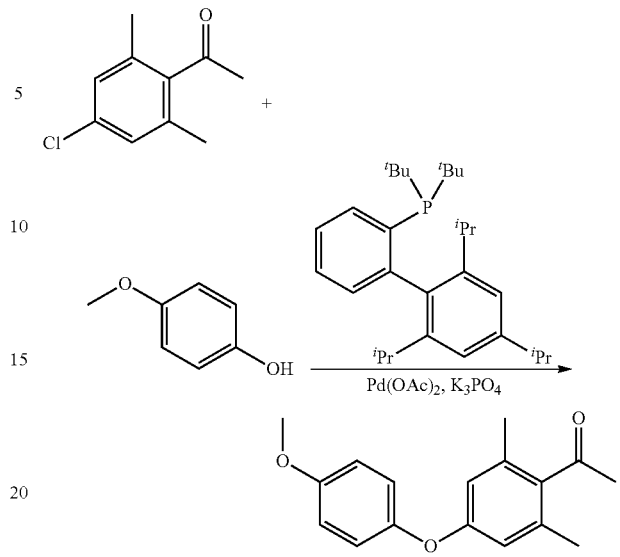

1-(4-(4-Methoxyphenoxy)-2,6-dimethylphenyl)ethanone. To a solution of 1-(4-chloro-2,6-dimethylphenyl)ethanone (10.0 g, 54.8 mmol), K₃PO₄ (23.2 g, 110 mmol) 4-methoxyphenol (8.16 g, 65.7 mmol) in toluene (78.2 mL), was added 2-di-tert-Butylphosphino-2',4',6'-triisopropylbiphenyl (349 mg, 0.82 mmol), Pd(OAc)₂ (259 mg, 1.15 mmol). The reaction was heated at 100° C. for 5.0 h under N₂. The solution was cooled to room temperature and filtered through a small pad of Celite. The cake was washed with ethyl acetate (50 mL) and combined filtrate was concentrated under reduced pressure. The residue was recrystallized in MeOH to give 1-(4-(4-methoxyphenoxy)-2,6-dimethylphenyl)ethanone (11.1 g) as white solids in 75.0%: $^1$H NMR (500 MHz, CDCl₃) δ 6.96 (m, 2 H), 6.88 (m, 2 H), 6.57 (s, 2 H), 3.81 (s, 3 H), 2.46 (s, 3 H), 2.20 (s, 6 H).

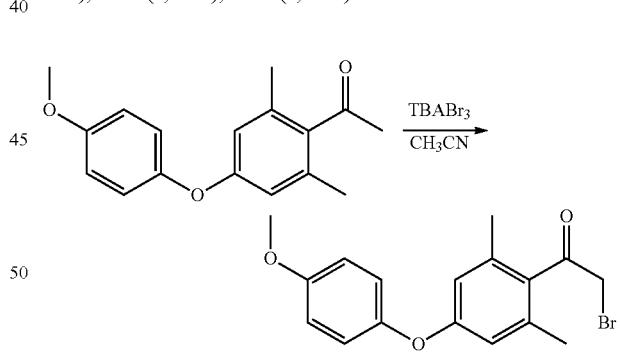

2-Bromo-1-(4-(4-methoxyphenoxy)-2,6-dimethylphenyl) ethanone. To a solution of 1-(4-(4-methoxyphenoxy)-2,6-dimethylphenyl)ethanone (3.80 g, 14.1 mmol) in acetonitrile (28.1 mL) was added tetrabutylammoniumtribromide (TBABr₃, 7.46 g, 15.5 mmol). The reaction was stirred at room temperature overnight. The solution was concentrated under reduced pressure, added with water, and extracted with ethyl acetate. The organic layer was washed with brine, dried over anhydrous MgSO₄(s), and concentrated under reduced pressure to give 2-bromo-1-(4-(4-methoxyphenoxy)-2,6-dimethylphenyl)ethanone (5.25 g), which was used directly for the next step without further purification.

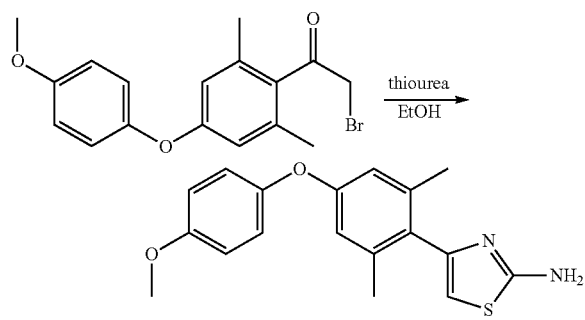

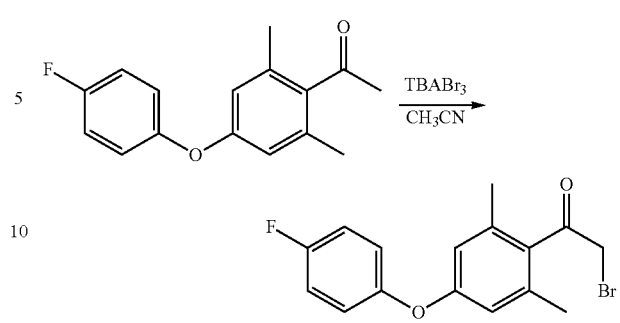

4-(4-(4-Methoxyphenoxy)-2,6-dimethylphenyl)thiazol-2-amine. A mixture of 2-bromo-1-(4-(4-methoxyphenoxy)-2,6-dimethylphenyl)ethanone (4.90 g, 14.0 mmol) and thiourea (1.07 g, 14.1 mmol) in 95% EtOH (20.0 mL) was heated at reflux for 100 min. The solution was concentrated and added with water (100 mL) and saturated aqueous $Na_2CO_3$ (5.0 mL). The resultant precipitate was filtered and recrystallized in toluene. The solids were filtered and dried under vacuum to give 4-(4-(4-methoxyphenoxy)-2,6-dimethylphenyl)thiazol-2-amine (3.10 g) as yellow solids in 68% yield: $^1$H NMR (500 MHz, CDCl3) δ 6.98 (m, 2 H), 6.88 (m, 2 H), 6.64 (s, 2 H), 6.27 (s, 1 H), 5.40 (bs, 2 H), 3.81 (s, 3 H), 2.13 (s, 6 H).

2-Bromo-1-(4-(4-fluorophenoxy)-2,6-dimethylphenyl)ethanone. To a solution of 1-(4-(4-fluorophenoxy)-2,6-dimethylphenyl)ethanone (4.40 g, 17.0 mmol) in acetonitrile (34.1 mL) was added tetrabutylammoniumtribromide (TBABr$_3$, 9.04 g, 18.8 mmol). The reaction was stirred at room temperature overnight. The solution was concentrated under reduced pressure, added with water, and extracted with ethyl acetate. The organic layer was washed with brine, dried over anhydrous $MgSO_4(s)$, and concentrated under reduced pressure to give 2-bromo-1-(4-(4-fluorophenoxy)-2,6-dimethylphenyl)ethanone (5.8 g), which was used directly for the next step without further purification.

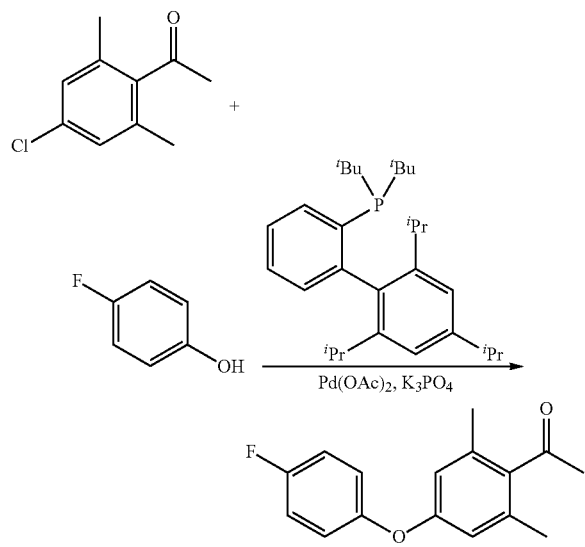

1-(4-(4-Fluorophenoxy)-2,6-dimethylphenyl)ethanone. To a solution of 1-(4-chloro-2,6-dimethylphenyl)ethanone (4.50 g, 24.6 mmol), $K_3PO_4$ (10.5 g, 49.3 mmol), 4-fluorophenol (3.31 g, 29.5 mmol) in toluene (49.3 mL), was added 2-di-tert-butylphosphino-2',4',6'-triisopropylbiphenyl (314 mg, 0.74 mmol), Pd(OAc)$_2$ (233 mg, 1.04 mmol). The reaction was heated at 100° C. overnight under $N_2$. The solution was cooled to room temperature and filtered through a small pad of Celite. The cake was washed with ethyl acetate (100 mL), and combined filtrate was concentrated under reduced pressure. The residue was purified by flash column chromatography on silica gel to give 1-(4-(4-Fluorophenoxy)-2,6-dimethylphenyl)ethanone (4.40 g) as yellow oil in 68% yield: $^1$H NMR (500 MHz, CDCl$_3$) δ 7.03 (m, 2 H), 6.98 (m, 2 H), 6.60 (s, 2 H), 2.47 (s, 3 H), 2.22 (s, 6 H).

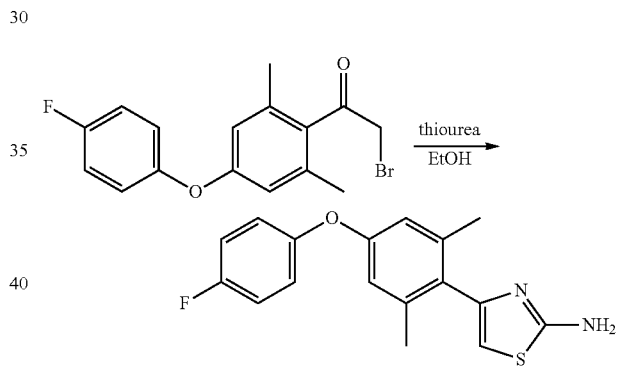

4-(4-(4-Fluorophenoxy)-2,6-dimethylphenyl)thiazol-2-amine. A mixture of 2-bromo-1-(4-(4-fluorophenoxy)-2,6-dimethylphenyl)ethanone (5.74 g, 17.0 mmol) and thiourea (1.30 g, 17.1 mmol) in 95% EtOH (24.3 mL) was heated at reflux for 60 min. The solution was concentrated and added with water (100 mL) and saturated aqueous $Na_2CO_3$ (5.0 mL). The resultant precipitate was filtered and recrystallized in toluene. The solids were filtered and dried under vacuum to give 4-(4-(4-fluorophenoxy)-2,6-dimethylphenyl)thiazol-2-amine (4.50 g) as yellow solids in 84% yield: $^1$H NMR (500 MHz, CDCl3) δ 7.05-6.97 (m, 4 H), 6.66 (s, 2 H), 6.28 (s, 1 H), 5.95 (bs, 2 H), 2.14 (s, 6 H).

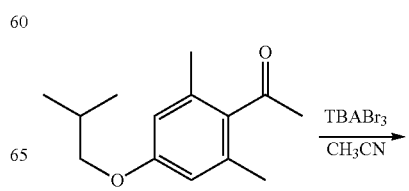

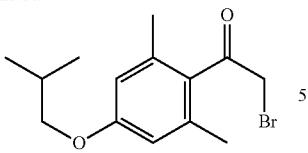

2-Bromo-1-(4-isobutoxy-2,6-dimethylphenyl)ethanone. To a solution of 1-(4-isobutoxy-2,6-dimethylphenyl)ethanone (4.3 g, 19.5 mmol) in acetonitrile (39 mL) was added tetrabutylammoniumtribromide (TBABr$_3$, 9.41 g, 19.5 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 1-(4-isobutoxy-2,6-dimethylphenyl)ethanone (6.1 g), which was used directly for the next step without further purification.

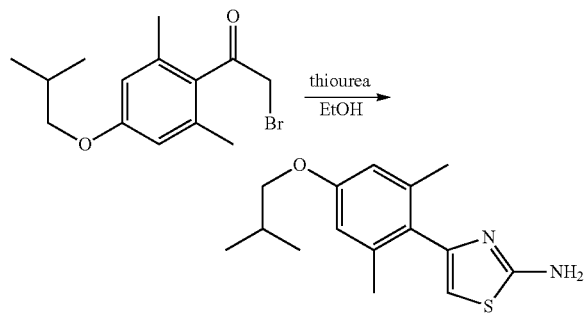

4-(4-Isobutoxy-2,6-dimethylphenyl)thiazol-2-amine. A mixture of 2-bromo-1-(4-isobutoxy-2,6-dimethylphenyl)ethanone (5.84 g, 19.5 mmol) and thiourea (1.49 g, 19.6 mmol) in 95% EtOH (28 mL) was heated at reflux for 60 min. The solution was concentrated and added with water (50 mL) and saturated aqueous Na$_2$CO$_3$ (5.0 mL). The resultant precipitate was filtered and recrystallized in toluene (30 mL). The solids were filtered and dried under vacuum to give 4-(4-isobutoxy-2,6-dimethylphenyl)thiazol-2-amine (4.4 g) as white solids in 82% yield: $^1$H NMR (500 MHz, CDCl3) δ 6.61 (s, 2 H), 6.24 (s, 1 H), 3.70 (d, J=6.5 Hz, 2 H), 2.15 (s, 6 H), 2.07 (m, 1 H), 1.01 (d, J=6.7 Hz, 6 H).

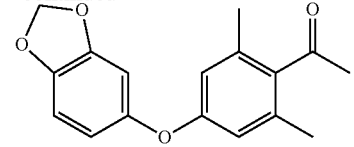

1-(4-(Benzo[d][1,3]dioxol-5-yloxy)-2,6-dimethylphenyl)ethanone. To a solution of 1-(4-chloro-2,6-dimethylphenyl)ethanone (5.0 g, 27.4 mmol), K$_3$PO$_4$ (11.6 g, 54.7 mmol), sesamol (4.54 g, 32.9 mmol) in toluene (54.8 mL), was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of Celite. The cake was washed with ethyl acetate (50 mL) and combined filtrate was concentrated under reduced pressure. The residue was recrystallized in MeOH to give 1-(4-(benzo[d][1,3]dioxol-5-yloxy)-2,6-dimethylphenyl)ethanone (4.80 g) as white solids in 62% yield: $^1$H NMR (500 MHz, CDCl3) δ 6.77 (d, J=8.5 Hz, 1 H), 6.59 (s, 2 H), 6.56 (s, 1 H), 6.48 (m, 1 H), 5.98 (s, 2 H), 2.46 (s, 3 H), 2.21 (s, 6 H).

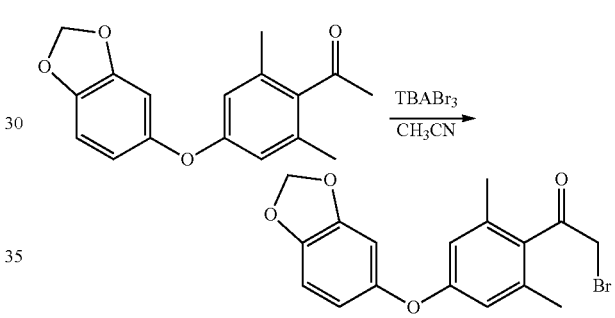

1-(4-(Benzo[d][1,3]dioxol-5-yloxy)-2,6-dimethylphenyl)-2-bromoethanone. To a solution of 1-(4-(benzo[d][1,3]dioxol-5-yloxy)-2,6-dimethylphenyl)ethanone (4.80 g, 16.9 mmol) in acetonitrile (33.8 mL) was added tetrabutylammoniumtribromide (TBABr$_3$, 8.14 g, 16.9 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 1-(4-(benzo[d][1,3]dioxol-5-yloxy)-2,6-dimethylphenyl)-2-bromoethanone (6.70 g), which was used directly for the next step without further purification.

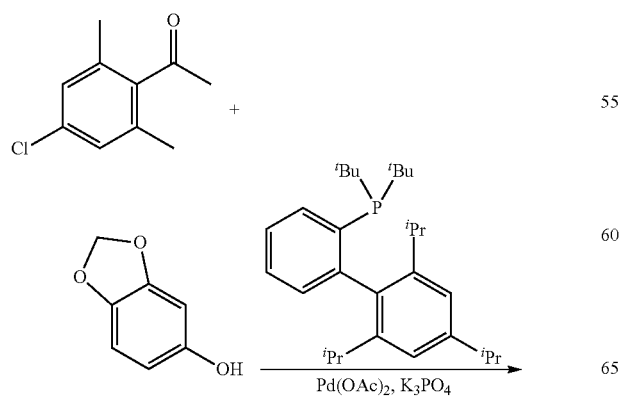

4-(4-(Benzo[d][1,3]dioxol-5-yloxy)-2,6-dimethylphenyl)thiazol-2-amine. A mixture of 1-(4-(benzo[d][1,3]dioxol-5-yloxy)-2,6-dimethylphenyl)-2-bromoethanone (6.13 g, 16.9 mmol) and thiourea (1.29 g, 16.9 mmol) in 95% EtOH (24.1 mL) was heated at reflux for 90 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(benzo[d][1,3]dioxol-5-yloxy)-2,6-dimethylphenyl)thiazol-2-amine (5.50 g) as yellow solids in 96% yield: $^1$H NMR (500 MHz, CDCl3) δ 6.75 (d, J=8.5 Hz, 1 H), 6.66 (s, 2 H), 6.58 (m, 1 H), 6.49 (m, 1 H), 6.28 (s, 1 H), 5.98 (s, 2 H), 5.05 (bs, 2 H), 2.13 (s, 6 H).

2-Bromo-1-(4-(3,5-dimethylphenoxy)-2,6-dimethylphenyl)ethanone. To a solution of 1-(4-(3,5-dimethylphenoxy)-2,6-dimethylphenyl)ethanone (6.30 g, 23.5 mmol) in acetonitrile (47.0 mL) was added tetrabutylammoniumtribromide (TBABr$_3$, 11.9 g, 24.7 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(3,5-dimethylphenoxy)-2,6-dimethylphenyl)ethanone (8.3 g), which was used directly for the next step without further purification.

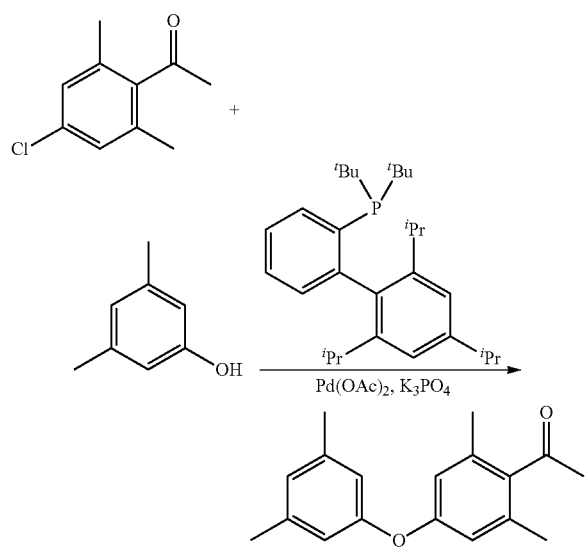

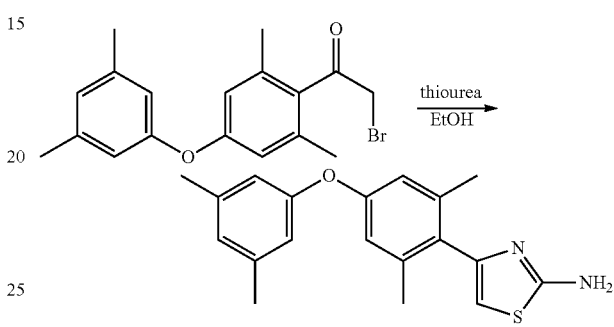

4-(4-(3,5-Dimethylphenoxy)-2,6-dimethylphenyl)thiazol-2-amine. A mixture of 2-bromo-1-(4-(3,5-dimethylphenoxy)-2,6-dimethylphenyl)ethanone (8.15 g, 23.5 mmol) and thiourea (1.79 g, 23.5 mmol) in 95% EtOH (33.5 mL) was heated at reflux for 120 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(3,5-dimethylphenoxy)-2,6-dimethylphenyl)thiazol-2-amine (4.50 g) as yellow solids in 59% yield: $^1$H NMR (500 MHz, CDCl3) δ 6.76 (s, 1 H), 6.68 (s, 2 H), 6.64 (s, 2 H), 6.26 (s, 1 H), 2.29 (s, 6 H), 2.16 (s, 6 H).

1-(4-(3,5-Dimethylphenoxy)-2,6-dimethylphenyl)ethanone. To a solution of 1-(4-chloro-2,6-dimethylphenyl)ethanone (5.0 g, 27.4 mmol), K$_3$PO$_4$ (11.6 g, 54.7 mmol), 3,5-dimethylphenol (4.01 g, 32.8 mmol) in toluene (54.8 mL), was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of Celite. The cake was washed with ethyl acetate (50 mL) and combined filtrate was concentrated under reduced pressure. The residue was purified by flash column chromatography on silica gel to give 1-(4-(3,5-dimethylphenoxy)-2,6-dimethylphenyl)ethanone (6.3 g) as yellow solids in 86% yield: $^1$H NMR (500 MHz, CDCl$_3$) δ 6.76 (s, 1 H), 6.63 (s, 2 H), 6.62 (s, 2 H), 2.48 (s, 3 H), 2.29 (s, 6 H), 2.22 (s, 6 H).

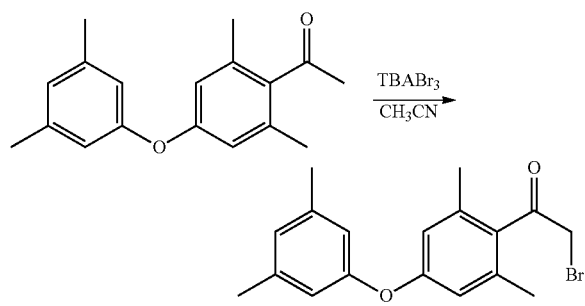

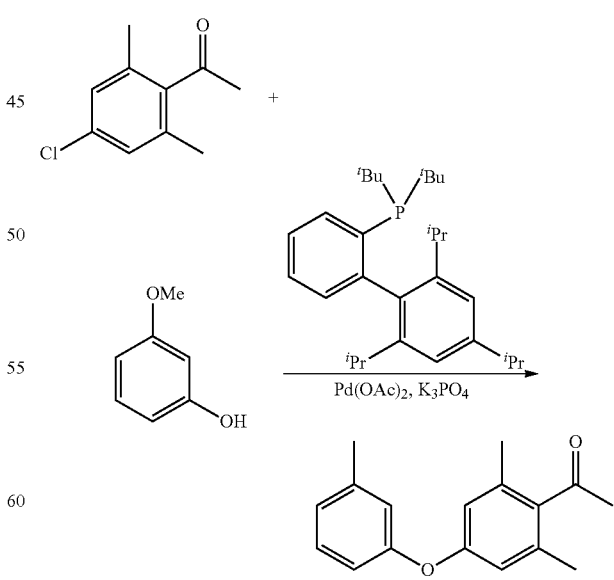

1-(4-(3-Methoxyphenoxy)-2,6-dimethylphenyl)ethanone. To a solution of 1-(4-chloro-2,6-dimethylphenyl)ethanone (5.00 g, 27.4 mmol), K$_3$PO$_4$ (11.6 g, 54.7 mmol), 3-methoxyphenol (4.08 g, 32.9 mmol) in toluene (54.8 mL) was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of Celite. The cake was washed with ethyl acetate (50 mL) and combined filtrate was concentrated under reduced pressure. The residue was purified by flash column chromatography on silica gel to give 1-(4-(3-methoxyphenoxy)-2,6-dimethylphenyl)ethanone (5.4 g) as yellow oil in 73% yield: $^1$H NMR (500 MHz, CDCl$_3$) δ 7.24 (m, 1 H), 6.68-6.66 (m, 3 H), 6.57-6.56 (m, 2 H), 3.79 (s, 3 H), 2.48 (s, 3 H), 2.22 (s, 6 H).

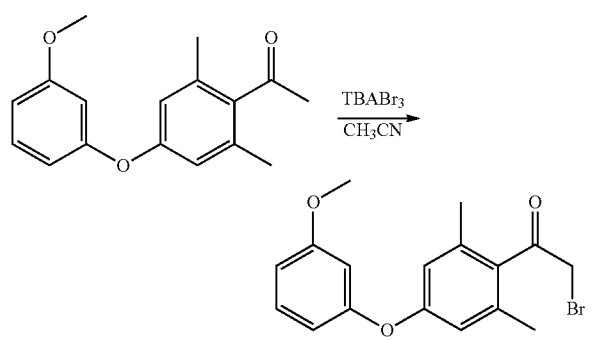

2-Bromo-1-(4-(3-methoxyphenoxy)-2,6-dimethylphenyl) ethanone. To a solution of 1-(4-(3-methoxyphenoxy)-2,6-dimethylphenyl)ethanone (5.40 g, 20.0 mmol) in acetonitrile (40.0 mL) was added tetrabutylammoniumtribromide (TBABr$_3$, 10.1 g, 21.0 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(3-methoxyphenoxy)-2,6-dimethylphenyl)ethanone (7.00 g), which was used directly for the next step without further purification.

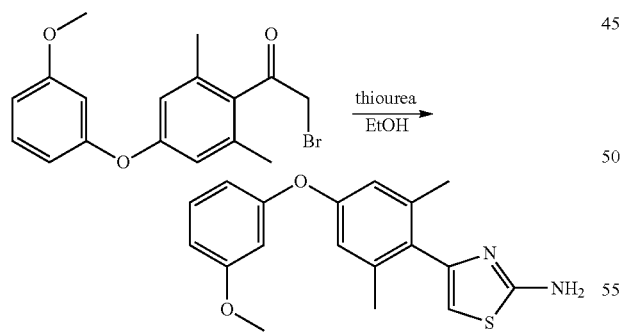

4-(4-(3-Methoxyphenoxy)-2,6-dimethylphenyl)thiazol-2-amine. A mixture of 2-bromo-1-(4-(3-methoxyphenoxy)-2,6-dimethylphenyl)ethanone (6.98 g, 20.0 mmol) and thiourea (1.52 g, 20.0 mmol) in 95% EtOH (28.5 mL) was heated at reflux for 5.0 h. The solution was concentrated and added with water (50 mL) and saturated aqueous Na$_2$CO$_3$ (1.0 mL), and extracted with ethyl acetate (100 ml). The organic layer was washed with brine, dried over anhydrous MgSO$_4$(s), and concentrated under reduced pressure to give 4-(4-(3-methox- yphenoxy)-2,6-dimethylphenyl)thiazol-2-amine (4.30 g) as deep-brown oil, which was used directly for the next step without further purification.

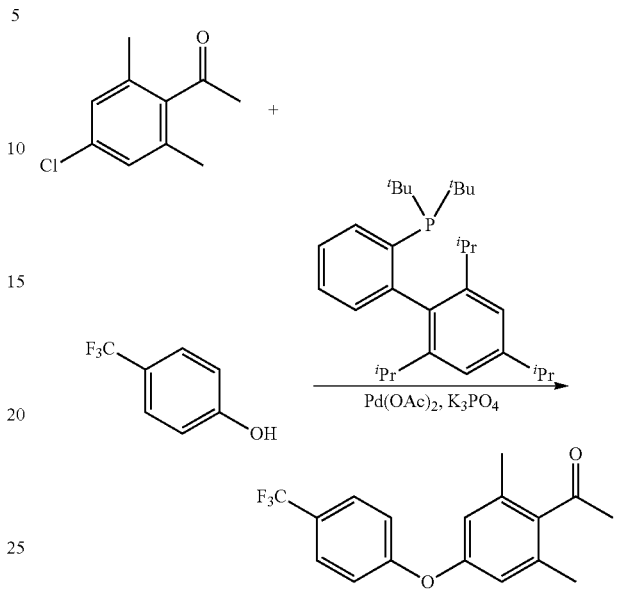

1-(2,6-Dimethyl-4-(4-(trifluoromethyl)phenoxy)phenyl) ethanone. To a solution of 1-chloro-4-(trifluoromethyl)benzene (6.60 g, 36.6 mmol), K$_3$PO$_4$ (12.9 g, 60.9 mmol), 1-(4-hydroxy-2,6-dimethylphenyl)ethanone (5.00 g, 30.5 mmol) in toluene (60.9 mL) was added 2-di-tert-butylphosphino-2',4',6'-triisopropylbiphenyl (388 mg, 0.91 mmol) and Pd(OAc)$_2$ (288 mg, 1.28 mmol). The reaction was heated at 100° C. for 120 min under N$_2$. The solution was cooled to room temperature and filtered through a small pad of Celite. The cake was washed with ethyl acetate (50 mL) and combined filtrate was concentrated under reduced pressure. The residue was purified by flash column chromatography on silica gel to give 1-(2,6-dimethyl-4-(4-(trifluoromethyl)phenoxy)phenyl)ethanone (1.8 g) as yellow oil in 19% yield: $^1$H NMR (500 MHz, CDCl3) δ 7.58 (d, J=8.5 Hz, 2 H), 7.04 (d, J=8.5 Hz, 2 H), 6.70 (s, 2 H), 2.50 (s, 3 H), 2.25 (s, 6 H).

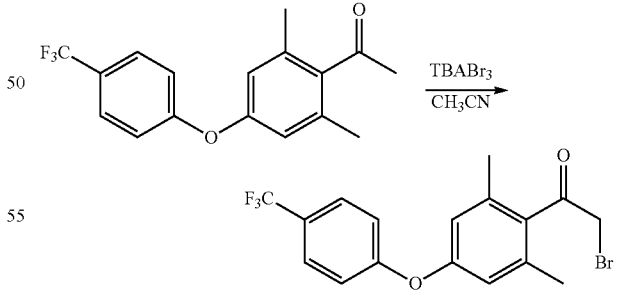

2-Bromo-1-(2,6-dimethyl-4-(4-(trifluoromethyl)phenoxy)phenyl)ethanone. To a solution of 1-(2,6-dimethyl-4-(4-(trifluoromethyl)phenoxy)phenyl)ethanone (1.80 g, 5.84 mmol) in acetonitrile (11.7 mL) was added tetrabutylammoniumtribromide (TBABr$_3$, 2.82 g, 5.84 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,6-dimethyl-4-(4-(trifluoromethyl)phenoxy)phenyl)ethanone (2.16 g), which was used directly for the next step without further purification.

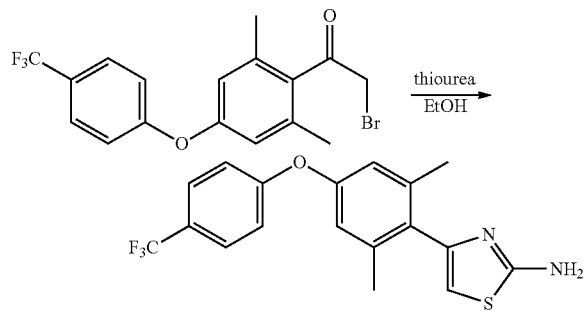

4-(2,6-Dimethyl-4-(4-(trifluoromethyl)phenoxy)phenyl) thiazol-2-amine. A mixture of 2-bromo-1-(2,6-dimethyl-4-(4-(trifluoromethyl)phenoxy)phenyl)ethanone (2.20 g, 5.68 mmol) and thiourea (0.43 g, 5.68 mmol) in 95% EtOH (8.1 mL) was heated at reflux for 60 min. The solution was concentrated and added with water (50 mL) and saturated aqueous Na$_2$CO$_3$ (1.0 mL). The resultant precipitate was filtered and recrystallized in toluene. The solids were filtered and dried under vacuum to give 4-(2,6-dimethyl-4-(4-(trifluoromethyl)phenoxy)phenyl)thiazol-2-amine (1.30 g) as yellow solids in 63% yield: $^1$H NMR (500 MHz, CDCl3) δ 7.56 (d, J=8.5 Hz, 2 H), 7.05 (d, J=8.5 Hz, 2 H), 6.76 (s, 2 H), 6.32 (s, 1 H), 5.03 (s, 2 H), 2.17 (s, 6 H).

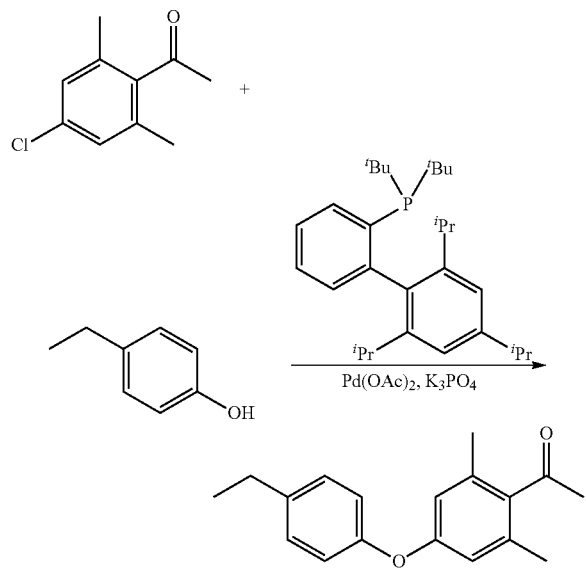

1-(4-(4-Ethylphenoxy)-2,6-dimethylphenyl)ethanone. To a solution of 1-(4-chloro-2,6-dimethylphenyl)ethanone (5.0 g, 27.4 mmol), K$_3$PO$_4$ (11.6 g, 54.7 mmol), 4-ethylphenol (4.01 g, 32.8 mmol) in toluene (54.8 mL) was added 2-di-tert-butylphosphino-2',4',6'-triisopropylbiphenyl (349 mg, 0.82 mmol) and Pd(OAc)$_2$ (259 mg, 1.15 mmol). The reaction was heated at 100° C. overnight under N$_2$. The solution was cooled to room temperature and filtered through a small pad of Celite. The cake was washed with ethyl acetate (50 mL) and combined filtrate was concentrated under reduced pressure. The residue was purified by flash column chromatography on silica gel to give 1-(4-(4-ethylphenoxy)-2,6-dimethylphenyl)ethanone (6.0 g) as yellow oil in 82% yield: $^1$H NMR (500 MHz, CDCl$_3$) δ 7.17 (d, J=8.5 Hz, 2 H), 6.93 (d, J=8.5 Hz, 2 H), 6.63 (s, 2 H), 2.64 (q, J=7.5 Hz, 2 H), 2.47 (s, 3 H), 2.21 (s, 6 H), 1.25 (t, J=7.5 Hz, 3 H).

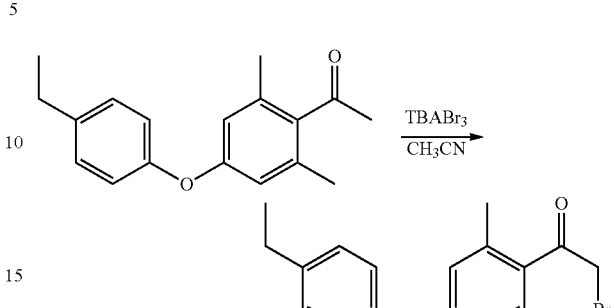

2-Bromo-1-(4-(4-ethylphenoxy)-2,6-dimethylphenyl) ethanone. To a solution of 1-(4-(4-ethylphenoxy)-2,6-dimethylphenyl)ethanone (6.00 g, 22.4 mmol) in acetonitrile (44.7 mL) was added tetrabutylammoniumtribromide (TBABr$_3$, 10.8 g, 22.4 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(4-ethylphenoxy)-2,6-dimethylphenyl)ethanone (8.2 g), which was used directly for the next step without further purification.

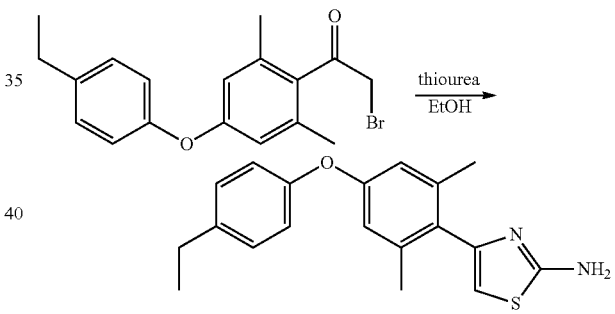

4-(4-(4-Ethylphenoxy)-2,6-dimethylphenyl)thiazol-2-amine. A mixture of 2-bromo-1-(4-(4-ethylphenoxy)-2,6-dimethylphenyl)ethanone (7.70 g, 22.2 mmol) and thiourea (1.69 g, 22.2 mmol) in 95% EtOH (31.7 mL) was heated at reflux for 180 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(4-ethylphenoxy)-2,6-dimethylphenyl)thiazol-2-amine (6.30 g) as yellow solids in 88% yield: $^1$H NMR (500 MHz, CDCl$_3$) δ 7.18 (d, J=7.5 Hz, 2 H), 6.95 (d, J=8.5, 2 H), 6.71 (s, 2 H), 6.29 (s, 1 H), 5.45 (bs, 2 H), 2.64 (q, J=7.5 Hz, 2 H), 2.14 (s, 6 H), 1.25 (t, J=8.0 Hz, 3 H).

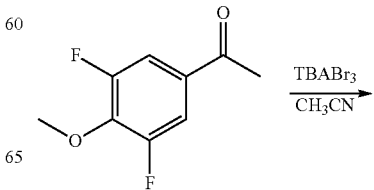

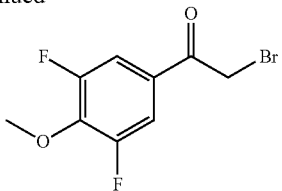

2-Bromo-1-(3,5-difluoro-4-methoxyphenyl)ethanone. To a CH$_3$CN solution (56 mL) containing 1-(3,5-difluoro-4-methoxyphenyl)ethanone (5.0 g, 26.9 mmol, 1.0 equiv) was added TBABr$_3$ (12.95 g, 26.9 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (2.0% EtOAc in hexanes as eluant) to provide 2-bromo-1-(3,5-difluoro-4-methoxyphenyl)ethanone (5.05 g, 19.0 mmol) as white solids in 71% yield: $^1$H NMR (DMSO-d$_6$, 500 MHz) δ 7.76-7.81 (m, 2 H), 4.91 (s, 2 H), 4.07 (s, 3 H).

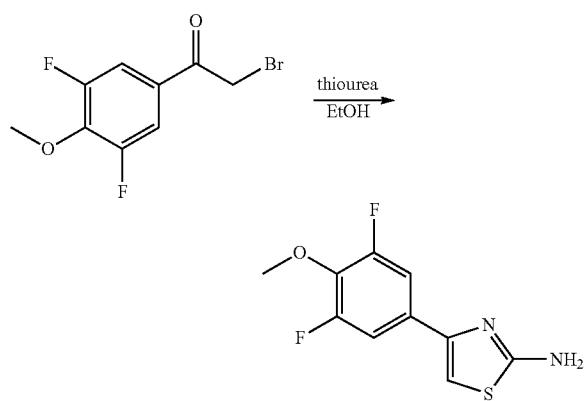

4-(3,5-Difluoro-4-methoxyphenyl)thiazol-2-amine. A reaction mixture containing 2-bromo-1-(3,5-difluoro-4-methoxyphenyl)ethanone (2.0 g, 7.5 mmol, 1.0 equiv) and thiourea (0.57 g, 7.5 mmol, 1.0 equiv) in EtOH (20.0 mL) was heated at reflux for 3.0 h. The residue was basified with saturated aqueous NaHCO$_3$ (20 mL) and extracted with EtOAc (3×30 mL). The organic layer was separated, dried over MgSO$_4$(s), and concentrated under reduced pressure. The resultant solids were washed with hexanes to give 4-(3,5-difluoro-4-methoxyphenyl)thiazol-2-amine (1.54 g, 6.4 mmol) as white solids in 84% yield: $^1$H NMR (DMSO-d$_6$, 500 MHz) δ 7.49-7.54 (m, 2 H), 7.12-7.14 (m, 3 H), 3.92 (s, 3 H); ESI-MS: m/z 243.0 (M+H)$^+$.

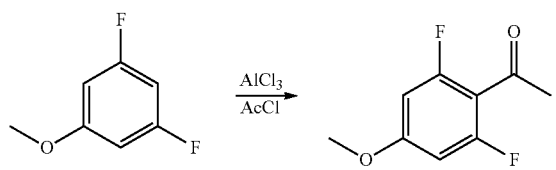

1-(2,6-Difluoro-4-methoxyphenyl)ethanone. A mixture of aluminium chloride (10.0 g, 69.4 mmol, 5.0 equiv) and acetyl chloride (2.0 mL, 28 mmol, 2.0 equiv) in CH$_2$Cl$_2$ (50.0 mL) was stirred at 0° C. for 30 min. The reaction mixture was slowly added with 1,3-difluoro-5-methoxy-benzene (2.0 g, 13.9 mmol, 1.0 equiv) in CH$_2$Cl$_2$ (10.0 mL), and the resultant solution was stirred at room temperature for additional 2.0 h. The solution was basified with saturated aqueous NaHCO$_3$ (20 mL) to pH 8-9. The organic layer was separated, dried over MgSO$_4$(s), and concentrated under reduced pressure. The residue was purified by column chromatography on silica gel (15% EtOAc in hexanes as eluant) at give 1-(2,6-difluoro-4-methoxyphenyl)ethanone (1.5 g, 8.1 mmol) as yellow oil in 58% yield: $^1$H NMR (CDCl$_3$, 500 MHz) δ 6.46-6.48 (m, 2 H), 3.83 (s, 3 H), 2.56 (s, 3 H); ESI-MS: m/z 187.0 (M+H)+.

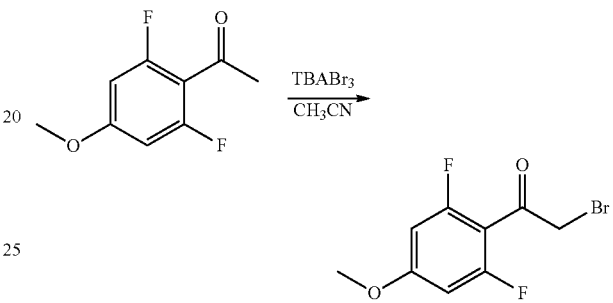

2-Bromo-1-(2,5-difluoro-4-methoxyphenyl)ethanone. A CH$_3$CN solution (20 mL) containing 1-(2,6-difluoro-4-methoxyphenyl)ethanone (1.5 g, 8.1 mmol, 1.0 equiv) was added with TBABr$_3$ (3.88 g, 8.1 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (2.0% EtOAc in hexanes as eluant) to provide 2-bromo-1-(2,5-difluoro-4-methoxyphenyl)ethanone (5.05 g, 19.1 mmol) as yellow oil in 84% yield: $^1$H NMR (CDCl$_3$, 500 MHz) δ 6.50-6.52 (m, 2 H), 4.34 (s, 2 H), 3.85 (s, 3 H).

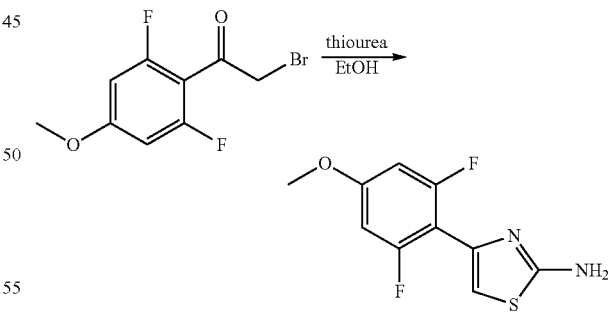

4-(2,6-Difluoro-4-methoxyphenyl)thiazol-2-amine. A reaction mixture containing 2-bromo-1-(2,5-difluoro-4-methoxyphenyl)ethanone (1.5 g, 5.7 mmol, 1.0 equiv) and thiourea (430.8 mg, 5.7 mmol, 1.0 equiv) in EtOH (15.0 mL) was heated at reflux for 6.0 h. The residue was basified with saturated aqueous NaHCO$_3$ (20 mL) and extracted with EtOAc (3×30 mL). The organic layer was separated, dried over MgSO$_4$(s), and concentrated under reduced pressure. The residue was purified by column chromatography on silica gel (3.0% EtOAc in hexanes as eluant) to provide 4-(2,6- difluoro-4-methoxy-phenyl)-thiazol-2-amine (928.6 mg, 3.8 mmol) as white solids in 68% yield: 1H NMR (CDCl3, 500 MHz) δ 6.68 (s, 1 H), 6.50-6.52 (m, 2 H), 5.07 (brs, 2 H), 3.81 (s, 3 H); ESI-MS: m/z 243.7 (M+H)+.

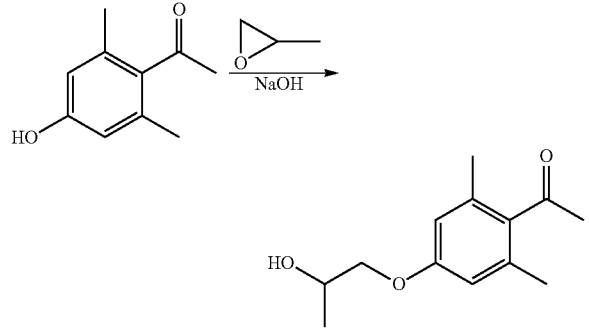

1-(4-(2-Hydroxypropoxy)-2,6-dimethylphenyl)ethanone. A pressure glass vessel charged with 1-(4-hydroxy-2,6-dimethylphenyl)ethanone (500 mg, 3.1 mmol, 1.0 equiv) and 2-methyloxirane (0.22 mL, 3.1 mmol, 1.0 equiv) in 50% aqueous NaOH solution (5.0 mL) was stirred at 140° C. for 4.0 h. The mixture was diluted with H₂O (20 mL) and extracted with EtOAc. The organic layer was collected, dried over MgSO₄(s), and concentrated under reduced pressure. The residue was purified by column chromatography on silica gel (30% EtOAc in hexanes as eluant) to provide 1-(4-(2-hydroxypropoxy)-2,6-dimethylphenyl)ethanone (445.9 mg, 2.1 mmol) as yellow oil in 66% yield: $^1$H NMR (CDCl₃, 500 MHz) δ 6.57 (s, 2 H), 4.10-4.20 (brs, 1 H), 3.90-3.93 (m, 2 H), 3.75-3.79 (m, 1 H), 2.45 (s, 3 H), 2.23 (s, 6 H), 1.25-1.28 (m, 3 H); ESI-MS: m/z 223.4 (M+H)⁺.

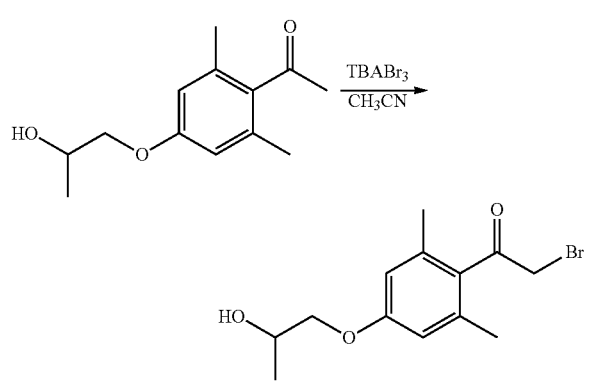

2-Bromo-1-(4-(2-hydroxypropoxy)-2,6-dimethylphenyl) ethanone. To a CH₃CN solution (6.0 mL) containing 1-(4-(2-hydroxypropoxy)-2,6-dimethylphenyl)ethanone (445.9 mg, 2.0 mmol, 1.0 equiv) was added TBABr₃ (967.3 mg, 2.0 mmol, 1.0 equiv). The reaction mixture was stirred at room temperature for 16 h. The solvent was concentrated under reduced pressure, and the residue was re-dissolved in EtOAc (50 mL). The solution was washed with saturated aqueous NaHCO₃ (30 mL), dried over MgSO₄, and concentrated under reduced pressure.
2-Bromo-1-(4-(2-hydroxypropoxy)-2,6-dimethylphenyl) ethanone (547.8 mg, 1.8 mmol) was obtained as brown oil in 91% yield: 1H NMR (CDCl₃, 500 MHz) δ 6.60 (s, 2 H), 4.25 (s, 2 H), 4.10-4.20 (brs, 1 H), 3.91-3.94 (m, 2 H), 3.79-3.80 (s, 1 H), 2.24 (s, 6 H), 1.27-1.29 (m, 3 H).

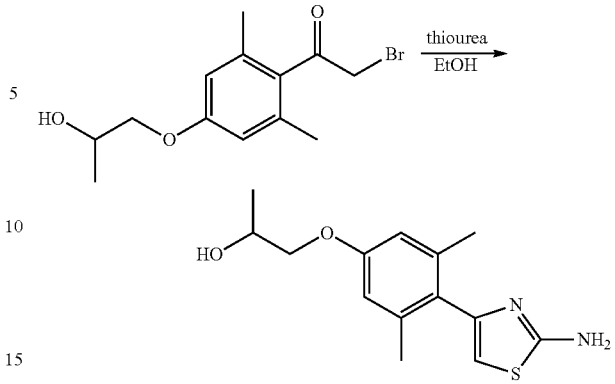

1-(4-(2-Aminothiazol-4-yl)-3,5-dimethylphenoxy)propan-2-ol. A reaction mixture containing 2-bromo-1-(2,5-difluoro-4-methoxyphenyl)ethanone (547.8 mg, 1.8 mmol, 1.0 equiv) and thiourea (138.5 mg, 1.8 mmol, 1.0 equiv) in EtOH (3.0 mL) was heated at reflux for 16 h. The solution was concentrated under reduced pressure, and the residue was re-dissolved in EtOAc (30 mL). The solution was washed with saturated aqueous NaHCO₃ (30 mL), dried over MgSO₄, and concentrated under reduced pressure. The residue was purified by column chromatography on silica gel (30% EtOAc in hexanes as eluant) to provide 1-(4-(2-aminothiazol-4-yl)-3,5-dimethylphenoxy)propan-2-ol (332.5 mg, 1.2 mmol) as yellow oil in 66% yield: 1H NMR (CDCl₃, 500 MHz) δ 6.62 (s, 2 H), 6.26 (s, 1 H), 4.95 (brs, 2 H), 4.10-4.20 (brs, 1 H), 3.91-3.94 (m, 2 H), 3.75-3.79 (m, 1 H), 2.15 (s, 6 H), 1.26-1.28 (m, 3 H); ESI-MS: m/z 279.7 (M+H)⁺.

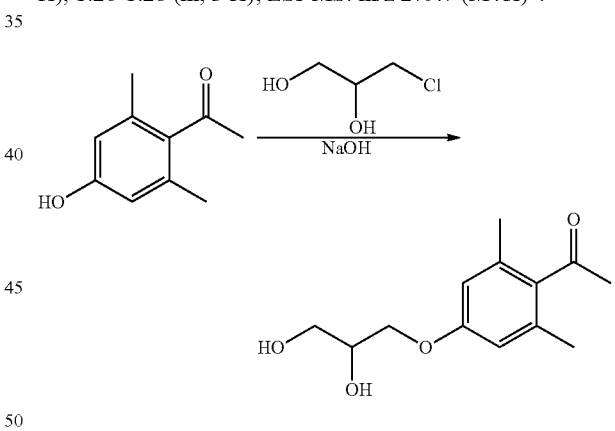

1-(4-(2,3-Dihydroxypropoxy)-2,6-dimethylphenyl)ethanone. A pressure glass vessel charged with 1-(4-hydroxy-2,6-dimethylphenyl)ethanone (2.00 g, 12.2 mmol, 1.0 equiv) and 3-chloropropane-1,2-diol (1.02 mL, 12.2 mmol, 1.0 equiv) in 50% aqueous NaOH solution (20.0 mL) was heated at 140° C. for 16 h. The mixture was diluted with H₂O (20 mL) and extracted with EtOAc. The organic layer was collected, dried over MgSO₄(s), and concentrated under reduced pressure. The residue was purified by column chromatography on silica gel (30% EtOAc in hexanes as eluant) to provide 1-(4-(2,3-dihydroxypropoxy)-2,6-dimethylphenyl)ethanone (1.66 g, 7.0 mmol) as yellow oil in 57% yield: $^1$H NMR (CDCl₃, 500 MHz) δ 6.57 (s, 2 H), 4.10-4.11 (m, 1 H), 4.08-4.09 (m, 2 H), 4.01-4.02 (m, 1 H), 3.74-3.75 (m, 1 H), 2.58-2.59 (brs, 1 H), 2.45 (s, 3 H), 2.23 (s, 6 H), 2.05-2.10 (brs, 1 H); ESI-MS: m/z 239.9 (M+H)⁺.

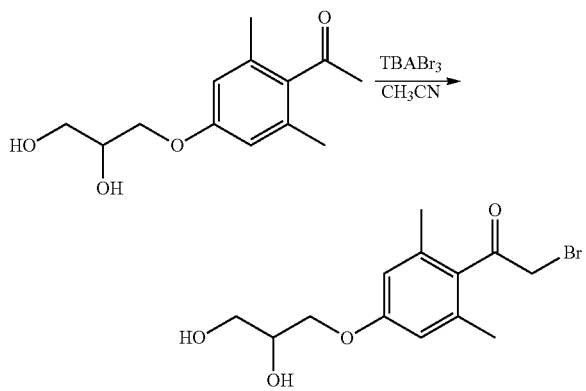

2-Bromo-1-(4-(2,3-dihydroxypropoxy)-2,6-dimethylphenyl)ethanone. To a CH$_3$CN solution (10.0 mL) containing 1-(4-(2,3-dihydroxypropoxy)-2,6-dimethylphenyl)ethanone (1.0 g, 4.2 mmol, 1.0 equiv) was added TBABr$_3$ (2.04 g, 4.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure.
2-Bromo-1-(4-(2,3-dihydroxypropoxy)-2,6-dimethylphenyl)ethanone (741.9 mg, 2.3 mmol) was obtained as yellow solids in 56% yield: $^1$H NMR (CDCl$_3$, 500 MHz) δ 6.60 (s, 2 H), 4.25 (s, 2 H), 4.10-4.11 (m, 1 H), 4.03-4.04 (m, 2 H), 3.82-3.85 (m, 1 H), 3.75-3.76 (m, 1 H), 2.24 (s, 6 H).

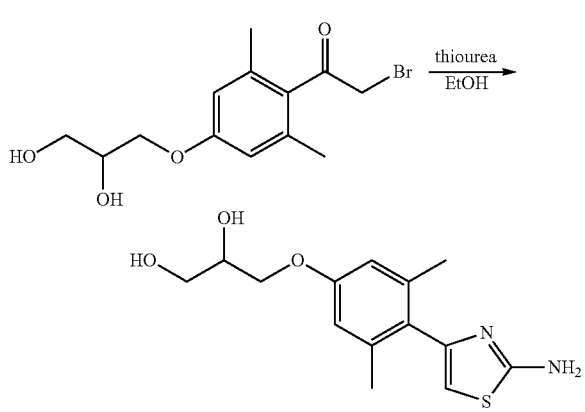

3-(4-(2-Aminothiazol-4-yl)-3,5-dimethylphenoxy)propane-1,2-diol. A reaction mixture containing 2-bromo-1-(4-(2,3-dihydroxypropoxy)-2,6-dimethylphenyl)ethanone (741.9 mg, 2.3 mmol, 1.0 equiv) and thiourea (178.1 mg, 2.3 mmol, 1.0 equiv) in EtOH (10.0 mL) was heated at reflux for 16 h. The solution was concentrated under reduced pressure, and the residue was re-dissolved in EtOAc (30 mL). The solution was washed with saturated aqueous NaHCO$_3$ (30 mL), dried over MgSO$_4$, and concentrated under reduced pressure. The residue was purified by column chromatography on silica gel (30.0% EtOAc in hexanes as eluant) to provide 3-(4-(2-aminothiazol-4-yl)-3,5-dimethylphenoxy)propane-1,2-diol (694.1 mg, 2.4 mmol) as yellow solids in >99% yield: $^1$H NMR (CDCl$_3$, 500 MHz) δ 6.76 (s, 2 H), 5.31-5.32 (m, 1 H), 3.99-4.00 (m, 1 H), 3.79-3.87 (m, 1 H), 3.78-3.79 (m, 1 H), 3.43-3.44 (m, 2 H), 3.37 (brs, 2 H), 2.15 (s, 6 H); ESI-MS: m/z 295.6 (M+H)$^+$.

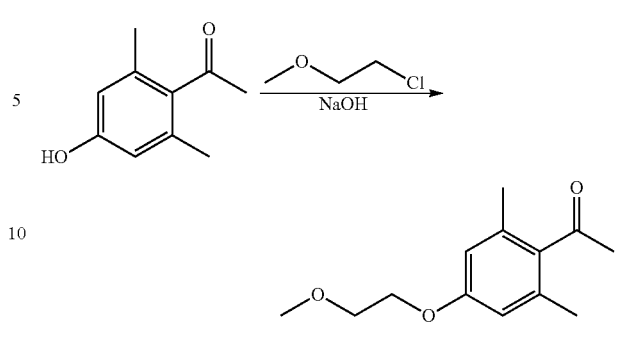

1-(4-(2-Methoxyethoxy)-2,6-dimethylphenyl)ethanone.
A pressure glass vessel charged with 1-(4-hydroxy-2,6-dimethylphenyl)ethanone (500 mg, 3.1 mmol, 1.0 equiv) and 1-chloro-2-methoxyethane (0.28 mL, 3.1 mmol, 1.0 equiv) in 50% aqueous NaOH solution (5.0 mL) was heated at 140° C. for 16 h. The residue was diluted with H$_2$O (20 mL) and extracted with EtOAc (3×30 mL). The organic layer was separated, dried with MgSO$_4$, and concentrated under reduced pressure to give 1-(4-(2-methoxyethoxy)-2,6-dimethylphenyl)ethanone (430.9 mg, 1.9 mmol) as yellow oil in 64% yield: $^1$H NMR (CDCl3, 500 MHz) δ 6.58 (s, 2 H), 4.09-4.10 (m, 2 H), 3.72-3.74 (m, 2 H), 3.44 (s, 3 H), 2.45 (s, 3 H), 2.23 (s, 6 H); ESI-MS: m/z 223.6 (M+H)$^+$.

2-Bromo-1-(4-(2-methoxyethoxy)-2,6-dimethylphenyl)ethanone. To a CH$_3$CN solution (6.0 mL) containing 1-(4-(2-methoxyethoxy)-2,6-dimethylphenyl)ethanone (400 mg, 1.8 mmol, 1.0 equiv) was added TBABr$_3$ (867.7 mg, 1.8 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. 2-Bromo-1-(4-(2-methoxyethoxy)-2,6-dimethylphenyl)ethanone (322.9 mg, 1.1 mmol) was obtained as yellow solids in 60% yield: $^1$H NMR (CDCl$_3$, 500 MHz) δ 6.61 (s, 2 H), 4.25 (s, 2 H), 4.09-4.11 (m, 2 H), 3.73-3.75 (m, 2 H), 3.45 (s, 3 H), 2.24 (s, 6 H).

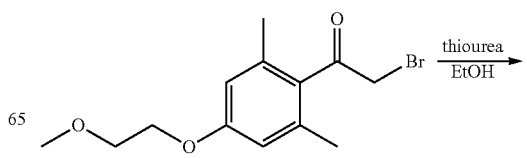

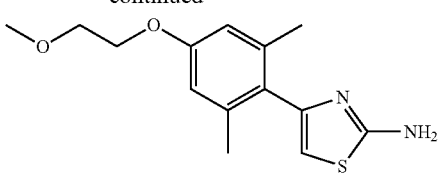

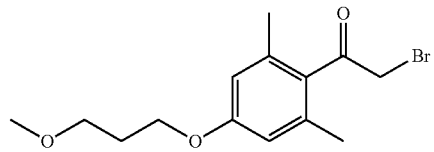

4-(4-(2-Methoxyethoxy)-2,6-dimethylphenyl)thiazol-2-amine. A reaction mixture containing 2-bromo-1-(4-(2-methoxyethoxy)-2,6-dimethylphenyl)ethanone (322.9 mg, 1.1 mmol, 1.0 equiv) and thiourea (81.61 mg, 1.1 mmol, 1.0 equiv) in EtOH (3.0 mL) was heated at reflux for 16 h. The solution was concentrated under reduced pressure, and the residue was re-dissolved in EtOAc (20 mL). The solution was washed with saturated aqueous $NaHCO_3$ (30 mL), dried over $MgSO_4$, and concentrated under reduced pressure. The residue was purified by column chromatography on silica gel (30% EtOAc in hexanes as eluant) to provide 4-(4-(2-methoxyethoxy)-2,6-dimethylphenyl)thiazol-2-amine (281.0 mg, 1.0 mmol) as yellow solids in 94% yield: $^1$H NMR (DMSO-$d_6$, 500 MHz) δ 6.76 (s, 2 H), 5.31-5.33 (m, 1 H), 4.09-4.11 (m, 2 H), 3.64-3.65 (m, 2 H), 3.30 (s, 3 H), 2.12 (s, 6 H); ESI-MS: m/z 279.7 (M+H)$^+$.

2-Bromo-1-(4-(3-methoxypropoxy)-2,6-dimethylphenyl)ethanone. To a $CH_3CN$ solution (15.0 mL) containing 1-(4-(3-methoxypropoxy)-2,6-dimethylphenyl)ethanone (987.8 mg, 4.2 mmol, 1.0 equiv) was added $TBABr_3$ (2.02 g, 4.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous $NaHCO_3$ (30 mL), dried over $MgSO_4$, and concentrated under reduced pressure. 2-Bromo-1-(4-(3-methoxypropoxy)-2,6-dimethylphenyl)ethanone (1.23 g, 3.9 mmol) was obtained as yellow oil in 93% yield: $^1$H NMR (CDCl$_3$, 500 MHz) δ 6.58 (s, 2 H), 4.24-4.35 (m, 2 H), 4.03-4.05 (m, 2 H), 3.53-3.55 (m, 2 H), 3.35 (s, 3 H), 2.24 (s, 6 H), 2.01-2.06 (m, 2 H).

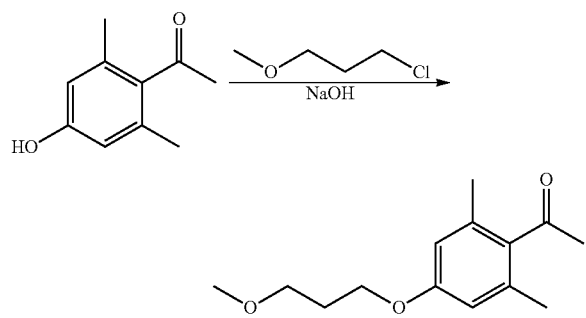

1-(4-(3-Methoxypropoxy)-2,6-dimethylphenyl)ethanone. A pressure glass vessel charged with 1-(4-hydroxy-2,6-dimethylphenyl)ethanone (800 mg, 4.9 mmol, 1.0 equiv) and 1-chloro-3-methoxypropane (528.97 mg, 4.9 mmol, 1.0 equiv) in 50% aqueous NaOH solution (10.0 mL) was stirred at 140° C. for 16 h. The residue was diluted with $H_2O$ (20 mL) and extracted with EtOAc (3×30 mL). The organic layer was separated, dried over $MgSO_4$(s), and concentrated under reduced pressure to give 1-(4-(3-methoxypropoxy)-2,6-dimethylphenyl)ethanone (987.8 mg, 4.2 mmol) as yellow oil in 86% yield: $^1$H NMR (DMSO-$d_6$, 500 MHz) δ 6.56 (s, 2 H), 4.02-4.04 (m, 2 H), 3.53-3.55 (m, 2 H), 3.36 (s, 3 H), 2.45 (s, 3 H), 2.23 (s, 6 H), 2.02-2.04 (m, 3H); ESI-MS: m/z 237.7 (M+H)$^+$.

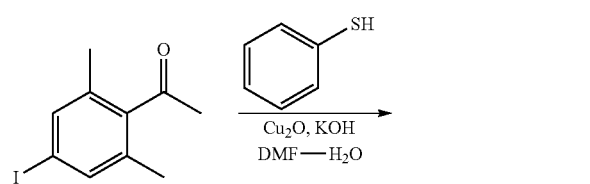

4-(4-(3-Methoxypropoxy)-2,6-dimethylphenyl)thiazol-2-amine. A reaction mixture containing 2-bromo-1-(4(3-methoxypropoxy)-2,6-dimethylphenyl)ethanone (500.0 mg, 1.6 mmol, 1.0 equiv) and thiourea (126.8 mg, 1.6 mmol, 1.0 equiv) in EtOH (10.0 mL) was heated at reflux for 16 h. The solution was concentrated under reduced pressure, and the residue was re-dissolved in EtOAc (50 mL). The solution was washed with saturated aqueous $NaHCO_3$ (30 mL), dried over $MgSO_4$, and concentrated under reduced pressure. The residue was purified by column chromatography on silica gel (30% EtOAc in hexanes as eluant) to provide 4-(4-(3-methoxypropoxy)-2,6-dimethylphenyl)thiazol-2-amine (328.9 mg, 1.1 mmol) as yellow solids in 71% yield: $^1$H NMR (CDCl$_3$, 500 MHz) δ 9.35 (brs, 1 H), 9.00 (brs, 1 H), 6.64 (s, 2 H), 6.22 (s, 1 H), 4.04-4.05 (m, 2 H), 3.54-3.56 (m, 2 H), 3.37 (s, 3 H), 2.19 (s, 6 H), 2.03-2.06 (m, 2 H); ESI-MS m/z 293.8 (M+H)$^+$.

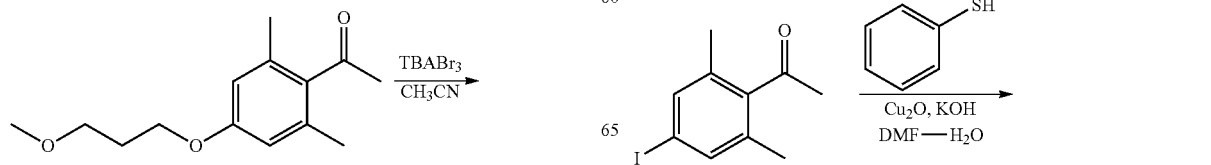

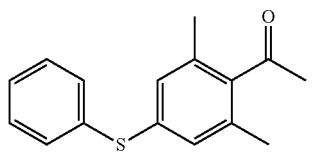

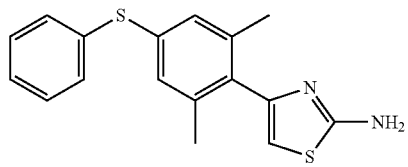

1-(2,6-Dimethyl-4-(phenylthio)phenyl)ethanone. A mixture of 1-(4-iodo-2,6-dimethylphenyl)ethanone (1.5 g, 5.5 mmol, 1.0 equiv), benzenethiol (0.60 mL, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and $H_2O$ (1.1 mL) was heated at reflux for 20 h. The mixture was quenched with $H_2O$ (10 mL) and extracted with ether (2×20 mL). The organic layer was collected, dried over $MgSO_4$(s), and concentrated under reduced pressure. The residue was purified by column chromatography on silica gel (3.0% EtOAc in hexanes as eluant) to provide 1-(2,6-dimethyl-4-(phenylthio)phenyl)ethanone (931 mg, 3.6 mmol) as yellow oil in 66% yield: 1H NMR ($CD_3OD$, 500 MHz) δ 7.34-7.35 (m, 5 H), 6.97 (s, 2 H), 2.46 (s, 3 H), 2.17 (s, 6 H); ESI-MS: m/z 257.0 $(M+H)^+$.

4-(2,6-Dimethyl-4-(phenylthio)phenyl)thiazol-2-amine. A reaction mixture containing 2-bromo-1-(2,6-dimethyl-4-(phenylthio)phenyl)ethanone (591.7 mg, 1.8 mmol, 1.0 equiv) and thiourea (134.3 mg, 1.8 mmol, 1.0 equiv) in EtOH (15.0 mL) was heated at reflux for 16 h. The solution was concentrated under reduced pressure, and the residue was re-dissolved in EtOAc (50 mL). The solution was washed with saturated aqueous $NaHCO_3$ (30 mL), dried over $MgSO_4$, and concentrated under reduced pressure. The residue was purified by column chromatography on silica gel (5.0% EtOAc in hexanes as eluant) to provide 4-(2,6-dimethyl-4-(phenylthio)phenyl)thiazol-2-amine (483.7 mg, 1.6 mmol) as yellow solids in 88% yield: $^1$H NMR (DMSO-$d_6$, 500 MHz) δ 7.33-7.38 (m, 2 H), 7.29-7.33 (m, 3 H), 7.06 (brs, 2 H), 6.89 (s, 2 H), 6.38 (s, 1 H), 2.07 (s, 6 H); ESI-MS: m/z 313.8 $(M+H)^+$.

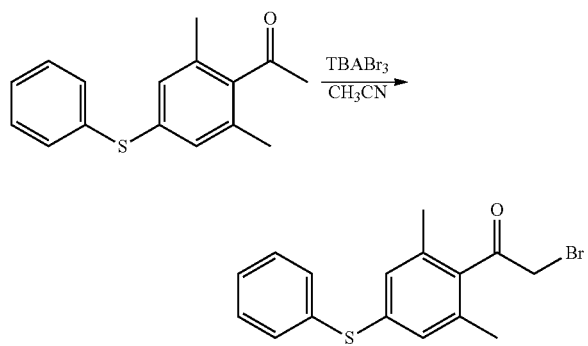

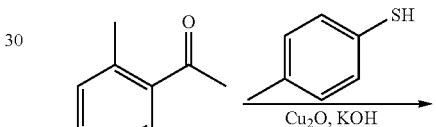

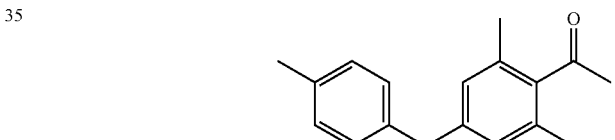

2-Bromo-1-(2,6-dimethyl-4-(phenylthio)phenyl)ethanone. To a $CH_3CN$ solution (15.0 mL) containing 1-(2,6-dimethyl-4-(phenylthio)phenyl)ethanone (816.3 mg, 3.2 mmol, 1.0 equiv) was added $TBABr_3$ (1.54 g, 3.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous $NaHCO_3$ (30 mL), dried over $MgSO_4$, and concentrated under reduced pressure. The residue was purified by column chromatography on silica gel (3.0% EtOAc in hexanes as the eluant) to provide 2-bromo-1-(2,6-dimethyl-4-(phenylthio)phenyl)ethanone (591.7 mg, 1.6 mmol) as yellow oil in 55% yield: $^1$H NMR (DMSO-$d_6$, 500 MHz) δ 7.36-7.42 (m, 5 H), 7.01 (s, 2 H), 4.75 (s, 2 H), 2.13 (s, 6 H).

1-(2,6-Dimethyl-4-(p-tolylthio)phenyl)ethanone. A mixture of 1-(4-iodo-2,6-dimethylphenyl)ethanone (1.5 g, 5.5 mmol, 1.0 equiv), 4-methylbenzenethiol (1.02 g, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and $H_2O$ (1.1 mL) was heated at reflux for 20 h. The mixture was quenched with $H_2O$ (10 mL) and extracted with ether (2×20 mL). The organic layer was collected, dried over $MgSO_4$(s), and concentrated under reduced pressure. The residue was purified by column chromatography on silica gel (3.0% EtOAc in hexanes as eluant) to provide 1-(2,6-dimethyl-4-(p-tolylthio)phenyl)ethanone (1.16 g, 4.3 mmol) as yellow oil in 79% yield: $^1$H NMR (CD3OD, 500 MHz) δ 7.29 (d, J=8.0 Hz, 2 H), 7.20 (d, J=8.0 Hz, 2 H), 6.88 (s, 2 H), 2.45 (s, 3 H), 2.35 (s, 3 H), 2.15 (s, 6 H); ESI-MS: m/z 271.8 $(M+H)^+$.

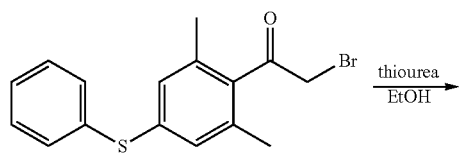

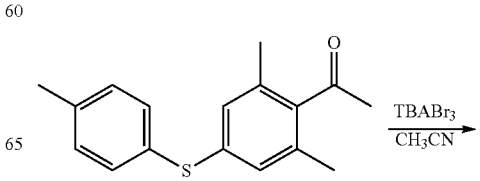

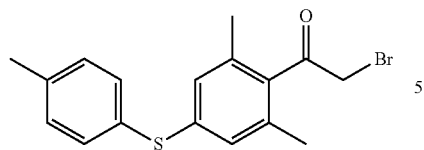

2-Bromo-1-(2,6-dimethyl-4-(p-tolylthio)phenyl)ethanone. To a CH₃CN solution (20.0 mL) containing 1-(2,6-dimethyl-4-(p-tolylthio)phenyl)ethanone (1.0 g, 3.7 mmol, 1.0 equiv) was added TBABr$_3$ (1.79 g, 3.7 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (3.0% EtOAc in hexanes as the eluant) to provide 2-bromo-1-(2,6-dimethyl-4-(p-tolylthio)phenyl)ethanone (394.8 mg, 1.1 mmol) as yellow oil in 31% yield: $^1$H NMR (DMSO-d$_6$, 500 MHz) δ 7.33 (d, J=8.0 Hz, 2 H), 7.25 (d, J=8.0 Hz, 2 H), 6.92 (s, 2 H), 4.76 (s, 2 H), 2.32 (s, 3 H), 2.11 (s, 6 H).

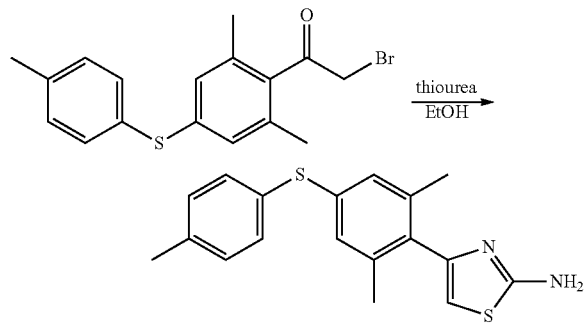

4-(2,6-Dimethyl-4-(p-tolylthio)phenyl)thiazol-2-amine. A reaction mixture containing 2-bromo-1-(2,6-dimethyl-4-(p-tolylthio)phenyl)ethanone (394.8 mg, 1.1 mmol, 1.0 equiv) and thiourea (86.04 mg, 1.1 mmol, 1.0 equiv) in EtOH (10.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (5.0% EtOAc in hexanes as eluant) to provide 4-(2,6-dimethyl-4-(p-tolylthio)phenyl)thiazol-2-amine (371.9 mg, 1.1 mmol) as yellow solids in >99% yield: $^1$H NMR (DMSO-d$_6$, 500 MHz) δ 7.27 (d, J=8.0 Hz, 2 H), 7.21 (d, J=8.0 Hz, 2 H), 6.97 (s, 2 H), 6.87 (s, 2 H), 6.36 (s, 1 H), 2.30 (s, 3 H), 2.05 (s, 6 H); ESI-MS: m/z 327.0 (M+H)$^+$.

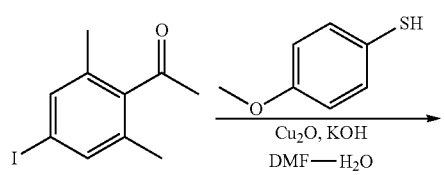

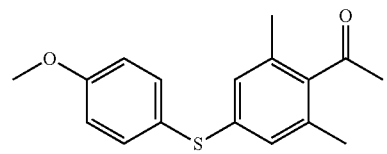

1-(4-(4-Methoxyphenylthio)-2,6-dimethylphenyl)ethanone. A mixture of 1-(4-iodo-2,6-dimethylphenyl)ethanone (1.5 g, 5.5 mmol, 1.0 equiv), 4-methoxybenzenethiol (1.01 mL, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and H2O (1.1 mL) was heated at reflux for 20 h. The mixture was quenched with H$_2$O (10 mL) and extracted with ether (2×20 mL). The organic layer was collected, dried over MgSO$_4$(s), and concentrated under reduced pressure. The residue was purified by column chromatography on silica gel (3.0% EtOAc in hexanes as eluant) to provide 1-(4-(4-methoxyphenylthio)-2,6-dimethylphenyl)ethanone (1.41 g, 4.9 mmol) as yellow oil in 90% yield: $^1$H NMR (DMSO-d$_6$, 500 MHz) δ 7.39 (d, J=8.5 Hz, 2 H), 6.96 (d, J=8.5 Hz, 2 H), 6.79 (s, 2 H), 3.82 (s, 3 H), 2.43 (s, 3 H), 2.13 (s, 6 H); ESI-MS: m/z 287.6 (M+H)$^+$.

2-Bromo-1-(4-(4-methoxyphenylthio)-2,6-dimethylphenyl)ethanone. To a CH₃CN solution (20.0 mL) containing 1-(4-(4-methoxyphenylthio)-2,6-dimethylphenyl)ethanone (1.0 g, 3.5 mmol, 1.0 equiv) was added TBABr$_3$ (1.684 g, 3.5 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (3.0% EtOAc in hexanes as eluant) to provide 2-bromo-1-(4-(4-methoxyphenylthio)-2,6-dimethylphenyl)ethanone (1.06 g, 2.9 mmol) as yellow oil in 83% yield: $^1$H NMR (DMSO-d$_6$, 500 MHz) δ 7.44 (d, J=8.7 Hz, 2 H), 7.03 (d, J=8.7 Hz, 2 H), 6.83 (s, 2 H), 4.71 (s, 2 H), 3.80 (s, 3 H), 2.10 (s, 6 H).

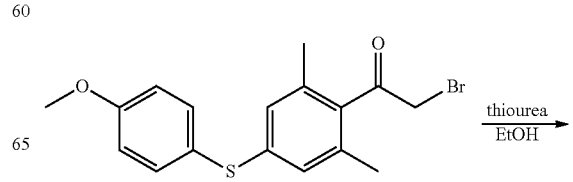

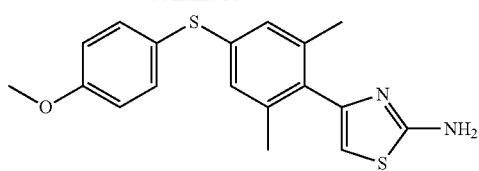
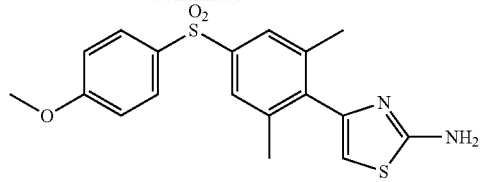

4-(4-(4-Methoxyphenylthio)-2,6-dimethylphenyl)thiazol-2-amine. A reaction mixture containing 2-bromo-1-(4-(4-methoxyphenylthio)-2,6-dimethylphenyl)ethanone (1.06 g, 2.9 mmol, 1.0 equiv) and thiourea (221.5 mg, 2.9 mmol, 1.0 equiv) in EtOH (20.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (5.0% EtOAc in hexanes as eluant) to provide 4-(4-(4-methoxyphenylthio)-2,6-dimethylphenyl)thiazol-2-amine (890.9 mg, 2.6 mmol) as yellow solids in 90% yield: $^1$H NMR (DMSO-d$_6$, 500 MHz) δ 7.40 (d, J=8.7 Hz, 2 H), 7.00 (d, J=8.7 Hz, 2 H), 6.86-6.87 (m, 4 H), 6.33 (s, 1 H), 3.78 (s, 3 H), 2.03 (s, 6 H); ESI-MS m/z 343.9 (M+H)$^+$.

4-(4-(4-Methoxyphenylsulfonyl)-2,6-dimethylphenyl)thiazol-2-amine. A reaction mixture containing 2-bromo-1-(4-(4-methoxyphenylsulfonyl)-2,6-dimethylphenyl)ethanone (1.33 g, 3.4 mmol, 1.0 equiv) and thiourea (254.8 mg, 3.4 mmol, 1.0 equiv) in EtOH (5.0 mL) was heated at reflux for 1.0 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The resultant solids were washed with hexanes to give 4-(4-(4-methoxyphenylsulfonyl)-2,6-dimethylphenyl)thiazol-2-amine (839.2 mg, 2.2 mmol) as yellow solids in 65% yield: $^1$H NMR (DMSO-d$_6$, 500 MHz) δ 7.89 (d, J=8.9 Hz, 2 H), 7.61 (s, 2 H), 7.13 (d, J=8.9 Hz, 2 H), 6.95 (brs, 2 H), 6.43 (s, 1 H), 3.83 (s, 3 H), 2.16 (s, 6 H); ESI-MS: m/z 375.6 (M+H)$^+$.

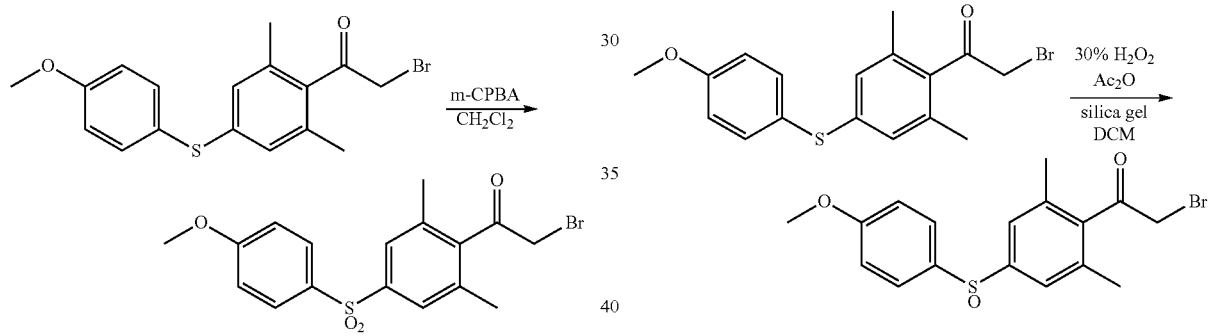

2-Bromo-1-(4-(4-methoxyphenylsulfonyl)-2,6-dimethylphenyl)ethanone. A mixture of 2-bromo-1-(4-(4-methoxyphenylthio)-2,6-dimethylphenyl)ethanone (1.0 g, 2.7 mmol, 1.0 equiv) and m-chloroperoxybenzoic acid (1.69 g, 6.8 mmol, 2.5 equiv) in dichloromethane (10.0 mL) was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure to give 2-bromo-1-(4-(4-methoxyphenylsulfonyl)-2,6-dimethylphenyl)ethanone (1.09 g, 2.7 mmol) as white solids in >99% yield: $^1$H NMR (CDCl$_3$, 500 MHz) δ 7.85-7.90 (m, 2 H), 7.57-7.60 (m, 2 H), 6.97-6.90 (m, 2 H), 4.21 (s, 2 H), 3.85 (s, 3 H), 2.30 (s, 6 H).

2-Bromo-1-(4-(4-methoxyphenylsulfinyl)-2,6-dimethylphenyl)ethanone. A mixture of 2-bromo-1-(4-(4-methoxyphenylthio)-2,6-dimethylphenyl)ethanone (500.0 mg, 1.3 mmol, 1.0 equiv), acetic anhydride (0.14 mL, 1.5 mmol, 1.1 equiv), 30% hydrogen peroxide (55.86 mg, 1.6 mmol, 1.2 equiv) and silica gel (273.75 mg, 230-400 mesh) in dichloromethane (10.0 mL) was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure to give 2-bromo-1-(4-(4-methoxyphenylsulfinyl)-2,6-dimethylphenyl)ethanone (235.4 mg, 0.6 mmol) as pale-yellow oil in 48% yield: $^1$H NMR (DMSO-d$_6$, 500 MHz) δ 7.65 (d, J=8.8 Hz, 2 H), 7.41 (s, 2 H), 7.09 (d, J=8.8 Hz, 2 H), 4.78 (s, 2 H), 3.79 (s, 3 H), 2.21 (s, 6 H).

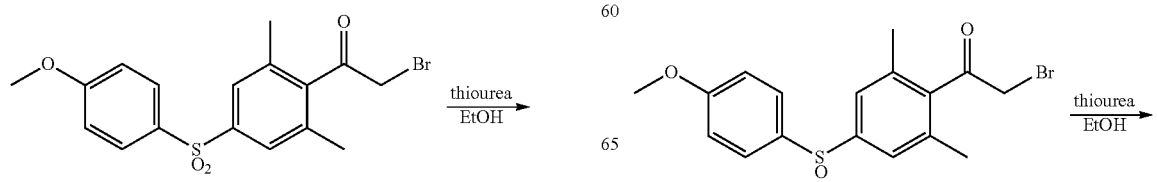

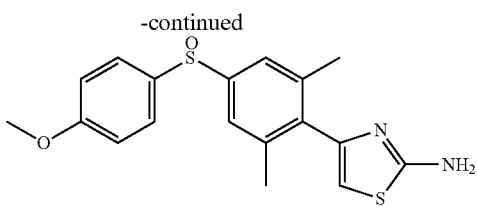

N-(4-(4-(4-Methoxyphenylsulfinyl)-2,6-dimethylphenyl) thiazol-2-yl)isonicotinamide. A reaction mixture containing 2-bromo-1-(4-(4-methoxyphenylsulfinyl)-2,6-dimethylphenyl)ethanone (235.4 mg, 0.6 mmol, 1.0 equiv) and thiourea (47.0 mg, 0.60 mmol, 1.0 equiv) in EtOH (5.0 mL) was heated at reflux for 1.0 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The resultant solids were washed with hexanes to give N-(4-(4-(4-methoxyphenylsulfinyl)-2,6-dimethylphenyl)thiazol-2-yl)isonicotinamide (236.7 mg, 0.70 mmol) as yellow solids in >99% yield: $^1$H NMR (DMSO-d$_6$, 500 MHz) δ 7.64 (d, J=8.9 Hz, 2 H), 7.34 (s, 2 H), 7.09 (d, J=8.9 Hz, 2 H), 6.90 (brs, 2 H), 6.39 (s, 1 H), 3.79 (s, 3 H), 2.13 (s, 6 H); ESI-MS m/z 359.0 (M+H)$^+$.

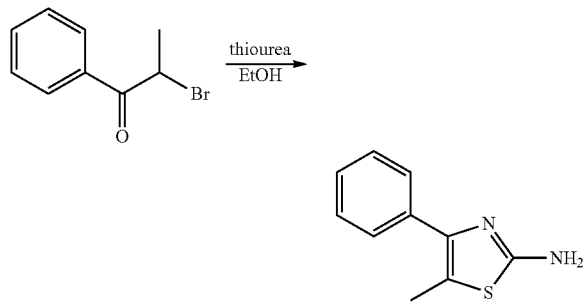

5-Methyl-4-phenylthiazol-2-amine. A mixture of 2-bromo-1-phenylpropan-1-one (3.00 g, 19.5 mmol) and thiourea (1.56 g, 20.5 mmol) in 95% EtOH (30 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 5-methyl-4-phenylthiazol-2-amine (4.07 g) as yellow solids in 77% yield: $^1$H NMR (500 MHz, DMSO-d$_6$) δ 8.85 (s, 2 H), 7.54-7.49 (m, 5 H), 2.28 (s, 3 H).

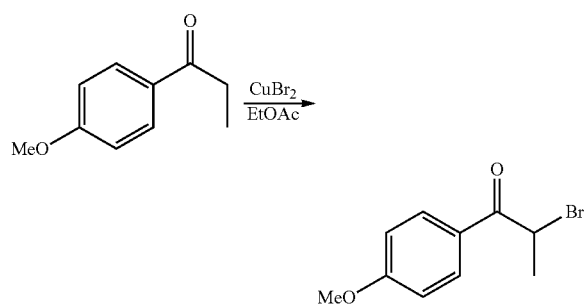

2-Bromo-1-(4-methoxyphenyl)propan-1-one. To a solution of 1-(4-methoxyphenyl)propan-1-one (5.01 g, 30.2 mol) in EtOAc (120 mL) was added copper(II) bromide (CuBr$_2$, 13.6 g, 6.8 mmol). The reaction mixture was heated at reflux for 90 min. The solution was allowed to cool down, and the resultant solids were filtered off and washed with EtOAc. The filtrate was concentrated under reduced pressure to give crude 2-bromo-1-(4-methoxyphenyl)propan-1-one (10.4 g) as yellow oil: $^1$H NMR (500 MHz, CDCl$_3$) δ 8.02 (2 H, m), 6.96 (2 H, m), 5.28-5.25 (m, 1 H), 3.89 (s, 3 H), 1.89 (d, 3 H).

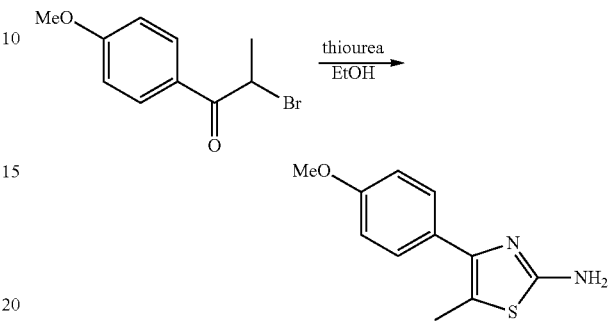

4-(4-Methoxyphenyl)-5-methylthiazol-2-amine. A mixture of 2-bromo-1-(4-methoxyphenyl)propan-1-one (10.4 g, 36.1 mmol) and thiourea (2.76 g, 36.2 mmol) in 95% EtOH (70 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 4-(4-methoxyphenyl)-5-methylthiazol-2-amine (6.16 g) as yellow solids in 78% yield: $^1$H NMR (500 MHz, DMSO-d$_6$) δ 8.90 (s, 2 H), 7.46-7.44 (m, 2 H), 7.09-7.07 (m, 2 H), 3.81 (s, 3 H), 2.47 (s, 3 H).

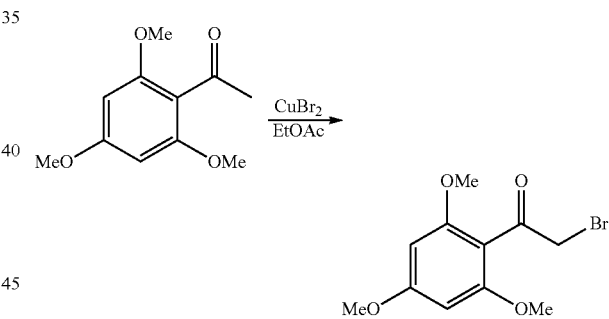

2-Bromo-1-(2,4,6-trimethoxyphenyl)ethanone. To a solution of 1-(2,4,6-trimethoxyphenyl)ethanone (5.0 g, 23.3 mmol) in EtOAc (100 mL) was added copper(II) bromide (CuBr$_2$, 10.4 g, 46.7 mmol). The reaction mixture was heated at reflux for 90 min. The solution was allowed to cool down, and the resultant solids were filtered off and washed with EtOAc. The filtrate was concentrated under reduced pressure to give crude 2-bromo-1-(2,4,6-trimethoxyphenyl)ethanone (2.70 g) 2-bromo-1-(2,4,6-trimethoxyphenyl)ethanone as yellow oil: $^1$H-NMR (500 MHz, CDCl$_3$) δ 6.11 (m, 2 H), 4.36 (m, 2 H), 3.86 (s, 3 H), 3.82 (s, 6 H).

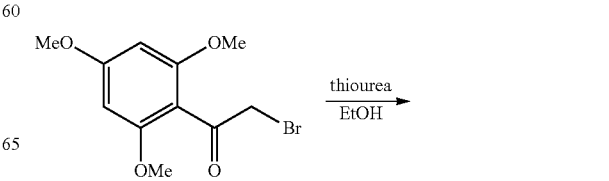

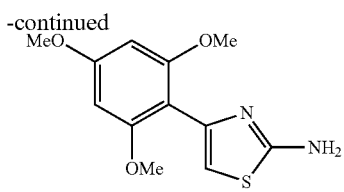

4-(2,4,6-Trimethoxyphenyl)thiazol-2-amine. A mixture of 2-bromo-1-(2,4,6-trimethoxyphenyl)ethanone (2.49 g, 8.6 mmol) and thiourea (0.67 g, 8.7 mmol) in 95% EtOH (16 mL) was heated at reflux for 60 min. The solution was concentrated and mixed with water (100 mL) and saturated aqueous $Na_2CO_3$ (5.0 mL). The resultant precipitate was filtered and recrystallized in toluene. The solids were filtered and dried under vacuum to give 4-(2,4,6-trimethoxyphenyl)thiazol-2-amine (1.75 g) as yellow solids in >99% yield: $^1$H NMR (500 MHz, DMSO-$d_6$) δ 9.00 (s, 2 H), 6.78 (s, 1 H), 6.36 (s, 2 H), 3.84 (s, 3 H), 3.79 (s, 6 H).

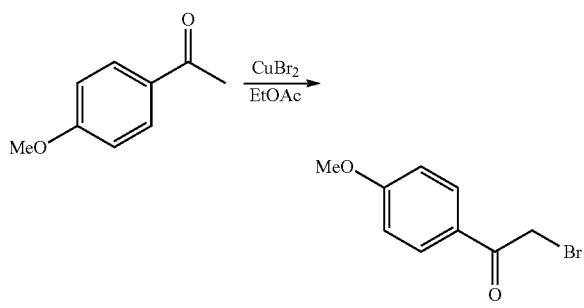

2-Bromo-1-(4-methoxyphenyl)ethanone. To a solution of 1-(4-methoxyphenyl)ethanone (15.2 g, 0.10 mol) in EtOAc (250 mL) was added copper(II) bromide ($CuBr_2$, 45.1 g, 0.20 mol). The reaction mixture was heated at reflux for 90 min. The solution was allowed to cool down, and the resultant solids were filtered off and washed with EtOAc. The filtrate was concentrated under reduced pressure to give crude 2-bromo-1-(4-methoxyphenyl)ethanone (15.8 g) as yellow oil: $^1$H NMR (500 MHz, $CDCl_3$) δ 7.98 (m, 2 H), 6.97 (m, 2 H), 4.41 (s, 3 H), 3.89 (s, 6 H).

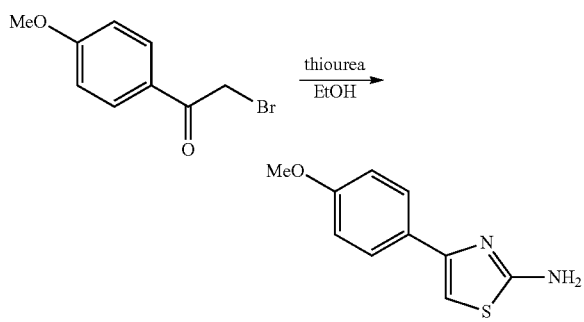

4-(4-Methoxyphenyl)thiazol-2-amine. A mixture of 2-bromo-1-(4-methoxyphenyl)ethanone (5.00 g, 21.8 mmol) and thiourea (1.72 g, 22.6 mmol) in 95% EtOH (40 mL) was heated at reflux for 60 min. The solution was concentrated and mixed with water (100 mL) and saturated aqueous $Na_2CO_3$ (5.0 mL). The resultant precipitate was filtered and recrystallized in toluene. The solids were filtered and dried under vacuum to give 4-(4-methoxyphenyl)thiazol-2-amine (5.24 g) as yellow solids in >99% yield: $^1$H NMR (500 MHz, DMSO-$d_6$) δ 7.72 (d, 2 H), 6.99 (s, 2 H), 6.92-6.91 (m, 2 H), 6.82 (s, 1 H), 3.76 (s, 3 H).

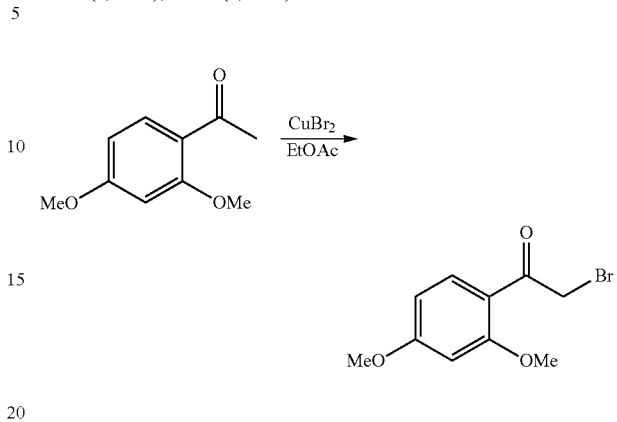

2-Bromo-1-(2,4-dimethoxyphenyl)ethanone. To a solution of 1-(2,4-dimethoxyphenyl)ethanone (10.0 g, 54.4 mmol) in EtOAc (220 mL) was added copper(II) bromide ($CuBr_2$, 24.3 g, 0.11 mol). The reaction mixture was heated at reflux for 90 min. The solution was allowed to cool down, and the resultant solids were filtered off and washed with EtOAc. The filtrate was concentrated under reduced pressure to give crude 2-bromo-1-(2,4-dimethoxyphenyl)ethanone (14.5 g) as yellow oil: $^1$H NMR (500 MHz, $CDCl_3$) δ 7.91 (m, 2 H), 6.52 (m, 2 H), 4.57 (s, 3 H), 3.98 (s, 3 H), 3.85 (s, 3 H).

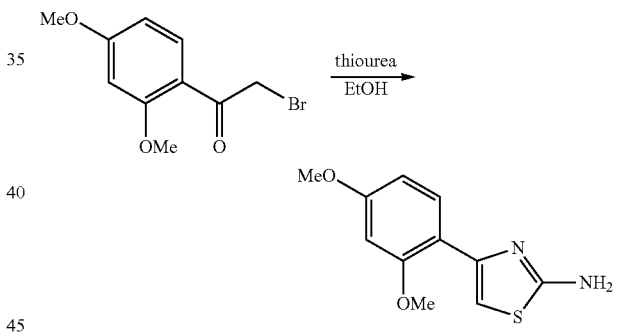

4-(2,4-Dimethoxyphenyl)thiazol-2-amine. A mixture of 2-bromo-1-(2,4-dimethoxyphenyl)ethanone (14.5 g, 55.8 mmol) and thiourea (4.32 g, 56.7 mmol) in 95% EtOH (110 mL) was heated at reflux for 60 min. The solution was concentrated and mixed with water (100 mL) and saturated aqueous $Na_2CO_3$ (5.0 mL). The resultant precipitate was filtered and recrystallized in toluene. The solids were filtered and dried under vacuum to give 4-(2,4-dimethoxyphenyl)thiazol-2-amine (10.9 g) as yellow solids in 62% yield: $^1$H NMR (500 MHz, DMSO-$d_6$) δ 8.60 (s, 2 H), 7.53 (s, 1 H), 6.97 (s, 1 H), 6.69 (s, 1 H), 6.67-6.63 (m, 1 H), 3.86 (s, 3 H), 3.80 (s, 3 H).

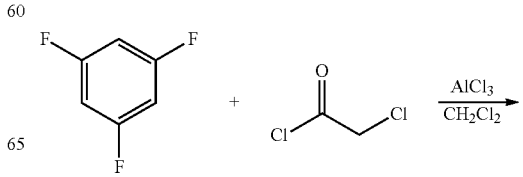

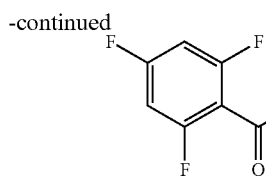

2-Chloro-1-(2,4,6-trifluorophenyl)ethanone. To a mechanically stirred solution of 1,3,5-trifluorobenzene (6.0 mL, 58 mmol) in dichloroethane (14.0 mL) was added gradually AlCl$_3$ (15.5 g, 116 mmol) in a period of 15 min with caution. Violent bumping and HCl gas evolution was observed. The mixture was carefully heated to reflux, and chloroacetyl chloride (5.5 mL, 69 mmol) was added drop wisely in a period of 45 min. The reaction mixture was heated at reflux for additional 6.0 h. The solution was cooled, carefully poured onto an ice/water slush (200 mL) and the aqueous solution was extracted with ether (3×50 mL). The combined ethereal layers were washed with 10% aqueous HCl (2×30 mL), 1.0 N aqueous NaOH (3×30 mL), and brine (25 mL). The solution was dried over MgSO$_4$ and concentrated under reduced pressure to give 2-chloro-1-(2,4,6-trifluorophenyl)ethanone (5.28 g) as yellow solids in 51% yield: $^1$H NMR (500 MHz, CDCl$_3$) δ 6.79-6.76 (m, 2 H), 4.50 (s, 2 H).

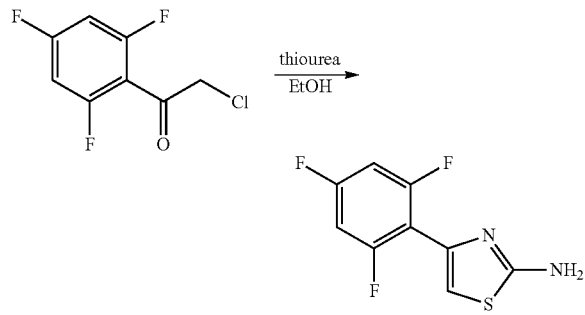

4-(2,4,6-Trifluorophenyl)thiazol-2-amine. A mixture of 2-chloro-1-(2,4,6-trifluorophenyl)ethanone (9.04 g, 43.5 mmol) and thiourea (3.51 g, 46.1 mmol) in 95% EtOH (50 mL) was heated at reflux overnight. The solution was concentrated and mixed with water (100 mL) and saturated aqueous Na$_2$CO$_3$ (5.0 mL). The solids were filtered and dried under vacuum to give 4-(2,4,6-trifluorophenyl)thiazol-2-amine (9.71 g) as pink-white solids in 97% yield: $^1$H NMR (500 MHz, DMSO-d$_6$) δ 7.26-7.22 (m, 2 H), 7.09 (s, 2 H), 6.77 (s, 1 H).

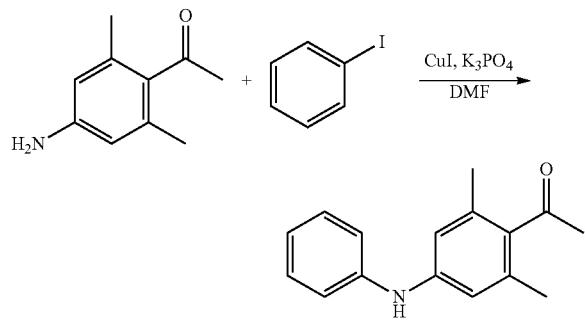

1-(2,6-Dimethyl-4-(phenylamino)phenyl)ethanone. To a solution of 1-(4-amino-2,6-dimethylphenyl)ethanone (3.26 g, 20.0 mmol), K$_3$PO$_4$ (9.2 g, 40 mmol), and 1-iodobenzene (4.08 g, 20.0 mmol) in DMF (35.0 mL) was added CuI (761.8 mg, 40 mmol). The reaction was heated at 110° C. overnight under N$_2$. The solution was cooled to room temperature and filtered through a small pad of Celite. The cake was washed with ethyl acetate (50 mL) and the combined filtrate was concentrated under reduced pressure. The residue was purified by flash column chromatography on silica gel to give 1-(2,6-dimethyl-4-(phenylamino)phenyl)ethanone as red-brown syrup: $^1$H NMR (500 MHz, CDCl$_3$) δ 7.30 (d, J=8.2 Hz, 2 H), 7.10 (d, J=7.7 Hz, 2 H), 6.99 (d, J=4.2 Hz, 1 H), 6.71 (s, 1 H), 2.47 (s, 3 H), 2.18 (s, 6 H); ESI-MS: m/z 239.5 (M+H)$^+$.

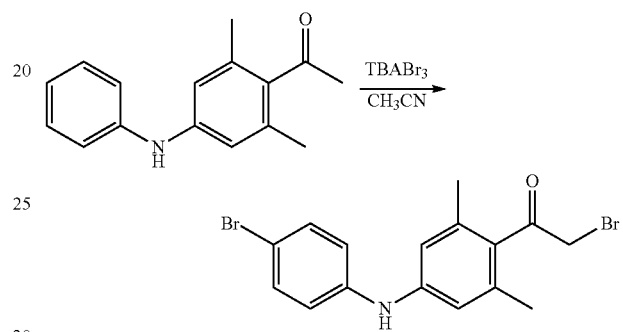

1-(4-(4-Bromophenylamino)-2,6-dimethylphenyl)-2-bromoethanone. To a solution of 1-(2,6-dimethyl-4-(phenylamino)phenyl)ethanone (2.10 g, 8.78 mmol) in acetonitrile (50 mL) was added tetrabutylammoniumtribromide (TBABr$_3$, 4.24 g, 8.78 mmol). The reaction was stirred at room temperature for 60 min. The solution was concentrated under reduced pressure, added with water, and extracted with ethyl acetate. The organic layer was washed with brine, dried over anhydrous MgSO$_4$(s), and concentrated under reduced pressure to give 1-(4-(4-bromophenylamino)-2,6-dimethylphenyl)-2-bromoethanone (2.01 g), which was used directly for the next step without further purification.

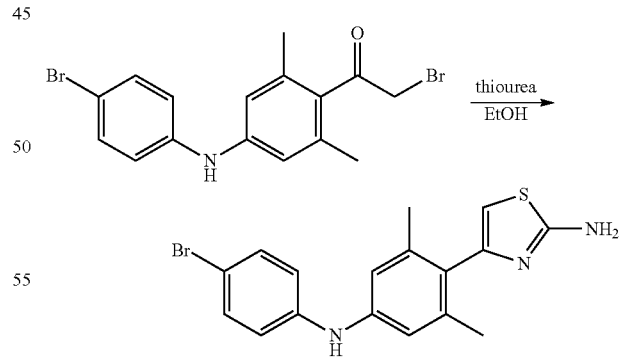

4-(4-(4-Bromophenylamino)-2,6-dimethylphenyl)thiazol-2-amine. A solution of 1-(4-(4-bromophenylamino)-2,6-dimethylphenyl)-2-bromoethanone (1.6 g, 4.0 mmol) and thiourea (0.79 g, 7.2 mmol) in acetonitrile (30 mL) was heated at reflux for 90 min. The solution was concentrated and added with water (50 mL) and saturated aqueous Na$_2$CO$_3$ (1.0 mL), and extracted with ethyl acetate. The organic layer was washed with brine, dried over anhydrous MgSO$_4$(s), and concentrated under reduced pressure to give product (1.1 g), which was used directly for the next step without further purification.

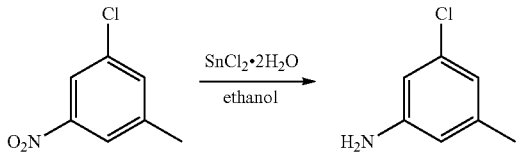

3-Chloro-5-methyl-phenylamine. An ethanol solution (75 mL) containing 1-chloro-3-methyl-5-nitro-benzene (5.0 g, 29 mmol) are added with SnCl$_2$.2 H2O (32.8 g, 146 mmol). The reaction mixture was reflux for 3.0 h. The solution was concentrated under vacuum, and the residue was re-dissolved in aqueous NaOH, filtered, and extracted with EtOAc. The organic layer was collected, washed with brine, dried over MgSO$_4$, and concentrated under reduced pressure. The residue was purified by column chromatography on silica gel to give 3-chloro-5-methyl-phenylamine (4.0 g) as light yellow solids in 97% yield: $^1$H NMR (500 MHz, CDCl3) δ 6.56 (s, 1 H), 6.48 (s, 1 H), 6.36 (s, 1 H), 3.66 (bs, 2 H), 2.23 (s, 3 H); ESI-MS: m/z 141.7 (M+H)$^+$.

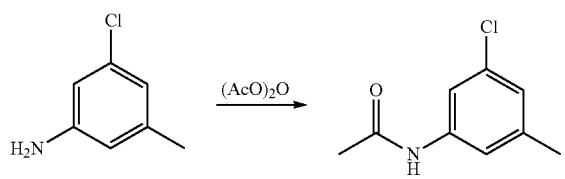

N-(3-Chloro-5-methyl-phenyl)-acetamide. Acetic anhydride (6.7 mL) and 3-chloro-5-methyl-phenylamine (5.0 g, 35 mmol) was mixed and stand for 2.0 h. The reaction mixture was cooled to room temperature to give N-(3-chloro-5-methyl-phenyl)acetamide (5.1 g) as light yellow solids in 79% yield: $^1$H NMR (500 MHz, CDCl$_3$) δ 7.38 (s, 1 H), 7.19 (s, 1 H), 7.12 (s, 1 H), 6.91 (s, 1 H), 2.31 (s, 3 H), 2.16 (s, 3 H).

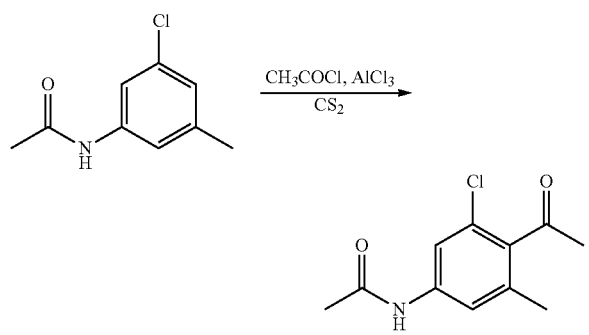

N-(4-Acetyl-3-chloro-5-methyl-phenyl)-acetamide. A dry CS$_2$ solution (30 mL) containing N-(3-chloro-5-methyl-phenyl)acetamide (5.0 g, 27 mmol) and acetyl chloride (2.9 ml, 40.8 mmol) was slowly added with aluminum chloride (9.1 g, 68 mmol). The reaction mixture was heated at reflux for 30 min, cooled to room temperature, and stand for 4.0 h. The CS$_2$ was decanted and the remaining syrup was poured into icy HCl. The resultant solids were collected, re-dissolved in EtOH, and decolorized by charcoal. The solution was filtered and the filtrate was concentrated under vacuum to give N-(4-acetyl-3-chloro-5-methylphenyl)acetamide (5.2 g) as light yellow solids in 85% yield: $^1$H NMR (500 MHz, CDCl$_3$) δ 7.48 (s, 1 H), 7.26 (s, 1 H), 7.21 (s, 1 H), 2.52 (s, 3 H), 2.24 (s, 3 H), 2.18 (s, 3 H).

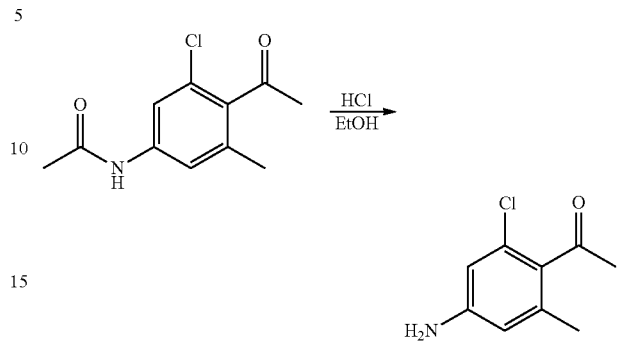

1-(4-Amino-2-chloro-6-methylphenyl)ethanone. An ethanol solution (4.0 mL) containing N-(4-acetyl-3-chloro-5-methylphenyl)acetamide (0.53 g, 2.3 mmol) and concentrated hydrochloric acid (1.6 mL) was heated at reflux for 15 h. The solution was added with 10% aqueous NaOH and the resultant solids were collected to give 1-(4-amino-2-chloro-6-methylphenyl)ethanone (0.37 g) as light yellow solids in 88% yield: $^1$H NMR (500 MHz, CDCl$_3$) δ 6.46 (d, J=1.77 Hz, 1 H), 6.34 (s, 1 H), 3.85 (bs, 2 H), 2.49 (s, 3 H), 2.14 (s, 3 H): ESI-MS: m/z 183.4 (M+H)$^+$.

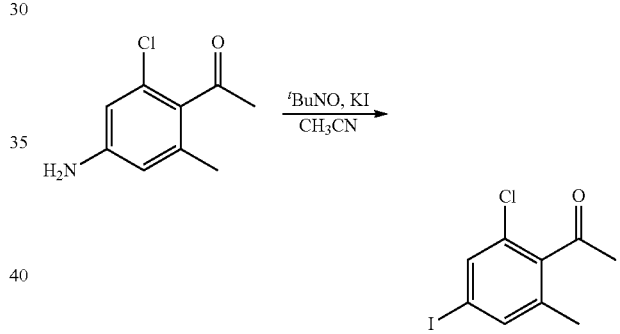

1-(2-Chloro-4-iodo-6-methyl-phenyl)-ethanone. A CH$_3$CN solution (20 mL) containing KI (2.5 g, 15 mmol) and tert-butyl nitrite (2.00 mL, 16.9 mmol) was added with 1-(4-amino-2-chloro-6-methyl-phenyl)ethanone (2.3 g, 12.5 mmol) in CH$_3$CN (13 mL) at −10° C. The reaction mixture was warmed to room temperature and poured into aqueous HCl (20%, 23 mL). The solution was extracted with EtOAc (20 mL), and the organic layer was separated, washed with H2O (23 mL), dried over MgSO$_4$(s), and concentrated under reduced pressure. The residue was purified by flash column chromatography on silica gel to give 1-(2-chloro-4-iodo-6-methylphenyl)ethanone (1.28 g) as yellow oil in 35% yield: $^1$H NMR (500 MHz, CDCl3) δ 7.58 (s, 1 H), 7.49 (s, 1 H), 2.51 (s, 3 H), 2.21 (s, 3 H).

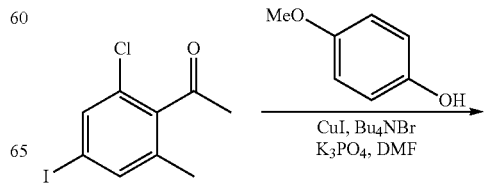

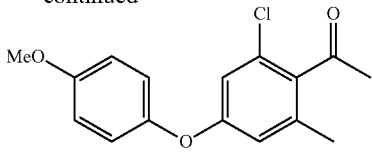

1-[2-Chloro-4-(4-methoxy-phenoxy)-6-methyl-phenyl]ethanone. To a solution of 1-(2-chloro-4-iodo-6-methylphenyl)ethanone (1.1 g, 3.7 mmol), $K_3PO_4$ (1.6 g, 7.4 mmol), and 4-methoxyphenol (0.55 g, 4.44 mmol) in DMF (55 mL) was added tetrabutylammomium bromide (0.12 g, 0.37 mmol) and copper(I) iodide (70 mg, 0.37 mmol). The reaction was heated at reflux for 22 h. The solution was extracted with EtOAc (10 mL), and the organic layer was separated, washed with $H_2O$ (11 mL), dried over $MgSO_4(s)$, and concentrated under reduced pressure. The residue was purified by flash column chromatography on silica gel to give 1-[2-chloro-4-(4-methoxyphenoxy)-6-methylphenyl]ethanone as yellow oil in 19% yield: $^1H$ NMR (500 MHz, $CDCl_3$) δ 6.97 (m, 2 H), 6.90 (m, 2 H), 6.73 (d, J=2.19 Hz, 1 H), 6.67 (d, J=1.99 Hz, 1 H), 3.81 (s, 3 H), 2.52 (s, 3 H), 2.20 (s, 3 H).

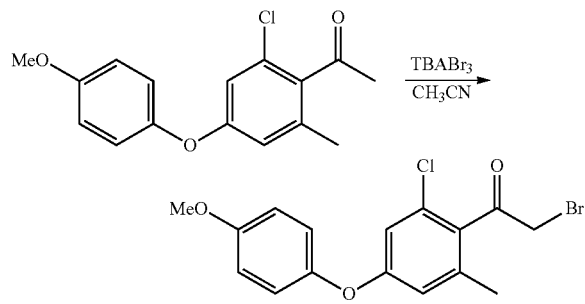

2-Bromo-1-[2-chloro-4-(4-methoxyphenoxy)-6-methylphenyl]ethanone. To a solution of 1-[2-chloro-4-(4-methoxyphenoxy)-6-methylphenyl]ethanone (0.20 g, 0.69 mmol) in acetonitrile (6.0 mL) was added $TBABr_3$ (0.33 g, 0.69 mmol). The reaction was stirred at room temperature for 30 min. The solution was concentrated under reduced pressure, added with water, and extracted with ethyl acetate. The organic layer was washed with brine, dried over anhydrous $MgSO_4(s)$, and concentrated under reduced pressure to give 2-bromo-1-(2,6-dimethyl-4-phenoxyphenyl)ethanone, which was used directly for the next step without further purification.

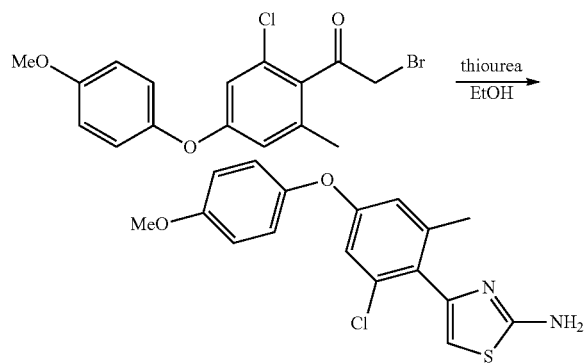

4-[2-Chloro-4-(4-methoxy-phenoxy)-6-methyl-phenyl]-thiazol-2-ylamine. A mixture of 2-bromo-1-(2,6-dimethyl-4-phenoxyphenyl)ethanone and thiourea (63 mg, 0.83 mmol) in 95% EtOH (3.0 mL) was heated at reflux for 60 min. The solution was concentrated and added with water (50 mL) and saturated aqueous $NaHCO_3$ (5.0 mL). The resultant precipitate was filtered and recrystallized in toluene (30 mL). The solids were filtered and dried under vacuum to give 4-[2-chloro-4-(4-methoxyphenoxy)-6-methylphenyl]thiazol-2-ylamine (0.10 g) as yellow solids in 42% yield: 1H NMR (500 MHz, $CDCl_3$) δ 6.98 (m, 2 H), 6.90 (m, 2 H), 6.83 (d, J=2.4 Hz, 1 H), 6.73 (d, J=2.3 Hz, 1 H), 6.41 (s, 1 H), 4.97 (brs, 2 H), 3.81 (s, 3 H), 2.16 (s, 3 H).

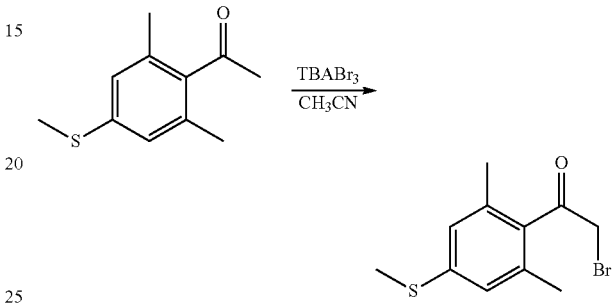

2-Bromo-1-(2,6-dimethyl-4-(methylthio)phenyl)ethanone. To a solution of 1-(4-(cyclopentyloxy)-2,6-dimethylphenyl)ethanone (3.30 g, 17.0 mmol) in acetonitrile (34.0 mL) was added tetrabutylammoniumtribromide ($TBABr_3$, 8.19 g, 17.0 mmol). The reaction was stirred at room temperature overnight. The solution was concentrated under reduced pressure, added with water, and extracted with ethyl acetate. The organic layer was washed with brine, dried over anhydrous $MgSO_4(s)$, and concentrated under reduced pressure to give 2-bromo-1-(2,6-dimethyl-4-(methylthio)phenyl)ethanone (5.2 g), which was used directly for the next step without further purification.

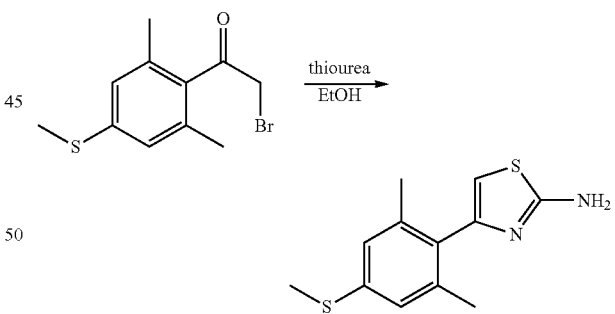

4-(2,6-Dimethyl-4-(methylthio)phenyl)thiazol-2-amine. A mixture of 2-bromo-1-(2,6-dimethyl-4-(methylthio)phenyl)ethanone (4.64 g, 17.0 mmol) and thiourea (1.29 g, 17.0 mmol) in 95% EtOH (24.3 mL) was heated at reflux for 120 min. The solution was concentrated and added with water (50 mL) and saturated aqueous $Na_2CO_3$ (4.0 mL). The resultant precipitate was filtered and recrystallized in toluene (30 mL). The solids were filtered and dried under vacuum to give 4-(2,6-dimethyl-4-(methylthio)phenyl)thiazol-2-amine (1.9 g) as light yellow solids in 45% yield: $^1H$ NMR (500 MHz, $CDCl_3$) δ 6.97 (s, 2 H), 6.26 (s, 1 H), 2.47 (s, 3 H), 2.15 (s, 6 H).

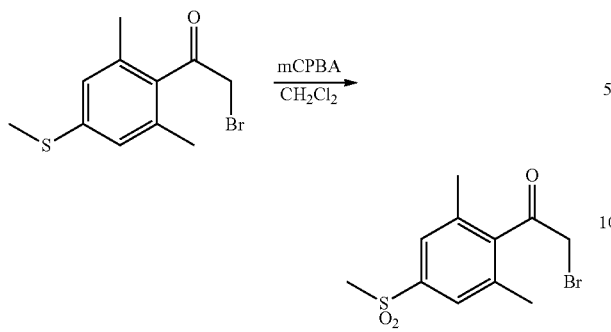

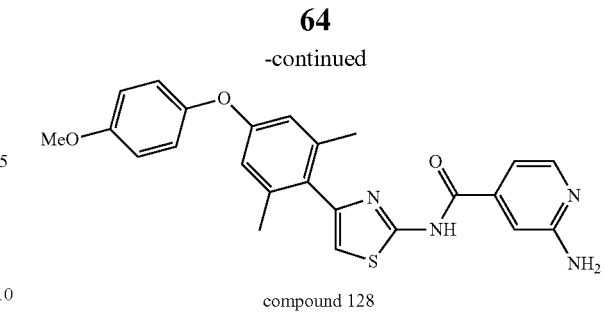

compound 128

2-Bromo-1-(2,6-dimethyl-4-(methylsulfonyl)phenyl) ethanone.

To a solution of 2-bromo-1-(2,6-dimethyl-4-(methylthio)phenyl)ethanone (4.92 g, 0.653 mol) in CH$_2$Cl$_2$ (36 mL) at 0° C. was added mCPBA (70%, 11.1 g, 1.63 mol). The mixture was stirred at room temperature for 7.0 h. The solution was filtered, and the filtrate was added with saturated aqueous NaHCO$_3$ (50 mL). The organic layer was dried over anhydrous MgSO$_4$(s) and concentrated under reduced pressure to give 2-bromo-1-(2,6-dimethyl-4-(methylsulfonyl) phenyl)ethanone (7.6 g), which was used directly for the next step without further purification.

2-Amino-N-(4-(4-(4-methoxyphenoxy)-2,6-dimethylphenyl)thiazol-2-yl)isonicotinamide.

A mixture of N-(4-(4-(4-methoxyphenoxy)-2,6-dimethylphenyl)thiazol-2-yl)-2-nitroisonicotinamide (0.20 g, 0.40 mmol) and Pd/C (0.15 g, 10% w/w) in ethanol (10 mL) was stirred under H$_2$ overnight. The reaction was filtered through diatomaceous earth and concentrated under reduced pressure to afford 2-amino-N-(4-(4-(4-methoxyphenoxy)-2,6-dimethylphenyl)thiazol-2-yl) isonicotinamide (0.11 g) as yellow solids in 59% yield: $^1$H-NMR (500 MHz, DMSO-d$_6$) δ 7.88-7.89 (m, 1 H), 7.10-7.11 (m, 2 H), 6.95-6.97 (m, 2 H), 6.62 (s, 1 H), 5.76 (s, 1 H), 3.29 (s, 3 H), 2.03 (s, 6 H); ESI-MS: m/z 446.6 [M+H]$^+$.

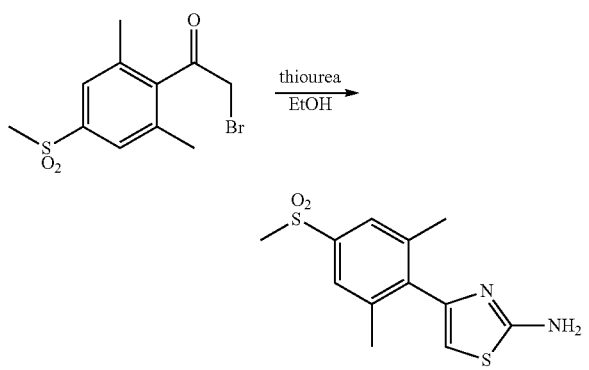

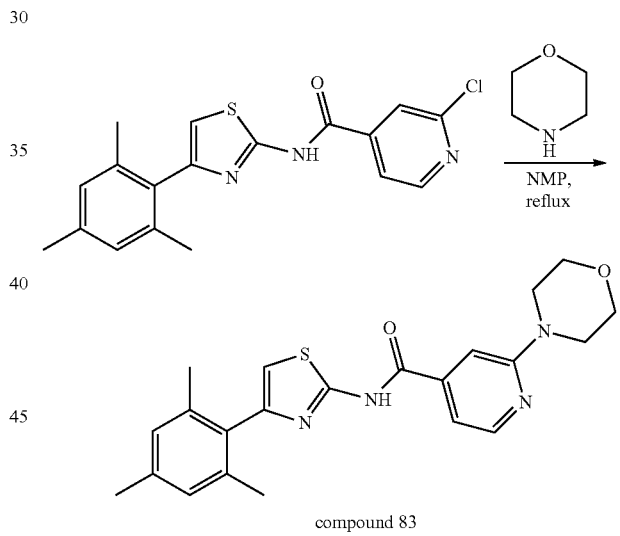

compound 83

4-(2,6-Dimethyl-4-(methylsulfonyl)phenyl)thiazol-2-amine.

A mixture of 2-bromo-1-(2,6-dimethyl-4-(methylsulfonyl)phenyl)ethanone (7.60 g, 24.9 mmol) and thiourea (1.90 g, 25.0 mmol) in 95% EtOH (35.6 mL) was heated at reflux for 90 min. The solution was concentrated and added with water (100 mL) and saturated aqueous Na$_2$CO$_3$ (5.0 mL). The resultant precipitate was filtered and recrystallized in toluene (20 mL). The solids were filtered and dried under vacuum to give 4-(2,6-dimethyl-4-(methylsulfonyl)phenyl) thiazol-2-amine (3.28 g) as yellow solids in 47% yield: $^1$H NMR (500 MHz, CDCl3) δ 7.64 (s, 2 H), 6.34 (s, 1 H), 5.19 (m, 1 H), 3.04 (s, 3 H), 2.26 (s, 6 H).

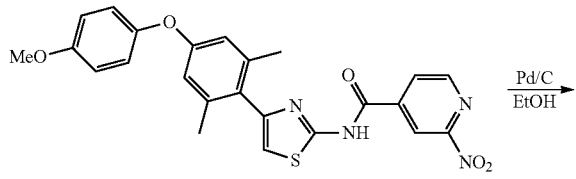

N-(4-Mesitylthiazol-2-yl)-2-morpholinoisonicotinamide.

A mixture of 2-chloro-N-(4-mesitylthiazol-2-yl)isonicotinamide (500.0 mg, 1.4 mmol, 1.0 equiv) and morpholine (1.5 mL, 16.8 mmol, 12 equiv) in methylpyrrolidone (15.0 mL) was stirred at 150° C. for 16 h. The mixture was poured into icy H$_2$O (20.0 mL), and the resultant solids were filtered to provide N-(4-mesitylthiazol-2-yl)-2-morpholinoisonicotinamide (358.6 mg, 0.90 mmol) as yellow solids in 63% yield: $^1$H NMR (DMSO-d$_6$, 500 MHz) δ 8.30 (d, J=5.1 Hz, 2 H), 7.50 (s, 1 H), 7.22 (d, J=5.1 Hz, 2 H), 7.10 (s, 1 H), 6.92 (s, 2 H), 3.70-3.73 (m, 4 H), 3.53-3.55 (m, 4 H), 2.26 (s, 3 H), 2.05 (s, 6 H); ESI-MS: m/z 409.3 (M+H)$^+$.

500 MHz) δ 8.29 (d, J=5.1 Hz, 1 H), 7.15 (s, 1 H), 6.83-6.90 (m, 3 H), 6.79 (s, 1 H), 3.61-3.63 (m, 4 H), 2.31 (s, 3 H), 2.08 (s, 6 H), 1.57-1.67 (m, 6 H); ESI-MS: m/z 407.2 (M+H)+.

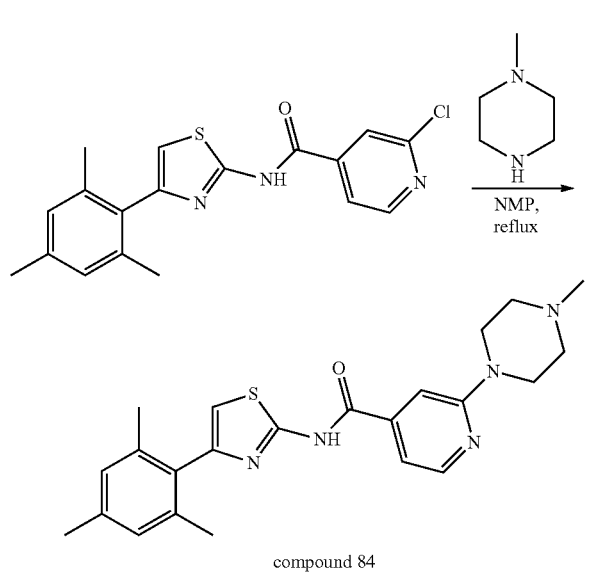

compound 84

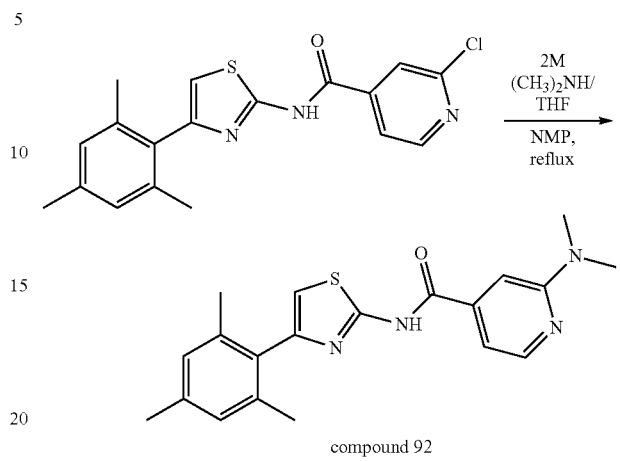

compound 92

N-(4-Mesylthiazol-2-yl)-2-(4-methylpiperazin-1-yl)isonicotinamide. A mixture of 2-chloro-N-(4-mesitylthiazol-2-yl)isonicotinamide (300.0 mg, 0.8 mmol, 1.0 equiv) and 1-methylpiperazine (1.12 mL, 10.1 mmol, 12 equiv) in methylpyrrolidone (9.0 mL) was stirred at 150° C. for 16 h. The mixture was poured into icy H$_2$O (15.0 mL) and the resultant solids were filtered to provide N-(4-mesitylthiazol-2-yl)-2-(4-methylpiperazin-1-yl)isonicotinamide (95.6 mg, 0.20 mmol) as yellow solids in 27% yield: $^1$H NMR (CDCl3, 500 MHz) δ 8.27 (d, J=5.1 Hz, 1 H), 7.12 (s, 1 H), 6.83-6.86 (m, 3 H), 6.78 (s, 1 H), 3.63-3.65 (m, 4 H), 2.35 (s, 3 H), 2.27 (s, 3 H), 2.04 (s, 6 H); ESI-MS: m/z 422.1 (M+H)+.

2-(Dimethylamino)-N-(4-mesitylthiazol-2-yl)isonicotinamide. A mixture of 2-chloro-N-(4-mesitylthiazol-2-yl)isonicotinamide (200 mg, 0.60 mmol, 1.0 equiv), caesium carbonate (2.73 g, 0.6 mmol, 15 equiv) and 2.0 M dimethylamine in THF (3.4 mL, 6.7 mmol, 12 equiv) in DMF (6.0 mL) was heated at reflux for 16 h. The mixture was poured into icy H$_2$O (10.0 mL) and extracted with EtOAc. The organic layer was collected, dried over MgSO4(s), and concentrated under reduced pressure. The residue was purified by column chromatography on silica gel (15% EtOAc in hexanes as eluant) to provide 2-(dimethylamino)-N-(4-mesityl-thiazol-2-yl)isonicotinamide (5.5 mg, 0.10 mmol) as yellow solids in 3.0% yield: $^1$H NMR (CDCl3, 500 MHz) δ 8.32 (d, J=5.1 Hz, 1 H), 7.02 (s, 1 H), 6.92 (s, 2 H), 6.85 (d, J=5.1 Hz, 1 H), 6.80 (s, 1 H), 3.16 (s, 6 H), 2.31 (s, 3 H), 2.09 (s, 6 H); ESI-MS: m/z 367.1 (M+H)+.

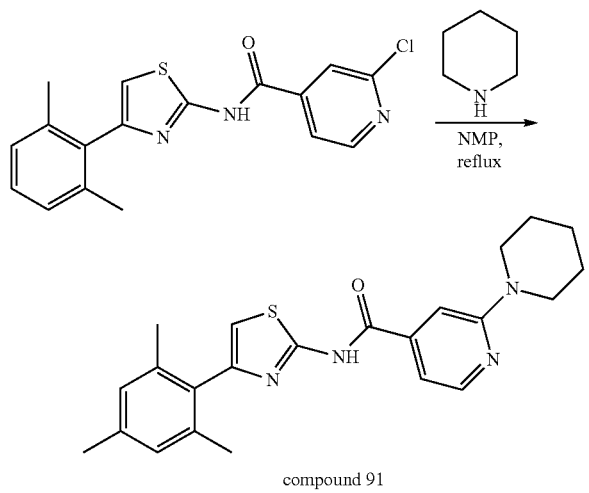

compound 91

N-(4-Mesitylthiazol-2-yl)-2-(piperidin-1-yl)isonicotinamide. A mixture of 2-chloro-N-(4-mesitylthiazol-2-yl)isonicotinamide (200 mg, 0.60 mmol, 1.0 equiv) and piperidine (0.70 mL, 6.7 mmol, 12 equiv) in methylpyrrolidone (6.0 mL) was stirred at 150° C. for 16 h. The mixture was poured into icy H$_2$O (10.0 mL) and the resultant solids were filtered. The solids were purified by column chromatography on silica gel (15% EtOAc in hexanes as eluant) to provide N-(4-mesitylthiazol-2-yl)-2-(piperidin-1-yl)isonicotinamide (87.2 mg, 0.20 mmol) as yellow solids in 38% yield: $^1$H NMR (CDCl$_3$, compound 118

N-(4-(4-Benzyl-2,6-dimethylphenyl)thiazol-2-yl)isonicotinamide. A THF solution of benzylzinc(II) bromide (4.0 mL, 2.0 mmol) was added to a degassed solution of N-(4-(4-iodo-2,6-dimethylphenyl)thiazol-2-yl)isonicotinamide (435 mg, 1.0 mmol) and tetrakistriphenylphosphine palladium (57.8 mg, 0.10 mmol) in THF (5.0 mL). The reaction mixture was heated at reflux for 16 h under N$_2$ and then poured into saturated aqueous NaHCO$_3$. The mixture was extracted with ethyl acetate, washed with brine, dried MgSO$_4$, and concentrated under reduced pressure. The residue was purified by flash column chromatography on silica gel to give N-(4-(4-benzyl-2,6-dimethylphenyl)thiazol-2-yl)isonicotinamide:

$^1$H NMR (500 MHz, CDCl$_3$) δ 8.70 (d, J=4.9 Hz, 2 H), 7.67 (d, J=4.9 Hz, 2 H), 7.33 (d, J=8.6 Hz, 2 H), 7.10-7.26 (m, 3 H), 6.80 (s, 1H), 6.24 (s, 1 H), 3.86 (s, 2 H), 2.04 (s, 6 H); ESI-MS: m/z 399.9 (M+H)+.

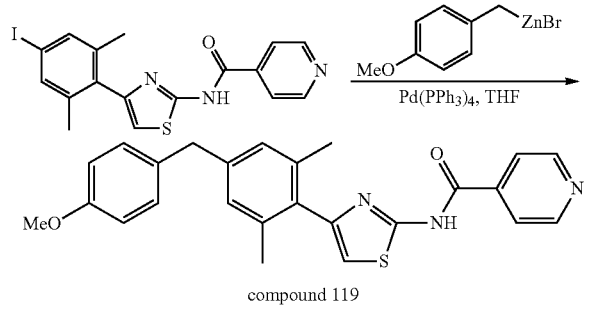

compound 119

N-(4-(4-(4-Methoxybenzyl)-2,6-dimethylphenyl)thiazol-2-yl)isonicotinamide. A THF solution of 4-methoxylbenzylzinc(II) bromide (4.0 mL, 2.0 mmol) was added to a degassed solution of N-(4-(4-iodo-2,6-dimethylphenyl)thiazol-2-yl)isonicotinamide (435 mg, 1.0 mmol) and tetrakistriphenylphosphine palladium (57.8 mg, 0.10 mmol) in THF (5.0 mL). The reaction mixture was heated at reflux for 16 h under N$_2$ then poured into saturated aqueous NaHCO$_3$. The mixture was extracted with ethyl acetate, washed with brine, dried MgSO$_4$, and concentrated under reduced pressure. The residue was purified by flash column chromatography on silica gel to give N-(4-(4-(4-methoxybenzyl)-2,6-dimethylphenyl)thiazol-2-yl)isonicotinamide: $^1$H NMR (500 MHz, CDCl$_3$) δ 8.69 (d, J=5.2 Hz, 2 H), 7.66 (d, J=4.9 Hz, 2 H), 7.11 (d, J=8.4 Hz, 2 H), 6.86 (d, 2 H), 6.80 (s, 1 H), 6.75 (s, 2 H), 3.80 (s, 2 H), 3.78 (s, 2 H), 1.98(s, 6 H); ESI-MS: m/z 399.9 (M+H)+.

Exemplary Compounds and Physicochemical Data compound 4

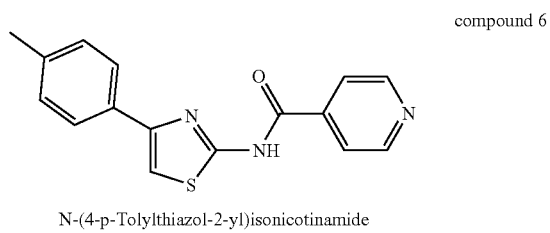 [SMILES: Cc1ccc(-c2csc(NC(=O)c3ccncc3)n2)cc1]

4-Cyano-N-(4-mesitylthiazol-2-yl)benzamide

Yield: 67%; $^1$H NMR (500 MHz, DMSO-d$_6$) δ 8.23 (d, 2 H), 8.02 (d, 2 H), 7.09 (s, 1 H), 6.92 (s, 2 H), 2.26 (s, 3 H), 2.05 (s, 6 H); ESI-MS: m/z 348.0 (M+H)+.

compound 5

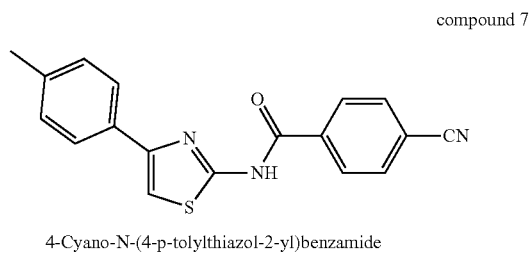 [SMILES: Cc1ccc(-c2csc(NC(=O)c3ccc(C#N)cc3)n2)cc1]

N-(4-mesitylthiazol-2-yl)pyrimidine-4-carboxamide

Yield: 62%; $^1$H NMR (500 MHz, DMSO-d$_6$) δ 9.41 (s, 1 H), 9.15 (d, 1 H), 8.14 (d, 1 H), 7.17 (s, 1 H), 6.89 (s, 2 H), 2.25 (s, 3 H), 2.03 (s, 6 H); ESI-MS: m/z 325.1 (M+H)+.

compound 6

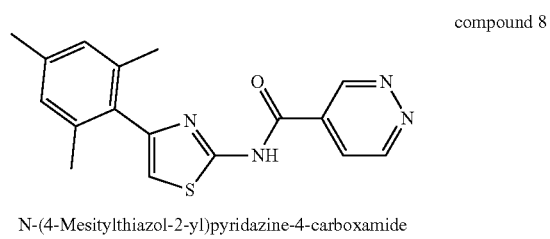 [SMILES: Cc1cc(C)c(-c2csc(NC(=O)c3ccnnc3)n2)c(C)c1]

N-(4-p-Tolylthiazol-2-yl)isonicotinamide

Yield: 8.6%; $^1$H NMR (500 MHz, CDCl$_3$) δ 8.70 (d, J=5.5 Hz, 2 H), 7.65-7.63 (m, 2 H), 7.60 (d, J=8.0 Hz, 2 H), 7.17 (s, 1 H), 7.14 (d, J=7.5 Hz, 2 H), 2.34 (s, 6 H); ESI-MS: m/z 295.9 (M+H)+.

compound 7

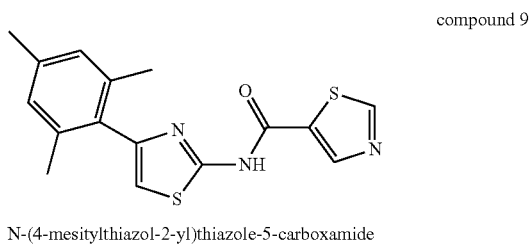 [SMILES: Cc1cc(C)c(-c2csc(NC(=O)c3cncs3)n2)c(C)c1]

4-Cyano-N-(4-p-tolylthiazol-2-yl)benzamide

Yield: 63%; $^1$H NMR (500 MHz, CDCl$_3$) δ 7.89 (d, J=8.5 Hz, 2 H), 7.62 (d, J=8.5 Hz, 2 H), 7.55 (d, J=8.5 Hz, 2 H), 7.17 (s, 1 H), 7.12 (d, J=8.0 Hz, 2 H), 2.34 (s, 6 H); ESI-MS: m/z 317.9 (M−H)−.

compound 8

N-(4-Mesitylthiazol-2-yl)pyridazine-4-carboxamide

Yield: 62%; $^1$H NMR (500 MHz, DMSO-d$_6$) δ 9.72 (s, 1 H), 9.50 (d, 1 H), 8.21 (m, 1 H), 7.13 (s, 1 H), 6.94 (s, 2 H), 2.27 (s, 3 H), 2.06 (s, 6 H); ESI-MS: m/z 324.5 (M+H)+.

compound 9

N-(4-mesitylthiazol-2-yl)thiazole-5-carboxamide

Yield: 40%; $^1$H NMR (500 MHz, DMSO-d$_6$) δ 9.36 (s, 1 H), 8.82 (brs, 1 H), 7.06 (s, 1 H), 6.93 (s, 2 H), 2.26 (s, 3 H), 2.05 (s, 6 H); ESI-MS: m/z 329.3 (M+H)+.

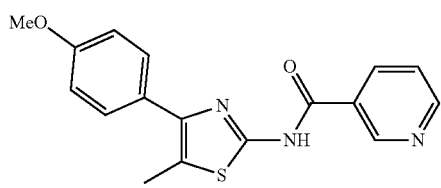

compound 14

N-(4-(4-Methoxyphenyl)-5-methylthiazol-2-yl)nicotinamide

Yield: 74%; $^1$H NMR (500 MHz, CDCl$_3$) δ 9.09 (d, 1 H), 8.73-8.72 (m, 1 H), 8.15-8.14 (m, 1 H), 7.42-7.41 (m, 2 H), 7.35 (m, 1 H), 6.87-6.85 (m, 2 H), 3.82 (s, 3 H), 2.51 (s, 6 H); ESI-MS: m/z 325.3 [M+H]+.

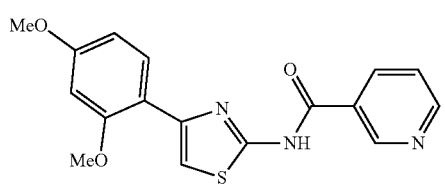

compound 15

N-(4-(2,4-Dimethoxyphenyl)thiazol-2-yl)nicotinamide

Yield: 87%; $^1$H NMR (500 MHz, CDCl$_3$) δ 9.30 (s, 1 H), 8.82-8.81 (m, 1 H), 8.39-8.36 (m, 1 H), 7.80-7.79 (m, 1 H), 7.48-7.46 (m, 1 H), 7.43-7.39 (m, 1 H), 6.58-6.55 (m, 2 H), 3.92 (s, 3 H), 3.86 (s, 3 H); ESI-MS: m/z 341.4 [M+H]+.

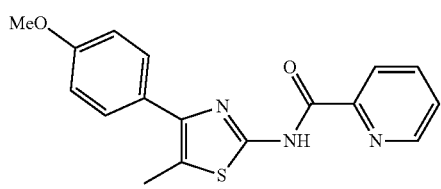

compound 16

N-(4-(4-Methoxyphenyl)-5-methylthiazol-2-yl)picolinamide

Yield: >99%; $^1$H NMR (500 MHz, CDCl$_3$) δ 10.55 (s, 1 H), 8.65-8.64 (m, 1 H), 8.30-8.29 (m, 1 H), 7.93 (m, 1 H), 7.60-7.58 (m, 2 H), 7.54-7.53 (m, 1 H), 6.99-6.98 (m, 2 H), 3.86 (s, 3 H), 2.54 (s, 3 H); ESI-MS: m/z 325.6 [M+H]+.

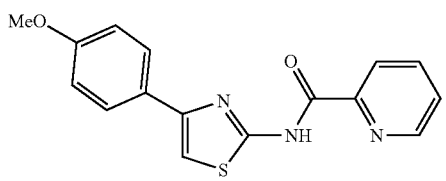

compound 17

N-(4-(4-Methoxyphenyl)thiazol-2-yl)picolinamide

Yield: >99%; $^1$H NMR (500 MHz, DMSO-d$_6$) δ 11.98 (s, 1 H), 8.78-8.77 (m, 1 H), 8.19-8.17 (m, 1 H), 8.11-8.09 (m, 1 H), 7.89-7.87 (m, 2 H), 7.74-7.71 (m, 1 H), 7.58 (m, 1 H), 7.00-6.99 (m, 2 H), 3.79 (s, 3 H), 2.54 (s, 3 H); ESI-MS: m/z 310.0 [M−H]−.

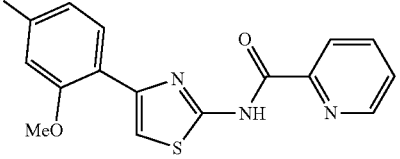

compound 18

N-(4-(2,4-Dimethoxyphenyl)thiazol-2-yl)picolinamide

Yield: 89%; $^1$H NMR (500 MHz, DMSO-d$_6$) δ 11.9 (s, 1 H), 8.79-8.78 (m, 1 H), 8.20-8.19 (m, 1 H), 8.12-8.07 (m, 1 H), 7.75-7.74 (m, 2 H), 7.61 (s, 1 H), 6.68-6.63 (m, 2 H), 3.92 (s, 3 H), 3.82 (s, 3 H); ESI MS: m/z 340.3 [M−H]−.

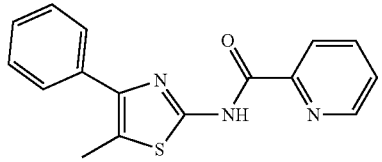

compound 19

N-(5-Methyl-4-phenylthiazol-2-yl)picolinamide

Yield 90%; $^1$H NMR (500 MHz, DMSO-d$_6$) δ 11.9 (s, 1 H), 8.76-8.77 (m, 1 H), 8.18-8.19 (m, 1 H), 8.10 (m, 1 H), 7.69-7.73 (m, 3 H), 7.45-7.48 (m, 1 H), 7.36-7.38 (m, 1 H), 2.50 (s, 3 H); ESI-MS: m/z 295.4 [M+H]+.

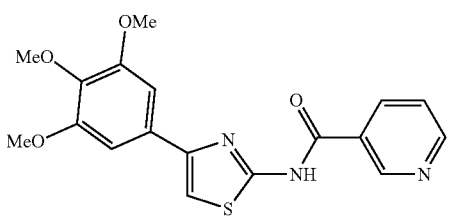

compound 20

N-(4-(3,4,5-Trimethoxyphenyl)thiazol-2-yl)nicotinamide

Yield 78%: $^1$H NMR (500 MHz, DMSO-d$_6$) δ 9.24 (d, 1 H), 8.79 (t, 1 H), 8.44 (d, 1 H), 7.75 (s, 1 H), 7.58-7.60 (m, 1 H), 7.26 (s, 2 H), 3.85 (s, 6 H), 3.69 (s, 3 H); ESI-MS: m/z 372.5 [M+H]+.

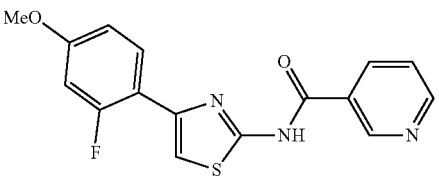

compound 21

N-(4-(2-Fluoro-4-methoxyphenyl)thiazol-2-yl)nicotinamide

Yield 81%: $^1$H NMR (500 MHz, DMSO-d$_6$) δ 9.23 (d, 1 H), 8.80 (t, 1 H), 8.44 (d, 1 H), 8.00-8.03 (m, 1 H), 7.58-7.60 (m, 1 H), 7.46 (d, 1 H), 6.90-6.98 (m, 2 H), 3.82 (s, 3 H); ESI-MS: m/z 330.0 [M+H]+.

compound 22

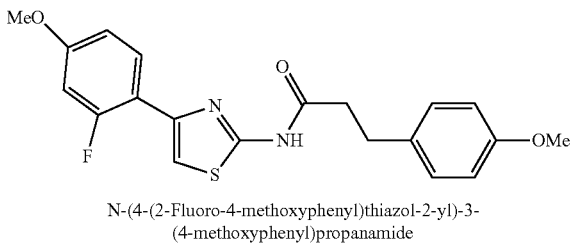

N-(4-(2-Fluoro-4-methoxyphenyl)thiazol-2-yl)-3-(4-methoxyphenyl)propanamide

Yield 53%: $^1$H NMR (500 MHz, CDCl$_3$) δ 11.01 (s, 1 H), 7.82-7.86 (m, 1 H), 7.27 (d, 1 H), 6.63-6.84 (m, 6 H), 3.80 (s, 3 H), 3.76 (s, 3 H), 2.77 (t, 2 H), 2.29 (t, 3 H); ESI-MS: m/z 387.0 [M+H]+.

compound 23

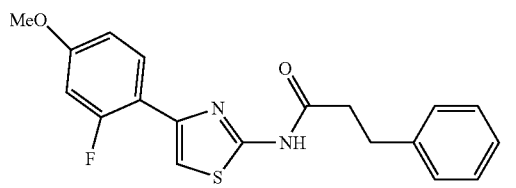

N-(4-(2-Fluoro-4-methoxyphenyl)thiazol-2-yl)-3-phenylpropanamide

Yield 45%: $^1$H NMR (500 MHz, CDCl$_3$) δ 10.87 (s, 1 H), 7.83-7.87 (m, 1 H), 7.15-7.27 (m, 5 H), 7.95 (d, 2 H), 6.62-6.73 (m, 2 H), 3.80 (s, 3 H), 2.86 (t, 2 H), 2.36 (t, 2 H); ESI-MS: m/z 356.0 [M+H]+.

compound 24

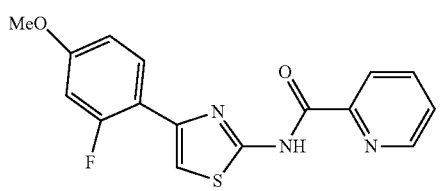

N-(4-(2-Fluoro-4-methoxyphenyl)thiazol-2-yl)picolinamide

Yield 77%: $^1$H NMR (500 MHz, DMSO-d$_6$) δ 12.04 (s, 1 H), 8.79 (d, 2 H), 8.02-8.21 (m, 3 H), 7.74 (t, 1 H), 7.49 (d, 2 H), 6.90-6.97 (m, 2 H), 3.82 (s, 3 H); ESI-MS: m/z 330.0 [M+H]+.

compound 25

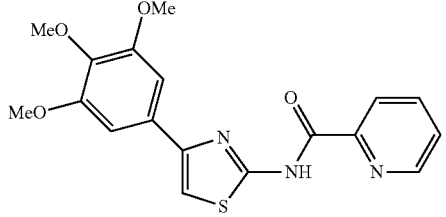

N-(4-(3,4,5-Trimethoxyphenyl)thiazol-2-yl)picolinamide

Yield 75%: $^1$H NMR (500 MHz, DMSO-d$_6$) δ 12.04 (s, 1 H), 8.78 (s, 1 H), 8.18 (d, 1 H), 8.11 (t, 1 H), 7.78-7.82 (m, 2 H), 7.28 (s, 2 H), 3.86 (s, 6 H), 3.69 (s, 3 H); ESI-MS: m/z 372.0 [M+H]+.

compound 26

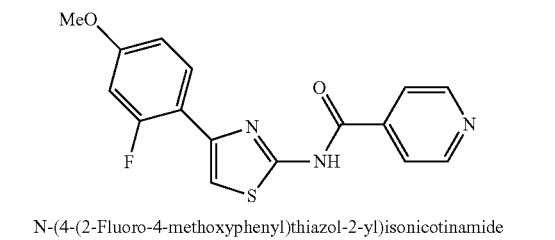

N-(4-(2-Fluoro-4-methoxyphenyl)thiazol-2-yl)isonicotinamide

Yield 84%: $^1$H NMR (500 MHz, DMSO-d$_6$) δ 8.82 (d, 2 H), 7.99-8.03 (m, 3 H), 7.48 (d, 1H), 6.91-6.98 (m, 2 H), 3.83 (s, 3 H); ESI-MS: m/z 330.0 [M+H]+.

compound 27

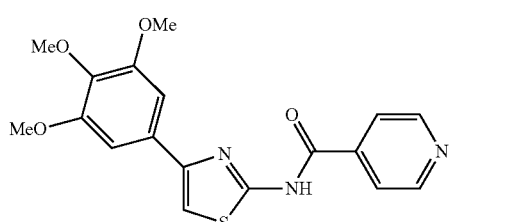

N-(4-(3,4,5-Trimethoxyphenyl)thiazol-2-yl)isonicotinamide

Yield 82%: $^1$H NMR (500 MHz, DMSO-d$_6$) δ 8.79 (d, 2 H), 8.00-8.01 (m, 2 H), 7.71 (s, 1 H), 7.26 (s, 2 H), 3.85 (s, 6 H), 3.70 (s, 3 H); ESI-MS: m/z 372.0 [M+H]+.

compound 28

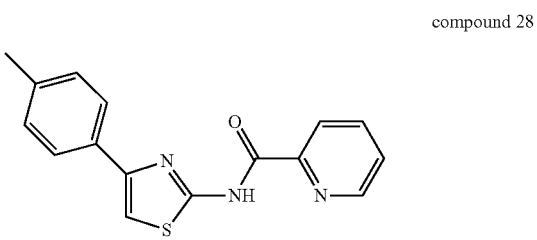

N-(4-p-Tolylthiazol-2-yl)picolinamide

Yield: 6.7%; $^1$H NMR (500 MHz, CDCl$_3$) δ 10.96 (bs, 1 H), 9.11 (bs, 1 H), 8.75 (bs, 1 H), 8.14 (d, J=8.0 Hz, 1 H), 7.60 (d, J=7.5 Hz, 2 H), 7.34 (s, 1 H), 7.15 (s, 1 H), 7.12 (d, J=7.5 Hz, 2 H), 2.33 (s, 6 H); ESI-MS: m/z 293.7 (M−H)−.

compound 29

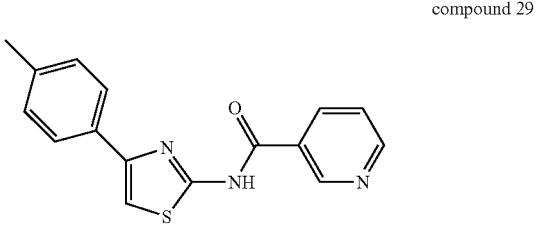

N-(4-p-Tolylthiazol-2-yl)nicotinamide

Yield: 83%; $^1$H NMR (500 MHz, CDCl$_3$) δ 11.24 (s, 1 H), 8.68 (d, J=4.5 Hz, 1 H), 8.31 (d, J=8.0 Hz, 1 H), 7.95 (m, 1 H), 7.78 (d, J=8.0 Hz, 2 H), 7.54 (m, 1 H), 7.24 (m, 2 H), 7.17 (s, 1 H), 2.39 (s, 6 H); ESI-MS: m/z 295.6 (M+H)+.

compound 30

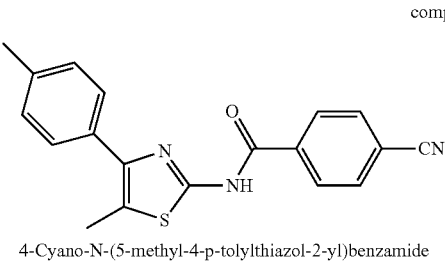

4-Cyano-N-(5-methyl-4-p-tolylthiazol-2-yl)benzamide

Yield: 36%; ¹H NMR (500 MHz, CDCl₃) δ 7.72 (d, J=8.5 Hz, 2 H), 7.49 (d, J=8.5 Hz, 2 H), 7.20 (d, J=8.0 Hz, 2 H), 6.99 (d, J=8.0 Hz, 2 H), 2.51 (s, 3 H), 2.27 (s, 3 H); ESI-MS: m/z 332.0 (M−H)−.

compound 31

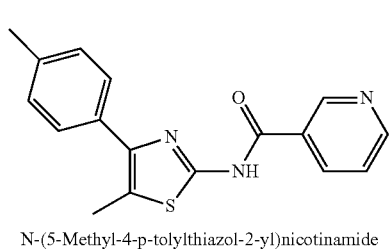

N-(5-Methyl-4-p-tolylthiazol-2-yl)nicotinamide

Yield: 56%; ¹H NMR (500 MHz, CDCl₃) δ 8.99 (s, 1 H), 8.63 (d, J=5.0 Hz, 1 H), 8.01 (d, J=7.9 Hz, 1 H), 7.29-7.21 (m, 3 H), 7.03 (d, J=7.8 Hz, 2 H), 2.49 (s, 3 H), 2.29 (s, 3 H); ESI-MS: m/z 310.3 (M+H)+.

compound 32

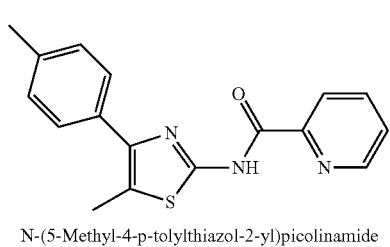

N-(5-Methyl-4-p-tolylthiazol-2-yl)picolinamide

Yield: 79%; ¹H NMR (500 MHz, CDCl₃) δ 11.11 (s, 1 H), 8.64 (d, J=4.5 Hz, 1 H), 8.29 (d, J=7.5 Hz, 1 H), 7.93 (t, J=8.0 Hz, 1 H), 7.55-7.51 (m, 3 H), 7.25 (d, J=7.5 Hz, 1 H), 2.54 (s, 3 H), 2.40 (s, 3 H); ESI-MS: m/z 309.0 (M−H)−.

compound 33

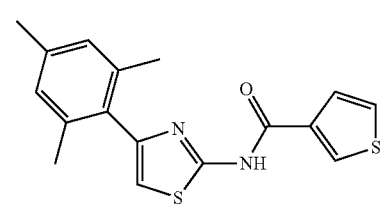

N-(4-Mesitylthiazol-2-yl)thiophene-3-carboxamide

Yield: 37%; ¹H NMR (500 MHz, DMSO-d₆) δ 12.59 (s, 1 H), 8.60 (s, 1 H), 7.69-7.76 (m, 2 H), 7.04 (s, 1 H), 6.93 (s, 2 H), 2.27 (s, 3 H), 2.06 (s, 6 H); ESI-MS: m/z 327.1 (M−H)−.

compound 34

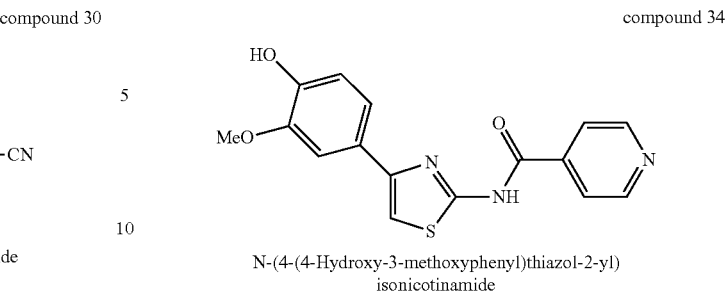

N-(4-(4-Hydroxy-3-methoxyphenyl)thiazol-2-yl)isonicotinamide

Yield: 54%; ¹H NMR (500 MHz, DMSO-d₆) δ 8.89 (d, 2 H), 8.00 (d, 2 H), 7.57 (d, 1 H), 7.44-7.46 (m, 1 H), 7.26 (d, 1 H), 7.11 (s, 3 H), 3.81 (s, 3 H); ESI-MS: m/z 327.9 (M+H)+.

compound 35

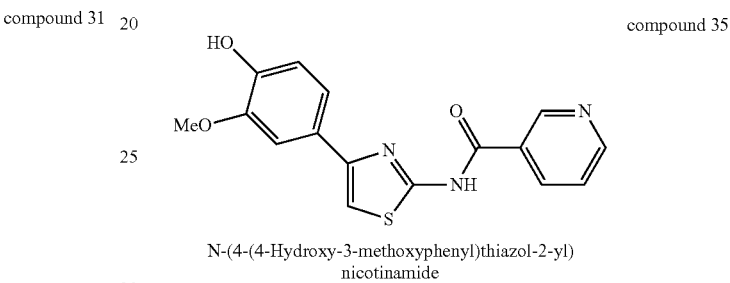

N-(4-(4-Hydroxy-3-methoxyphenyl)thiazol-2-yl)nicotinamide

Yield: 44%; ¹H NMR (500 MHz, DMSO-d₆) δ 9.25 (s, 1 H), 8.91 (s, 1 H), 8.45-8.48 (m, 1 H), 7.65-7.67 (m, 1 H), 7.57 (d, 1 H), 7.44-7.46 (m, 1 H), 7.26 (d, 1 H), 7.10 (s, 2 H), 3.81 (s, 3 H); ESI-MS: m/z 328.0 (M+H)⁺.

compound 36

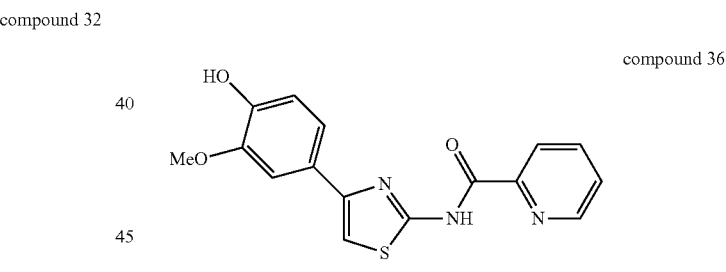

N-(4-(4-Hydroxy-3-methoxyphenyl)thiazol-2-yl)picolinamide

Yield: 37%; ¹H NMR (500 MHz, DMSO-d₆) δ 8.82 (d, 1 H), 8.23 (d, 1 H), 8.08 (d, 1 H), 7.74-7.75 (m, 1 H), 7.57 (d, 1 H), 7.44-7.46 (m, 1 H), 7.23 (d, 1 H), 7.10 (s, 2 H), 3.81 (s, 3 H); ESI-MS: m/z 328.1 (M+H)+.

compound 37

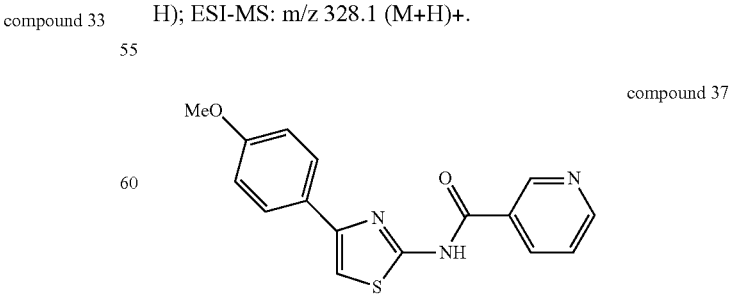

N-(4-(4-Methoxyphenyl)thiazol-2-yl)nicotinamide

Yield: 94%; ¹H NMR (500 MHz, DMSO-d₆) δ 12.98 (s, 1 H), 9.23 (m, 1 H), 8.80 (m, 1 H), 8.46-8.43 (m, 1 H), 7.90-7.88 (m, 2 H), 7.61-7.56 (m, 1 H), 7.02-7.00 (m, 2 H), 3.80 (s, 3 H); ESI-MS: m/z 310.0 [M−H]−.

Yield: 76%; ¹H NMR (500 MHz, CDCl₃) δ 8.90 (s, 1 H), 7.56-7.55 (m, 2 H), 7.43-7.40 (m, 2 H), 7.34-7.33 (m, 1 H), 7.26-7.22 (m, 1 H), 3.77 (s, 3 H), 3.47 (s, 2 H), 2.49 (s, 3 H); ESI-MS: m/z 339.2 [M+H]+.

compound 38

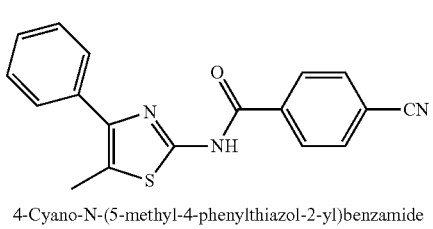

4-Cyano-N-(5-methyl-4-phenylthiazol-2-yl)benzamide

Yield: 99%; ¹H NMR (500 MHz, DMSO-d₆) δ 7.82-7.80 (m, 2 H), 7.60-7.58 (m, 2 H), 7.41-7.40 (m, 2 H), 7.30-7.29 (m, 2 H), 7.22-7.19 (m, 1 H), 2.54 (s, 3 H); ESI-MS: m/z 320.0 [M+H]+.

compound 42

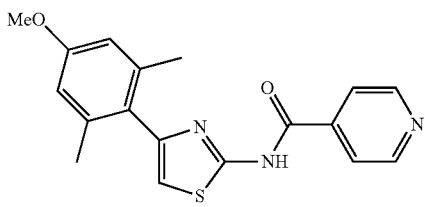

N-(4-(4-Methoxy-2,6-dimethylphenyl)thiazol-2-yl)isonicotinamide

Yield: 69%; ¹H NMR (500 MHz, CDCl₃) δ 8.67 (d, J=5.5 Hz, 2 H), 7.55 (d, J=6.0 Hz, 2 H), 6.77 (s, 1 H), 6.32 (s, 2 H), 3.73 (s, 3 H), 1.91 (s, 6 H); ESI-MS: m/z 340.0 (M+H)+.

compound 39

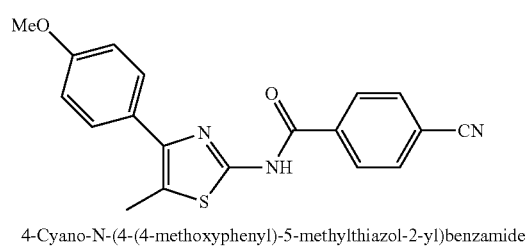

4-Cyano-N-(4-(4-methoxyphenyl)-5-methylthiazol-2-yl)benzamide

Yield: 66%; ¹H NMR (500 MHz, CD₃OD) δ 8.18-8.17 (m, 2 H), 7.92-7.90 (m, 2 H), 7.60-7.58 (m, 2 H), 7.01-7.00 (m, 2 H), 3.84 (s, 3 H), 2.50 (s, 2 H); ESI-MS m/z 349.5 [M+H]+.

compound 43

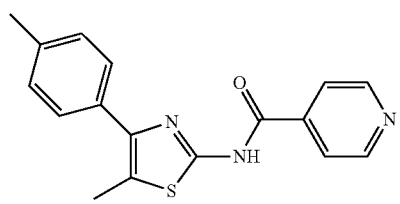

N-(5-Methyl-4-p-tolylthiazol-2-yl)isonicotinamide

Yield: 54%; ¹H NMR (500 MHz, CDCl₃) δ 8.57 (d, J=5.0 Hz, 2 H), 7.46 (d, J=5.5 Hz, 2 H), 7.25 (d, J=4.5 Hz, 2 H), 7.02 (d, J=7.5 Hz, 2 H), 2.51 (s, 3 H), 2.28 (s, 3 H); ESI-MS: m/z 309.9 (M+H)+.

compound 40

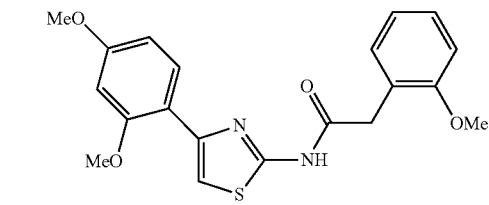

N-(4-(2,4-Dimethoxyphenyl)thiazol-2-yl)-2-(2-methoxyphenyl)acetamide

Yield: 85%; ¹H NMR (500 MHz, DMSO-d₆) δ 12.3 (s, 1 H), 7.99-7.97 (m, 1 H), 7.64 (s, 1 H), 7.24 (m, 1 H), 6.91 (m, 2 H), 6.90 (m, 1 H), 6.66-6.61 (m, 2 H), 3.89 (s, 3 H), 3.80 (s, 3 H), 3.75-3.74 (m, 5 H); ESI-MS: m/z 385.1 [M+H]+.

compound 44

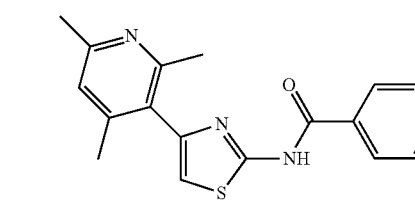

N-(4-(2,4,6-Trimethylpyridin-3-yl)thiazol-2-yl)isonicotinamide

Yield: 51%; ¹H NMR (500 MHz, CDCl₃) δ 8.79 (d, J=5.5 Hz, 2 H), 7.70 (d, J=5.5 Hz, 2 H), 6.86 (s, 1 H), 6.77 (s, 1 H), 2.45 (s, 3 H), 2.23 (s, 3 H), 2.03 (s, 3 H); ESI-MS: m/z 324.5 (M+H)+.

compound 41

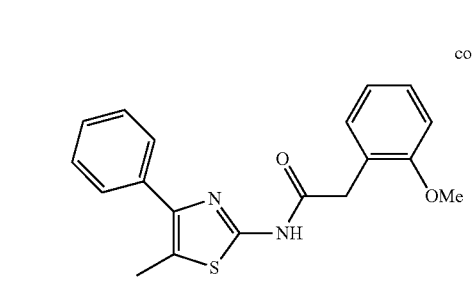

2-(2-Methoxyphenyl)-N-(5-methyl-4-phenylthiazol-2-yl)acetamide compound 45

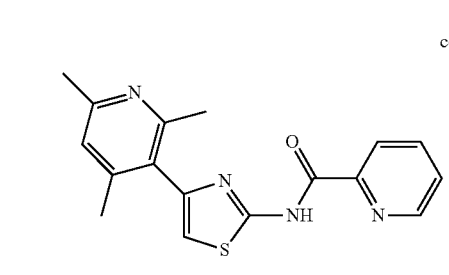

N-(4-(2,4,6-Trimethylpyridin-3-yl)thiazol-2-yl)picolinamide

Yield: 18%; $^1$H NMR (500 MHz, CDCl$_3$) δ 11.22 (s, 1 H), 8.65 (d, J=4.5 Hz, 1 H), 8.31 (d, J=7.5 Hz, 1 H), 7.96 (t, J=7.5 Hz, 1 H), 7.54 (m, 1 H), 6.92 (s, 1 H), 6.85 (s, 1 H), 2.52 (s, 3 H), 2.37 (s, 3 H), 2.133 (s, 3 H); ESI-MS: m/z 325.0 (M+H)+.

compound 46

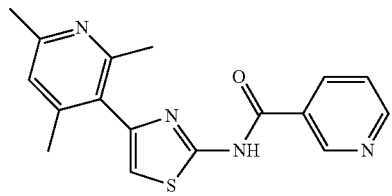

N-(4-(2,4,6-Trimethylpyridin-3-yl)thiazol-2-yl)nicotinamide

Yield: 18%; $^1$H NMR (500 MHz, CDCl$_3$) δ 9.11 (s, 1 H), 8.77 (s, 1 H), 8.17 (d, J=7.5 Hz, 1 H), 7.42 (m, 1 H), 6.85 (s, 1 H), 6.78 (s, 1 H), 2.45 (s, 3 H), 2.27 (s, 3 H), 2.02 (s, 3 H); ESI-MS: m/z 325.1 (M+H)+.

compound 47

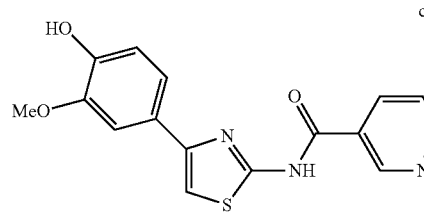

N-(4-(4-Hydroxy-3-methoxyphenyl)thiazol-2-yl) pyridazine-4-carboxamide

Yield: 54%; $^1$H NMR (500 MHz, DMSO-d$_6$) δ 9.75 (s, 1 H), 9.61 (s, 1 H), 8.28-8.30 (m, 1 H), 7.58 (d, 1 H), 7.46-7.48 (m, 1 H), 7.29 (d, 1 H), 7.12 (s, 3 H), 3.82 (s, 3 H); ESI-MS: m/z 329.4 (M+H)+.

compound 48

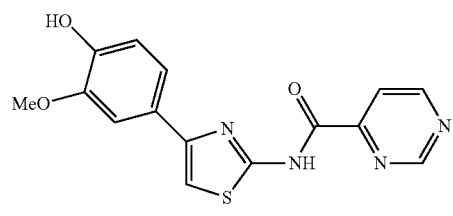

N-(4-(4-Hydroxy-3-methoxyphenyl)thiazol-2-yl) pyrimidine-4-carboxamide

Yield: 44%; $^1$H NMR (500 MHz, DMSO-d$_6$) δ 9.49 (d, 1 H), 9.19 (d, 1 H), 8.22-8.23 (m, 1 H), 7.58 (d, 1 H), 7.45-7.47 (m, 1 H), 7.27 (d, 1 H), 7.12 (s, 3 H), 3.82 (s, 3 H); ESI-MS: m/z 328.9 (M+H)+.

compound 49

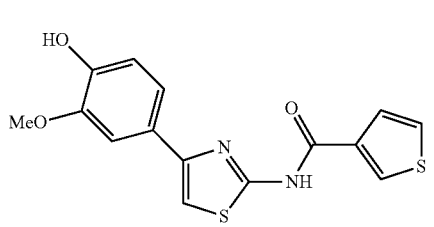

N-(4-(4-Hydroxy-3-methoxyphenyl)thiazol-2-yl) thiophene-3-carboxamide

Yield: 37%; $^1$H NMR (500 MHz, DMSO-d$_6$) δ 8.58 (d, 1 H), 7.73-7.75 (m, 1 H), 7.60 (d, 1 H), 7.55 (d, 1 H), 7.42-7.44 (m, 1 H), 7.18 (d, 1 H), 7.09 (m, 3 H); ESI-MS: m/z 333.0 (M+H)+.

compound 50

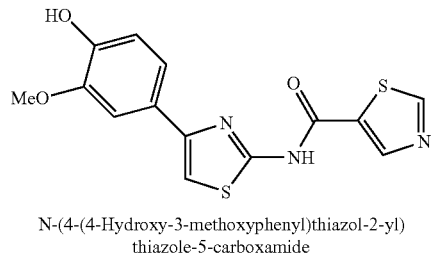

N-(4-(4-Hydroxy-3-methoxyphenyl)thiazol-2-yl) thiazole-5-carboxamide

Yield: 37%; $^1$H NMR (500 MHz, DMSO-d$_6$) δ 9.49 (s, 1 H), 8.75 (s, 1 H), 7.56 (s, 1 H), 7.43-7.45 (m 1 H), 7.24 (d, 1 H), 7.11 (m, 3 H), 3.81 (s, 3 H); ESI-MS: m/z 333.9 (M+H)+.

compound 51

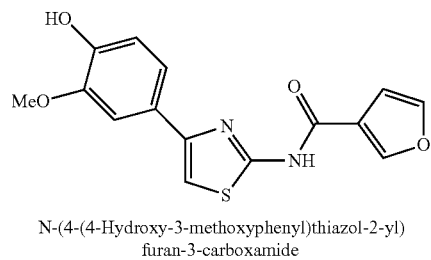

N-(4-(4-Hydroxy-3-methoxyphenyl)thiazol-2-yl) furan-3-carboxamide

Yield: 32%; $^1$H NMR (500 MHz, DMSO-d$_6$) δ 8.63 (s, 1 H), 7.91 (s, 1 H), 7.54 (s, 1 H), 7.41-7.43 (m, 1 H), 7.08-7.18 (m, 4 H), 6.93 (s, 1 H), 3.80 (s, 3 H); ESI-MS: m/z 316.9 (M+H)+.

compound 52

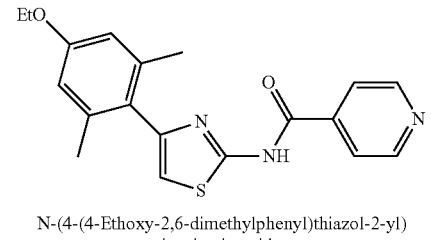

N-(4-(4-Ethoxy-2,6-dimethylphenyl)thiazol-2-yl) isonicotinamide

Yield: 88%; $^1$H NMR (500 MHz, CDCl$_3$) δ 8.70 (d, J=6.0 Hz, 2 H), 7.58 (d, J=6.0 Hz, 2 H), 6.78 (s, 1 H), 6.37 (s, 2 H), 3.95 (q, J=7.0 Hz, 2 H), 1.94 (s, 6 H), 1.41 (t, J=7.0 Hz, 3 H); ESI-MS: m/z 353.6 (M+H)+.

compound 53

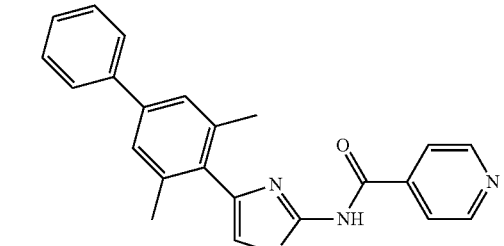

N-(4-(3,5-Dimethylbiphenyl-4-yl)thiazol-2-yl) isonicotinamide

Yield: 78%; ¹H NMR (500 MHz, CDCl₃) δ 8.58 (m, 2 H), 7.53-7.44 (m, 5 H), 7.37 (m, 1 H), 7.03 (s, 2 H), 6.86 (s, 1 H), 2.02 (s, 6 H); ESI-MS: m/z 385.7 (M+H)+.

compound 55

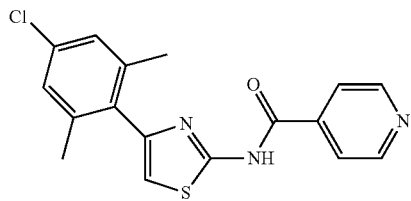

N-(4-(4-Chloro-2,6-dimethylphenyl)thiazol-2-yl)isonicotinamide

Yield: 89%; ¹H NMR (500 MHz, CDCl₃) δ 8.76 (d, J=6.0 Hz, 2 H), 7.57 (m, 2 H), 6.81 (m, 3 H), 1.92 (s, 6 H); ESI-MS: m/z 343.8 (M+H)+.

compound 56

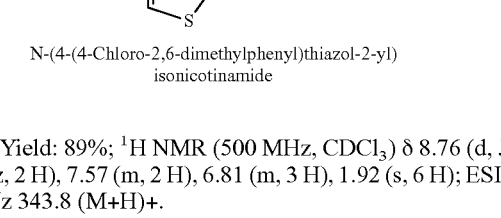

4-Cyano-N-(4-(4-hydroxyphenyl)thiazol-2-yl)benzamide

Yield: 38%; ¹H NMR (500 MHz, DMSO-d₆) δ 8.28 (d, 2 H), 8.09 (d, 2 H), 7.88 (d, 2 H), 7.31 (d, 2 H), 7.04-7.08 (m, 3 H); ESI-MS: m/z 322.0 (M+H)+.

compound 57

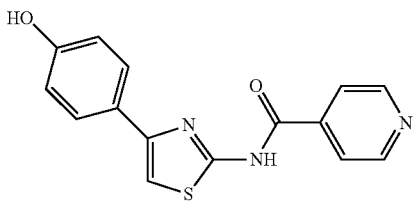

N-(4-(4-Hydroxyphenyl)thiazol-2-yl)isonicotinamide

Yield: 75%; ¹H NMR (500 MHz, DMSO-d₆) δ 8.89 (d, 2 H), 8.01-8.06 (m, 2 H), 7.89 (d, 2 H), 7.32 (d, 2 H), 7.05-7.09 (m, 3 H); ESI-MS: m/z 297.6 (M+H)+.

compound 58

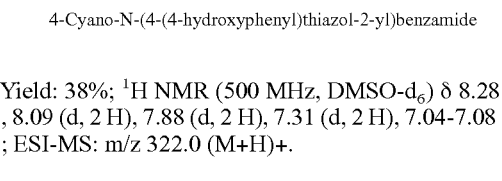

N-(4-(4-Hydroxyphenyl)thiazol-2-yl)pyrimidine-4-carboxamide

Yield: 48%; ¹H NMR (500 MHz, DMSO-d₆) δ 9.49 (s, 1 H), 9.18 (d, 1 H), 8.23 (d, 1 H), 7.86-7.91 (m, 2 H), 7.33 (d, 2 H), 7.06-7.09 (m, 3 H); ESI-MS: m/z 192.5 (M-106, aminothiazole).

compound 59

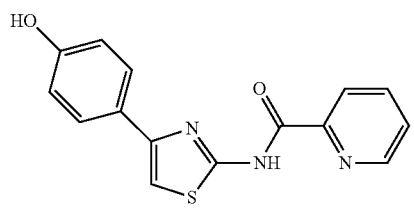

N-(4-(4-Hydroxyphenyl)thiazol-2-yl)picolinamide

Yield: 49%; ¹H NMR (500 MHz, DMSO-d₆) δ 8.82 (d, 1 H), 8.24 (d, 1 H), 8.07-8.10 (m, 1 H), 7.88 (d, 2 H), 7.73-7.75 (m, 1 H), 7.30 (d, 2 H), 7.05-7.08 (m, 3 H); ESI-MS: m/z 297.7 (M+H)+.

compound 60

N-(4-(4-Hydroxyphenyl)thiazol-2-yl)nicotinamide

Yield: 49%; ¹H NMR (500 MHz, DMSO-d₆) δ 9.26 (d, 1 H), 8.91 (d, 1 H), 8.47 (d, 1 H), 7.89 (d, 2 H), 7.65-7.67 (m, 1 H), 7.32 (d, 2 H), 7.05-7.08 (m, 3 H); ESI-MS: m/z 297.6 (M+H)+.

compound 61

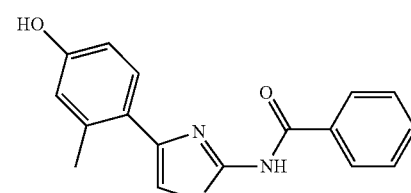

4-Cyano-N-(4-(4-hydroxy-2-methylphenyl)thiazol-2-yl)benzamide

Yield: 48%; ¹H NMR (500 MHz, DMSO-d₆) δ 8.24-8.30 (m, 2 H), 8.04-8.11 (m, 2 H), 7.63 (d, 1 H), 7.00-7.20 (m, 4 H), 6.67 (s, 1 H); ESI-MS: m/z 335.7 (M+H)+.

compound 62

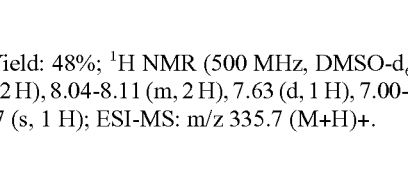

N-(4-(3,5-Difluoro-4-methoxyphenyl)thiazol-2-yl)isonicotinamide

Yield: 67%; ¹H NMR (DMSO-d₆, 500 MHz) δ 13.10 (s, 1 H), 8.82 (d, J=5.6 Hz, 2 H), 8.00 (d, J=5.6 Hz, 2 H), 7.88 (s, 1 H), 7.70-7.72 (m, 2 H), 3.96 (s, 3 H); ESI-MS m/z 348.0 (M+H)+.

compound 67

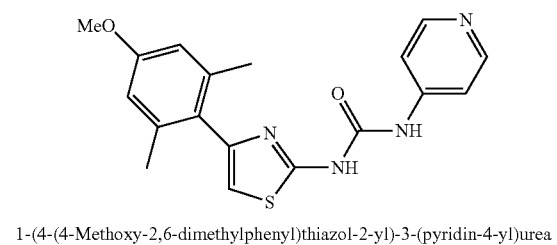

1-(4-(4-Methoxy-2,6-dimethylphenyl)thiazol-2-yl)-3-(pyridin-4-yl)urea

Yield: 40%; $^1$H NMR (500 MHz, DMSO-d$_6$) δ 10.49 (bs, 1 H), 8.54 (d, J=6.5 Hz, 2 H), 7.94 (s, 2 H), 6.88 (s, 1 H), 6.74 (s, 2 H), 3.76 (s, 3 H), 2.10 (s, 6 H); ESI-MS: m/z 354.8 (M+H)+.

compound 68

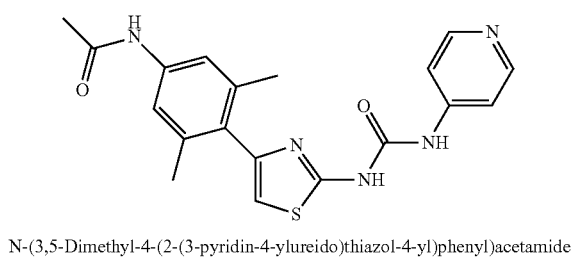

N-(3,5-Dimethyl-4-(2-(3-pyridin-4-ylureido)thiazol-4-yl)phenyl)acetamide

Yield: 73%; $^1$H NMR (500 MHz, DMSO-d$_6$) δ 9.87 (s, 1 H), 9.40 (s, 1 H), 8.39 (d, J=6.0 Hz, 2 H), 7.49 (d, J=6.5 Hz, 2 H), 7.32 (s, 2 H), 6.92 (s, 1 H), 2.06 (s, 6 H), 2.04 (s, 3 H); ESI-MS: m/z 381.8 (M+H)+.

compound 73

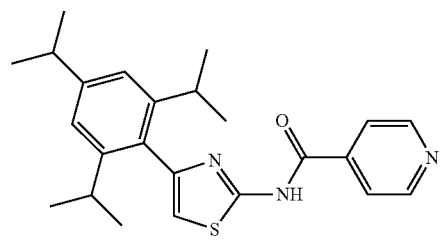

N-(4-(2,4,6-Triisopropylphenyl)thiazol-2-yl)isonicotinamide

Yield: 62%; $^1$H NMR (500 MHz, CDCl$_3$) δ 8.83 (d, J=5.5 Hz, 2 H), 7.83 (d, J=6.0 Hz, 2H), 7.06 (s, 2 H), 6.82 (s, 1 H), 2.94 (m, 1 H), 2.64 (m, 2 H), 1.29 (d, J=7.0 Hz, 6 H), 1.13 (d, J=7.0 Hz, 12 H); ESI-MS: m/z 407.9 (M+H)+.

compound 74

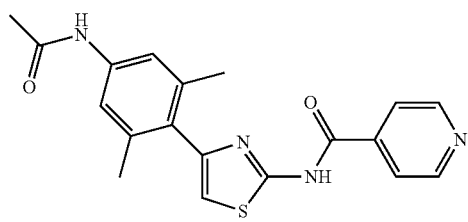

N-(4-(4-Acetamido-2,6-dimethylphenyl)thiazol-2-yl)isonicotinamide

Yield: 39%; $^1$H NMR (500 MHz, DMSO-d$_6$) δ 13.03 (bs, 1 H), 9.86 (s, 1 H), 8.80 (d, J=5.5 Hz, 2 H), 7.99 (d, J=5.5 Hz, 2 H), 7.34 (s, 2 H), 7.13 (s, 1 H), 2.06 (s, 6 H); ESI-MS: m/z 385.7 (M+H)+.

compound 77

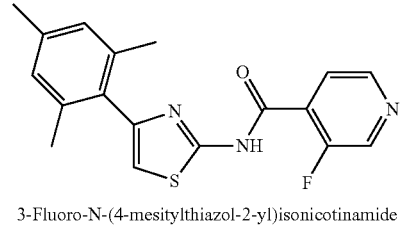

3-Fluoro-N-(4-mesitylthiazol-2-yl)isonicotinamide

Yield: 23%; $^1$H NMR (500 MHz, CDCl$_3$) δ 11.32 (bs, 1 H), 8.57 (m, 2 H), 7.80 (t, J=5.5 Hz, 1 H), 6.80 (s, 1 H), 6.71 (s, 2 H), 2.23 (s, 3 H), 1.96 (s, 6 H); ESI-MS: m/z 341.9 (M+H)+.

compound 78

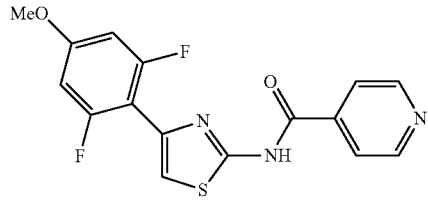

N-(4-(2,6-Difluoro-4-methoxyphenyl)thiazol-2-yl)isonicotinamide

Yield: 49%; $^1$H NMR (DMSO-d$_6$, 500 MHz) δ 13.13 (s, 1 H), 8.81 (d, J=5.9 Hz, 2 H), 8.00 (d, J=5.9 Hz, 2 H), 7.46 (s, 1 H), 6.86-6.88 (m, 2 H), 3.83 (s, 3 H); ESI-MS: m/z 348.7 (M+H)+.

compound 79

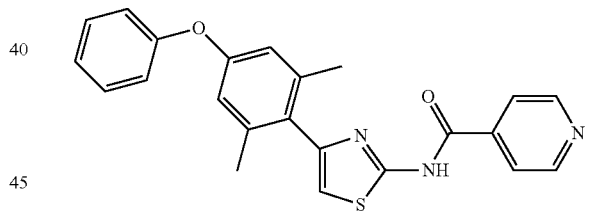

N-(4-(2,6-Dimethyl-4-phenoxyphenyl)thiazol-2-yl)isonicotinamide

Yield: 30%; $^1$H NMR (500 MHz, CDCl$_3$) δ 8.81 (d, J=5.5 Hz, 2 H), 7.99 (d, J=5.5 Hz, 2 H), 7.41 (t, J=8.0 Hz, 2 H), 7.19 (s, 1 H), 7.15 (t, J=7.5 Hz, 1 H), 7.04 (d, J=8.2 Hz, 2 H), 6.78 (s, 2 H), 2.07 (s, 6 H); ESI-MS: m/z 401.8 (M+H)+.

compound 82

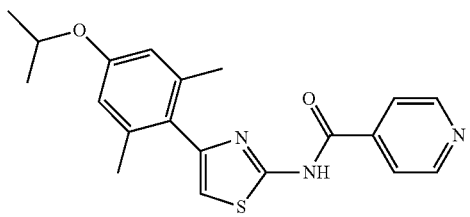

N-(4-(4-Isopropoxy-2,6-dimethylphenyl)thiazol-2-yl)isonicotinamide

Yield: 80%; ¹H NMR (500 MHz, CDCl₃) δ 8.67 (d, J=6.0 Hz, 2 H), 7.55 (d, J=6.0 Hz, 2 H), 6.77 (s, 1 H), 6.30 (s, 2 H), 4.43 (m, 1 H), 1.89 (s, 6 H), 1.31(d, J=6.0 Hz, 6 H); ESI-MS: m/z 368.1 (M+H)+.

compound 85

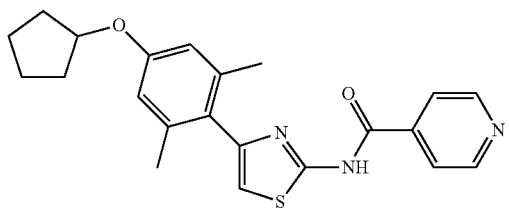

N-(4-(4-(Cyclopentyloxy)-2,6-dimethylphenyl)thiazol-2-yl)isonicotinamide

Yield: 62%; ¹H NMR (500 MHz, CDCl₃) δ 8.71 (d, J=6.0 Hz, 2 H), 7.60 (d, J=6.0 Hz, 2 H), 6.78 (s, 1 H), 6.37 (s, 2 H), 4.68 (m, 1 H), 1.95 (s, 6 H), 1.80-1.92 (m, 6 H), 0.85 (m, 2 H); ESI-MS: m/z 394.1 (M+H)+.

compound 94

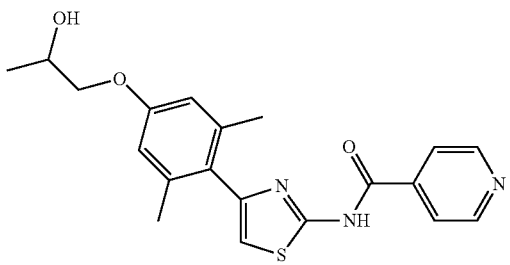

N-(4-(4-(2-Hydroxypropoxy)-2,6-dimethylphenyl)thiazol-2-yl)isonicotinamide

Yield: 4.0%; ¹H NMR (CDCl₃, 500 MHz) δ 8.80 (d, J=5.9 Hz, 2 H), 7.69 (d, J=5.9 Hz, 2H), 6.81 (s, 1 H), 6.55 (s, 2 H), 4.19-4.25 (brs, 1 H), 4.10-4.15 (m, 1 H), 3.91-3.98 (m, 1 H), 3.78-3.82 (m, 1 H), 2.05 (s, 6 H), 1.28 (s, 3 H); ESI-MS: m/z 384.7 (M+H)+.

compound 95

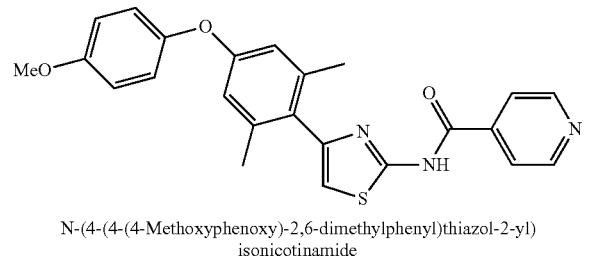

N-(4-(4-(4-Methoxyphenoxy)-2,6-dimethylphenyl)thiazol-2-yl)isonicotinamide

Yield: 95%; ¹H NMR (500 MHz, CDCl₃) δ 8.73 (m, 2 H), 7.62 (m, 2 H), 6.90-6.96 (m, 4 H), 6.80 (s, 1 H), 6.45 (s, 2 H), 3.83 (s, 3 H), 1.92 (s, 6 H); ESI-MS: m/z 431.7 (M+H)+.

compound 96

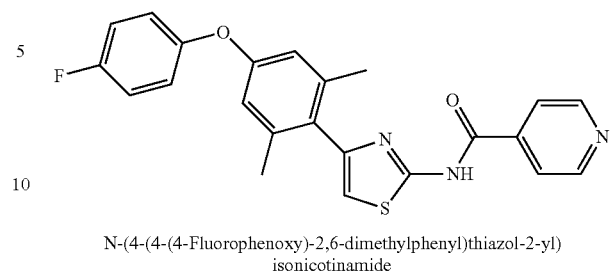

N-(4-(4-(4-Fluorophenoxy)-2,6-dimethylphenyl)thiazol-2-yl)isonicotinamide

Yield: 17%; ¹H NMR (500 MHz, CDCl₃) δ 8.72 (d, J=5.5 Hz, 2 H), 7.60 (d, J=5.5 Hz, 2 H), 7.04 (m, 2 H), 6.94 (m, 2 H), 6.81 (s, 1 H), 6.43 (s, 2 H), 1.92 (s, 6 H); ESI-MS: m/z 420.2 (M+H)+.

compound 97

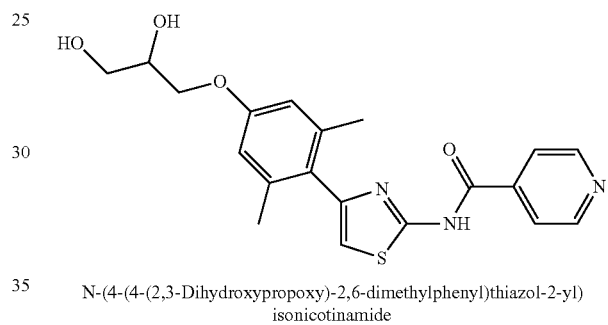

N-(4-(4-(2,3-Dihydroxypropoxy)-2,6-dimethylphenyl)thiazol-2-yl)isonicotinamide

Yield: 12%; ¹H NMR (DMSO-d₆, 500 MHz) δ 8.78 (d, J=4.5 Hz, 2 H), 7.98 (d, J=4.5 Hz, 2 H), 7.15 (s, 1 H), 6.69 (s, 2 H), 4.95-4.96 (m, 1 H), 4.68-4.69 (m, 1 H), 3.97-3.98 (m, 1 H), 3.84-3.85 (m, 1 H), 3.78-3.79 (m, 1 H), 2.06 (s, 6 H); ESI-MS: m/z 400.7 (M+H)+.

compound 100

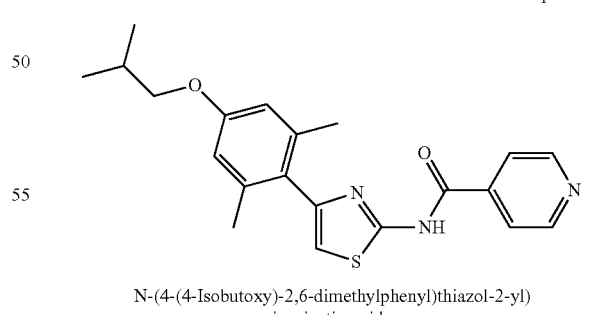

N-(4-(4-Isobutoxy)-2,6-dimethylphenyl)thiazol-2-yl)isonicotinamide

Yield: 99%; ¹H NMR (500 MHz, CDCl₃) δ 8.68 (d, J=6.0 Hz, 2 H), 7.56 (d, J=6.0 Hz, 2 H), 6.77 (s, 1 H), 6.33 (s, 2 H), 3.62 (d, J=6.5 Hz, 2 H), 2.08 (m, 1 H), 1.91 (s, 6 H), 1.05 (d, J=6.7 Hz, 6 H); ESI-MS: m/z 381.1 (M+H)+.

compound 101

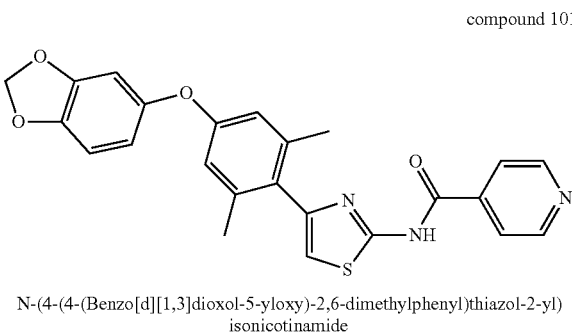 [SMILES: Cc1cc(Oc2ccc3c(c2)OCO3)cc(C)c1-c1csc(NC(=O)c2ccncc2)n1]

N-(4-(4-(Benzo[d][1,3]dioxol-5-yloxy)-2,6-dimethylphenyl)thiazol-2-yl)
isonicotinamide Yield: 92%; $^1$H NMR (500 MHz, CDCl$_3$) δ 8.73 (m, 2 H), 7.62 (m, 2 H), 6.81 (s, 1 H), 6.78 (d, J=8.5 Hz, 1 H), 6.43-6.52 (m, 4 H), 6.00 (s, 2 H), 1.93 (s, 6 H); ESI-MS: m/z 445.9 (M+H)+.

compound 108

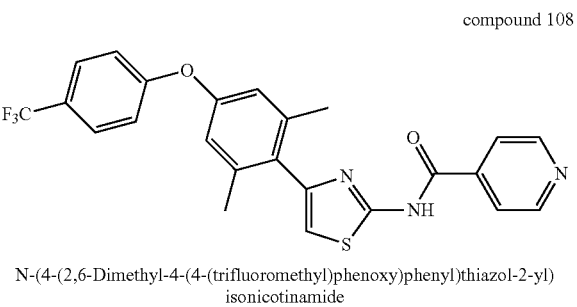 [SMILES: Cc1cc(Oc2ccc(C(F)(F)F)cc2)cc(C)c1-c1csc(NC(=O)c2ccncc2)n1]

N-(4-(2,6-Dimethyl-4-(4-(trifluoromethyl)phenoxy)phenyl)thiazol-2-yl)
isonicotinamide Yield: 87%; $^1$H NMR (500 MHz, CDCl$_3$) δ 8.76 (m, 2 H), 7.64 (m, 2 H), 7.58 (d, J=8.5 Hz, 2 H), 7.01 (d, J=8.5 Hz, 2 H), 6.86 (s, 1 H), 6.57 (s, 2 H), 1.98 (s, 6 H); ESI-MS: m/z 469.7 (M+H)+.

compound 102

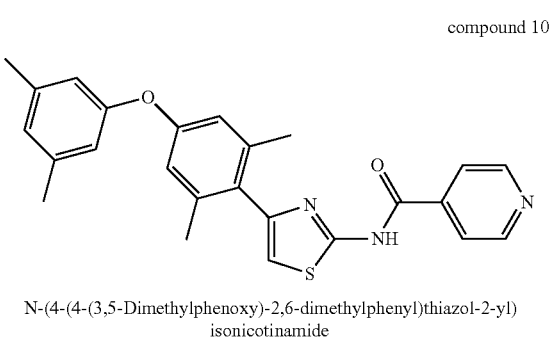

N-(4-(4-(3,5-Dimethylphenoxy)-2,6-dimethylphenyl)thiazol-2-yl)
isonicotinamide

Yield: 94%; $^1$H NMR (500 MHz, CDCl$_3$) δ 8.81 (d, J=5.1 Hz, 2 H), 7.78 (d, J=5.6 Hz, 2 H), 6.84 (s, 1 H), 6.78 (s, 1 H), 6.64 (s, 2 H), 6.61 (s, 2 H), 2.31 (s, 6 H), 2.02 (s, 6 H); ESI-MS: m/z 429.8 (M+H)+.

compound 111

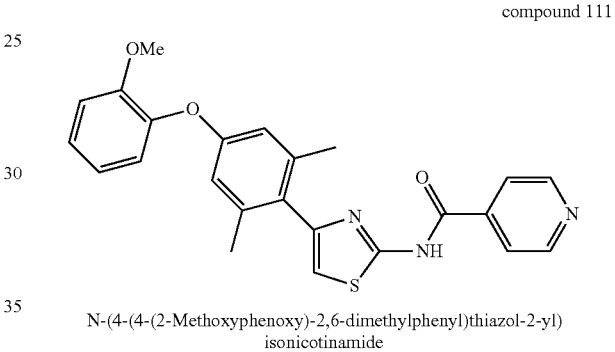

N-(4-(4-(2-Methoxyphenoxy)-2,6-dimethylphenyl)thiazol-2-yl)
isonicotinamide

Yield: 85%; $^1$H NMR (500 MHz, DMSO-d$_6$) δ 8.80-8.81 (m, 2 H), 7.98-7.99 (m, 2 H), 7.16-7.21 (m, 3 H), 6.99-7.06 (m, 2 H), 6.59 (s, 2 H), 3.76 (s, 3 H), 2.03 (s, 6 H); ESI-MS: m/z 431.5 [M+H]+.

compound 107

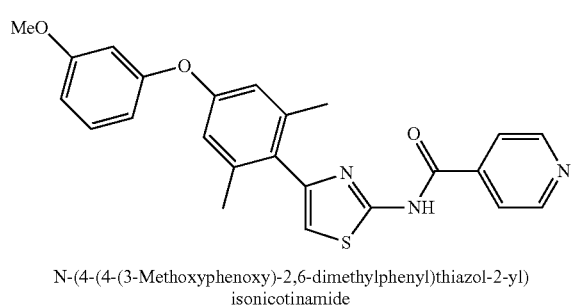

N-(4-(4-(3-Methoxyphenoxy)-2,6-dimethylphenyl)thiazol-2-yl)
isonicotinamide

Yield: 51%; $^1$H NMR (500 MHz, CDCl$_3$) δ 8.75 (m, 2 H), 7.62 (m, 2 H), 7.25 (m, 1 H), 6.82 (s, 1 H), 6.69 (m, 1 H), 6.56 (d, 1 H), 6.51 (m, 2 H), 6.47 (s, 2 H), 3.81 (s, 3 H), 1.94 (s, 6 H); ESI-MS: m/z 431.6 (M+H)+.

compound 112

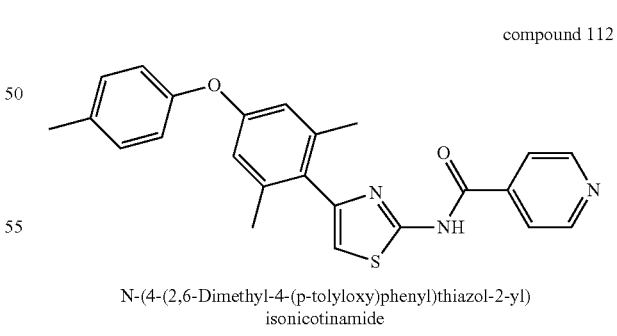

N-(4-(2,6-Dimethyl-4-(p-tolyloxy)phenyl)thiazol-2-yl)
isonicotinamide

Yield: 89%; $^1$H NMR (500 MHz, DMSO-d$_6$) δ 8.80-8.81 (m, 2 H), 7.98-7.99 (m, 2 H), 7.18-7.22 (m, 3 H), 6.94-6.95 (m, 2 H), 6.73 (s, 2 H), 2.30 (s, 3 H), 2.06 (s, 6 H); ESI-MS: m/z 414.9 [M−H]−.

compound 113

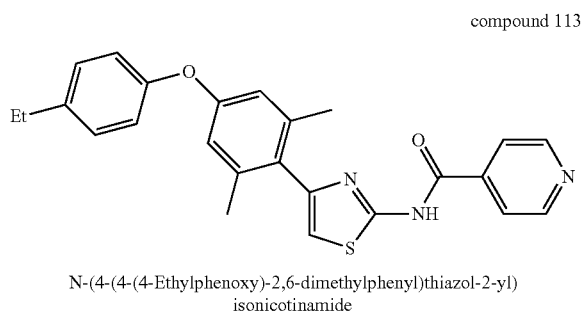 [SMILES: CCc1ccc(Oc2cc(C)c(-c3csc(NC(=O)c4ccncc4)n3)c(C)c2)cc1]

N-(4-(4-(4-Ethylphenoxy)-2,6-dimethylphenyl)thiazol-2-yl)
isonicotinamide

Yield: 91%; $^1$H NMR (500 MHz, CDCl$_3$) δ 8.78 (d, J=6.0 Hz, 2 H), 8.67 (m, 2 H), 7.18 (d, J=8.0 Hz, 2 H), 6.93 (d, J=8.5 Hz, 2 H), 6.83 (s, 1 H), 6.56 (s, 2 H), 2.65 (m, 2 H), 1.98 (s, 6 H), 1.26 (t, J=7.5 Hz, 3 H); ESI-MS: m/z 429.6 (M+H)+.

compound 114

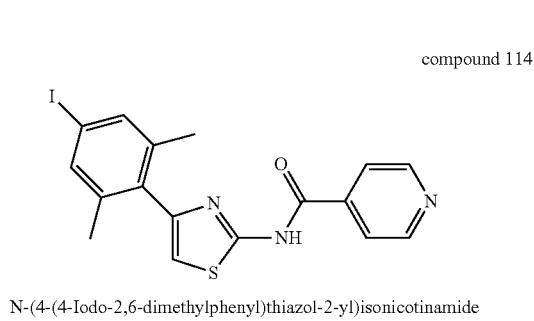 [SMILES: Cc1cc(I)cc(C)c1-c1csc(NC(=O)c2ccncc2)n1]

N-(4-(4-Iodo-2,6-dimethylphenyl)thiazol-2-yl)isonicotinamide

Yield: 61%; $^1$H NMR (500 MHz, CDCl$_3$) δ 8.76 (m, 2 H), 7.52 (m, 2 H), 7.11 (s, 2 H), 6.80 (s, 1 H), 1.84 (s, 6 H); ESI-MS: m/z 435.6 (M+H)+.

compound 115

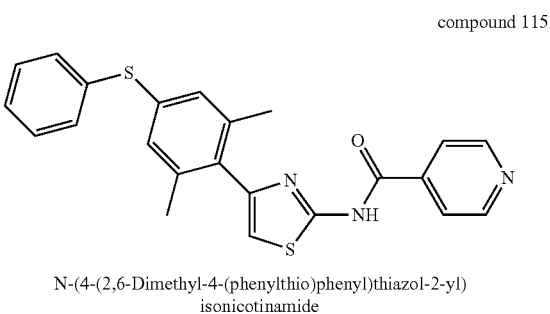 [SMILES: Cc1cc(Sc2ccccc2)cc(C)c1-c1csc(NC(=O)c2ccncc2)n1]

N-(4-(2,6-Dimethyl-4-(phenylthio)phenyl)thiazol-2-yl)
isonicotinamide

Yield: 63%; $^1$H NMR (DMSO-d$_6$, 500 MHz) δ 8.77 (d, J=5.4 Hz, 2 H), 7.98 (d, J=5.4 Hz, 2 H), 7.38-7.40 (m, 2 H), 7.31-7.35 (m, 3 H), 7.11 (s, 3 H), 2.07 (s, 6 H); ESI-MS: m/z 418.8 (M+H)+.

compound 116

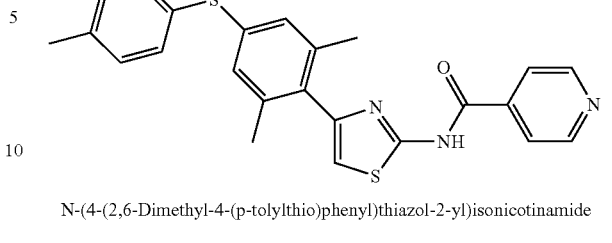

N-(4-(2,6-Dimethyl-4-(p-tolylthio)phenyl)thiazol-2-yl)isonicotinamide

Yield: 84%; $^1$H NMR (DMSO-d$_6$, 500 MHz) δ 8.78 (d, J=5.2 Hz, 2 H), 7.98 (d, J=5.2 Hz, 2 H), 7.30 (d, J=8.0 Hz, 2 H), 7.23 (d, J=8.0 Hz, 2 H), 7.10 (s, 1 H), 7.02 (s, 2 H), 2.36 (s, 3 H), 2.04 (s, 6 H); ESI-MS: m/z 432.5 (M+H)+.

compound 117

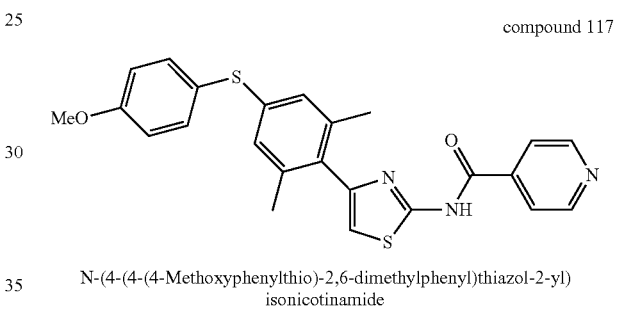

N-(4-(4-(4-Methoxyphenylthio)-2,6-dimethylphenyl)thiazol-2-yl)
isonicotinamide

Yield: 64%; $^1$H NMR (DMSO-d$_6$, 500 MHz) δ 8.79 (d, J=5.0 Hz, 2 H), 7.98 (d, J=5.0 Hz, 2 H), 7.43 (d, J=8.4 Hz, 2 H), 7.12 (s, 1 H), 7.02 (d, J=8.4 Hz, 2 H), 6.92 (s, 2 H), 3.79 (s, 3 H), 2.02 (s, 6 H); ESI-MS: m/z 448.1 (M+H)+.

compound 121

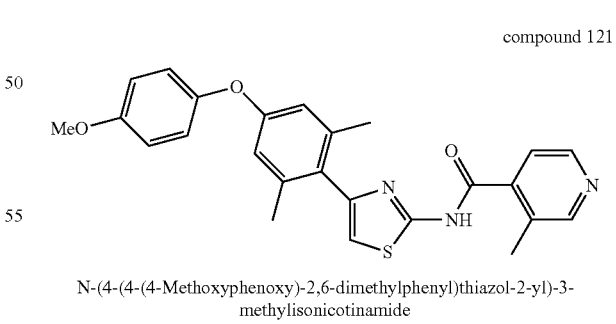

N-(4-(4-(4-Methoxyphenoxy)-2,6-dimethylphenyl)thiazol-2-yl)-3-
methylisonicotinamide Yield: 62%; $^1$H NMR (500 MHz, DMSO-d$_6$) δ 12.8 (s, 1 H), 8.54-8.58 (m, 2 H), 7.55-7.56 (m, 1 H), 7.14 (s, 1 H), 6.96-7.03 (m, 4 H), 6.67 (s, 2 H), 3.76 (s, 3 H), 2.40 (s, 3 H), 2.05 (s, 6 H); ESI-MS: m/z 445.7 [M+H]+.

compound 122

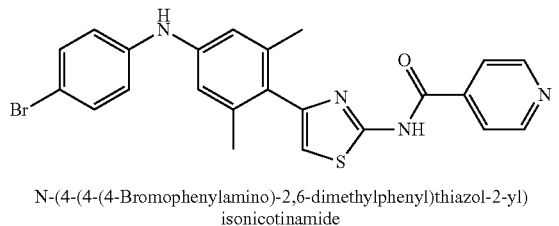

N-(4-(4-(4-Bromophenylamino)-2,6-dimethylphenyl)thiazol-2-yl)isonicotinamide

Yield: 60%; $^1$H NMR (500 MHz, CDCl$_3$) δ 8.79 (d, J=4.5 Hz, 2 H), 7.85 (d, J=4.5 Hz, 2 H), 7.39 (d, J=8.6 Hz, 2 H), 6.97 (d, J=8.6 Hz, 2 H), 6.83 (s, 1 H), 2.05 (s, 6 H); ESI-MS: m/z 479.2 (M+H)+.

compound 123

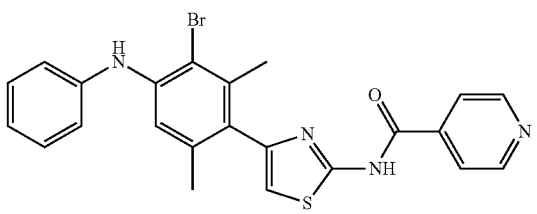

N-(4-(3-Bromo-2,6-dimethyl-4-(phenylamino)phenyl)thiazol-2-yl)isonicotinamide

Yield: 58%; $^1$H NMR (500 MHz, CDCl$_3$) δ 8.87 (d, J=4.5 Hz, 2 H), 8.02 (d, J=4.5 Hz, 2 H), 7.47 (d, J=8.6 Hz, 2 H), 7.08 (d, J=8.6 Hz, 2 H), 6.89 (s, 1 H), 6.85 (s, 1 H), 6.24 (s, 1 H), 2.04 (s, 6 H); ESI-MS: m/z 479.3 (M+H)+.

compound 124

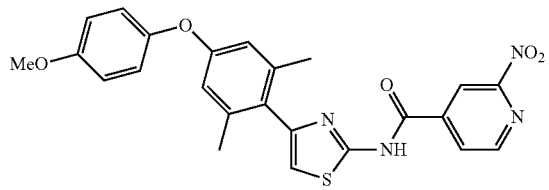

N-(4-(4-(4-Methoxyphenoxy)-2,6-dimethylphenyl)thiazol-2-yl)-2-nitroisonicotinamide Yield: 94%; $^1$H NMR (500 MHz, DMSO-d$_6$) δ 8.82 (s, 1 H), 8.71-8.72 (m, 1 H), 8.39-8.40 (m, 1 H), 7.01-7.03 (m, 2 H), 6.96-6.99 (m, 2 H), 6.64-6.67 (m, 3 H), 3.75 (s, 3 H), 2.03 (s, 6 H); ESI-MS: m/z 476.8 [M+H]+.

compound 125

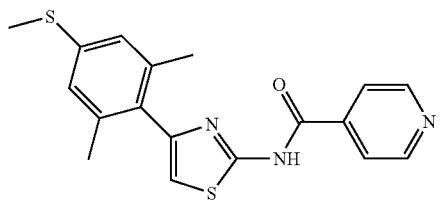

N-(4-(2,6-Dimethyl-4-(methylthio)phenyl)thiazol-2-yl)isonicotinamide

Yield: 94%; $^1$H NMR (500 MHz, CDCl$_3$) δ 8.66-8.68 (m, 2 H), 7.49-7.50 (m, 2 H), 6.77 (s, 1 H), 6.57 (s, 2 H), 2.42 (s, 3 H), 1.87 (s, 6 H); ESI-MS: m/z 355.6 (M+H)+.

compound 127

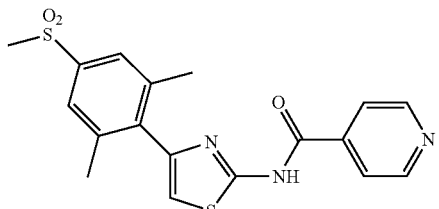

N-(4-(2,6-Dimethyl-4-(methylsulfonyl)phenyl)thiazol-2-yl)isonicotinamide

Yield: 39%; $^1$H NMR (500 MHz, CDCl$_3$) δ 8.80-8.81 (m, 2 H), 7.98-8.00 (m, 2 H), 7.70 (s, 2 H), 7.30 (s, 1 H), 3.30 (s, 1 H), 2.20 (s, 6 H); ESI-MS: m/z 387.6 (M+H)+.

compound 129

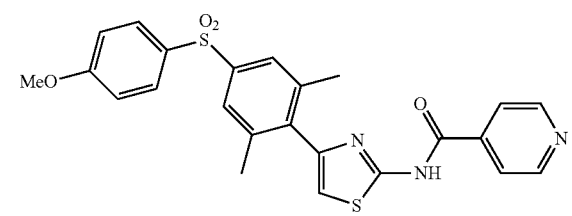

N-(4-(4-(4-Methoxyphenylsulfonyl)-2,6-dimethylphenyl)thiazol-2yl)isonicotinamide Yield: 61%; $^1$H NMR (DMSO-d$_6$, 500 MHz) δ 8.79 (s, 2 H), 7.97 (d, J=6.0 Hz, 2 H), 7.91 (d, J=8.9 Hz, 2 H), 7.69 (s, 2 H), 7.27 (s, 1 H), 7.15 (d, J=8.9 Hz, 2 H), 3.84 (s, 3 H), 2.16 (s, 6 H); ESI-MS: m/z 480.6 (M+H)+.

compound 130

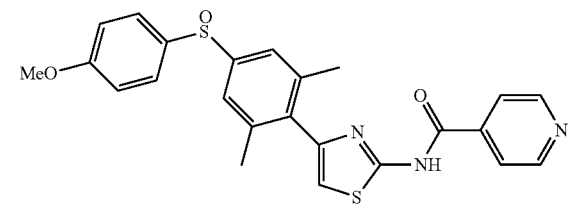

N-(4-(4-(4-Methoxyphenylsulfinyl)-2,6-dimethylphenyl)thiazol-2-yl)isonicotinamide Yield: 43%; $^1$H NMR (DMSO-d$_6$, 500 MHz) δ 13.1 (brs, 1 H), 8.80 (d, J=6.0 Hz, 2 H), 7.97 (d, J=6.0 Hz, 2 H), 7.66 (d, J=8.8 Hz, 2 H), 7.42 (s, 2 H), 7.23 (s, 1 H), 7.10 (d, J=8.8 Hz, 2 H), 3.80 (s, 3 H), 2.13 (s, 6 H); ESI-MS: m/z 464.7 (M+H)+.

compound 131

N-(4-(4-(4-methoxyphenoxy)-2,6-dimethylphenyl)thiazol-2-yl)isonicotinamide

Yield: 24%; ¹H NMR (500 MHz, CDCl₃) δ 8.80 (s, 2 H), 7.70 (d, J=5.1 Hz, 2 H), 6.97 (m, 2 H), 6.92 (m, 3 H), 6.70 (d, J=2.4 Hz, 1 H), 6.61 (d, J=2.3, 1 H), 3.83 (s, 3 H), 2.02 (s, 3 H); ESI-MS: m/z 452.4 (M+H)+.

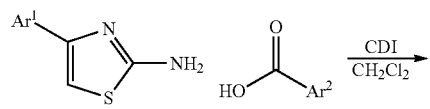

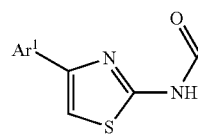

General Procedure II for the Synthesis of 4-Aryl-2-amidothiazoles. To a suspension of arylcarboxylic acid (1.5 equiv) in dichloromethane was added 1,1'-carbonyldiimidazole (CDI, 3.0 equiv). After being stirred at room temperature for 2.0 h, the solution was added with 4-arylthiazol-2-amine (q.0 equiv). The reaction mixture was stirred at room temperature overnight. The solution was concentrated and the residue was re-dissolved in dichloromethane. The solution was washed with brine, dried over MgSO₄, and concentrated under reduced pressure to give the corresponding 4-aryl-2-amidothiazoles.

compound 1

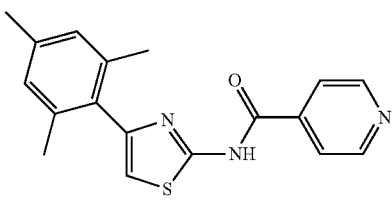

N-(4-Mesitylthiazol-2-yl)isonicotinamide

Yield: 77%; ¹H NMR (500 MHz, CD₃OD) δ 8.75-8.76 (m, 2 H), 7.96-7.99 (m, 2 H), 6.90-6.92 (m, 3 H), 2.29 (s, 3 H), 2.08 (s, 6 H); ESI-MS: m/z 324.0 [M+H]+.

compound 2

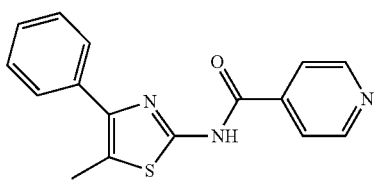

N-(5-Methyl-4-phenylthiazol-2-yl)isonicotinamide

Yield: 77%; ¹H NMR (500 MHz, CDCl₃) δ 11.7 (s, 1 H), 8.61-8.62 (m, 2 H), 7.51-7.53 (m, 2 H), 7.41-7.43 (m, 2 H), 7.26-7.30 (m, 2 H), 7.20-7.22 (m, 1 H), 2.54 (s, 3 H); ESI-MS: m/z 295.3 [M+H]+.

compound 3

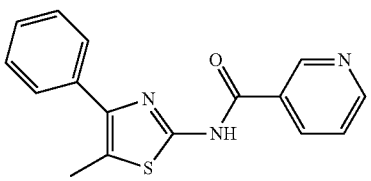

N-(5-Methyl-4-phenylthiazol-2-yl)nicotinamide

Yield: 15%; ¹H NMR (500 MHz, CDCl₃) δ 11.7 (s, 1 H), 9.03 (s, 1 H), 8.68-8.69 (m, 1 H), 8.06-8.08 (m, 1 H), 7.45-7.47 (m, 2 H), 7.22-7.31 (m, 4 H), 2.54 (s, 3 H); ESI-MS: m/z 295.9 [M+H]+.

compound 10

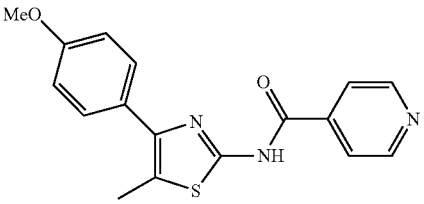

N-(4-(4-Methoxyphenyl)-5-methylthiazol-2-yl)isonicotinamide

Yield: 12%; ¹H NMR (500 MHz, DMSO-d₆) δ 12.9 (s, 1 H), 8.80-8.81 (m, 2 H), 7.99-8.00 (m, 2 H), 7.61-7.63 (m, 2 H), 7.02-7.04 (m, 2 H), 3.80 (s, 3 H), 2.49 (s, 3 H); ESI-MS: m/z 326.0 [M+H]+.

compound 11

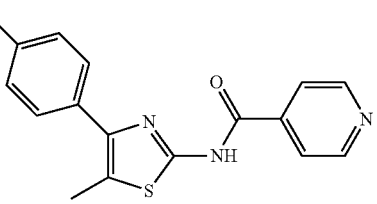

N-(4-(2,4,6-Trimethoxyphenyl)thiazol-2-yl)isonicotinamide

Yield: 12%; ¹H NMR (500 MHz, DMSO-d₆) δ 13.0 (s, 1 H), 8.78 (s, 2 H), 7.98-8.00 (m, 2 H), 6.98 (s, 1 H), 6.29 (s, 2 H), 3.82 (s, 3 H), 3.68 (s, 3 H); ESI-MS: m/z 369.9 [M−H]−.

compound 12

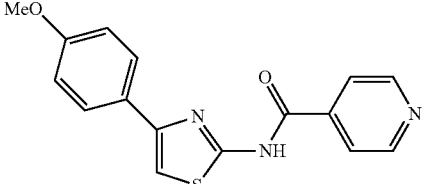

N-(4-(4-Methoxyphenyl)thiazol-2-yl)isonicotinamide

Yield: 50%; ¹H NMR (500 MHz, CDCl₃) δ 11.7 (s, 1 H), 8.61-8.62 (m, 2 H), 7.51-7.53 (m, 2 H), 7.41-7.43 (m, 2 H), 7.26-7.30 (m, 2 H), 7.20-7.22 (m, 1 H), 2.54 (s, 3 H); ESI-MS: m/z 310.1 [M−H]−.

compound 13

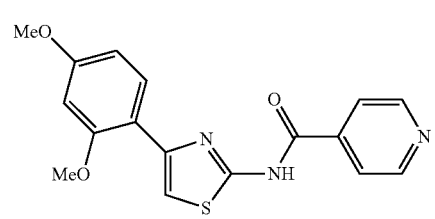

N-(4-(2,4-Dimethoxyphenyl)thiazol-2-yl)isonicotinamide

Yield: 10%; ¹H NMR (500 MHz, DMSO-d$_6$) δ 12.97 (s, 1 H), 8.81-8.82 (m, 2 H), 8.00-8.07 (m, 3 H), 7.59 (s, 1 H), 6.64-6.68 (m, 2 H), 3.92 (s, 3 H), 3.81 (s, 3 H); ESI-MS: m/z 340.3 [M−H]−.

compound 54

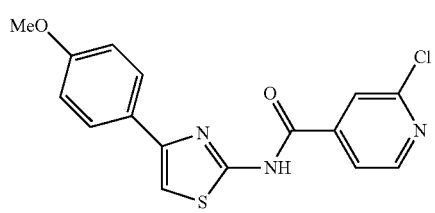

2-Chloro-N-(4-(4-Methoxyphenyl)thiazol-2-yl)isonicotinamide

Yield: 95%; ¹H NMR (500 MHz, CDCl$_3$) δ 8.33-8.34 (m, 1 H), 7.47-7.54 (m, 4 H), 7.11 (s, 1 H), 6.79-6.80 (m, 2 H), 3.81 (s, 3 H); ESI-MS: m/z 345.7 [M+H]+.

compound 63

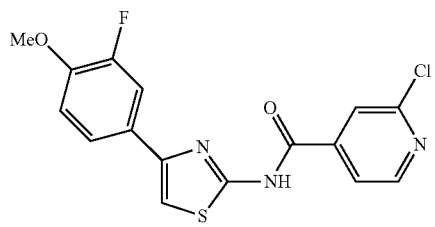

2-Chloro-N-(4-(3-fluoro-4-methoxyphenyl)thiazol-2-yl)isonicotinamide

Yield: 83%; ¹H NMR (500 MHz, CDCl$_3$) δ 8.52-8.53 (m, 1 H), 7.69-7.70 (m, 1 H), 7.59-7.60 (m, 1 H), 7.28-7.47 (m, 2 H), 7.16 (s, 1 H), 6.93-6.97 (m, 1 H), 3.93 (s, 3 H); ESI-MS: m/z 363.7 [M+H]+.

compound 64

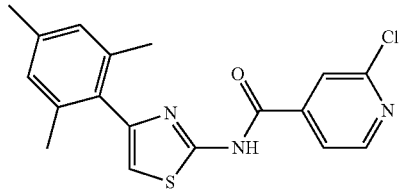

2-Chloro-N-(4-mesitylthiazol-2-yl)isonicotinamide

Yield: 87%; ¹H NMR (500 MHz, CDCl$_3$) δ 8.49-8.50 (m, 1 H), 7.74 (m, 1 H), 7.62 (m, 1 H), 6.83 (s, 1 H), 6.72 (m, 2 H), 2.26 (s, 3 H), 1.97 (s, 6 H); ESI-MS: m/z 357.7 [M+H]+.

compound 65

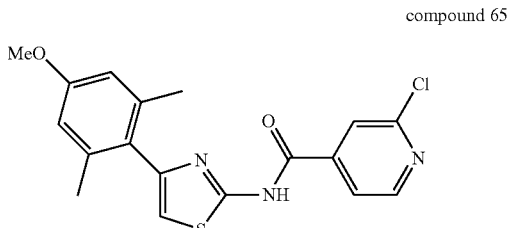

2-Chloro-N-(4-(4-methoxy-2,6-dimethylphenyl)thiazol-2-yl)isonicotinamide

Yield: 63%; ¹H NMR (500 MHz, CDCl$_3$) δ 8.60-8.61 (m, 1 H), 7.91-7.96 (m, 2 H), 6.87 (s, 1 H), 6.58 (m, 2 H), 3.81 (s, 3 H), 2.11 (s, 6 H); ESI-MS: m/z 373.9 [M+H]+.

compound 66

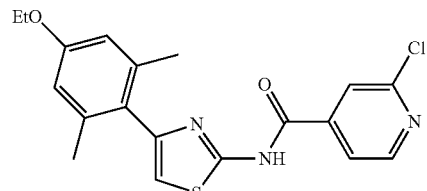

2-Chloro-N-(4-(4-ethoxy-2,6-dimethylphenyl)thiazol-2-yl)isonicotinamide

Yield: 95%; ¹H NMR (500 MHz, CDCl$_3$) δ 8.53-8.54 (m, 1 H), 7.74-7.84 (m, 2 H), 6.83 (s, 1 H), 6.48 (m, 2 H), 3.98-4.02 (m, 2 H), 2.01 (s, 6 H), 1.41-1.44 (m, 3 H); ESI-MS: m/z 387.9 [M+H]+.

compound 69

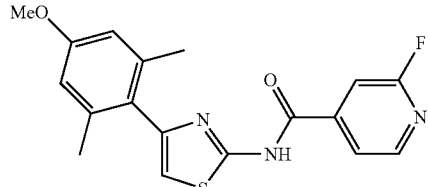

2-Fluoro-N-(4-(4-methoxy-2,6-dimethylphenyl)thiazol-2-yl)isonicotinamide

Yield: 68%; ¹H NMR (500 MHz, CDCl$_3$) δ 8.36-8.38 (m, 1 H), 7.72 (s, 1 H), 7.42 (s, 1 H), 6.84 (s, 1 H), 6.48 (s, 2 H), 3.78 (s, 3 H), 2.03 (s, 6 H); ESI-MS: m/z 357.5 [M+H]+.

compound 70

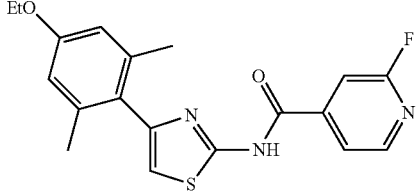

N-(4-(4-Ethoxy-2,6-dimethylphenyl)thiazol-2-yl)-2-fluoroisonicotinamide

Yield: 94%; ¹H NMR (500 MHz, CDCl₃) δ 8.39-8.40 (m, 1 H), 7.78 (s, 1 H), 7.48 (s, 1 H), 6.85 (s, 1 H), 6.50 (s, 2 H), 3.98-4.01 (q, 2 H), 2.05(s, 6 H), 1.42-1.44 (t, 3 H); ESI-MS: m/z 371.8 [M+H]+.

compound 71

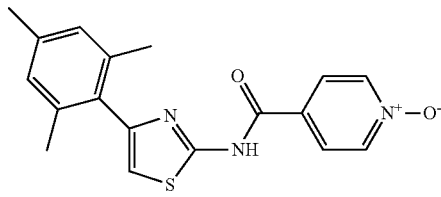

4-(4-Mesitylthiazol-2-ylcarbamoyl)pyridine 1-oxide

Yield: 75%; ¹H NMR (500 MHz, CDCl₃) δ 8.15-8.16 (d, 2 H), 7.78-7.79 (d, 2 H), 6.83 (s, 1 H), 6.80 (s, 2 H), 2.23 (s, 3 H), 2.01 (s, 6 H); ESI-MS: m/z 340.1 [M+H]+.

compound 72

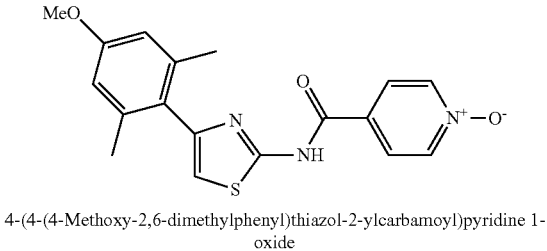

4-(4-(4-Methoxy-2,6-dimethylphenyl)thiazol-2-ylcarbamoyl)pyridine 1-oxide

Yield: 43%; ¹H NMR (500 MHz, CDCl₃) δ 8.23 (s, 2 H), 8.04 (s, 2 H), 6.85 (s, 1 H), 6.60 (s, 2 H), 3.80 (s, 3 H), 2.12 (s, 6 H); ESI-MS: m/z 355.8 [M+H]+.

compound 75

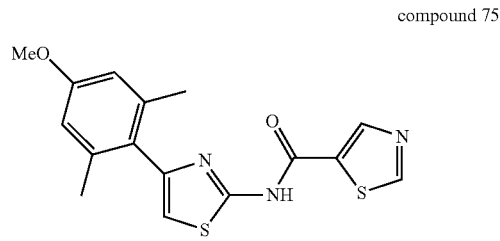

N-(4-(4-Methoxy-2,6-dimethylphenyl)thiazol-2-yl)thiazole-5-carboxamide

Yield: 18%; ¹H NMR (500 MHz, CDCl₃) δ 9.01 (s, 1 H), 8.66 (s, 1 H), 6.82 (s, 1 H), 6.59 (s, 2 H), 3.81 (s, 3 H), 2.13 (s, 6 H); ESI-MS: m/z 345.6 [M+H]+.

compound 76

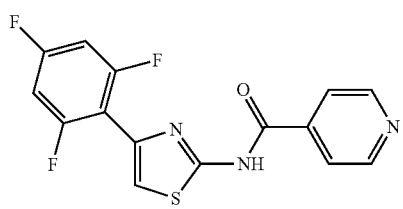

N-(4-(2,4,6-Trifluorophenyl)thiazol-2-yl)isonicotinamide

Yield: 46%; ¹H NMR (500 MHz, CDCl₃) δ 8.78-8.79 (m, 2 H), 7.73-7.74 (m, 2 H), 7.26-7.28 (m, 1 H), 6.76-6.79 (m, 1 H), 6.67-6.70 (m, 2 H); ESI-MS: m/z 335.5 [M+H]+.

compound 80

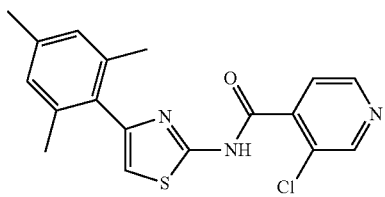

3-Chloro-N-(4-mesitylthiazol-2-yl)isonicotinamide

Yield: 21%; ¹H NMR (500 MHz, CDCl₃) δ 8.68 (s, 1 H), 8.59-8.60 (m, 1 H), 7.54-7.55 (m, 1 H), 6.81-6.83 (m, 2 H), 2.30 (s, 3 H), 2.01 (s, 6 H); ESI-MS: m/z 357.8 [M+H]+.

compound 81

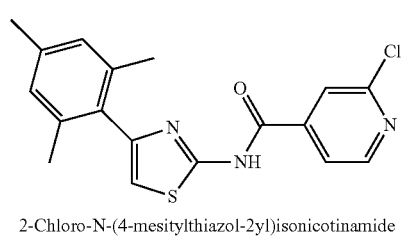

2-Chloro-N-(4-mesitylthiazol-2yl)isonicotinamide

Yield: 42%; ¹H NMR (500 MHz, DMSO-d₆) δ 8.63-8.64 (m, 1 H), 8.11 (s, 1 H), 7.98-7.99 (m, 1 H), 7.12 (s, 1 H), 6.93 (m, 2 H), 2.50 (s, 3 H), 2.05 (s, 6 H); ESI-MS: m/z 357.9 [M+H]+.

compound 86

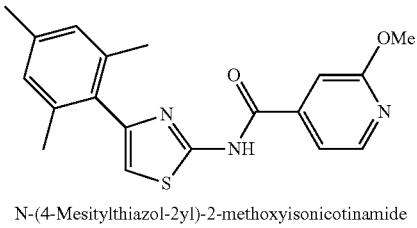

N-(4-Mesitylthiazol-2yl)-2-methoxyisonicotinamide

Yield: 40%; ¹H NMR (500 MHz, CDCl₃) δ 8.38-8.39 (m, 1 H), 7.55-7.56 (m, 1 H), 7.41 (s, 1 H), 6.91-6.93 (m, 2 H), 6.86 (s, 1 H), 5.30 (s, 1 H), 4.00 (s, 3 H), 2.32 (s, 3 H), 2.12 (s, 6 H); ESI-MS: m/z 355.0 [M+H]+.

compound 87

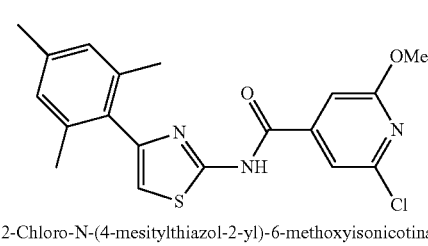

2-Chloro-N-(4-mesitylthiazol-2-yl)-6-methoxyisonicotinamide

Yield: 63%; ¹H NMR (500 MHz, CDCl₃) δ 7.31 (s, 1 H), 7.06 (s, 1 H), 6.81 (s, 1 H), 6.76 (s, 2 H), 4.00 (s, 3 H), 2.32 (s, 3 H), 1.98 (s, 6 H); ESI-MS: m/z 387.9 [M+H]+.

compound 88

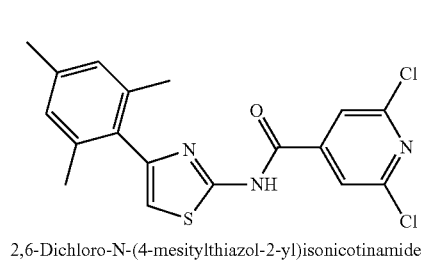

2,6-Dichloro-N-(4-mesitylthiazol-2-yl)isonicotinamide

Yield: 70%; ¹H¹H NMR (500 MHz, CDCl₃) δ 7.61 (s, 2 H), 6.80 (s, 1 H), 6.73 (s, 2 H), 2.29 (s, 3 H), 1.94 (s, 6 H); ESI-MS: m/z 392.0 [M+H]+.

compound 89

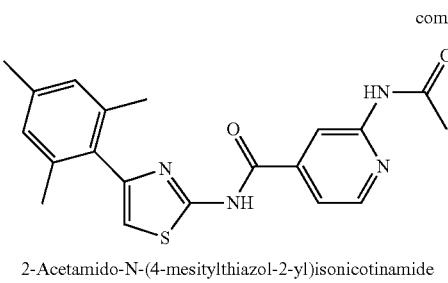

2-Acetamido-N-(4-mesitylthiazol-2-yl)isonicotinamide

Yield: 61%; ¹H¹H-NMR (500 MHz, CDCl₃) δ 8.81 (s, 1 H), 8.37 (s, 1 H), 7.80-7.77 (m, 1 H), 6.91 (s, 2 H), 6.80 (s, 1 H), 2.30 (s, 3 H), 2.26 (s, 3 H), 2.11 (s, 6 H); ESI-MS: m/z 381.2 [M+H]+.

compound 90

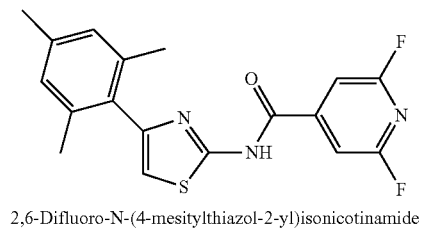

2,6-Difluoro-N-(4-mesitylthiazol-2-yl)isonicotinamide

Yield: 67%; ¹H¹H-NMR (500 MHz, CDCl₃) δ 7.11 (s, 2 H), 6.81 (s, 1 H), 6.68 (s, 1 H), 2.30 (s, 3 H), 1.91 (s, 6 H); ESI-MS: m/z 360.0 [M+H]+.

compound 93

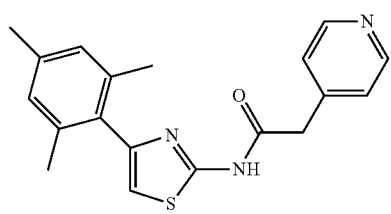

N-(4-Mesitylthiazol-2-yl)-2-(pyridin-4-yl)acetamide

Yield: 65%; ¹H¹H-NMR (500 MHz, DMSO-d₆) δ 8.52-8.53 (m, 2 H), 7.35-7.36 (m, 2 H), 6.99 (s, 1 H), 6.91 (s, 1 H), 3.84 (s, 1 H), 2.25 (s, 3 H), 2.02 (s, 6 H); ESI-MS: m/z 338.1 [M+H]+.

compound 98

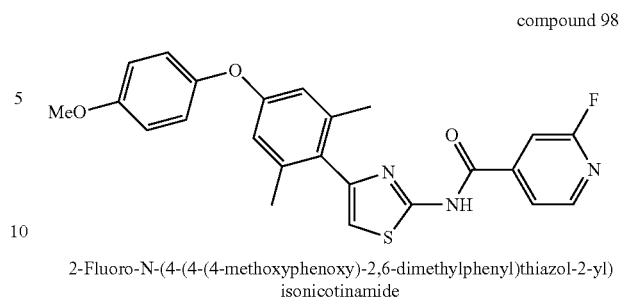

2-Fluoro-N-(4-(4-(4-methoxyphenoxy)-2,6-dimethylphenyl)thiazol-2-yl)isonicotinamide Yield: 70%; ¹H¹H-NMR (500 MHz, CDCl₃) δ 8.38-8.40 (m, 1 H), 7.66-7.67 (m, 2 H), 7.43 (s, 1 H), 6.98-7.00 (m, 2 H), 6.91-6.93 (m, 2 H), 6.84 (s, 1 H), 6.54 (s, 1 H), 3.83 (s, 3 H), 2.0 (s, 6 H); ESI-MS: m/z 450.0 [M+H]+.

compound 99

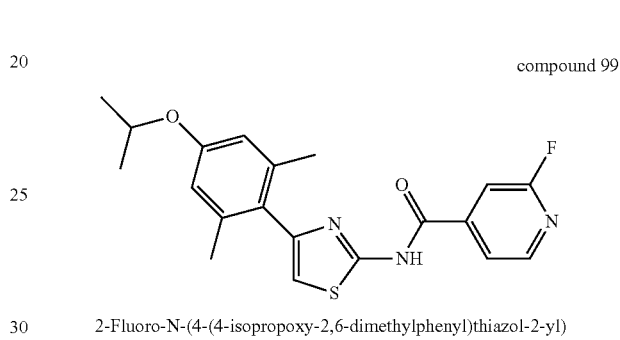

2-Fluoro-N-(4-(4-isopropoxy-2,6-dimethylphenyl)thiazol-2-yl)isonicotinamide

Yield: 83%; ¹H¹H-NMR (500 MHz, CDCl₃) δ 8.40 (m, 1 H), 7.78 (s, 1 H), 7.50 (s, 1 H), 6.84 (s, 1 H), 6.53 (s, 2 H), 4.52-4.56 (m, 1 H), 2.06 (s, 6 H), 1.33 (s, 6 H); ESI-MS: m/z 385.8 [M+H]+.

compound 103

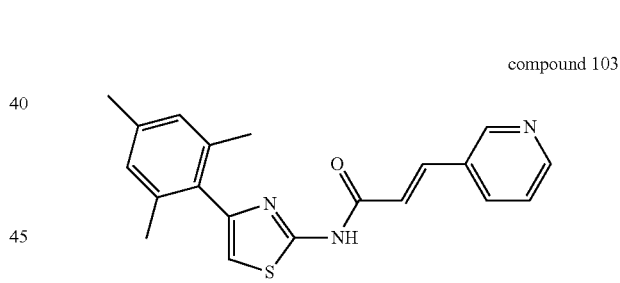

(E)-N-(4-Mesitylthiazol-2-yl)-3-(pyridin-3-yl)acrylamide

Yield: 34% yield; ¹H NMR (DMSO-d₆, 500 MHz) δ 12.48 (brs, 1 H), 8.82-8.83 (m, 1 H), 8.60-8.61 (m, 1 H), 8.04-8.05 (m, 1 H), 7.76-7.79 (m, 1 H), 7.49-7.51 (m, 1 H), 7.00-7.03 (m, 2 H), 6.92 (s, 2 H), 2.26 (s, 3 H), 2.05 (s, 6 H); ESI-MS: m/z 350.7 (M+H)+.

compound 104

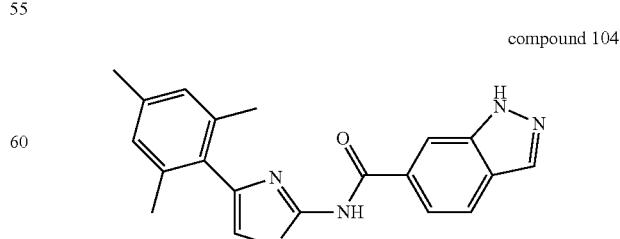

N-(4-Mesitylthiazol-2-yl)-1H-indazole-6-carboxamide

Yield: 25%; ¹H NMR (DMSO-d₆, 500 MHz) δ 13.20 (brs, 1 H), 8.36 (s, 1 H), 8.19 (s, 1 H), 7.87-7.88 (m, 1 H), 7.72-7.83 (m, 1 H), 7.00 (s, 1 H), 6.93 (s, 2 H), 2.27 (s, 3 H), 2.07 (s, 6 H); ESI-MS: m/z 363.9 (M+H)+.

compound 105

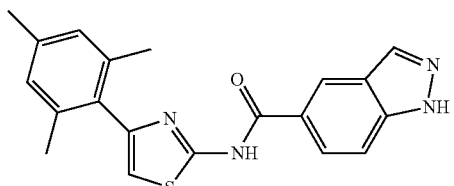

N-(4-Mesitylthiazol-2-yl)-1H-indazole-5-carboxamide

Yield: 38% yield; ¹H NMR (DMSO-d₆, 500 MHz) δ 13.20 (brs, 1 H), 8.66 (s, 1 H), 8.26 (s, 1 H), 8.08 (d, J=8.4 Hz, 1 H), 7.65 (d, J=8.4 Hz, 1 H), 7.02 (s, 1 H), 6.93 (s, 2 H), 2.36 (s, 3 H), 2.07 (s, 6 H); ESI-MS: m/z 363.9 (M+H)+.

compound 106

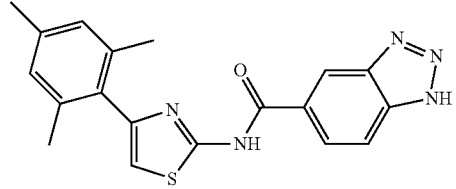

N-(4-Mesitylthiazol-2-yl)-1H-benzo[d][1,2,3]triazole-5-carboxamide

Yield: 41%; ¹H NMR (DMSO-d₆, 500 MHz) δ 8.78 (s, 1 H), 8.11 (d, J=8.4 Hz, 1 H), 7.96 (d, J=8.4 Hz, 1 H), 7.07 (s, 1 H), 6.93 (s, 2 H), 2.27 (s, 3 H), 2.07 (s, 6 H); ESI-MS: m/z 364.9 (M+H)+.

compound 109

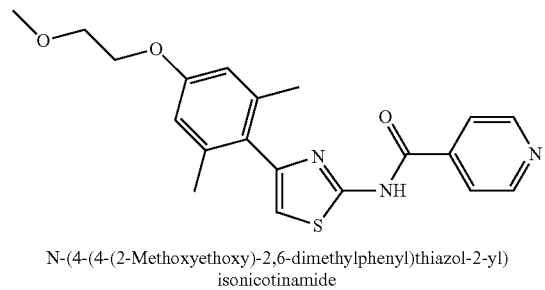

N-(4-(4-(2-Methoxyethoxy)-2,6-dimethylphenyl)thiazol-2-yl)isonicotinamide

Yield: 19%; ¹H NMR (DMSO-d₆, 500 MHz) δ 8.79-8.80 (m, 12 H), 7.98-7.99 (m, 2 H), 7.08 (s, 1 H), 6.70 (s, 2 H), 4.08-4.10 (m, 2 H), 3.65-3.66 (m, 2 H), 3.31 (s, 3 H), 2.06 (s, 6 H); ESI-MS: m/z 384.6 (M+H)+.

compound 110

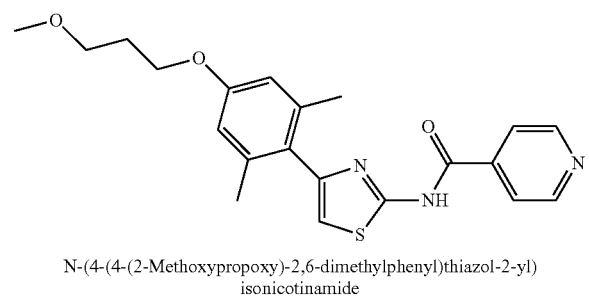

N-(4-(4-(2-Methoxypropoxy)-2,6-dimethylphenyl)thiazol-2-yl)isonicotinamide

Yield: 58%; ¹H NMR (DMSO-d₆, 500 MHz) δ 8.78-8.79 (m, 2 H), 7.98-7.99 (m, 2 H), 7.05 (s, 1 H), 6.69 (s, 2 H), 4.00-4.02 (m, 2 H), 3.46-3.48 (m, 2 H), 3.25 (s, 3 H), 2.06 (s, 6 H), 1.93-1.95 (m, 2 H); ESI-MS: m/z 398.8 (M+H)+.

compound 120

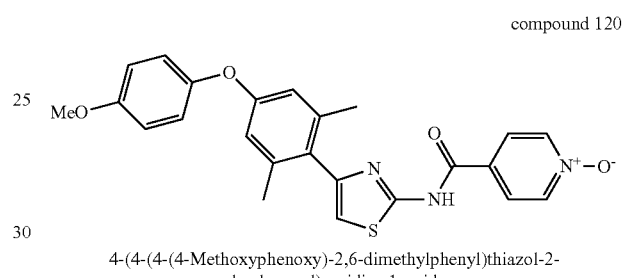

4-(4-(4-(4-Methoxyphenoxy)-2,6-dimethylphenyl)thiazol-2-ylcarbamoyl)pyridine 1-oxide Yield: 69%; ¹H NMR (500 MHz, CDCl₃) δ 8.46-8.48 (m, 1 H), 8.39-8.43 (m, 2 H), 8.32-8.33 (m, 1 H), 7.02-7.05 (m, 2 H), 6.93-6.95 (m, 3 H), 6.70 (s, 2 H), 3.84 (s, 3 H), 2.19 (s, 3 H), 2.16 (s, 3 H); ESI-MS: m/z 447.8 [M+H]+.

compound 126

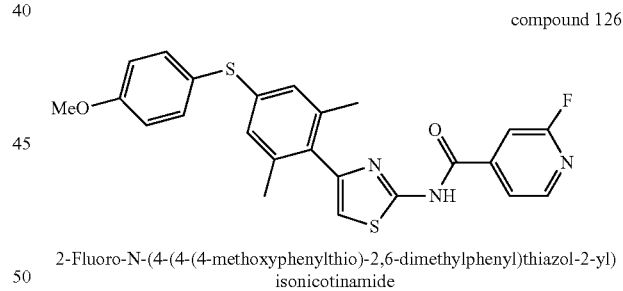

2-Fluoro-N-(4-(4-(4-methoxyphenylthio)-2,6-dimethylphenyl)thiazol-2-yl)isonicotinamide Yield: 65%; ¹H-NMR (500 MHz, DMSO-d₆) δ 13.1 (s, 1 H), 8.46-8.47 (m, 1 H), 7.93-7.94 (m, 1 H), 7.78 (s, 1 H), 7.42-7.44 (m, 2 H), 7.19 (s, 1 H), 7.01-7.03 (m, 2 H), 6.91 (s, 2 H), 3.79 (s, 3 H), 2.02 (s, 6 H); ESI-MS: m/z 465.4 [M+H]+.

Exemplary Compounds and Inhibitory Activity

The following table lists exemplary results for selected compounds illustrating the antiproliferative activity on selected cancer cells using exposure of the cells in growth medium with the compounds as indicated. Antiproliferative effect is expressed as IC50 values in microMolar final concentration.

| Compound | Structure | Antiproliferative IC$_{50}$ (μM) | | | |
|---|---|---|---|---|---|
| | | Hela | K562 | MDA-MB-468 | MDA-MB-231 |
| 1 | 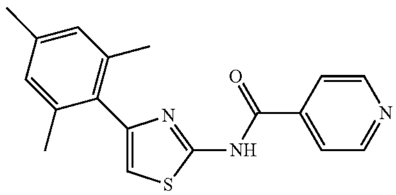 [SMILES: Cc1cc(C)c(-c2csc(NC(=O)c3ccncc3)n2)c(C)c1] | 0.67 | 0.43 | 0.35 | 0.30 |
| 2 | 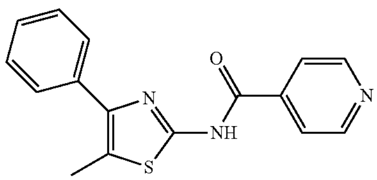 [SMILES: Cc1sc(NC(=O)c2ccncc2)nc1-c1ccccc1] | >10 | >10 | 8.15 | >10 |
| 3 | 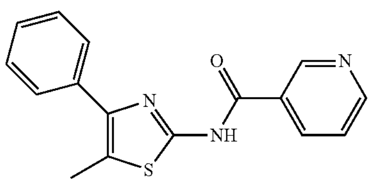 [SMILES: Cc1sc(NC(=O)c2cccnc2)nc1-c1ccccc1] | >10 | >10 | >10 | >10 |
| 4 | 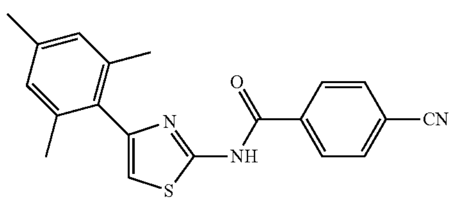 [SMILES: Cc1cc(C)c(-c2csc(NC(=O)c3ccc(C#N)cc3)n2)c(C)c1] | >10 | 2.07 | 0.79 | 0.61 |
| 5 | 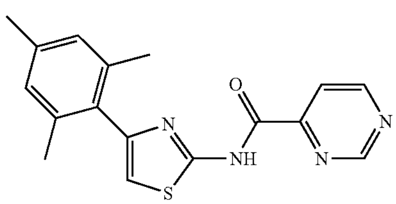 [SMILES: Cc1cc(C)c(-c2csc(NC(=O)c3ccncn3)n2)c(C)c1] | >10 | 5.74 | 4.57 | 7.37 |
| 6 | 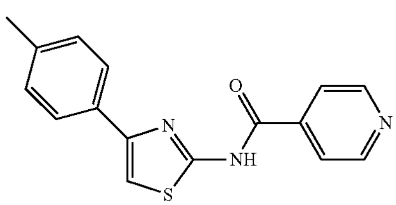 [SMILES: Cc1ccc(-c2csc(NC(=O)c3ccncc3)n2)cc1] | 1.05 | 1.48 | 1.14 | 0.67 |
| 7 | 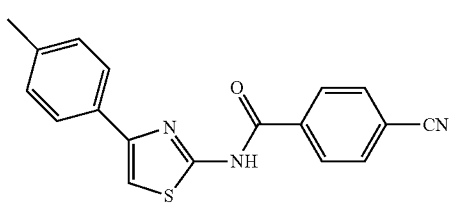 [SMILES: Cc1ccc(-c2csc(NC(=O)c3ccc(C#N)cc3)n2)cc1] | >10 | >10 | >10 | >10 |

-continued

| Compound | Structure | Antiproliferative IC$_{50}$ (μM) | | | |
|---|---|---|---|---|---|
| | | Hela | K562 | MDA-MB-468 | MDA-MB-231 |
| 8 | 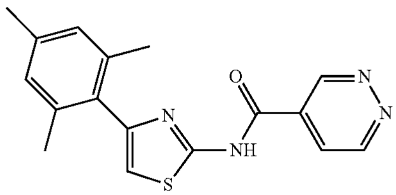 [SMILES: Cc1cc(C)c(-c2csc(NC(=O)c3ccnnc3)n2)c(C)c1] | 8.75 | 5.60 | 6.18 | 3.12 |
| 9 | 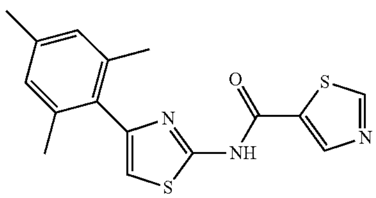 [SMILES: Cc1cc(C)c(-c2csc(NC(=O)c3cncs3)n2)c(C)c1] | 1.51 | 2.68 | 1.83 | 1.24 |
| 10 | 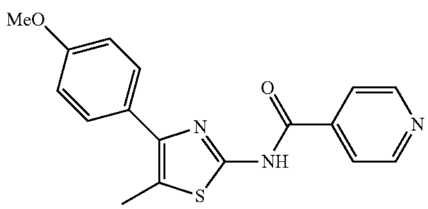 [SMILES: COc1ccc(-c2nc(NC(=O)c3ccncc3)sc2C)cc1] | >10 | >10 | 8.89 | 8.03 |
| 11 | 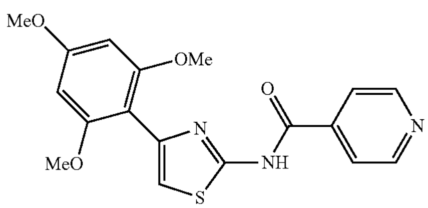 [SMILES: COc1cc(OC)c(-c2csc(NC(=O)c3ccncc3)n2)c(OC)c1] | >10 | >10 | >10 | >10 |
| 12 | 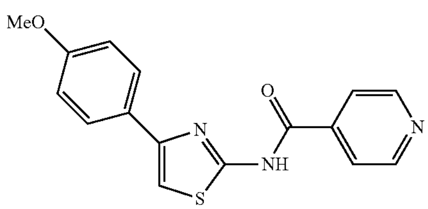 [SMILES: COc1ccc(-c2csc(NC(=O)c3ccncc3)n2)cc1] | >10 | 3.91 | 2.88 | 1.41 |
| 13 | 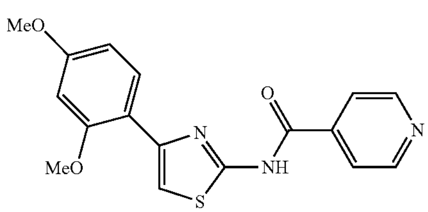 [SMILES: COc1ccc(-c2csc(NC(=O)c3ccncc3)n2)c(OC)c1] | >10 | >10 | >10 | >10 |
| 14 | 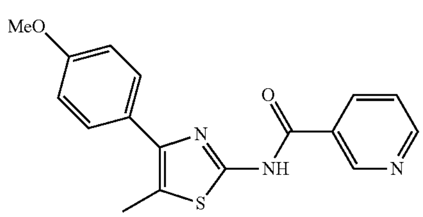 [SMILES: COc1ccc(-c2nc(NC(=O)c3cccnc3)sc2C)cc1] | >10 | >10 | >10 | >10 |

-continued
| Compound | Structure | Antiproliferative IC$_{50}$ (μM) | | | |
|---|---|---|---|---|---|
| | | Hela | K562 | MDA-MB-468 | MDA-MB-231 |
| 15 | 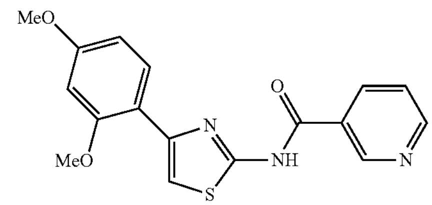 [SMILES: COc1ccc(-c2csc(NC(=O)c3cccnc3)n2)c(OC)c1] | >10 | >10 | >10 | >10 |
| 16 | 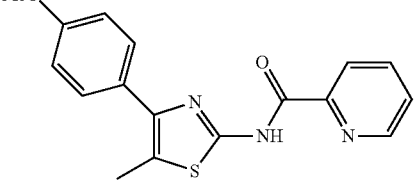 | >10 | >10 | >10 | >10 |
| 17 | 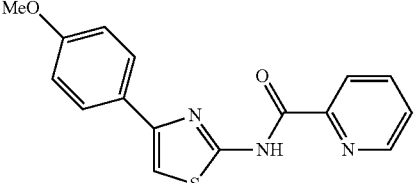 | >10 | >10 | >10 | >10 |
| 18 | 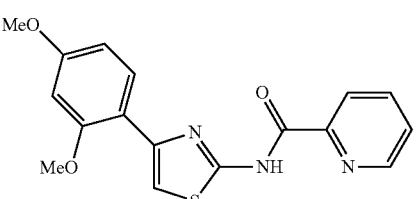 | >10 | >10 | >10 | >10 |
| 19 | 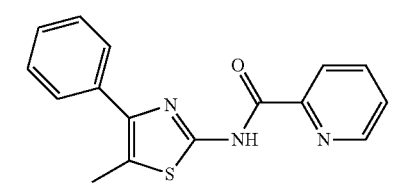 [SMILES: Cc1sc(NC(=O)c2ccccn2)nc1-c1ccccc1] | >10 | >10 | 6.85 | 6.75 |
| 20 | 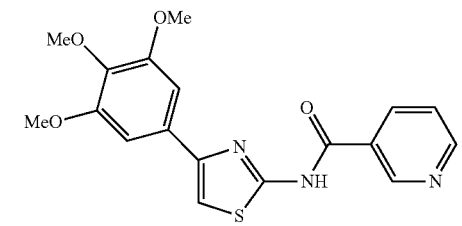 [SMILES: COc1cc(-c2csc(NC(=O)c3cccnc3)n2)cc(OC)c1OC] | >10 | >10 | >10 | >10 |
| 21 | 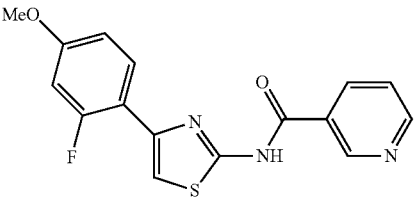 [SMILES: COc1ccc(-c2csc(NC(=O)c3cccnc3)n2)c(F)c1] | >10 | >10 | >10 | >10 |

-continued

| Compound | Structure | Antiproliferative IC$_{50}$ (μM) | | | |
|---|---|---|---|---|---|
| | | Hela | K562 | MDA-MB-468 | MDA-MB-231 |
| 22 | 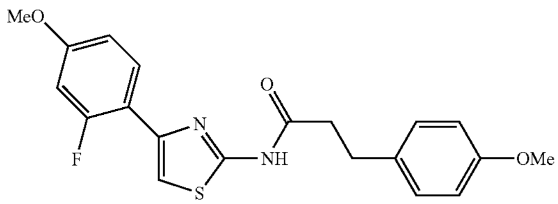 [SMILES: COc1ccc(CCC(=O)Nc2nc(-c3ccc(OC)cc3F)cs2)cc1] | >10 | >10 | 4.19 | >10 |
| 23 | 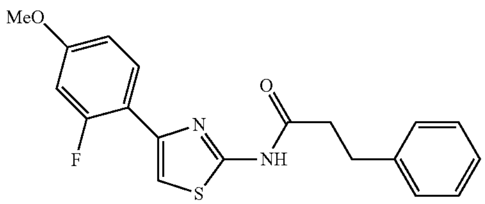 [SMILES: COc1ccc(-c2csc(NC(=O)CCc3ccccc3)n2)c(F)c1] | >10 | >10 | 7.12 | >10 |
| 24 | 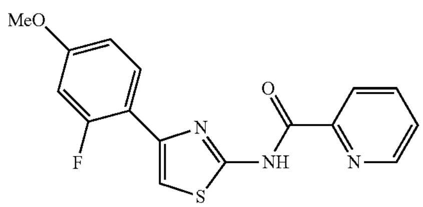 [SMILES: COc1ccc(-c2csc(NC(=O)c3ccccn3)n2)c(F)c1] | >10 | >10 | >10 | >10 |
| 25 | 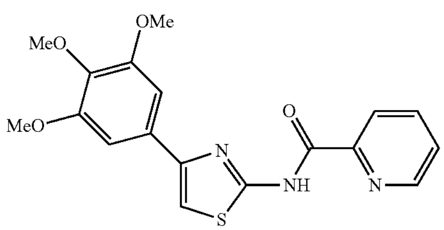 [SMILES: COc1cc(-c2csc(NC(=O)c3ccccn3)n2)cc(OC)c1OC] | >10 | >10 | >10 | >10 |
| 26 | 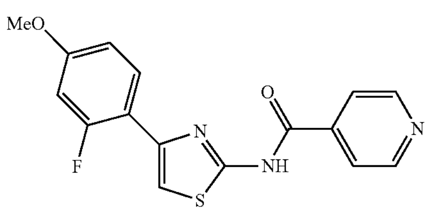 [SMILES: COc1ccc(-c2csc(NC(=O)c3ccncc3)n2)c(F)c1] | >10 | 2.43 | 2.25 | 6.85 |
| 27 | 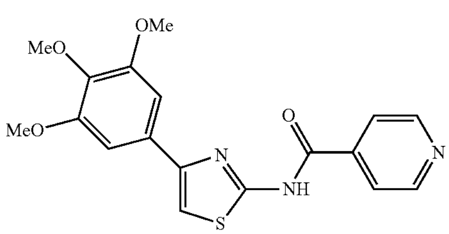 [SMILES: COc1cc(-c2csc(NC(=O)c3ccncc3)n2)cc(OC)c1OC] | >10 | >10 | >10 | >10 |
| 28 | 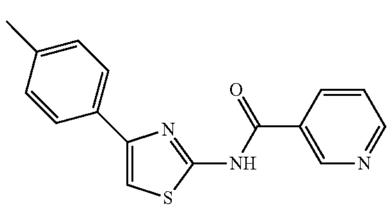 [SMILES: Cc1ccc(-c2csc(NC(=O)c3cccnc3)n2)cc1] | >10 | >10 | >10 | >10 |

-continued

| Compound | Structure | Antiproliferative IC$_{50}$ (μM) | | | |
| --- | --- | --- | --- | --- | --- |
| | | Hela | K562 | MDA-MB-468 | MDA-MB-231 |
| 29 | 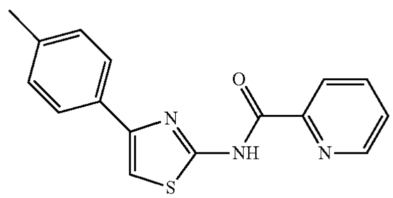 [SMILES: Cc1ccc(-c2csc(NC(=O)c3ccccn3)n2)cc1] | >10 | >10 | >10 | >10 |
| 30 | 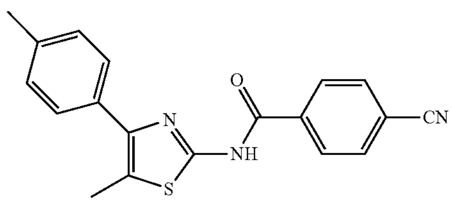 [SMILES: Cc1ccc(-c2nc(NC(=O)c3ccc(C#N)cc3)sc2C)cc1] | >10 | >10 | >10 | >10 |
| 31 | 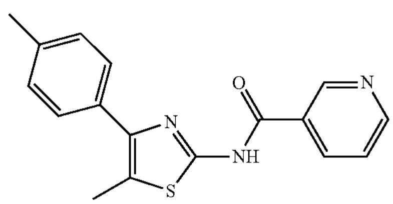 [SMILES: Cc1ccc(-c2nc(NC(=O)c3cccnc3)sc2C)cc1] | >10 | >10 | >10 | >10 |
| 32 | 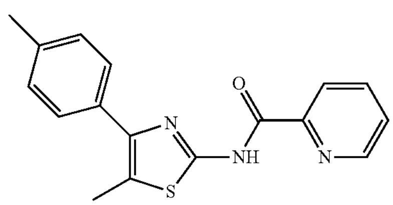 [SMILES: Cc1ccc(-c2nc(NC(=O)c3ccccn3)sc2C)cc1] | >10 | >10 | >10 | >10 |
| 33 | 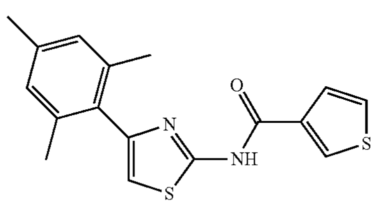 [SMILES: Cc1cc(C)c(-c2csc(NC(=O)c3ccsc3)n2)c(C)c1] | >10 | >10 | 0.79 | >10 |
| 34 | 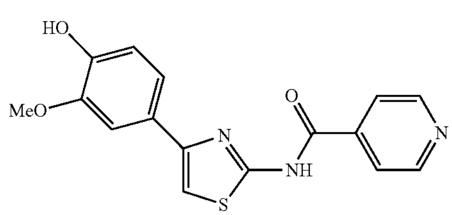 [SMILES: COc1cc(-c2csc(NC(=O)c3ccncc3)n2)ccc1O] | >10 | >10 | >10 | >10 |
| 35 | 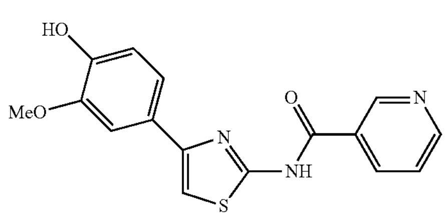 [SMILES: COc1cc(-c2csc(NC(=O)c3cccnc3)n2)ccc1O] | >10 | >10 | >10 | >10 |

-continued

| Compound | Structure | Antiproliferative IC$_{50}$ (μM) | | | |
|---|---|---|---|---|---|
| | | Hela | K562 | MDA-MB-468 | MDA-MB-231 |
| 36 | 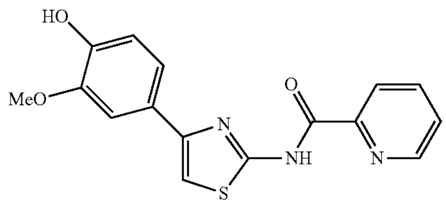 [SMILES: COc1cc(-c2csc(NC(=O)c3ccccn3)n2)ccc1O] | >10 | >10 | >10 | >10 |
| 37 | 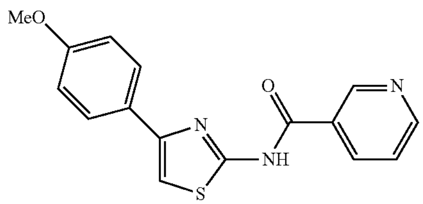 [SMILES: COc1ccc(-c2csc(NC(=O)c3cccnc3)n2)cc1] | >10 | >10 | >10 | >10 |
| 38 | 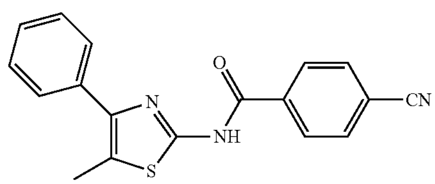 [SMILES: Cc1sc(NC(=O)c2ccc(C#N)cc2)nc1-c1ccccc1] | >10 | >10 | 3.40 | 5.68 |
| 39 | 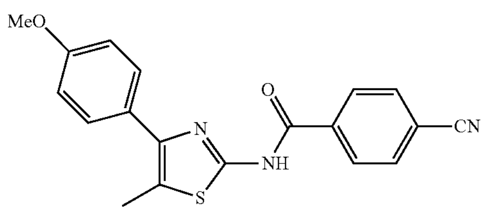 [SMILES: COc1ccc(-c2nc(NC(=O)c3ccc(C#N)cc3)sc2C)cc1] | >10 | >10 | >10 | >10 |
| 40 | 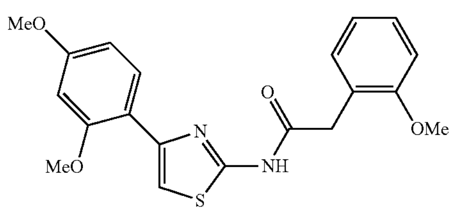 [SMILES: COc1ccc(-c2csc(NC(=O)Cc3ccccc3OC)n2)c(OC)c1] | >10 | >10 | >10 | >10 |
| 41 | 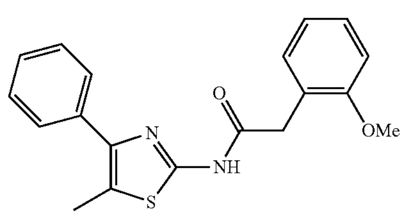 [SMILES: COc1ccccc1CC(=O)Nc1nc(-c2ccccc2)c(C)s1] | >10 | >10 | >10 | >10 |
| 42 | 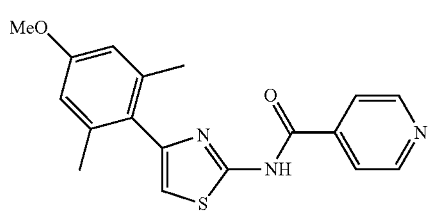 [SMILES: COc1cc(C)c(-c2csc(NC(=O)c3ccncc3)n2)c(C)c1] | 0.10 | 0.17 | 0.15 | 0.16 |

-continued

| Compound | Structure | Antiproliferative IC$_{50}$ (μM) | | | |
| --- | --- | --- | --- | --- | --- |
| | | Hela | K562 | MDA-MB-468 | MDA-MB-231 |
| 43 | 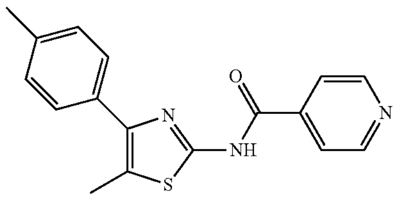 [SMILES: Cc1ccc(-c2nc(NC(=O)c3ccncc3)sc2C)cc1] | >10 | >10 | >10 | >10 |
| 44 | 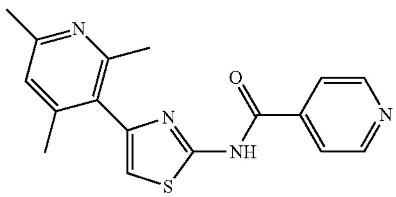 [SMILES: Cc1cc(C)c(-c2csc(NC(=O)c3ccncc3)n2)c(C)n1] | >10 | 1.96 | 1.01 | 1.24 |
| 45 | 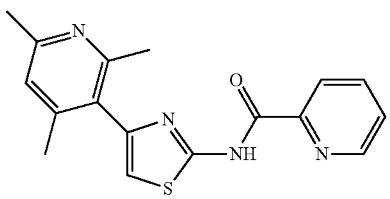 [SMILES: Cc1cc(C)c(-c2csc(NC(=O)c3ccccn3)n2)c(C)n1] | >10 | >10 | 7.68 | >10 |
| 46 | 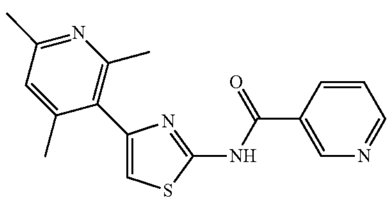 [SMILES: Cc1cc(C)c(-c2csc(NC(=O)c3cccnc3)n2)c(C)n1] | >10 | >10 | 7.19 | 7.41 |
| 47 | 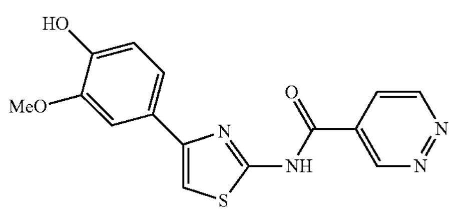 [SMILES: COc1cc(-c2csc(NC(=O)c3ccnnc3)n2)ccc1O] | >10 | >10 | >10 | >10 |
| 48 | 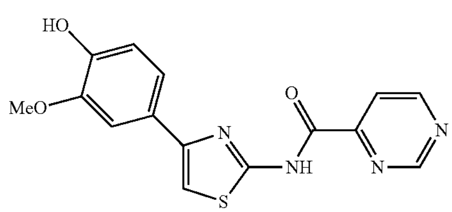 [SMILES: COc1cc(-c2csc(NC(=O)c3ccncn3)n2)ccc1O] | >10 | >10 | >10 | >10 |
| 49 | 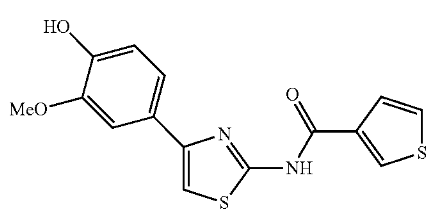 [SMILES: COc1cc(-c2csc(NC(=O)c3ccsc3)n2)ccc1O] | >10 | >10 | >10 | >10 |

-continued

| Compound | Structure | Antiproliferative IC$_{50}$ (μM) | | | |
|---|---|---|---|---|---|
| | | Hela | K562 | MDA-MB-468 | MDA-MB-231 |
| 50 | (HO, MeO-phenyl)-thiazole-NH-C(O)-thiazole | >10 | >10 | >10 | >10 |
| 51 | (HO, MeO-phenyl)-thiazole-NH-C(O)-furan | >10 | >10 | >10 | >10 |
| 52 | (EtO, dimethyl-phenyl)-thiazole-NH-C(O)-pyridine | 0.04 | 0.21 | 0.17 | 0.17 |
| 53 | (biphenyl, dimethyl)-thiazole-NH-C(O)-pyridine | 0.48 | 0.62 | 0.48 | 0.43 |
| 54 | (MeO-phenyl)-thiazole-NH-C(O)-(Cl-pyridine) | 5.92 | 6.65 | 6.95 | 4.56 |
| 55 | (Cl, dimethyl-phenyl)-thiazole-NH-C(O)-pyridine | 0.73 | 0.76 | 0.89 | 0.59 |
| 56 | (HO-phenyl)-thiazole-NH-C(O)-(CN-phenyl) | >10 | >10 | >10 | >10 |

| Compound | Structure | Antiproliferative IC$_{50}$ (μM) | | | |
| --- | --- | --- | --- | --- | --- |
| | | Hela | K562 | MDA-MB-468 | MDA-MB-231 |
| 57 | 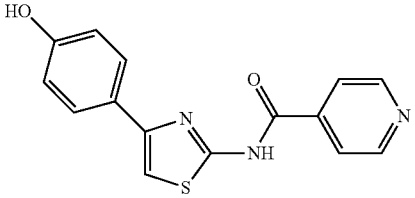 [SMILES: O=C(Nc1nc(-c2ccc(O)cc2)cs1)c1ccncc1] | >10 | >10 | >10 | >10 |
| 58 | 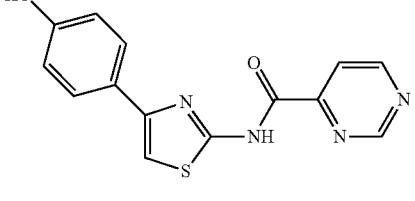 | >10 | >10 | >10 | >10 |
| 59 | 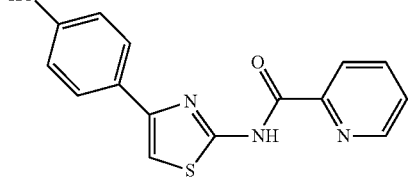 | >10 | >10 | >10 | >10 |
| 60 | 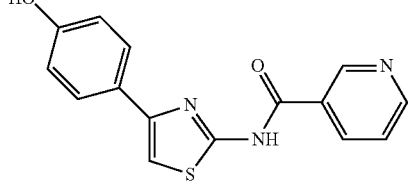 | >10 | >10 | >10 | >10 |
| 61 | 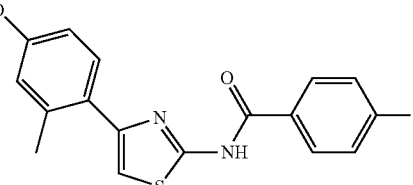 | >10 | >10 | >10 | >10 |
| 62 | 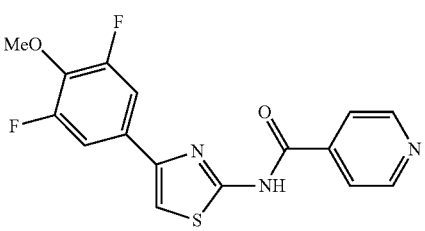 [SMILES: COc1c(F)cc(-c2csc(NC(=O)c3ccncc3)n2)cc1F] | >10 | 7.16 | 5.45 | 4.00 |
| 63 | 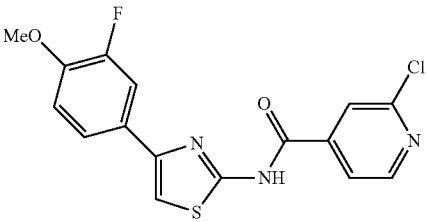 [SMILES: COc1ccc(-c2csc(NC(=O)c3ccnc(Cl)c3)n2)cc1F] | >10 | >10 | >10 | >10 |

-continued

| Compound | Structure | Antiproliferative IC$_{50}$ (μM) | | | |
|---|---|---|---|---|---|
| | | Hela | K562 | MDA-MB-468 | MDA-MB-231 |
| 64 | 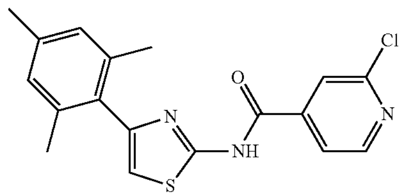 [SMILES: Cc1cc(C)c(-c2csc(NC(=O)c3ccnc(Cl)c3)n2)c(C)c1] | 0.84 | 0.93 | 0.98 | 0.62 |
| 65 | 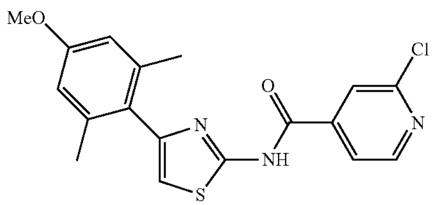 [SMILES: COc1cc(C)c(-c2csc(NC(=O)c3ccnc(Cl)c3)n2)c(C)c1] | 0.20 | 0.24 | 0.28 | 0.16 |
| 66 | 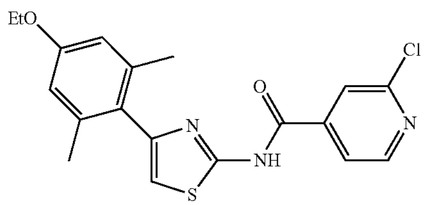 [SMILES: CCOc1cc(C)c(-c2csc(NC(=O)c3ccnc(Cl)c3)n2)c(C)c1] | 0.20 | 0.21 | 0.24 | 0.11 |
| 67 | 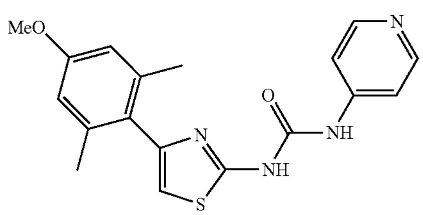 [SMILES: COc1cc(C)c(-c2csc(NC(=O)Nc3ccncc3)n2)c(C)c1] | >10 | 0.82 | 0.78 | 0.57 |
| 68 | 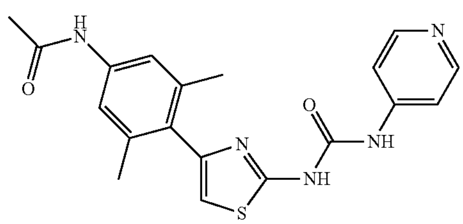 [SMILES: CC(=O)Nc1cc(C)c(-c2csc(NC(=O)Nc3ccncc3)n2)c(C)c1] | 5.13 | 4.96 | 3.61 | 4.24 |
| 69 | 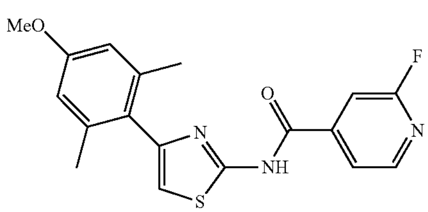 [SMILES: COc1cc(C)c(-c2csc(NC(=O)c3ccnc(F)c3)n2)c(C)c1] | 0.08 | 0.20 | 0.22 | 0.13 |
| 70 | 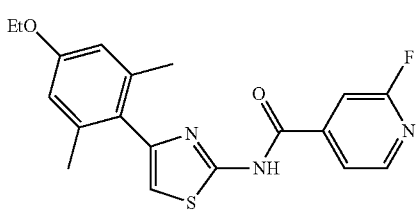 [SMILES: CCOc1cc(C)c(-c2csc(NC(=O)c3ccnc(F)c3)n2)c(C)c1] | 0.03 | 0.16 | 0.21 | 0.11 |

-continued

| Compound | Structure | Antiproliferative IC$_{50}$ (μM) | | | |
|---|---|---|---|---|---|
| | | Hela | K562 | MDA-MB-468 | MDA-MB-231 |
| 71 | 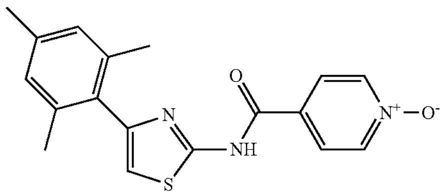 [SMILES: Cc1cc(C)c(-c2csc(NC(=O)c3cc[n+]([O-])cc3)n2)c(C)c1] | 2.29 | 4.58 | 4.18 | 3.57 |
| 72 | 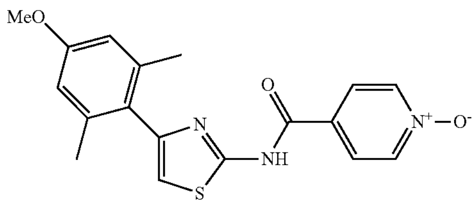 [SMILES: COc1cc(C)c(-c2csc(NC(=O)c3cc[n+]([O-])cc3)n2)c(C)c1] | 2.70 | 5.40 | 4.81 | 4.28 |
| 73 | 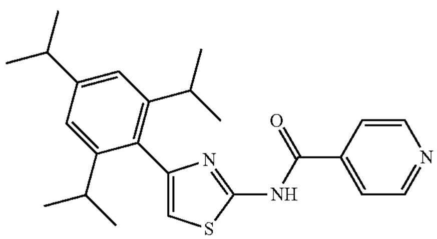 [SMILES: CC(C)c1cc(C(C)C)c(-c2csc(NC(=O)c3ccncc3)n2)c(C(C)C)c1] | >10 | >10 | >10 | >10 |
| 74 | 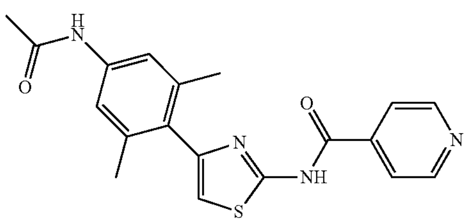 [SMILES: CC(=O)Nc1cc(C)c(-c2csc(NC(=O)c3ccncc3)n2)c(C)c1] | 1.59 | 2.13 | 1.27 | 1.46 |
| 75 | 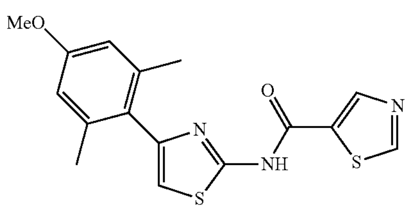 [SMILES: COc1cc(C)c(-c2csc(NC(=O)c3cncs3)n2)c(C)c1] | 2.93 | 3.70 | 4.34 | 2.37 |
| 76 | 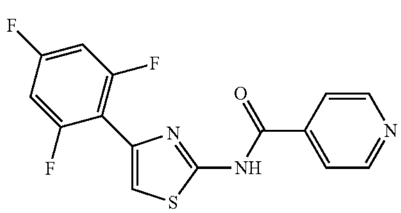 [SMILES: O=C(Nc1nc(-c2c(F)cc(F)cc2F)cs1)c1ccncc1] | 1.12 | 0.94 | 1.25 | 0.54 |
| 77 | 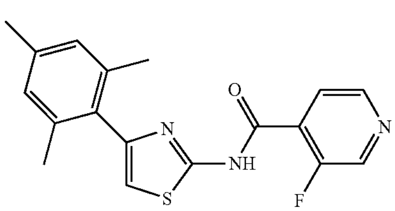 [SMILES: Cc1cc(C)c(-c2csc(NC(=O)c3ccncc3F)n2)c(C)c1] | 2.29 | 2.82 | 2.78 | 1.22 |

-continued

| Compound | Structure | Antiproliferative IC$_{50}$ (μM) | | | |
| --- | --- | --- | --- | --- | --- |
| | | Hela | K562 | MDA-MB-468 | MDA-MB-231 |
| 78 | 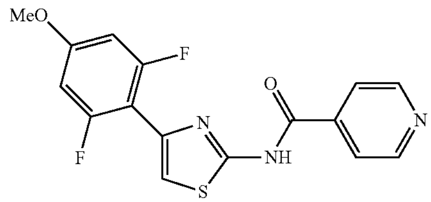 [SMILES: COc1cc(F)c(-c2csc(NC(=O)c3ccncc3)n2)c(F)c1] | 0.31 | 0.22 | 0.45 | 0.17 |
| 79 | 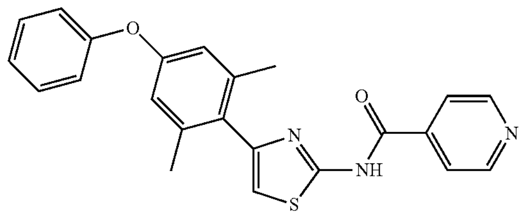 [SMILES: Cc1cc(Oc2ccccc2)cc(C)c1-c1csc(NC(=O)c2ccncc2)n1] | 0.24 | 0.09 | 0.15 | 0.17 |
| 80 | 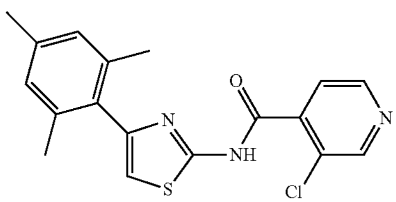 [SMILES: Cc1cc(C)c(-c2csc(NC(=O)c3ccncc3Cl)n2)c(C)c1] | 7.16 | 6.07 | 5.20 | 6.79 |
| 81 | 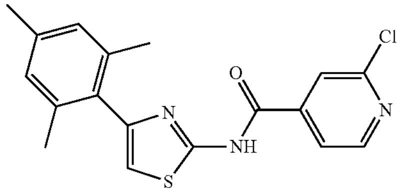 [SMILES: Cc1cc(C)c(-c2csc(NC(=O)c3ccnc(Cl)c3)n2)c(C)c1] | 0.86 | 0.79 | 0.82 | 0.72 |
| 82 | 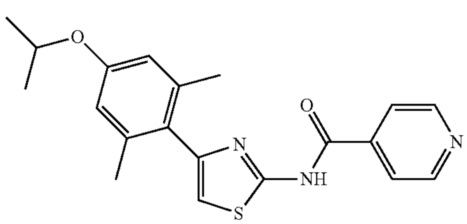 [SMILES: Cc1cc(OC(C)C)cc(C)c1-c1csc(NC(=O)c2ccncc2)n1] | 0.16 | 0.05 | 0.12 | 0.10 |
| 83 | 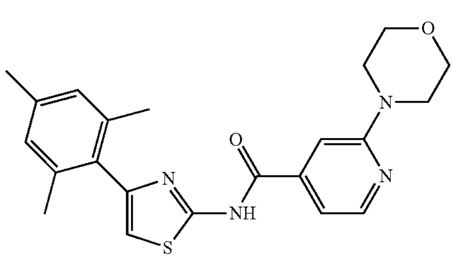 [SMILES: Cc1cc(C)c(-c2csc(NC(=O)c3ccnc(N4CCOCC4)c3)n2)c(C)c1] | 2.37 | 2.23 | 4.17 | 3.51 |

-continued

| Compound | Structure | Antiproliferative IC$_{50}$ (μM) | | | |
|---|---|---|---|---|---|
| | | Hela | K562 | MDA-MB-468 | MDA-MB-231 |
| 84 | 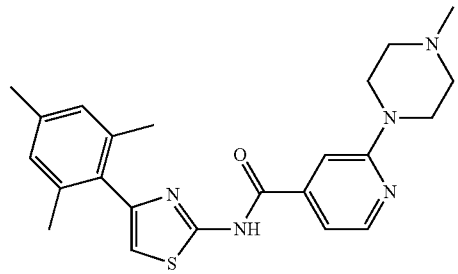 | >10 | >10 | 28.8 | >10 |
| 85 | 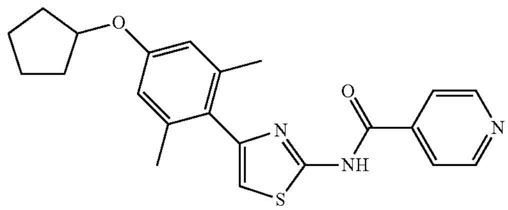 [SMILES: Cc1cc(OC2CCCC2)cc(C)c1-c1csc(NC(=O)c2ccncc2)n1] | 0.22 | 0.12 | 0.13 | 0.10 |
| 86 | 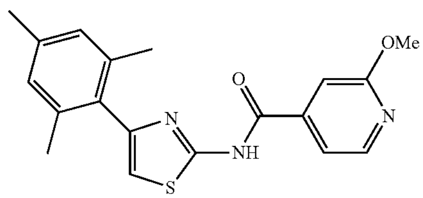 [SMILES: COc1cc(C(=O)Nc2nc(-c3c(C)cc(C)cc3C)cs2)ccn1] | 1.72 | 0.69 | 2.51 | 0.77 |
| 87 | 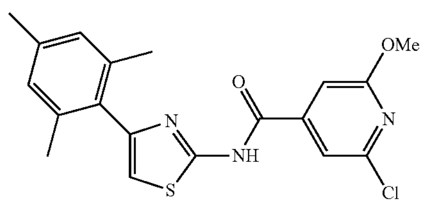 [SMILES: COc1cc(C(=O)Nc2nc(-c3c(C)cc(C)cc3C)cs2)cc(Cl)n1] | >10 | >10 | >10 | >10 |
| 88 | 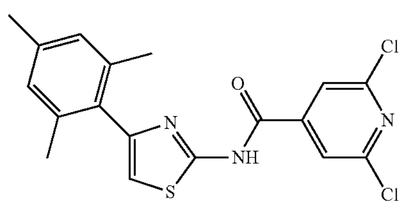 [SMILES: Cc1cc(C)c(-c2csc(NC(=O)c3cc(Cl)nc(Cl)c3)n2)c(C)c1] | >10 | 8.30 | 15.47 | 7.98 |
| 89 | 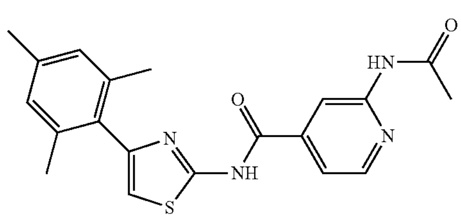 [SMILES: CC(=O)Nc1cc(C(=O)Nc2nc(-c3c(C)cc(C)cc3C)cs2)ccn1] | >10 | >10 | 8.20 | >10 |
| 90 | 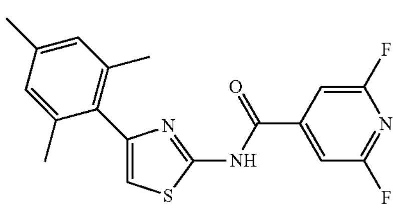 [SMILES: Cc1cc(C)c(-c2csc(NC(=O)c3cc(F)nc(F)c3)n2)c(C)c1] | 1.15 | 0.99 | 1.22 | 0.80 |

-continued

| Compound | Structure | Antiproliferative IC$_{50}$ (µM) | | | |
|---|---|---|---|---|---|
| | | Hela | K562 | MDA-MB-468 | MDA-MB-231 |
| 91 | 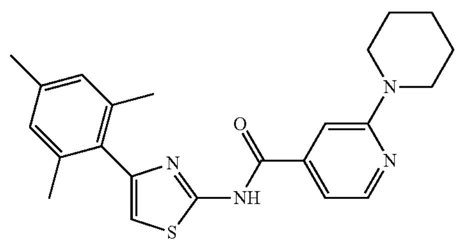 [SMILES: Cc1cc(C)c(-c2csc(NC(=O)c3ccnc(N4CCCCC4)c3)n2)c(C)c1] | >10 | 1.40 | 4.66 | 6.06 |
| 92 | 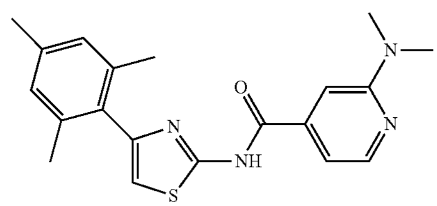 | >10 | 0.45 | 3.29 | 2.21 |
| 93 | 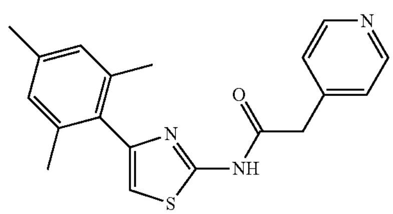 [SMILES: Cc1cc(C)c(-c2csc(NC(=O)Cc3ccncc3)n2)c(C)c1] | 0.62 | 0.38 | 0.30 | 0.31 |
| 94 | 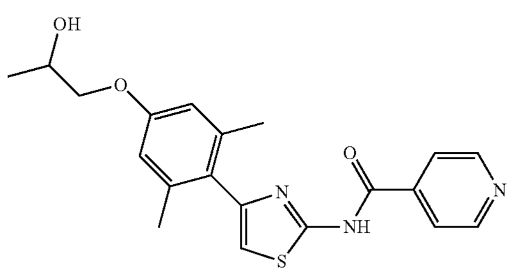 [SMILES: Cc1cc(OCC(C)O)cc(C)c1-c1csc(NC(=O)c2ccncc2)n1] | 0.23 | 0.23 | 0.39 | 0.30 |
| 95 | 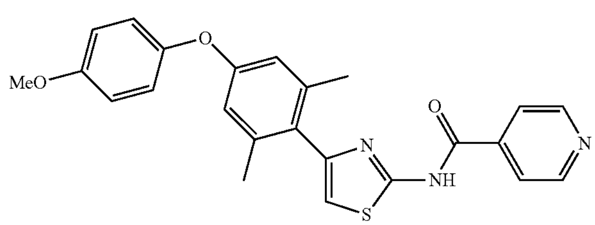 [SMILES: COc1ccc(Oc2cc(C)c(-c3csc(NC(=O)c4ccncc4)n3)c(C)c2)cc1] | 0.05 | 0.03 | 0.04 | 0.03 |
| 96 | 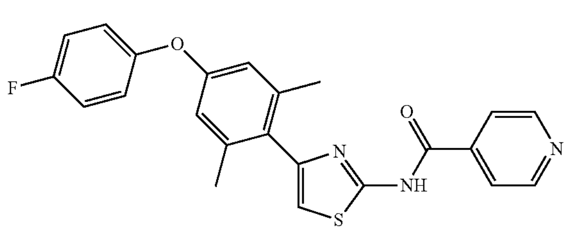 [SMILES: Cc1cc(Oc2ccc(F)cc2)cc(C)c1-c1csc(NC(=O)c2ccncc2)n1] | 0.26 | 0.28 | 0.25 | 0.24 |

-continued

| Compound | Structure | Antiproliferative IC$_{50}$ (μM) | | | |
| --- | --- | --- | --- | --- | --- |
| | | Hela | K562 | MDA-MB-468 | MDA-MB-231 |
| 97 | 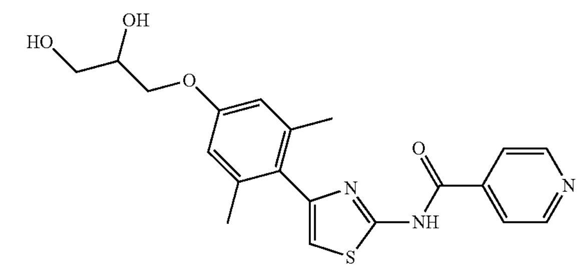 [SMILES: Cc1cc(OCC(O)CO)cc(C)c1-c1csc(NC(=O)c2ccncc2)n1] | 3.26 | 9.11 | 3.11 | 8.30 |
| 98 | 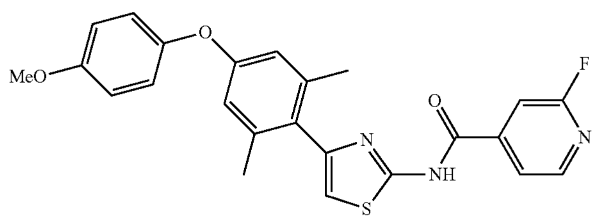 | 0.04 | 0.02 | 0.04 | 0.02 |
| 99 | 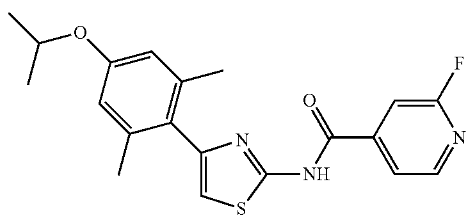 | 0.17 | 0.04 | 0.11 | 0.06 |
| 100 | 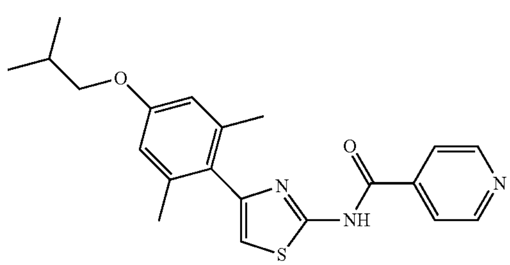 [SMILES: Cc1cc(OCC(C)C)cc(C)c1-c1csc(NC(=O)c2ccncc2)n1] | 0.28 | 0.11 | 0.39 | 0.28 |
| 101 | 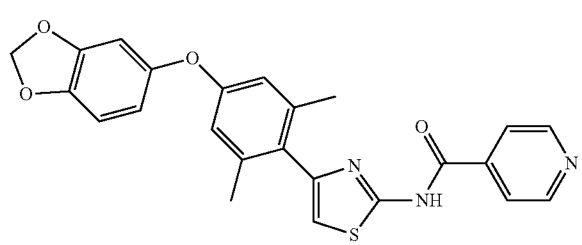 [SMILES: Cc1cc(Oc2ccc3c(c2)OCO3)cc(C)c1-c1csc(NC(=O)c2ccncc2)n1] | 0.11 | 0.05 | 0.13 | 0.07 |
| 102 | 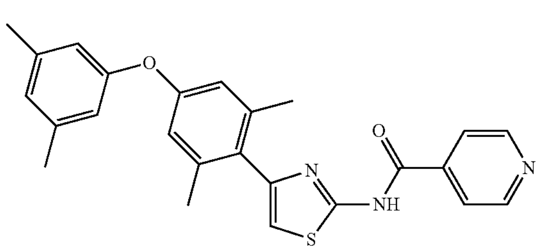 [SMILES: Cc1cc(C)cc(Oc2cc(C)c(-c3csc(NC(=O)c4ccncc4)n3)c(C)c2)c1] | 1.62 | 0.73 | 1.48 | 0.93 |

-continued

| Compound | Structure | Antiproliferative IC$_{50}$ (μM) | | | |
| --- | --- | --- | --- | --- | --- |
| | | Hela | K562 | MDA-MB-468 | MDA-MB-231 |
| 103 | 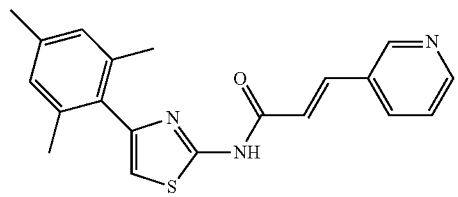 [SMILES: Cc1cc(C)c(-c2csc(NC(=O)/C=C/c3cccnc3)n2)c(C)c1] | >10 | 2.48 | 2.17 | 1.11 |
| 104 | 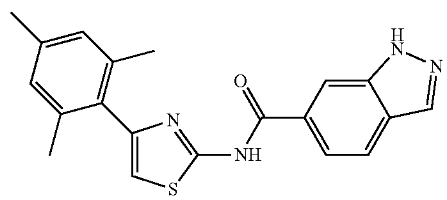 [SMILES: Cc1cc(C)c(-c2csc(NC(=O)c3ccc4cn[nH]c4c3)n2)c(C)c1] | >10 | 2.44 | 7.64 | 1.10 |
| 105 | 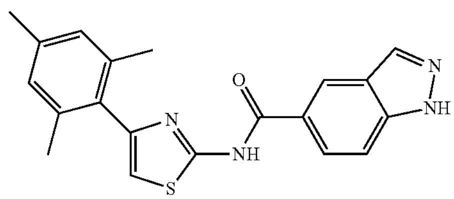 [SMILES: Cc1cc(C)c(-c2csc(NC(=O)c3ccc4[nH]ncc4c3)n2)c(C)c1] | >10 | >10 | 8.02 | >10 |
| 106 | 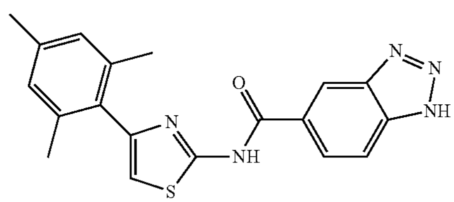 [SMILES: Cc1cc(C)c(-c2csc(NC(=O)c3ccc4[nH]nnc4c3)n2)c(C)c1] | >10 | >10 | >10 | 4.95 |
| 107 | 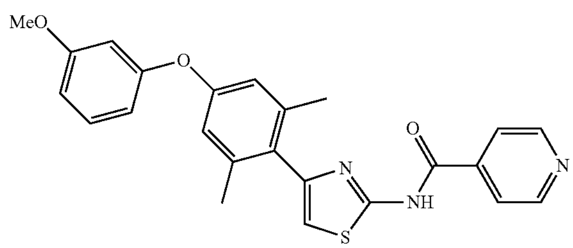 [SMILES: COc1cccc(Oc2cc(C)c(-c3csc(NC(=O)c4ccncc4)n3)c(C)c2)c1] | 0.25 | 0.10 | 0.20 | 0.20 |
| 108 | 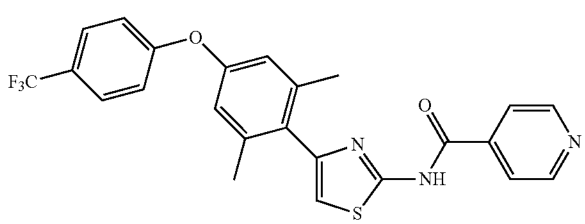 [SMILES: Cc1cc(Oc2ccc(C(F)(F)F)cc2)cc(C)c1-c1csc(NC(=O)c2ccncc2)n1] | 0.13 | 0.06 | 0.11 | 0.11 |
| 109 | 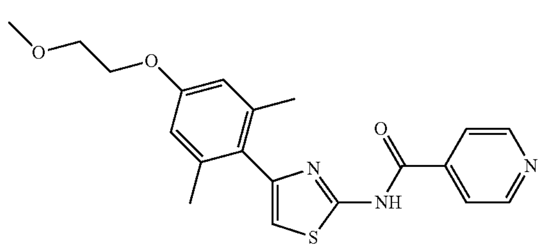 [SMILES: COCCOc1cc(C)c(-c2csc(NC(=O)c3ccncc3)n2)c(C)c1] | 0.31 | 0.24 | 0.28 | 0.26 |

-continued
| Compound | Structure | Antiproliferative IC$_{50}$ (μM) | | | |
|---|---|---|---|---|---|
| | | Hela | K562 | MDA-MB-468 | MDA-MB-231 |
| 110 | 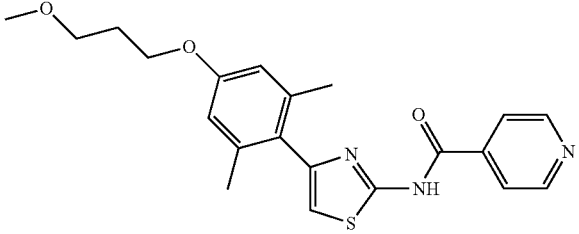 [SMILES: COCCCOc1cc(C)c(-c2csc(NC(=O)c3ccncc3)n2)c(C)c1] | 0.11 | 0.10 | 0.13 | 0.09 |
| 111 | 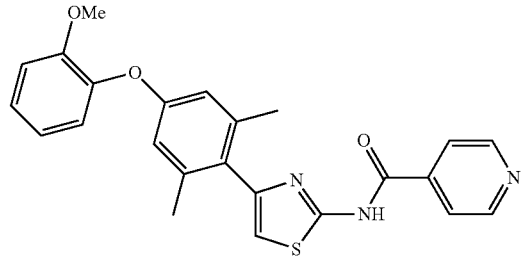 [SMILES: COc1ccccc1Oc1cc(C)c(-c2csc(NC(=O)c3ccncc3)n2)c(C)c1] | 0.33 | 0.18 | 0.33 | 0.25 |
| 112 | 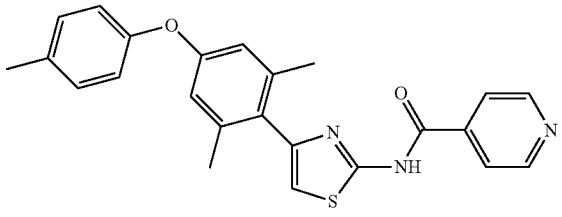 [SMILES: Cc1ccc(Oc2cc(C)c(-c3csc(NC(=O)c4ccncc4)n3)c(C)c2)cc1] | 0.24 | 0.13 | 0.22 | 0.14 |
| 113 | 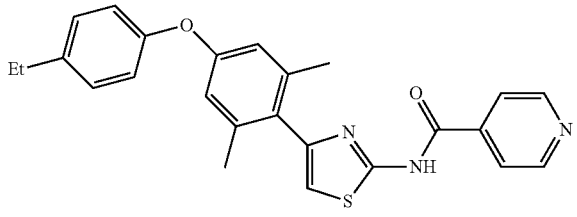 [SMILES: CCc1ccc(Oc2cc(C)c(-c3csc(NC(=O)c4ccncc4)n3)c(C)c2)cc1] | 0.18 | 0.17 | 0.17 | 0.17 |
| 114 | 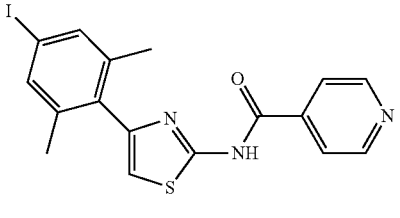 [SMILES: Cc1cc(I)cc(C)c1-c1csc(NC(=O)c2ccncc2)n1] | 0.40 | 0.23 | 0.55 | 0.30 |
| 115 | 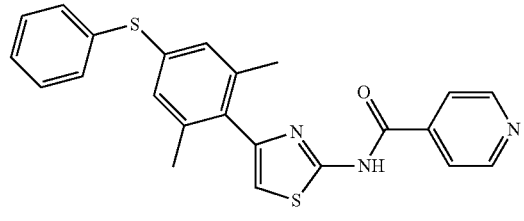 | 0.23 | 0.14 | 0.22 | 0.17 |

-continued

| Compound | Structure | Antiproliferative IC$_{50}$ (μM) | | | |
|---|---|---|---|---|---|
| | | Hela | K562 | MDA-MB-468 | MDA-MB-231 |
| 116 | 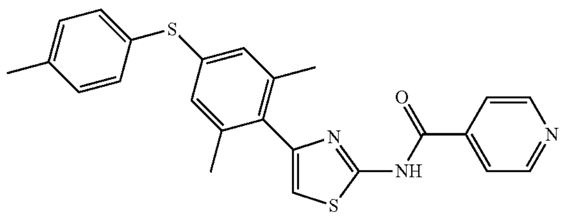 [SMILES: Cc1ccc(Sc2cc(C)c(-c3csc(NC(=O)c4ccncc4)n3)c(C)c2)cc1] | 0.15 | 0.11 | 0.13 | 0.12 |
| 117 | 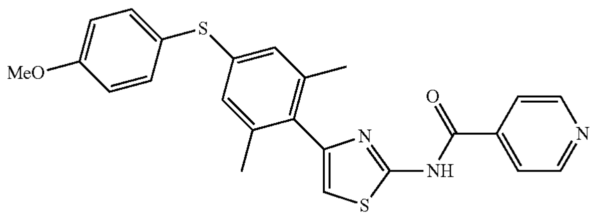 | 0.03 | 0.02 | 0.04 | 0.03 |
| 118 | 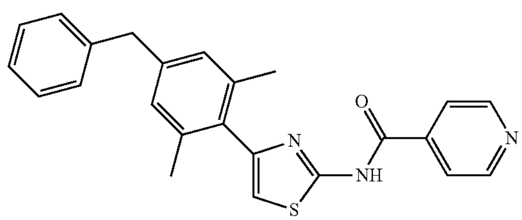 [SMILES: Cc1cc(Cc2ccccc2)cc(C)c1-c1csc(NC(=O)c2ccncc2)n1] | 0.27 | 0.15 | 0.22 | 0.24 |
| 119 | 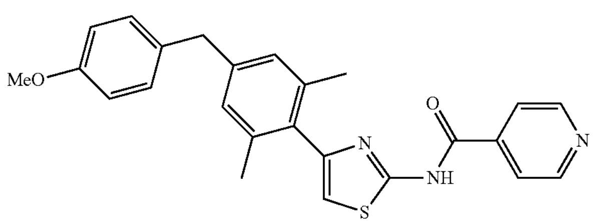 | 0.06 | 0.03 | 0.06 | 0.05 |
| 120 | 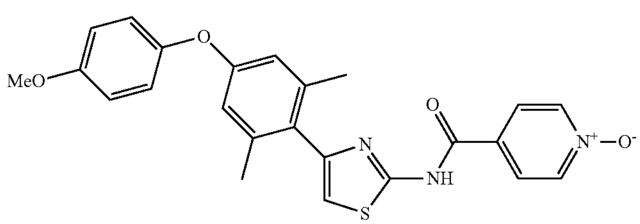 [SMILES: COc1ccc(Oc2cc(C)c(-c3csc(NC(=O)c4cc[n+]([O-])cc4)n3)c(C)c2)cc1] | 0.16 | 0.18 | 0.25 | 0.22 |
| 121 | 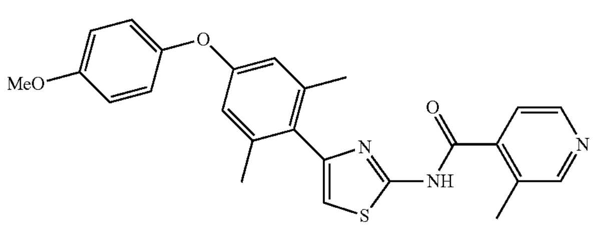 | 0.90 | 0.32 | 0.81 | 0.44 |

-continued

| Compound | Structure | Antiproliferative IC$_{50}$ (μM) | | | |
|---|---|---|---|---|---|
| | | Hela | K562 | MDA-MB-468 | MDA-MB-231 |
| 122 | 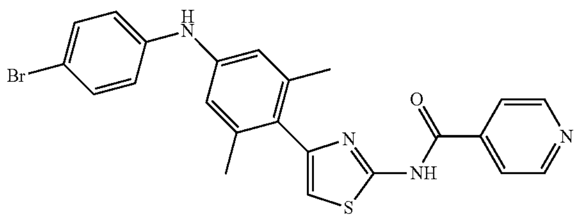 [SMILES: Cc1cc(Nc2ccc(Br)cc2)cc(C)c1-c1csc(NC(=O)c2ccncc2)n1] | 2.13 | 0.36 | 1.22 | 0.72 |
| 123 | 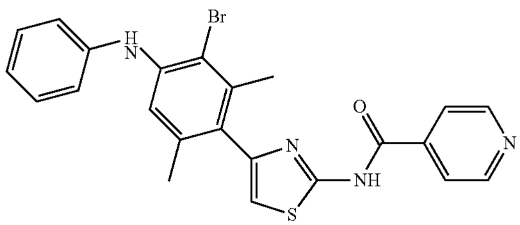 [SMILES: Cc1cc(Nc2ccccc2)c(Br)c(C)c1-c1csc(NC(=O)c2ccncc2)n1] | 0.87 | 0.33 | 0.88 | 0.61 |
| 124 | 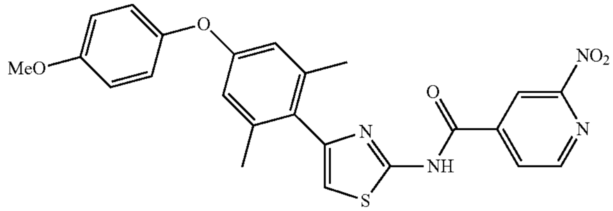 [SMILES: COc1ccc(Oc2cc(C)c(-c3csc(NC(=O)c4ccnc([N+](=O)[O-])c4)n3)c(C)c2)cc1] | 0.33 | 0.12 | 0.53 | 0.22 |
| 125 | 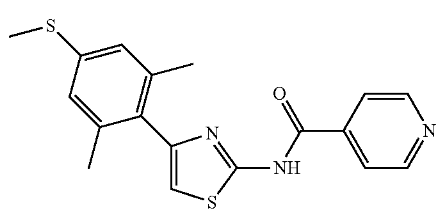 [SMILES: CSc1cc(C)c(-c2csc(NC(=O)c3ccncc3)n2)c(C)c1] | 0.27 | 0.18 | 0.25 | 0.16 |
| 126 | 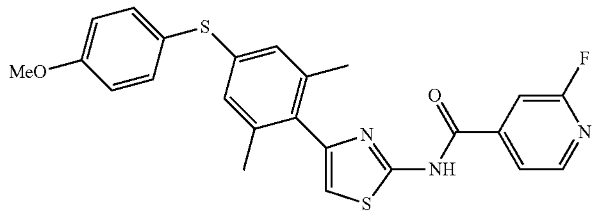 | 0.04 | 0.02 | 0.05 | 0.03 |
| 127 | 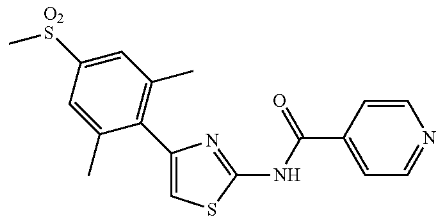 [SMILES: Cc1cc(S(C)(=O)=O)cc(C)c1-c1csc(NC(=O)c2ccncc2)n1] | 0.84 | 0.53 | 0.46 | 0.45 |

| Compound | Structure | Antiproliferative IC$_{50}$ (μM) | | | |
|---|---|---|---|---|---|
| | | Hela | K562 | MDA-MB-468 | MDA-MB-231 |
| 128 | MeO-C6H4-O-(2,6-diMe-phenyl)-thiazole-NH-C(O)-(2-amino-pyridin-4-yl) | 0.24 | 0.19 | 0.16 | 0.16 |
| 129 | MeO-C6H4-SO2-(2,6-diMe-phenyl)-thiazole-NH-C(O)-pyridin-4-yl | 0.27 | 0.19 | 0.27 | 0.20 |
| 130 | MeO-C6H4-S(O)-(2,6-diMe-phenyl)-thiazole-NH-C(O)-pyridin-4-yl | 0.18 | 0.08 | 0.14 | 0.09 |
| 131 | MeO-C6H4-O-(2-Cl-6-Me-phenyl)-thiazole-NH-C(O)-pyridin-4-yl | 0.06 | 0.04 | 0.05 | 0.04 |

Exemplary Biological Activities of Selected Compounds

The following data provide exemplary guidance with respect to the biological activity of certain compounds in vitro and in vivo. Where compounds are referenced by number, the number is with regard to the compounds listed in the table above.

Cytotoxicity and Antiproliferative Activity: Cells from established cell lines (e.g. from cell lines like MDA-MB-231, MDA-MB-468, Hela, and K562) were cultured in 10% FBS (Hylcone) in DMEM medium (Sigma, D5523). Cells were grown at 37° C. in a humidified atmosphere with 5% CO$_2$ and 95% air. Cells were seeded in 96 well tissue culture plates.

Compound treatment started after overnight incubation of cells (T0). Compound was prepared in an eight point 3× dilution from 10 μM to 4.6 nM. Compound was added to the plate in triplicate wells, and the plates were then incubated for 96 hours. DMSO (compounds diluents) was also included and added to the plate in control wells. Cell viability was then determined by MTS assay using CellTiter 96® AQueous non-radioactive cell proliferation assay system (Promega). A plate reader (Molecular Devices, Vmax) was used to read the optical densities, and the results were used to deduce concentration-response curves. All data represent the results of triplicate experiments, and are the mean of three separate determinations with variations of less than ±20%. The results were analyzed using linear regression software (GraphPad Prism 5; GraphPad Software Inc.).

The IC50 values refer to the concentration that causes 50% growth inhibition. The GI50 values (growth inhibitory activity) were determined to emphasize on the correction for the cell count at time zero; thus, the % inhibition of test drug were: [1−(T−T0)/(C−T0)]×100; and these value were used to plot the concentration-response curves, and then analyzed with linear regression software (GraphPad Prism 5).

As can be seen from FIG. 1A, selected compounds had significant cytotoxic and antiproliferative effect on multiple solid tumor cells as well as leukemia cells. In contrast, as can be taken from FIG. 1B, the same compounds at exhibited no significant cytotoxic and antiproliferative effect on several normal cell lines. Here, WI-38 is human normal lung fibroblast cell line, RPTEC is renal proximal tubule epithelial cells, HuVec is human umbilical vein endothelial cells, and HAoSMC is Human aortic smooth muscle cells.

Selected compounds disrupt Hec1/Nek2 Interaction, trigger Nek2 degradation, and increase Nek2 protein instability: Cells were resuspended in ice-cold Lysis buffer 250 (50 mM Tris-HCl, pH 7.4, 250 mM NaCl, 0.3% Nonidet P-40, 10 mM NaF, supplemented with protease inhibitors) were subjected to three freeze/thaw cycles and centrifuged at 14,000 rpm for 2 min at room temperature. The supernatants were used for lysate analysis or immunoprecipitation. For immunoprecipitation, supernatants were incubated with anti-Hec1 antibody mAb1 9G3 or mouse polyclonal anti-Nek2 for 1-h, then with protein A-Sepharose beads for another hour. Beads were collected and washed five times with lysis buffer containing hypertonic NaCl, and boiled in SDS-loading buffer for immunoblot analysis. After immunoblotting to Immobilon-P membrane (Millipore Corp., Bedford, Mass.), blots were probed with anti-Hec1 antibodies or anti-Nek2 antibodies (Genetex, Irvine, Calif.). Blots were developed using an ECL chemiluminescence kit (Amersham Biosciences). Additional details can be found elsewhere (Phosphorylation of the mitotic regulator protein Hec1 by Nek2 kinase is essential for faithful chromosome segregation. J Biol. Chem. 2002 Dec. 20; 277 (51):49408-16. Epub 2002 Oct. 16).

Figure 2B:
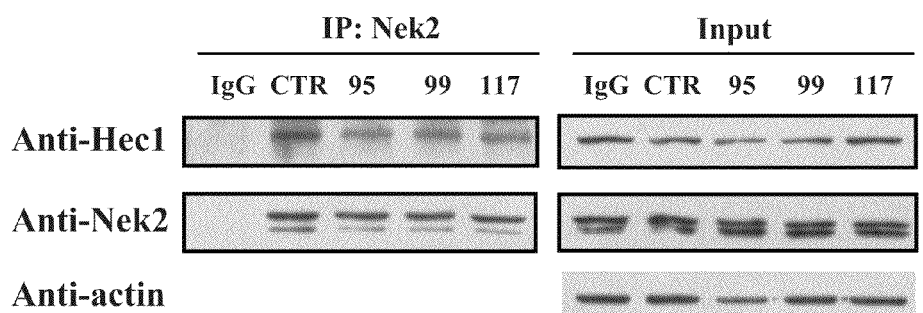
Figure 2C:
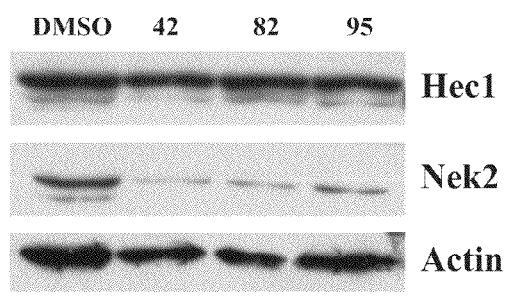
Figure 2D:
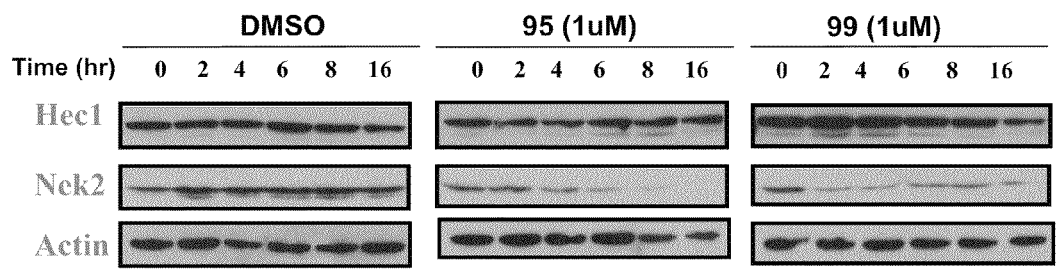

FIGS. 2A and 2B depicts an exemplary result of such experiment where it is readily apparent that selected compounds tested significantly disrupted Hec1/Nek2 interaction. FIG. 2C shows typical results of the Nek2 reduction upon incubation of K562 cells for 24 hrs with 1 mcM of tested compounds, and FIG. 2D depicts results demonstrating protein instability of Nek2 over time after treatment of K562 cells exposed to selected compounds at 1 mcM final concentration.

Selected compounds induce aberrant mitosis: Cells were grown on cover slips and gently washed with PEMG buffer [80 mM piperazine-N,N-bis(2-ethanesulfonic acid) (PIPES), pH 6.8, 5 mM EGTA, 1 mM $MgCl_2$, and 4 M glycerol] or phosphate-buffered saline (PBS). Cells were then fixed with 100% methanol at −20° C. or 4% paraformaldehyde in PEMG or PBS buffer and permeabilized with 0.4% Triton-X 100. Cells were blocked with 5% normal goat serum (NGS) in PBS and incubated with primary antibodies in PBS with 5% NGS (1-2 h at room temperature). Secondary antibodies were conjugated with Alexa 488 or 594 (Invitrogen, Carlsbad, Calif.). After incubation with secondary antibody, 4,6-Diamidino-2-phenylindole (DAPI) staining was applied and cells were mounted on cover slides with Prolong gold anti-fade reagent (Invitrogen). Images were captured with a Nikon H550L microscope equipped with digital cameras and SPOT digital imaging software (version 4, Diagnostic Instruments, Inc).

Further image analysis or quantification was performed with Image-Pro Plus (MediaCybernetics, Bethesda, Md.) or Adobe Photoshop software (Adobe Systems, Mountain View, Calif.). Further details are described elsewhere (Hec1 contributes to mitotic centrosomal microtubule growth for proper spindle assembly through interaction with Hicel. Mol Biol Cell. 2009 November; 20(22):4686-95. Epub 2009 Sep. 23).

Figure 3:
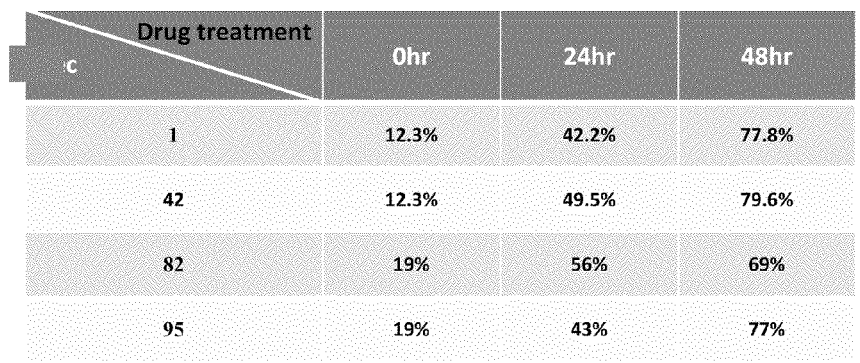
FIG. 3 is a table illustrating percentage of mitotic cells affected by contemplated compounds.

FIG. 3 is a table depicting the effect of selected compounds on mitosis. More specifically, the results are expressed as percentages of chromosome misalignment in mitotic cells over 48 hrs. As can be taken, the tested compounds substantially affected mitosis in a large number of cells.

Selected compounds are highly selective kinase inhibitors: Inhibition of kinase activity by test compound was measured by quantifying the amount of [$^{33}$P] incorporation of substrate in the present of test compound. The standard kinase assays were initiated with MgATP, in the presence of test compound (diluted in final concentration of 4% DMSO) or DMSO control, stopped by the addition of 3% phosphoric acid and harvested onto a filter plate using a unifilter harvester (PerkinElmer, Boston, Mass., U.S.A.) and counted using TopCount. For primary screening of kinase activity inhibition, each test compound was evaluated at two concentrations (10 mM and 1 mM) in duplication. The results were the average of duplicate measurements and expressed as percentage inhibition (compound treatment versus DMSO control). The available kinase assays are as followed: VEGFR2, PDGFR-β, FGFR1, Flt3, c-Met, CHK1, CHK2, Cdk1/Cyclin B, Aurora A, Aurora B, B-Raf, B-Raf (V600E), C-Raf, and mTOR. The ATP concentration used in most of the kinase assay is at or below the Km for ATP for each enzyme.

Despite the significant effects of contemplated compounds at very low IC50, the inhibitory profile was highly selective as can be seen from the table of FIG. 4.

Bioavailability: Selected compounds were administered to rats per os or via injection following well known procedures. For example, compound 82 was injected i.v. at a concentration of 2 mg/kg in a formulation containing 5% DMSO, 10% Cremophor, and 85% WFI. The table below lists exemplary pharmacokinetic data

| SD rat Number | $T_{1/2}$ (hr) | $C_0$ (ng/ml) | $AUC_{0-t}$ (hr*ng/ml) | $AUC_{0-inf}$ (hr*ng/ml) | Vss (ml/kg) | Vz (ml/kg) | CL (ml/hr/kg) | $MRT_{0-inf}$ (hrs) |
|---|---|---|---|---|---|---|---|---|
| No. 1 | 6.85 | 8181 | 10808 | 17849 | 985 | 1107 | 112 | 8.80 |
| No. 2 | 2.79 | 5590 | 10659 | 11974 | 561 | 672 | 167 | 3.36 |
| No. 3 | 5.78 | 7282 | 12797 | 19002 | 760 | 878 | 105 | 7.22 |
| Mean | 5.14 | 7017 | 11421 | 16275 | 769 | 885 | 128 | 6.46 |
| SD | 2.10 | 1316 | 1194 | 3770 | 212 | 218 | 34 | 2.80 |

Compound 82 was also orally administered at a concentration of 20 mg/kg in a formulation containing 1% methylcellulose. The table below lists exemplary pharmacokinetic data

| SD rat Number | $C_{max}$ (ng/ml) | $T_{max}$ (hr) | $T_{1/2}$ (hr) | $AUC_{0-t}$ (ng/ml hr) | $AUC_{0-inf}$ (ng/ml hr) | Vz (ml/kg) | CL (ml/hr/kg) | $MRT_{0-inf}$ (hrs) |
|---|---|---|---|---|---|---|---|---|
| No. 1 | 2870 | 4.00 | 4.53 | 18576 | 28893 | 1175 | 180 | 7.71 |
| No. 2 | 3770 | 4.00 | 2.94 | 22384 | 28922 | 763 | 180 | 5.76 |
| No. 3 | 4690 | 4.00 | 5.76 | 28408 | 52324 | 825 | 99 | 9.72 |
| Mean | 3777 | 4.00 | 4.41 | 23123 | 36713 | 921 | 153 | 7.73 |
| SD | 910 | 0.00 | 1.41 | 4957 | 13519 | 222 | 46 | 1.98 |

Similarly, PK data were obtained for compounds 42 and 95 with otherwise identical formulations and routes of administration. The following tables exemplarily illustrate the results.

Compound 42 i.v. and oral are shown in the respective tables below:

| SD rat Number | $T_{1/2}$ (hr) | $C_0$ (ng/ml) | $AUC_{0-t}$ (ng/ml hr) | $AUC_{0-inf}$ (ng/ml hr) | Vz (ml/kg) | CL (ml/hr/kg) | MRT (hrs) |
|---|---|---|---|---|---|---|---|
| No. 1 | 1.40 | 11495 | 11628 | 11770 | 344 | 170 | 1.30 |
| No. 2 | 0.99 | 11344 | 10782 | 10823 | 265 | 185 | 1.20 |
| No. 3 | 2.16 | 11625 | 10467 | 10730 | 582 | 186 | 1.28 |
| Mean | 1.52 | 11488 | 10959 | 11108 | 397 | 180 | 1.26 |
| SD | 0.59 | 141 | 600 | 575 | 165 | 9 | 0.05 |

| SD rat Number | $C_{max}$ (ng/ml) | $T_{max}$ (hr) | $T_{1/2}$ (hr) | $AUC_{0-t}$ (ng/ml hr) | $AUC_{0-inf}$ (ng/ml hr) | Vss (ml/kg) | CL (ml/hr/kg) | MRT (hrs) |
|---|---|---|---|---|---|---|---|---|
| No. 1 | 6880 | 1.5 | 3.28 | 24858 | 24926 | 781.0 | 165.3 | 3.46 |
| No. 2 | 4720 | 1 | 3.30 | 21467 | 21547 | 909.7 | 191.2 | 3.78 |
| No. 3 | 5730 | 1.5 | 2.97 | 22030 | 22051 | 800.7 | 186.8 | 2.83 |
| Mean | 5777 | 1.33 | 3.18 | 22785 | 22841 | 830.5 | 181.1 | 3.36 |
| SD | 1081 | 0.29 | 0.18 | 1817 | 1823 | 69.3 | 13.9 | 0.48 |

Compound 95 i.v. and oral are shown in the respective tables below:

| SD rat Number | $T_{1/2}$ (hr) | $C_0$ (ng/ml) | $AUC_{0-t}$ (ng/ml hr) | $AUC_{0-inf}$ (ng/ml hr) | Vz (ml/kg) | CL (ml/hr/kg) | MRT (hrs) |
|---|---|---|---|---|---|---|---|
| No. 1 | 9.46 | 2519 | 7683 | 15275 | 1601 | 1788 | 131 |
| No. 2 | 4.71 | 3144 | 7735 | 10570 | 1131 | 1286 | 189 |
| No. 3 | 7.90 | 5356 | 10881 | 18516 | 1043 | 1231 | 108 |
| Mean | 7.36 | 3673 | 8767 | 14787 | 1258 | 1435 | 143 |
| SD | 2.42 | 1491 | 1832 | 3996 | 300 | 307 | 42 |

| SD rat Number | $C_{max}$ (ng/ml) | $T_{max}$ (hr) | $T_{1/2}$ (hr) | $AUC_{0-t}$ (ng/ml hr) | $AUC_{0-inf}$ (ng/ml hr) | Vss (ml/kg) | CL (ml/hr/kg) | MRT (hrs) |
|---|---|---|---|---|---|---|---|---|
| No. 1 | 639 | 4.00 | 9.96 | 4041 | 11056 | 3225 | 224 | 4.40 |
| No. 2 | 1380 | 4.00 | 12.86 | 9183 | 29968 | 1536 | 83 | 4.38 |
| No. 3 | 1200 | 1.00 | 9.75 | 5774 | 13863 | 2517 | 179 | 3.92 |
| Mean | 1073 | 3.00 | 10.86 | 6333 | 18296 | 2426 | 162 | 4.24 |
| SD | 386 | 1.73 | 1.74 | 2616 | 10206 | 848 | 72 | 0.27 |

Selected compounds are effective in mouse xenograft model: The procedure was adapted from a previous published protocol (Small molecule targeting the Hec1Nek2 mitotic pathway suppresses tumor cell growth in culture and in animal. Cancer Res. 2008 Oct. 15; 68(20):8393-9). More specifically, female BALB/c nude (nu/nu) mice (5-8 weeks) were purchased from Lasco (Taiwan). The animals were maintained under specific pathogen-free conditions, and food and water were supplied ad libitum. Housing and all procedures involving animals were performed according to protocols approved by the IACUC in DCB. For subcutaneous implantation of MDA-MB-468 and MDA-MB-231 cells, cells ($1 \times 10^7$ in matrix gel/animal, and $0.5 \times 10^7$/animal, respectively) were injected subcutaneously into the right subaxillary region. After 10 days of tumor implantation, mice were treated (i.v., QD/21 cycles or p.o., QD/28 cycles in total) with vehicle A (5% DMSO, 10% Cremophor, 85% $H_2O$), or candidate compounds formulated in vehicle A (7.5-150 mg/kg body weight). Perpendicular diameter measurement of each tumor were made with digital calipers and the volume of the tumor calculated using formula (L×W×W)/2, in which L and W represent the length and the width, respectively. Body weights were measured three times weekly. Mean tumor growth inhibition of each treated group was compared with vehicle control and a Tumor growth inhibition value calculated using the formula: [1−(T/C)×100%].

Figure 5A:
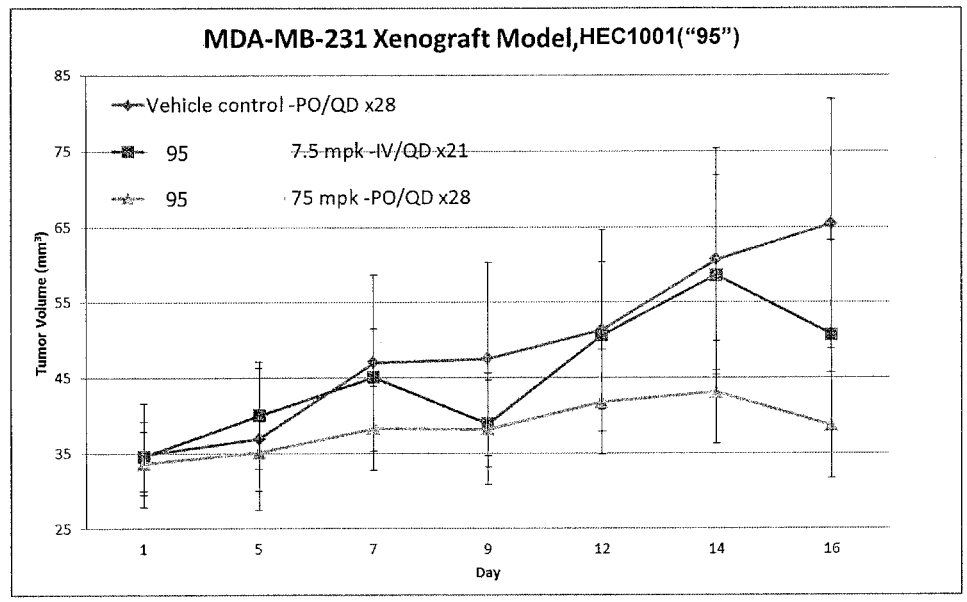
FIGS. 5A and 5B are graphs depicting in vivo effect of selected compounds on tumor volume in nude mice.
Figure 5B:
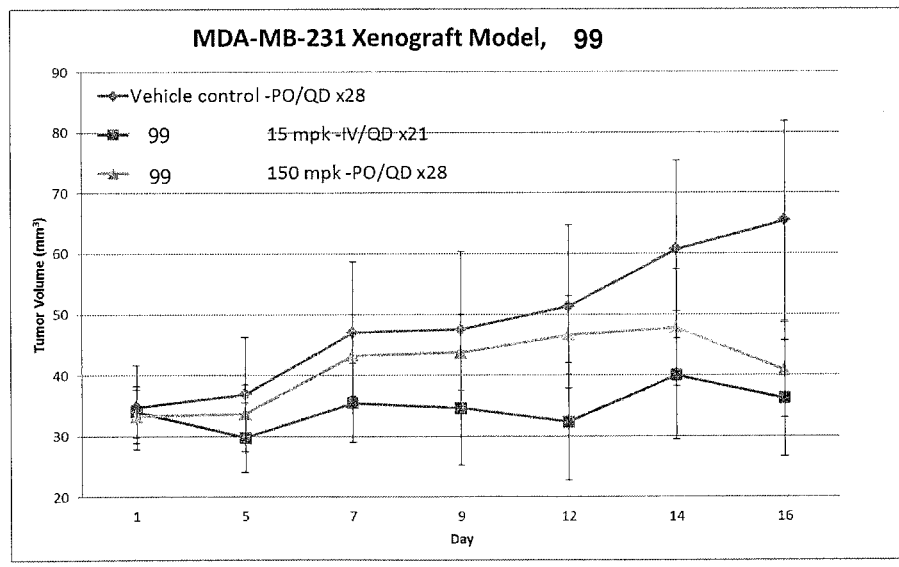

The in vivo effect of contemplated compounds on the tumor volume in nude mice is readily apparent from the graphs in FIGS. 5A and 5B. Despite the tumor reduction, body weight remained constant in all cases (data not shown).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A antineoplastic compound having a structure according to Formula I

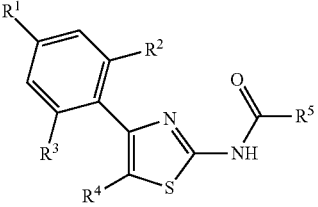

Formula I $R^1$ is $OR_a$, $SR_a$, or $—S(O)_2R_a$;

$R_a$ is alkyl, aryl, or aryl substituted with alkyl, fluoroalkyl, halogen, or alkoxy;

$R^2$ and $R^3$ are independently alkyl or halogen, and $R^4$ is hydrogen; and $R^5$ is optionally substituted pyridyl;

wherein each of $R^1$, $R^2$, $R^3$, $R^5$, and $R_a$ is independently optionally substituted with alkyl, fluoroalkyl, halogen, or alkoxy.

2. The compound of claim 1 wherein $R^1$ is $SR_a$, $OR_a$, or, —$S(O)_2R_a$, and wherein $R_a$ is aryl substituted with alkyl, fluoroalkyl, halogen, or alkoxy.

3. The compound of claim 2 wherein $R^1$ is $SR_a$ or $OR_a$, and wherein $R_a$ is aryl or aryl substituted with alkoxy.

4. The compound of claim 1 having a structure selected from the group consisting of

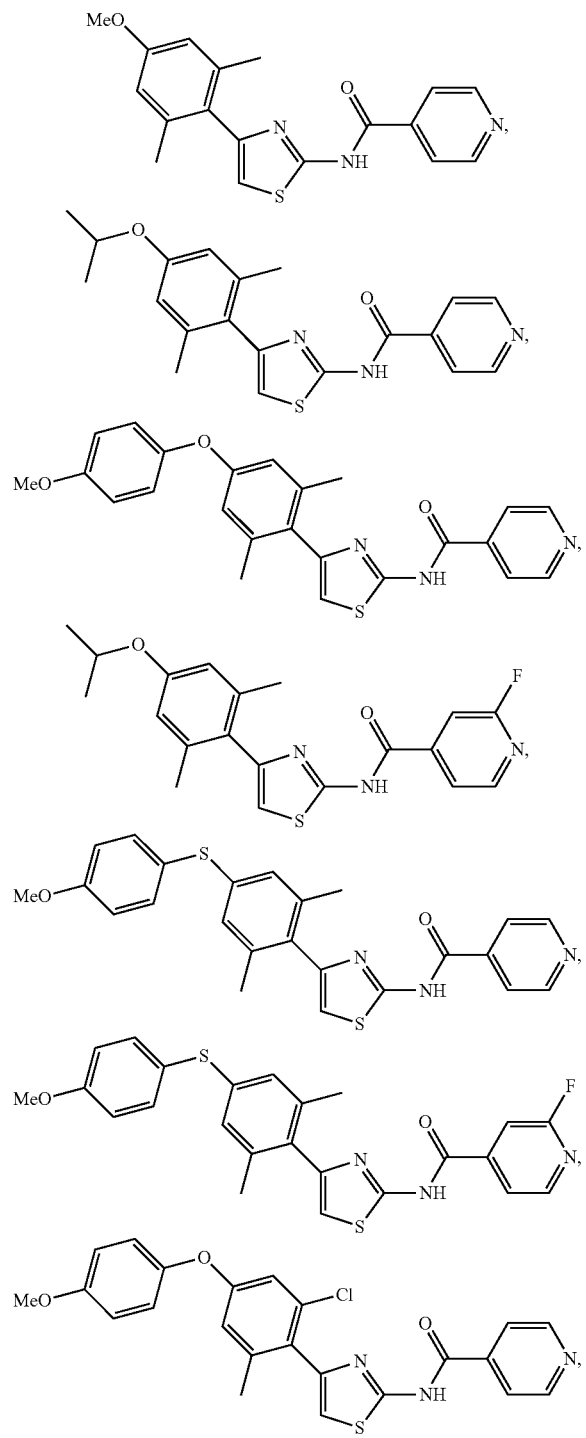

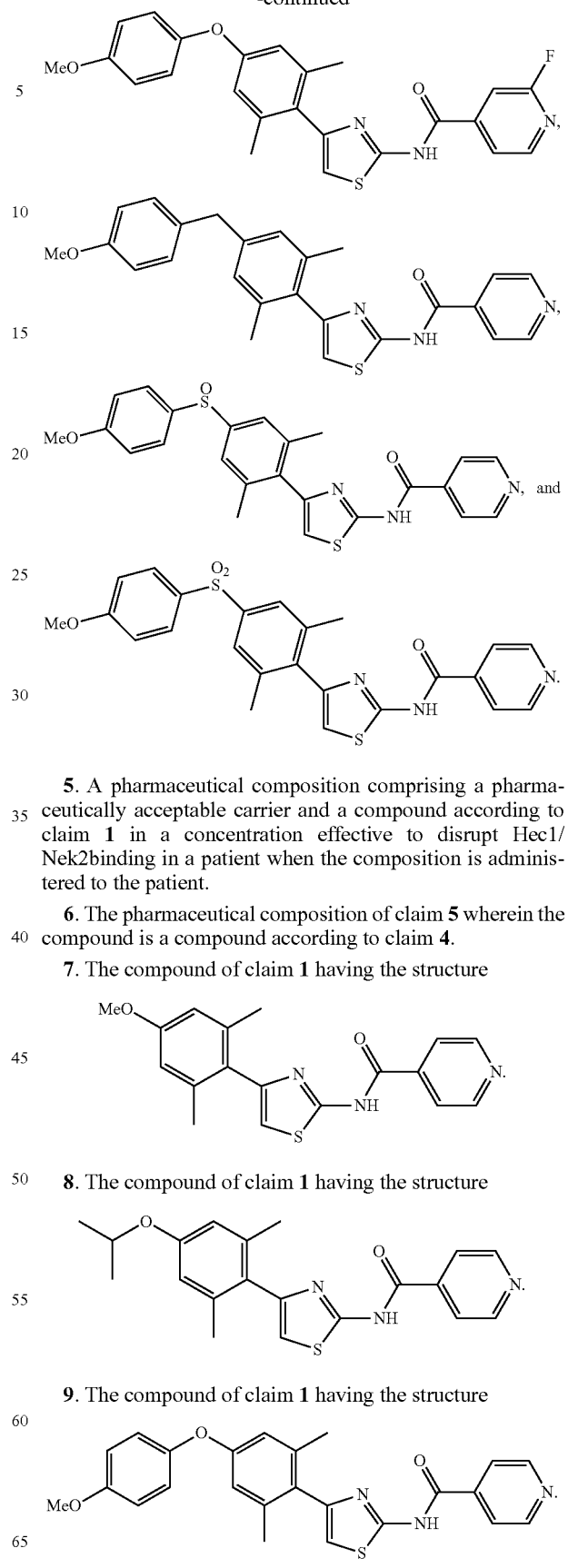

5. A pharmaceutical composition comprising a pharmaceutically acceptable carrier and a compound according to claim 1 in a concentration effective to disrupt Hec1/Nek2binding in a patient when the composition is administered to the patient.

6. The pharmaceutical composition of claim 5 wherein the compound is a compound according to claim 4.

7. The compound of claim 1 having the structure

8. The compound of claim 1 having the structure

9. The compound of claim 1 having the structure

10. The compound of claim 1 having the structure
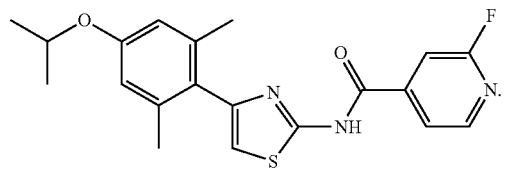 [SMILES: Cc1cc(OC(C)C)cc(C)c1-c1csc(NC(=O)c2ccnc(F)c2)n1]
11. The compound of claim 1 having the structure
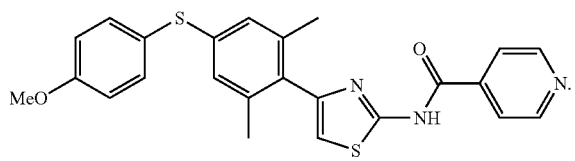 [SMILES: COc1ccc(Oc2cc(C)c(-c3csc(NC(=O)c4ccncc4)n3)c(Cl)c2)cc1]
12. The compound of claim 1 having the structure
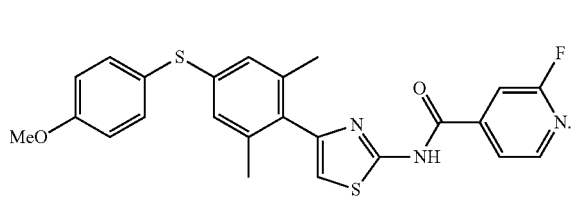 [SMILES: COc1ccc(Oc2cc(C)c(-c3csc(NC(=O)c4ccnc(F)c4)n3)c(C)c2)cc1]
13. The compound of claim 1 having the structure
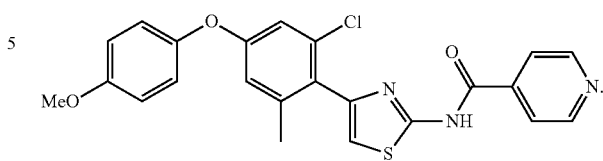
14. The compound of claim 1 having the structure
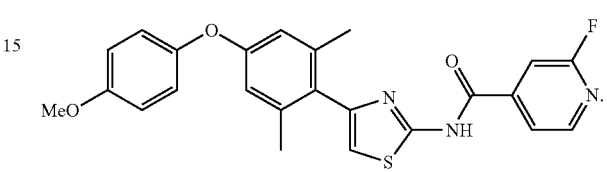
15. The compound of claim 1 having the structure
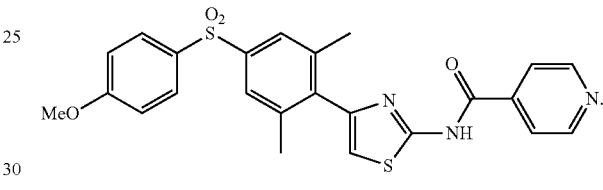
* * * * *